United States Patent
Probst et al.

(10) Patent No.: US 6,432,916 B1
(45) Date of Patent: Aug. 13, 2002

(54) COMPOUNDS AND METHODS FOR TREATMENT AND DIAGNOSIS OF CHLAMYDIAL INFECTION

(75) Inventors: Peter Probst; Ajay Bhatia, both of Seattle; Yasir A. W. Skeiky, Bellevue; Steven P. Fling, Bainbridge Island, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

(21) Appl. No.: 09/556,877

(22) Filed: Apr. 19, 2000

Related U.S. Application Data

(63) Continuation-in-part of application No. 09/454,684, filed on Dec. 3, 1999, which is a continuation-in-part of application No. 09/426,571, filed on Oct. 22, 1999, which is a continuation-in-part of application No. 09/410,568, filed on Oct. 1, 1999, which is a continuation-in-part of application No. 09/288,594, filed on Apr. 8, 1999, which is a continuation-in-part of application No. 09/208,277, filed on Dec. 8, 1998.

(51) Int. Cl.$^7$ .................. A61K 38/00; A61K 39/395; A61K 39/00; C07H 21/02; C07H 21/04; G01N 33/53

(52) U.S. Cl. .................. 514/2; 424/130.1; 424/184.1; 424/190.1; 536/23.1; 536/23.4; 435/7.1; 435/975

(58) Field of Search .................. 530/300; 514/44, 514/2; 424/130.1, 184.1, 190.1; 536/23.1, 23.4; 435/7.1, 975

(56) References Cited

U.S. PATENT DOCUMENTS

| | | | |
|---|---|---|---|
| 4,118,469 A | 10/1978 | Caldwell et al. | 424/1 |
| 4,497,863 A | 2/1985 | Armstrong et al. | 436/510 |
| 5,166,053 A | 11/1992 | Huguenel et al. | 435/7.36 |
| 5,318,892 A | 6/1994 | Watanabe et al. | 435/7.36 |
| 5,725,963 A | 3/1998 | Daniels | 424/263.1 |

FOREIGN PATENT DOCUMENTS

| | | |
|---|---|---|
| EP | 0784 059 A | 7/1997 |
| WO | WO 97/06263 | 2/1997 |
| WO | WO 98/02546 | 1/1998 |
| WO | WO 98/10789 | 3/1998 |
| WO | WO 99/27105 | 6/1999 |
| WO | WO 99/28475 | 6/1999 |
| WO | WO 99/51748 | 10/1999 |
| WO | WO 00/34483 | 6/2000 |

OTHER PUBLICATIONS

Stagg et al. Mol Med Today 1998 Apr.; 4:166–73.*
Stephens et al. Science 1998 Oct.;282:754–9.*
Kim et al. J Immunol 1999 Jun.; 162:6855–66.*
GenBank Accession No. AE001273, "Genome sequence of an obligate intracellular pathogen of humans: *Chlamydia trachomatis*," Oct. 30, 1999.
GenBank Accession No. AE001323, "Genome sequence of an obligate intracellular pathogen of humans: *Chlamydia trachomatis*," Oct. 30, 1999.
GenBank Accession No. AE001324, "Genome sequence of an obligate intracellular pathogen of humans: *Chlamydia trachomatis*," Oct. 30, 1999.

(List continued on next page.)

*Primary Examiner*—James Ketter
*Assistant Examiner*—Q Janice Li
(74) *Attorney, Agent, or Firm*—Seed Intellectual Property Law Group PLLC

(57) ABSTRACT

Compounds and methods for the diagnosis and treatment of Chlamydial infection are disclosed. The compounds provided include polypeptides that contain at least one antigenic portion of a Chlamydia antigen and DNA sequences encoding such polypeptides. Pharmaceutical compositions and vaccines comprising such polypeptides or DNA sequences are also provided, together with antibodies directed against such polypeptides. Diagnostic kits containing such polypeptides or DNA sequences and a suitable detection reagent may be used for the detection of Chlamydial infection in patients and in biological samples.

22 Claims, 11 Drawing Sheets

OTHER PUBLICATIONS

GenBank Accession No. AE001335, "Genome sequence of an obligate intracellular pathogen of humans: *Chlamydia trachomatis*," Oct. 30, 1999.

GenBank Accession No. E71500, "Genome sequence of an obligate intracellualr pathogen of humans: *Chlamydia trachomatis*," Oct. 8, 1999.

GenBank Accession No. H71501, "Genome sequence of an obligate intracellular pathogen of humans: *Chlamydia trachomatis*," Oct. 8, 1999.

GenBank Accession No. H71510, "Genome sequence of an obligate intracellular pathogen of humans: *Chlamydia trachomatis*" Oct. 8, 1999.

Levinson and Jawetz, *Medical Microbiology & Immunology*, 3d ed., Appleton & Lange, 1994, pp. 292–293.

Rank et al., *Infect. And Immunity*, 58(8):2599–2605, 1990.

Stephens et al., "Genome Sequence of an Obligate Intracellular Pathogen of Humans: *Chlamydia trachomatis*," *Science* 282:754–759, 1998.

Genbank Accession No. AE001316.

Genbank Accession No. AE001320.

Genbank Accession No. AE001326.

Gu et al., "*Chlamydia trachomatis* RNA polymerase α subunit: sequence and structural analysis," *J. Bacteriology* 177:2594–2601, May 1995.

Lalvani et al., "Rapid effector function in CD8+ memory T cells," *J. Exp. Med.* 186(6):859–865 Sep. 15, 1997.

Sanderson et al., "Identification of a CD4+ T Cell–stimulating Antigen of Pathogenic Bacteria by Expression Cloning," *J. Exp. Med.* 182(6):1751–1757, 1995.

Scudiero et al., "Evaluation of a soluble tetrazolium/formazan assay for cell growth and drug sensitivity in culture using human and other tumor cell lines," *Cancer Research* 48:4827–4833, Sep. 1, 1988.

Starnbach et al., "Protective cytotoxic T lymphocytes are induced during murine infection with *Chlamydia trachomatis*," *The Journal of Immunology* 153(11):5183–5189, Dec. 1, 1994.

Webb et al., "Molecular cloning of a novel protein antigen of Leishmania major that elicits a potent immune response in experimental murine leishmaniasis," *The Journal of Immunology* 157:5034–5041, 1996.

Baehr et al., "Mapping antigenic domains expressed by *chlamydia trachomatis* major outer membrane protein genes," *Proc Natl Acad Sci USA* 85(1):4000–4004, Jun. 1, 1998.

Brunham et al., "*Chlamydia trachomatis* antigens: role in immunity and pathogenesis," *Infectious Agents and Disease* 3(5):218–233, Oct. 1994.

Genbank Accession No. AE 001361, Jul. 22, 1998.

* cited by examiner

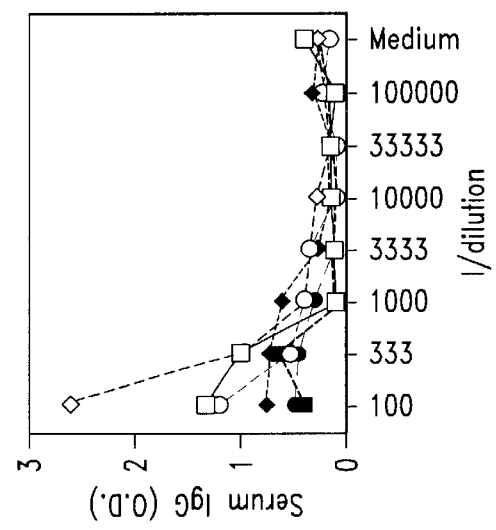
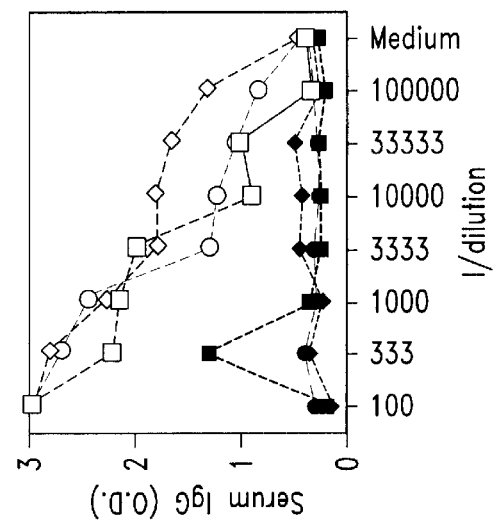
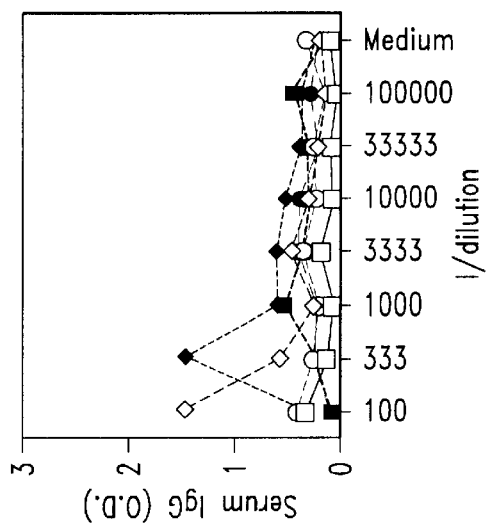
Fig. 4A
Fig. 4B
Fig. 4C

PRIMER SEQUENCES-CP SWIB AND CP S13

CP SWIB Nde (5' primer)
5' GATATACATATGCATCACCATCACCATCACATGAGTCAAAAAAATAAAAACTCT CP SWIB EcoRI (3' primer)
5' CTCGAGGAATTCTTATTTTACAATATGTTTGGA CP S13 Nde (5' primer)
5' GATATACATATGCATCACCATCACCATCACATGCCACGCATCATTGGAATGAT CP S13 EcoRI (3' primer)
5' CTCGAGGAATTCTTATTTCTTCTTACCTGC

*Fig. 6*

T cell line TCL-8 EBCD responds to *E. coli* expressing ribosomal S13 from *C. trachomatis* and from *C. pneumoniae*

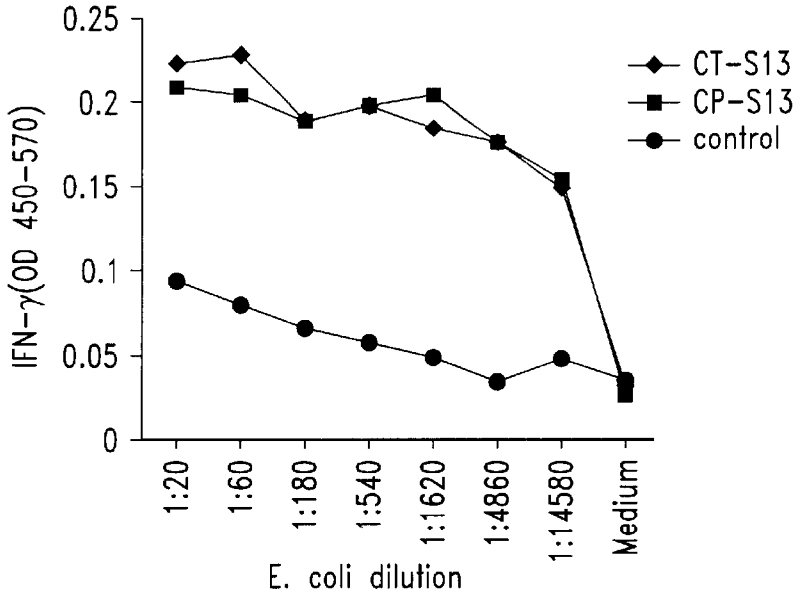

*Fig. 7A*

T cell line TCL-8 EBCD responds to *E. coli* expressing SWIB from *C. trachomatis* but not from *C. pneumoniae*

Identification of T cell epitopes in chlamydial ribosomal S13 protein with TCL8 EB/DC Proliferative responses were determined by stimulating $2.5 \times 10^4$ T cells in the pressence of $1 \times 10^4$ monocyte-derived dendritic cells and Ct-EB (1 μg/ml), Ct-, CpS13 (2 μg/ml) or the respective peptide (0.2 μg/ml). Assay was harvested after 4 days with a $^3$H-thymidine pulse for the last 18h.

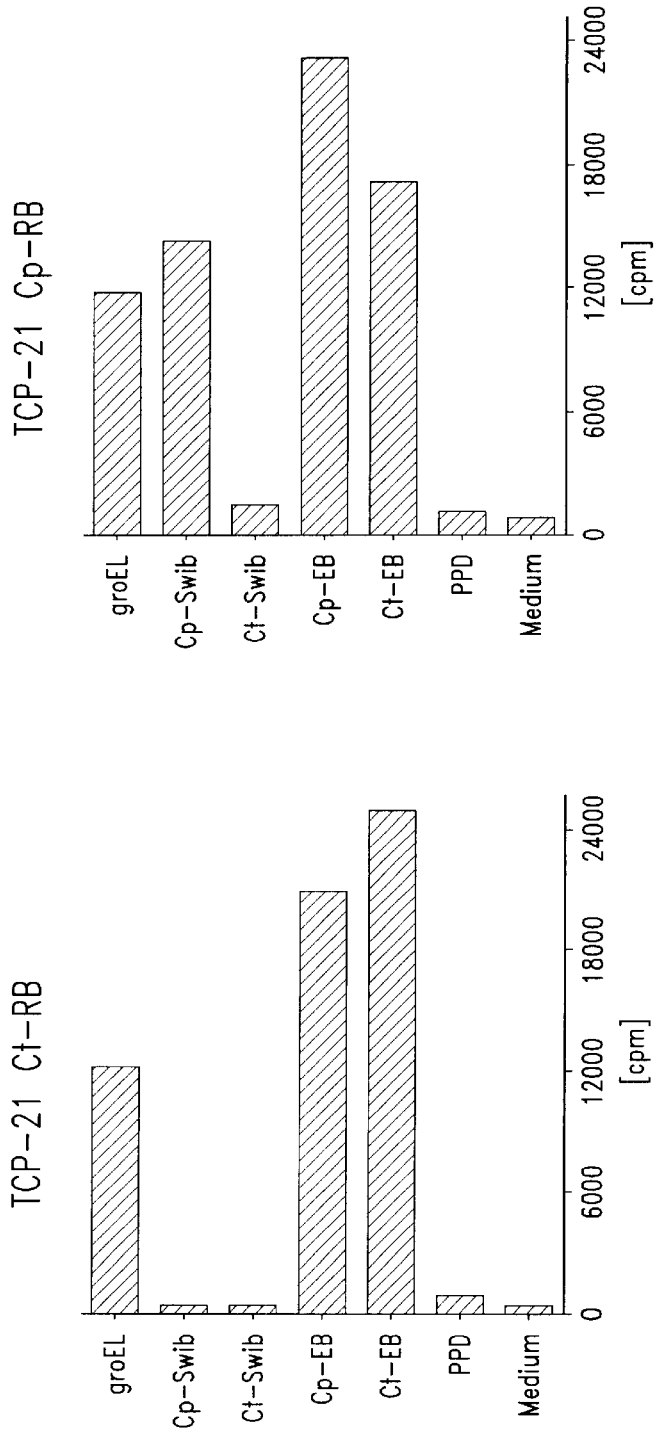

T cells lines were generated against monocyte-derived dendritic cells infected for 72h with C. trachomatis LGV II (Ct-RB) or C. pneumoniae (Cp-RB) respectively. Proliferative responses were determined by stimulating 2.5 x 10⁴ monocyte-derived dendritic cells and the respective antigen Ct-groEL 2µg/ml, Cp-groEL 2µg/ml, Ct-Swib 2µg/ml, Cp-EB 1µg/ml. Assay was harvested after 4 days with a ³H-thymidine pulse for the last 18h.

A primary T cell line (TCT-10 EB) from an asymptomatic donor has a *C. trachomatis*-specific Swib response

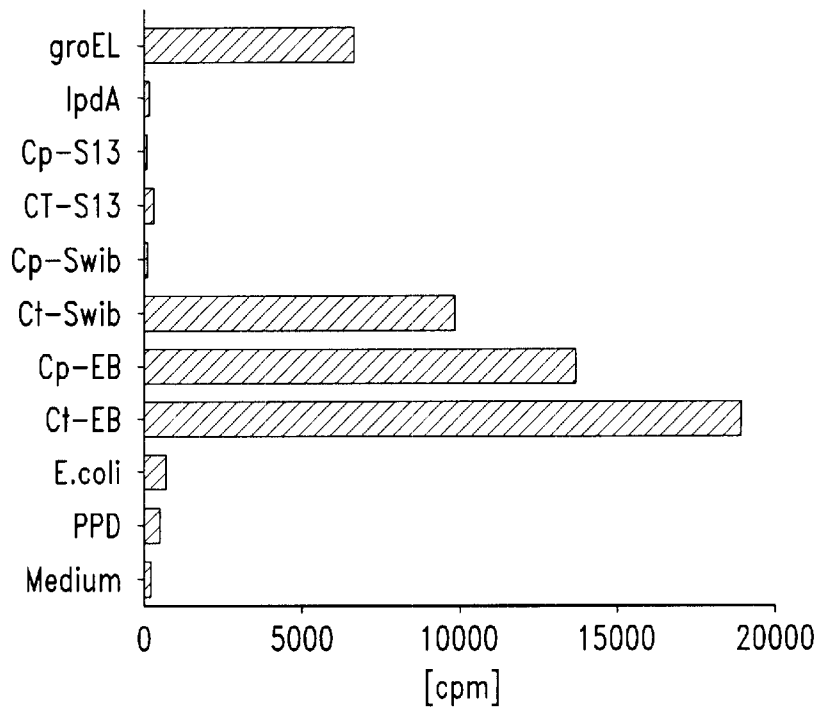

T cell line TCT-10 EB was generated by stimulating PBMC with 1 μg/ml killed C. trachomatis LGV2 elementary body (EB). Proliverative responses were determined by stimulating $2.5 \times 10^4$ T cells in the presence of $1 \times 10^4$ monocyte-derived dendritic cells and the respective antigen. Assay was harvested after 4 days with a $^3$H-thymidine pulse for the last 18h.

SEQUENCE LISTING

```
<160> NUMBER OF SEQ ID NOS:  305

<210> SEQ ID NO 1
<211> LENGTH: 481
<212> TYPE: DNA
<213> ORGANISM: Chlamydia trachomatis

<400> SEQUENCE: 1
ctgaagactt ggctatgttt tttattttga cgataaacct agttaaggca taaaagagtt     60
gcgaaggaag agccctcaac ttttcttatc accttcttta actaggagtc atccatgagt    120
caaaataaga actctgcttt catgcagcct gtgaacgtat ccgctgattt agctgccatc    180
```

```
gttggtgcag gacctatgcc tcgcacagag atcattaaga aatgtggga ttacattaag      240 gagaatagtc ttcaagatcc tacaaacaaa cgtaatatca atcccgatga taaattggct      300 aaagttttg gaactgaaaa acctatcgat atgttccaaa tgacaaaaat ggtttctcaa       360
cacatcatta aataaaatag aaattgactc acgtgttcct cgtctttaag atgaggaact      420
agttcattct ttttgttcgt ttttgtgggt attactgtat ctttaacaac tatcttagca      480
g                                                                     481

<210> SEQ ID NO 2
<211> LENGTH: 183
<212> TYPE: DNA
<213> ORGANISM: Chlamydia trachomatis

<400> SEQUENCE: 2
atcgttggtg caggacctat gcctcgcaca gagatcatta agaaaatgtg ggattacatt       60
aaggagaata gtcttcaaga tcctacaaac aaacgtaata tcaatcccga tgataaattg      120
gctaaagttt tggaactga aaaacctatc gatatgttcc aaatgacaaa aatggtttct       180
caa                                                                    183

<210> SEQ ID NO 3
<211> LENGTH: 110
<212> TYPE: DNA
<213> ORGANISM: Chlamydia trachomatis

<400> SEQUENCE: 3
gctgcgacat catgcgagct tgcaaaccaa catggacatc tccaatttcc ccttctaact       60
cgctctttgg aactaatgct gctaccgagt caatcacaat cacatcgacc                 110

<210> SEQ ID NO 4
<211> LENGTH: 555
<212> TYPE: DNA
<213> ORGANISM: Chlamydia trachomatis

<400> SEQUENCE: 4
cggcacgagc ctaagatgct tatactactt taagggaggc ccttcgtatg ccgcgcatca       60
ttggaataga tattcctgcg aaaaagaaat taaaataag tcttacatat atttatggaa       120
tagggccagc tctttctaaa gagattattg ctagattgca gttgaatccc gaagctagag      180
ctgcagagtt gactgaggaa gaggttggtc gactaaacgc tcttttacag tcggattacg      240
ttgttgaagg ggatttgcgc cgtcgtgtgc aatctgatat caaacgtctg attactatcc      300
atgcttatcg tggacaaaga catagacttt ctttgcctgt tcgtggtcag agaacaaaaa      360
caaattctcg cacgcgtaag ggtaaacgta aaactattgc aggtaagaag aataataat       420 ttttaggaga gagtgttttg gttaaaaatc aagcgcaaaa aagaggcgta aaagaaaac       480 aagtaaaaaa cattccttcg ggcgttgtcc atgttaaggc tacttttaat aatacaattg     540
taaccataac agacc                                                       555

<210> SEQ ID NO 5
<211> LENGTH: 86
<212> TYPE: PRT
<213> ORGANISM: Chlamydia trachomatis

<400> SEQUENCE: 5

Met Ser Gln Asn Lys Asn Ser Ala Phe Met Gln Pro Val Asn Val Ser
  1               5                  10                  15
```

```
Ala Asp Leu Ala Ala Ile Val Gly Ala Gly Pro Met Pro Arg Thr Glu
             20                  25                  30

Ile Ile Lys Lys Met Trp Asp Tyr Ile Lys Glu Asn Ser Leu Gln Asp
         35                  40                  45

Pro Thr Asn Lys Arg Asn Ile Asn Pro Asp Asp Lys Leu Ala Lys Val
     50                  55                  60

Phe Gly Thr Glu Lys Pro Ile Asp Met Phe Gln Met Thr Lys Met Val
 65                  70                  75                  80

Ser Gln His Ile Ile Lys
                 85

<210> SEQ ID NO 6
<211> LENGTH: 61
<212> TYPE: PRT
<213> ORGANISM: Chlamydia trachomatis

<400> SEQUENCE: 6

Ile Val Gly Ala Gly Pro Met Pro Arg Thr Glu Ile Ile Lys Lys Met
 1               5                  10                  15

Trp Asp Tyr Ile Lys Glu Asn Ser Leu Gln Asp Pro Thr Asn Lys Arg
             20                  25                  30

Asn Ile Asn Pro Asp Asp Lys Leu Ala Lys Val Phe Gly Thr Glu Lys
         35                  40                  45

Pro Ile Asp Met Phe Gln Met Thr Lys Met Val Ser Gln
     50                  55                  60

<210> SEQ ID NO 7
<211> LENGTH: 36
<212> TYPE: PRT
<213> ORGANISM: Chlamyida trachomatis

<400> SEQUENCE: 7

Ala Ala Thr Ser Cys Glu Leu Ala Asn Gln His Gly His Leu Gln Phe
 1               5                  10                  15

Pro Leu Leu Thr Arg Ser Leu Glu Leu Met Leu Leu Pro Ser Gln Ser
             20                  25                  30

Gln Ser His Arg
         35

<210> SEQ ID NO 8
<211> LENGTH: 18
<212> TYPE: PRT
<213> ORGANISM: Chlamydia trachomatis

<400> SEQUENCE: 8

Leu Arg His His Ala Ser Leu Gln Thr Asn Met Asp Ile Ser Asn Phe
 1               5                  10                  15

Pro Phe

<210> SEQ ID NO 9
<211> LENGTH: 5
<212> TYPE: PRT
<213> ORGANISM: Chlamydia trachomatis

<400> SEQUENCE: 9

Leu Ala Leu Trp Asn
 1               5

<210> SEQ ID NO 10
<211> LENGTH: 11
```

```
<212> TYPE: PRT
<213> ORGANISM: Chlamydia trachomatis

<400> SEQUENCE: 10

Cys Cys Tyr Arg Val Asn His Asn His Ile Asp
1               5                   10

<210> SEQ ID NO 11
<211> LENGTH: 36
<212> TYPE: PRT
<213> ORGANISM: Chlamydia trachomatis

<400> SEQUENCE: 11

Val Asp Val Ile Val Ile Asp Ser Val Ala Leu Val Pro Lys Ser
1               5                   10                  15

Glu Leu Glu Gly Glu Ile Gly Asp Val His Val Gly Leu Gln Ala Arg
            20                  25                  30

Met Met Ser Gln
            35

<210> SEQ ID NO 12
<211> LENGTH: 122
<212> TYPE: PRT
<213> ORGANISM: Chlamydia trachomatis

<400> SEQUENCE: 12

Met Pro Arg Ile Ile Gly Ile Asp Ile Pro Ala Lys Lys Lys Leu Lys
1               5                   10                  15

Ile Ser Leu Thr Tyr Ile Tyr Gly Ile Gly Pro Ala Leu Ser Lys Glu
            20                  25                  30

Ile Ile Ala Arg Leu Gln Leu Asn Pro Glu Ala Arg Ala Ala Glu Leu
            35                  40                  45

Thr Glu Glu Val Gly Arg Leu Asn Ala Leu Leu Gln Ser Asp Tyr
    50                  55                  60

Val Val Glu Gly Asp Leu Arg Arg Val Gln Ser Asp Ile Lys Arg
65                  70                  75                  80

Leu Ile Thr Ile His Ala Tyr Arg Gly Gln Arg His Arg Leu Ser Leu
            85                  90                  95

Pro Val Arg Gly Gln Arg Thr Lys Thr Asn Ser Arg Thr Arg Lys Gly
            100                 105                 110

Lys Arg Lys Thr Ile Ala Gly Lys Lys Lys
            115                 120

<210> SEQ ID NO 13
<211> LENGTH: 20
<212> TYPE: PRT
<213> ORGANISM: Chlamydia trachomatis

<400> SEQUENCE: 13

Asp Pro Thr Asn Lys Arg Asn Ile Asn Pro Asp Asp Lys Leu Ala Lys
1               5                   10                  15

Val Phe Gly Thr
            20

<210> SEQ ID NO 14
<211> LENGTH: 20
<212> TYPE: PRT
<213> ORGANISM: Chlamydia trachomatis

<400> SEQUENCE: 14
```

```
Asp Asp Lys Leu Ala Lys Val Phe Gly Thr Glu Lys Pro Ile Asp Met
  1               5                  10                  15

Phe Gln Met Thr
            20
```

<210> SEQ ID NO 15
<211> LENGTH: 161
<212> TYPE: DNA
<213> ORGANISM: Chlymidia trachomatis

<400> SEQUENCE: 15

```
atctttgtgt gtctcataag cgcagagcgg ctgcggctgt ctgtagcttc atcggaggaa    60
ttacctacct cgcgacattc ggagctatcc gtccgattct gtttgtcaac aaaatgctgg   120
cgcaaccgtt tctttcttcc caaactaaag caaatatggg a                       161
```

<210> SEQ ID NO 16
<211> LENGTH: 897
<212> TYPE: DNA
<213> ORGANISM: Chlymidia trachomatis

<400> SEQUENCE: 16

```
atggcttcta tatgcggacg tttagggtct ggtacaggga atgctctaaa agcttttttt    60
acacagccca acaataaaat ggcaagggta gtaaataaga cgaagggaat ggataagact   120
attaaggttg ccaagtctgc tgccgaattg accgcaaata ttttggaaca agctggaggc   180
gcgggctctt ccgcacacat tacagcttcc caagtgtcca aaggattagg ggatgcgaga   240
actgttgtcg ctttagggaa tgcctttaac ggagcgttgc caggaacagt tcaaagtgcg   300
caaagcttct tctctcacat gaaagctgct agtcagaaaa cgcaagaagg ggatgagggg   360
ctcacagcag atctttgtgt gtctcataag cgcagagcgg ctgcggctgt ctgtagcatc   420
atcggaggaa ttacctacct cgcgacattc ggagctatcc gtccgattct gtttgtcaac   480
aaaatgctgg caaaccgttt ctttcttcc caaactaaag caaatatggg atcttctgtt   540
agctatatta tggcggctaa ccatgcagcg tctgtggtgg gtgctggact cgctatcagt   600
gcggaaagag cagattgcga agcccgctgc gctcgtattg cgagagaaga gtcgttactc   660
gaagtgccgg gagaggaaaa tgcttgcgag aagaaagtcg ctggagagaa agccaagacg   720
ttcacgcgca tcaagtatgc actcctcact atgctcgaga gttttttgga atgcgttgcc   780
gacgttttca aattggtgcc gctgcctatt acaatgggta ttcgtgcgat gtggctgct   840
ggatgtacgt tcacttctgc aattattgga ttgtgcactt tctgcgccag agcataa    897
```

<210> SEQ ID NO 17
<211> LENGTH: 298
<212> TYPE: PRT
<213> ORGANISM: Chlamydia trachomatis

<400> SEQUENCE: 17

```
Met Ala Ser Ile Cys Gly Arg Leu Gly Ser Gly Thr Gly Asn Ala Leu
  1               5                  10                  15

Lys Ala Phe Phe Thr Gln Pro Asn Asn Lys Met Ala Arg Val Val Asn
             20                  25                  30

Lys Thr Lys Gly Met Asp Lys Thr Ile Lys Val Ala Lys Ser Ala Ala
         35                  40                  45

Glu Leu Thr Ala Asn Ile Leu Glu Gln Ala Gly Ala Gly Ser Ser
     50                  55                  60

Ala His Ile Thr Ala Ser Gln Val Ser Lys Gly Leu Gly Asp Ala Arg
```

```
              65                  70                  75                  80
Thr Val Val Ala Leu Gly Asn Ala Phe Asn Gly Ala Leu Pro Gly Thr
                     85                  90                  95

Val Gln Ser Ala Gln Ser Phe Ser His Met Lys Ala Ala Ser Gln
            100                 105                 110

Lys Thr Gln Glu Gly Asp Glu Gly Leu Thr Ala Asp Leu Cys Val Ser
        115                 120                 125

His Lys Arg Arg Ala Ala Ala Val Cys Ser Ile Ile Gly Gly Ile
    130                 135                 140

Thr Tyr Leu Ala Thr Phe Gly Ala Ile Arg Pro Ile Leu Phe Val Asn
145                 150                 155                 160

Lys Met Leu Ala Lys Pro Phe Leu Ser Ser Gln Thr Lys Ala Asn Met
                165                 170                 175

Gly Ser Ser Val Ser Tyr Ile Met Ala Ala Asn His Ala Ala Ser Val
            180                 185                 190

Val Gly Ala Gly Leu Ala Ile Ser Ala Glu Arg Ala Asp Cys Glu Ala
        195                 200                 205

Arg Cys Ala Arg Ile Ala Arg Glu Glu Ser Leu Leu Glu Val Pro Gly
    210                 215                 220

Glu Glu Asn Ala Cys Glu Lys Lys Val Ala Gly Glu Lys Ala Lys Thr
225                 230                 235                 240

Phe Thr Arg Ile Lys Tyr Ala Leu Leu Thr Met Leu Glu Lys Phe Leu
                245                 250                 255

Glu Cys Val Ala Asp Val Phe Lys Leu Val Pro Leu Pro Ile Thr Met
            260                 265                 270

Gly Ile Arg Ala Ile Val Ala Ala Gly Cys Thr Phe Thr Ser Ala Ile
        275                 280                 285

Ile Gly Leu Cys Thr Phe Cys Ala Arg Ala
    290                 295

<210> SEQ ID NO 18
<211> LENGTH: 18
<212> TYPE: PRT
<213> ORGANISM: Chlamydia trachomatis

<400> SEQUENCE: 18

Arg Ala Ala Ala Ala Ala Val Cys Ser Phe Ile Gly Gly Ile Thr
1               5                   10                  15

Tyr Leu

<210> SEQ ID NO 19
<211> LENGTH: 18
<212> TYPE: PRT
<213> ORGANISM: Chlamydia trachomatis

<400> SEQUENCE: 19

Cys Ser Phe Ile Gly Gly Ile Thr Tyr Leu Ala Thr Phe Gly Ala Ile
1               5                   10                  15

Arg Pro

<210> SEQ ID NO 20
<211> LENGTH: 216
<212> TYPE: PRT
<213> ORGANISM: Chlamydia trachomatis

<400> SEQUENCE: 20

Met Arg Gly Ser Gln Gln Ile Phe Val Cys Leu Ile Ser Ala Glu Arg
```

-continued

```
  1               5              10              15
Leu Arg Leu Ser Val Ala Ser Ser Glu Glu Leu Pro Thr Ser Arg His
                 20              25              30

Ser Glu Leu Ser Val Arg Phe Cys Leu Ser Thr Lys Cys Trp Gln Asn
                 35              40              45

Arg Phe Phe Leu Pro Lys Leu Lys Gln Ile Trp Asp Leu Leu Leu Ala
     50              55              60

Ile Leu Trp Arg Leu Thr Met Gln Arg Leu Trp Trp Val Leu Asp Ser
 65              70              75              80

Leu Ser Val Arg Lys Glu Gln Ile Ala Lys Pro Ala Ala Leu Val Leu
                 85              90              95

Arg Glu Lys Ser Arg Tyr Ser Lys Cys Arg Glu Arg Lys Met Leu Ala
                100             105             110

Arg Arg Lys Ser Leu Glu Arg Lys Pro Arg Arg Ser Arg Ala Ser Ser
                115             120             125

Met His Ser Ser Leu Cys Ser Arg Ser Phe Trp Asn Ala Leu Pro Thr
        130             135             140

Phe Ser Asn Trp Cys Arg Cys Leu Leu Gln Trp Val Phe Val Arg Leu
145             150             155             160

Trp Leu Leu Asp Val Arg Ser Leu Leu Gln Leu Leu Asp Cys Ala Leu
                165             170             175

Ser Ala Pro Glu His Lys Gly Phe Phe Lys Phe Leu Lys Lys Lys Ala
                180             185             190

Val Ser Lys Lys Lys Gln Pro Phe Leu Ser Thr Lys Cys Leu Ala Phe
            195             200             205

Leu Ile Val Lys Ile Val Phe Leu
        210             215
```

<210> SEQ ID NO 21
<211> LENGTH: 1256
<212> TYPE: DNA
<213> ORGANISM: Chlamydia trachomatis

<400> SEQUENCE: 21

```
ctcgtgccgg cacgagcaaa gaaatccctc aaaaaatggc cattattggc ggtggtgtga      60
tcggttgcga attcgcttcc ttattccata cgttaggctc cgaagtttct gtgatcgaag     120
caagctctca aatccttgct ttgaataatc cagatatttc aaaaaccatg ttcgataaat     180
tcacccgaca aggactccgt ttcgtactag aagcctctgt atcaaatatt gaggatatag     240
gagatcgcgt tcggttaact atcaatggga atgtcgaaga atacgattac gttctcgtat     300
ctataggacg ccgtttgaat acagaaaata ttggcttgga taaagctggt gttatttgtg     360
atgaacgcgg agtcatccct accgatgcca caatgcgcac aaacgtacct aacatttatg     420
ctattggaga tatcacagga aaatggcaac ttgcccatgt agcttctcat caaggaatca     480
ttgcagcacg gaatataggt ggccataaag aggaaatcga ttactctgct gtcccttctg     540
tgatctttac cttccctgaa gtcgcttcag taggcctctc cccaacagca gctcaacaac     600
atctccttct tcgcttactt tttctgaaaa atttgataca gaagaagaat tcctcgcaca     660
cttgcgagga ggagggcgtc tggaagacca gttgaattta gctaagtttt ctgagcgttt     720
tgattctttg cgagaattat ccgctaagct tggttacgat agcgatggag agactgggga     780
tttcttcaac gaggagtacg acgacgaaga gaggaaatc aaaccgaaga aaactacgaa     840
acgtggacgt aagaagagcc gttcataagc cttgctttta aggtttggta gttttacttc     900
```

-continued

| | |
|---|---|
| tctaaaatcc aaatggttgc tgtgccaaaa agtagtttgc gtttccggat agggcgtaaa | 960 |
| tgcgctgcat gaaagattgc ttcgagagcg gcatcgcgtg ggagatcccg gatactttct | 1020 |
| ttcagatacg aataagcata gctgttccca gaataaaaac ggccgacgct aggaacaaca | 1080 |
| agatttagat agagcttgtg tagcaggtaa actgggttat atgttgctgg gcgtgttagt | 1140 |
| tctagaatac ccaagtgtcc tccaggttgt aatactcgat acacttccct aagagcctct | 1200 |
| aatggatagg ataagttccg taatccatag gccatagaag ctaaacgaaa cgtatt | 1256 |

<210> SEQ ID NO 22
<211> LENGTH: 601
<212> TYPE: DNA
<213> ORGANISM: Chlamydia trachomatis

<400> SEQUENCE: 22

| | |
|---|---|
| ctcgtgccgg cacgagcaaa gaaatccctc aaaaaatggc cattattggc ggtggtgtga | 60 |
| tcggttgcga attcgcttcc ttattccata cgttaggctc cgaagtttct gtgatcgaag | 120 |
| caagctctca atccttgct ttgaataatc cagatatttc aaaaaccatg ttcgataaat | 180 |
| tcacccgaca aggactccgt ttcgtactag aagcctctgt atcaaatatt gaggatatag | 240 |
| gagatcgcgt tcggttaact atcaatggga atgtcgaaga atacgattac gttctcgtat | 300 |
| ctataggacg ccgtttgaat acagaaaata ttggcttgga taaagctggt gttatttgtg | 360 |
| atgaacgcgg agtcatccct accgatgcca caatgcgcac aaacgtacct aacatttatg | 420 |
| ctattggaga tatcacagga aaatggcaac ttgcccatgt agcttctcat caaggaatca | 480 |
| ttgcagcacg gaatataggt ggccataaag aggaaatcga ttactctgct gtcccttctg | 540 |
| tgatctttac cttccctgaa gtcgcttcag taggcctctc cccaacagca gctcaacaac | 600 |
| a | 601 |

<210> SEQ ID NO 23
<211> LENGTH: 270
<212> TYPE: DNA
<213> ORGANISM: Chlamydia trachomatis

<400> SEQUENCE: 23

| | |
|---|---|
| acatctcctt cttcgcttac tttttctgaa aaatttgata cagaagaaga attcctcgca | 60 |
| cacttgcgag gaggagggcg tctggaagac cagttgaatt tagctaagtt ttctgagcgt | 120 |
| tttgattctt tgcgagaatt atccgctaag cttggttacg atagcgatgg agagactggg | 180 |
| gatttcttca acgaggagta cgacgacgaa gaagaggaaa tcaaaccgaa gaaaactacg | 240 |
| aaacgtggac gtaagaagag ccgttcataa | 270 |

<210> SEQ ID NO 24
<211> LENGTH: 363
<212> TYPE: DNA
<213> ORGANISM: Chlamydia trachomatis

<400> SEQUENCE: 24

| | |
|---|---|
| ttacttctct aaaatccaaa tggttgctgt gccaaaaagt agtttgcgtt tccggatagg | 60 |
| gcgtaaatgc gctgcatgaa agattgcttc gagagcggca tcgcgtggga gatcccggat | 120 |
| actttctttc agatacgaat aagcatagct gttcccagaa taaaaacggc cgacgctagg | 180 |
| aacaacaaga tttagataga gcttgtgtag caggtaaact gggttatatg ttgctgggcg | 240 |
| tgttagttct agaatacccca agtgtcctcc aggttgtaat actcgataca cttccctaag | 300 |
| agcctctaat ggataggata agttccgtaa tccataggcc atagaagcta acgaaacgt | 360 |

```
att                                                                       363
```

<210> SEQ ID NO 25
<211> LENGTH: 696
<212> TYPE: DNA
<213> ORGANISM: Chlamydia trachomatis

<400> SEQUENCE: 25

```
gctcgtgccg gcacgagcaa agaaatccct caaaaaatgg ccattattgg cggtggtgtg    60
atcggttgcg aattcgcttc cttattccat acgttaggct ccgaagtttc tgtgatcgaa   120
gcaagctctc aaatccttgc tttgaataat ccagatattt caaaaaccat gttcgataaa   180
ttcacccgac aaggactccg tttcgtacta gaagcctctg tatcaaatat tgaggatata   240
ggagatcgcg ttcggttaac tatcaatggg aatgtcgaag aatacgatta cgttctcgta   300
tctataggac gccgtttgaa tacagaaaat attggcttgg ataaagctgg tgttatttgt   360
gatgaacgcg gagtcatccc taccgatgcc acaatgcgca caaacgtacc taacatttat   420
gctattggag atatcacagg aaaatggcaa cttgcccatg tagcttctca tcaaggaatc   480
attgcagcac ggaatatagg tggccataaa gaggaaatcg attactctgc tgtcccttct   540
gtgatcttta ccttccctga agtcgcttca gtaggcctct ccccaacagc agctcaacaa   600
catctccttc ttcgcttact ttttctgaaa aatttgatac agaagaagaa ttcctcgcac   660
acttgcgagg aggagggcgt ctggaagacc agttga                              696
```

<210> SEQ ID NO 26
<211> LENGTH: 231
<212> TYPE: PRT
<213> ORGANISM: Chlamydia trachomatis

<400> SEQUENCE: 26

```
Ala Arg Ala Gly Thr Ser Lys Glu Ile Pro Gln Lys Met Ala Ile Ile
  1               5                  10                  15

Gly Gly Gly Val Ile Gly Cys Glu Phe Ala Ser Leu Phe His Thr Leu
             20                  25                  30

Gly Ser Glu Val Ser Val Ile Glu Ala Ser Ser Gln Ile Leu Ala Leu
         35                  40                  45

Asn Asn Pro Asp Ile Ser Lys Thr Met Phe Asp Lys Phe Thr Arg Gln
 50                  55                  60

Gly Leu Arg Phe Val Leu Glu Ala Ser Val Ser Asn Ile Glu Asp Ile
 65                  70                  75                  80

Gly Asp Arg Val Arg Leu Thr Ile Asn Gly Asn Val Glu Glu Tyr Asp
                 85                  90                  95

Tyr Val Leu Val Ser Ile Gly Arg Arg Leu Asn Thr Glu Asn Ile Gly
            100                 105                 110

Leu Asp Lys Ala Gly Val Ile Cys Asp Glu Arg Gly Val Ile Pro Thr
        115                 120                 125

Asp Ala Thr Met Arg Thr Asn Val Pro Asn Ile Tyr Ala Ile Gly Asp
    130                 135                 140

Ile Thr Gly Lys Trp Gln Leu Ala His Val Ala Ser His Gln Gly Ile
145                 150                 155                 160

Ile Ala Ala Arg Asn Ile Gly Gly His Lys Glu Glu Ile Asp Tyr Ser
                165                 170                 175

Ala Val Pro Ser Val Ile Phe Thr Phe Pro Glu Val Ala Ser Val Gly
            180                 185                 190
```

```
Leu Ser Pro Thr Ala Ala Gln Gln His Leu Leu Arg Leu Leu Phe
        195                 200                 205

Leu Lys Asn Leu Ile Gln Lys Lys Asn Ser Ser His Thr Cys Glu Glu
    210                 215                 220

Glu Gly Val Trp Lys Thr Ser
225                 230

<210> SEQ ID NO 27
<211> LENGTH: 264
<212> TYPE: DNA
<213> ORGANISM: Chlamydia pneumoniae

<400> SEQUENCE: 27
atgagtcaaa aaataaaaa ctctgctttt atgcatcccg tgaatatttc cacagattta      60
gcagttatag ttggcaaggg acctatgccc agaaccgaaa ttgtaaagaa agtttgggaa   120
tacattaaaa aacacaactg tcaggatcaa aaaataaaac gtaatatcct tcccgatgcg   180
aatcttgcca agtctttgg ctctagtgat cctatcgaca tgttccaaat gaccaaagcc    240
ctttccaaac atattgtaaa ataa                                          264

<210> SEQ ID NO 28
<211> LENGTH: 87
<212> TYPE: PRT
<213> ORGANISM: Chlamydia pneumoniae

<400> SEQUENCE: 28

Met Ser Gln Lys Asn Lys Asn Ser Ala Phe Met His Pro Val Asn Ile
1               5                   10                  15

Ser Thr Asp Leu Ala Val Ile Val Gly Lys Gly Pro Met Pro Arg Thr
            20                  25                  30

Glu Ile Val Lys Lys Val Trp Glu Tyr Ile Lys Lys His Asn Cys Gln
        35                  40                  45

Asp Gln Lys Asn Lys Arg Asn Ile Leu Pro Asp Ala Asn Leu Ala Lys
    50                  55                  60

Val Phe Gly Ser Ser Asp Pro Ile Asp Met Phe Gln Met Thr Lys Ala
65                  70                  75                  80

Leu Ser Lys His Ile Val Lys
                85

<210> SEQ ID NO 29
<211> LENGTH: 369
<212> TYPE: DNA
<213> ORGANISM: Chlamydia pneumoniae

<400> SEQUENCE: 29
atgccacgca tcattggaat tgatattcct gcaaagaaaa agttaaaaat aagtctgaca    60
tatatttatg gaataggatc agctcgttct gatgaaatca ttaaaaagtt gaagttagat   120
cctgaggcaa gagcctctga attaactgaa gaagaagtag gacgactgaa ctctctgcta   180
caatcagaat ataccgtaga aggggatttg cgacgtcgtg ttcaatcgga tatcaaaaga   240
ttgatcgcca tccattctta tcgaggtcag agacatagac tttctttacc agtaagagga   300
caacgtacaa aaactaattc tcgtactcga aaaggtaaaa gaaaaacagt cgcaggtaag   360
agaaataa                                                           369

<210> SEQ ID NO 30
<211> LENGTH: 122
<212> TYPE: PRT
```

-continued

<213> ORGANISM: Chlamydia pneumoniae

<400> SEQUENCE: 30

```
Met Pro Arg Ile Ile Gly Ile Asp Ile Pro Ala Lys Lys Lys Leu Lys
 1               5                  10                  15

Ile Ser Leu Thr Tyr Ile Tyr Gly Ile Gly Ser Ala Arg Ser Asp Glu
            20                  25                  30

Ile Ile Lys Lys Leu Lys Leu Asp Pro Glu Ala Arg Ala Ser Glu Leu
        35                  40                  45

Thr Glu Glu Glu Val Gly Arg Leu Asn Ser Leu Leu Gln Ser Glu Tyr
    50                  55                  60

Thr Val Glu Gly Asp Leu Arg Arg Arg Val Gln Ser Asp Ile Lys Arg
65                  70                  75                  80

Leu Ile Ala Ile His Ser Tyr Arg Gly Gln Arg His Arg Leu Ser Leu
                85                  90                  95

Pro Val Arg Gly Gln Arg Thr Lys Thr Asn Ser Arg Thr Arg Lys Gly
            100                 105                 110

Lys Arg Lys Thr Val Ala Gly Lys Lys Lys
        115                 120
```

<210> SEQ ID NO 31
<211> LENGTH: 10
<212> TYPE: PRT
<213> ORGANISM: Artificial Sequence
<220> FEATURE:
<223> OTHER INFORMATION: Made in the lab

<400> SEQUENCE: 31

```
Cys Ser Phe Ile Gly Gly Ile Thr Tyr Leu
 1               5                  10
```

<210> SEQ ID NO 32
<211> LENGTH: 53
<212> TYPE: PRT
<213> ORGANISM: Chlamydia trachomatis

<400> SEQUENCE: 32

```
Leu Cys Val Ser His Lys Arg Arg Ala Ala Ala Ala Val Cys Ser Phe
 1               5                  10                  15

Ile Gly Gly Ile Thr Tyr Leu Ala Thr Phe Gly Ala Ile Arg Pro Ile
            20                  25                  30

Leu Phe Val Asn Lys Met Leu Ala Gln Pro Phe Leu Ser Ser Gln Thr
        35                  40                  45

Lys Ala Asn Met Gly
    50
```

<210> SEQ ID NO 33
<211> LENGTH: 161
<212> TYPE: DNA
<213> ORGANISM: Chlamydia trachomatis

<400> SEQUENCE: 33

```
atctttgtgt gtctcataag cgcagagcgg ctgcggctgt ctgtagcatc atcggaggaa     60
ttacctacct cgcgacattc ggagctatcc gtccgattct gtttgtcaac aaaatgctgg    120
caaaaccgtt tctttcttcc caaactaaag caaatatggg a                        161
```

<210> SEQ ID NO 34
<211> LENGTH: 53
<212> TYPE: PRT

-continued

<213> ORGANISM: Chlamydia trachomatis

<400> SEQUENCE: 34

```
Leu Cys Val Ser His Lys Arg Arg Ala Ala Ala Ala Val Cys Ser Ile
 1               5                  10                  15

Ile Gly Gly Ile Thr Tyr Leu Ala Thr Phe Gly Ala Ile Arg Pro Ile
            20                  25                  30

Leu Phe Val Asn Lys Met Leu Ala Lys Pro Phe Leu Ser Ser Gln Thr
        35                  40                  45

Lys Ala Asn Met Gly
    50
```

<210> SEQ ID NO 35
<211> LENGTH: 55
<212> TYPE: DNA
<213> ORGANISM: Chlamydia pneumoniae

<400> SEQUENCE: 35

```
gatatacata tgcatcacca tcaccatcac atgagtcaaa aaaaataaaa actct          55
```

<210> SEQ ID NO 36
<211> LENGTH: 33
<212> TYPE: DNA
<213> ORGANISM: Chlamydia pneumoniae

<400> SEQUENCE: 36

```
ctcgaggaat tcttatttta caatatgttt gga                                   33
```

<210> SEQ ID NO 37
<211> LENGTH: 53
<212> TYPE: DNA
<213> ORGANISM: Chlamydia pneumoniae

<400> SEQUENCE: 37

```
gatatacata tgcatcacca tcaccatcac atgccacgca tcattggaat gat            53
```

<210> SEQ ID NO 38
<211> LENGTH: 30
<212> TYPE: DNA
<213> ORGANISM: Chlamydia pneumoniae

<400> SEQUENCE: 38

```
ctcgaggaat tcttatttct tcttacctgc                                      30
```

<210> SEQ ID NO 39
<211> LENGTH: 16
<212> TYPE: PRT
<213> ORGANISM: Artificial Sequence
<220> FEATURE:
<223> OTHER INFORMATION: Made in the lab

<400> SEQUENCE: 39

```
Lys Arg Asn Ile Asn Pro Asp Asp Lys Leu Ala Lys Val Phe Gly Thr
 1               5                  10                  15
```

<210> SEQ ID NO 40
<211> LENGTH: 16
<212> TYPE: PRT
<213> ORGANISM: Artificial Sequence
<220> FEATURE:
<223> OTHER INFORMATION: made in the lab

<400> SEQUENCE: 40

Lys Arg Asn Ile Leu Pro Asp Ala Asn Leu Ala Lys Val Phe Gly Ser
1               5                   10                  15

<210> SEQ ID NO 41
<211> LENGTH: 15
<212> TYPE: PRT
<213> ORGANISM: Artificial Sequence
<220> FEATURE:
<223> OTHER INFORMATION: made in the lab

<400> SEQUENCE: 41

Lys Glu Tyr Ile Asn Gly Asp Lys Tyr Phe Gln Gln Ile Phe Asp
1               5                   10                  15

<210> SEQ ID NO 42
<211> LENGTH: 16
<212> TYPE: PRT
<213> ORGANISM: Artificial Sequence
<220> FEATURE:
<223> OTHER INFORMATION: made in the lab

<400> SEQUENCE: 42

Lys Lys Ile Ile Ile Pro Asp Ser Lys Leu Gln Gly Val Ile Gly Ala
1               5                   10                  15

<210> SEQ ID NO 43
<211> LENGTH: 15
<212> TYPE: PRT
<213> ORGANISM: Artificial Sequence
<220> FEATURE:
<223> OTHER INFORMATION: made in the lab

<400> SEQUENCE: 43

Lys Lys Leu Leu Val Pro Asp Asn Asn Leu Ala Thr Ile Ile Gly
1               5                   10                  15

<210> SEQ ID NO 44
<211> LENGTH: 509
<212> TYPE: DNA
<213> ORGANISM: Chlamydia

<400> SEQUENCE: 44
ggagctcgaa ttcggcacga gagtgcctat tgttttgcag gctttgtctg atgatagcga      60
taccgtacgt gagattgctg tacaagtagc tgttatgtat ggttctagtt gcttactgcg     120
cgccgtgggc gatttagcga aaaatgattc ttctattcaa gtacgcatca ctgcttatcg     180
tgctgcagcc gtgttggaga tacaagatct tgtgcctcat ttacgagttg tagtccaaaa     240
tacacaatta gatggaacgg aaagaagaga agcttggaga tctttatgtg ttcttactcg     300
gcctcatagt ggtgtattaa ctggcataga tcaagcttta atgacctgtg agatgttaaa     360
ggaatatcct gaaaagtgta cggaagaaca gattcgtaca ttattggctg cagatcatcc     420
agaagtgcag gtagctactt tacagatcat tctgagagga ggtagagtat tccggtcatc     480
ttctataatg gaatcggttc tcgtgccgg                                       509

<210> SEQ ID NO 45
<211> LENGTH: 481
<212> TYPE: DNA
<213> ORGANISM: Chlamydia
<220> FEATURE:
<221> NAME/KEY: unsure
<222> LOCATION: (23)
<223> OTHER INFORMATION: n=A,T,C or G

<400> SEQUENCE: 45

```
gatccgaatt cggcacgagg cantatttac tcccaacatt acggttccaa ataagcgata      60
aggtcttcta ataaggaagt taatgtaaga ggctttttta ttgcttttcg taaggtagta     120
ttgcaaccgc acgcgattga atgatacgca agccatttcc atcatggaaa agaaccettg     180 gacaaaaata caaggaggt tcactcctaa ccagaaaaag ggagagttag tttccatggg      240
ttttccttat atacacccgt tcacacaat taggagccgc gtctagtatt tggaatacaa      300
attgtcccca agcgaatttt gttcctgttt cagggatttc tcctaattgt tctgtcagcc    360
atccgcctat ggtaacgcaa ttagctgtag taggaagatc aactccaaac aggtcataga    420
aatcagaaag ctcataggtg cctgcagcaa taacaacatt cttgtctgag tgagcgaatt    480
g                                                                     481

<210> SEQ ID NO 46
<211> LENGTH: 427
<212> TYPE: DNA
<213> ORGANISM: Chlamydia
<220> FEATURE:
<221> NAME/KEY: unsure
<222> LOCATION: (20)
<223> OTHER INFORMATION: n=A,T,C or G

<400> SEQUENCE: 46
gatccgaatt cggcacgagn tttttcctgt tttttcttag tttttagtgt tcccggagca     60
ataacacaga tcaaagaacg gccattcagt ttaggctctg actcaacaaa acctatgtcc    120
tctaagccct gacacattct tgaacaacc ttatgcccgt gttcgggata agccaactct     180
cgcccccgaa acatacaaga aacctttact ttatttcctt tctcaataaa ggctctagct    240
tgctttgctt tcgtaagaaa gtcgttatca tcgatattag gcttaagctt aacctctttg    300
atacgcactt ggtgctgtgc tttcttacta tcttttttctt ttttagttat gtcgtaacga   360
tacttcccgt agtccatgat tttgcacaca ggaggctctg agtttgaagc aacctcgtgc    420
cgaattc                                                               427

<210> SEQ ID NO 47
<211> LENGTH: 600
<212> TYPE: DNA
<213> ORGANISM: Chlamydia
<220> FEATURE:
<221> NAME/KEY: unsure
<222> LOCATION: (522)
<223> OTHER INFORMATION: n=A,T,C or G

<400> SEQUENCE: 47
gatccgaatt cggcacgaga tgcttctatt acaattggtt tggatgcgga aaaagcttac     60
cagcttattc tagaaaagtt gggagatcaa attcttggtg gaattgctga tactattgtt    120
gatagtacag tccaagatat tttagacaaa atcacaacag acccttctct aggtttgttg    180 aaagcttttta caactttcc aatcactaat aaaattcaat gcaacgggtt attcactccc    240
aggaacattg aaactttatt aggaggaact gaaataggaa aattcacagt cacacccaaa    300
agctctggga gcatgttctt agtctcagca gatattattg catcaagaat ggaaggcggc    360
gttgttctag ctttggtacg agaaggtgat tctaagccct acgcgattag ttatggatac    420
tcatcaggcg ttcctaattt atgtagtcta agaaccagaa ttattaatac aggattgact    480
ccgacaacgt attcattacg tgtaggcggt ttagaaagcg gngtggtatg ggttaatgcc    540
ctttctaatg gcaatgatat tttaggaata acaaatcttc taatgtatct ttttttggagg   600
```

<210> SEQ ID NO 48
<211> LENGTH: 600
<212> TYPE: DNA
<213> ORGANISM: Chlamydia

<400> SEQUENCE: 48

| | | | | | |
|---|---|---|---|---|---|
| ggagctcgaa | ttcggcacga | gctctatgaa | tatccaattc | tctaaactgt | tcggataaaa | 60 |
| atgatgcagg | aattaggtcc | acactatctt | tttttgtttc | gcaaatgatt | gattttaaat | 120 |
| cgtttgatgt | gtatactatg | tcgtgtaagc | cttttt ggtt | acttctgaca | ctagccccca | 180 |
| atccagaaga | taaattggat | tgcgggtcta | ggtcagcaag | taacactttt | ttccctaaaa | 240 |
| attgggccaa | gttgcatccc | acgtttagag | aaagtgttgt | ttttccagtt | cctcccttaa | 300 |
| aagagcaaaa | aactaaggtg | tgcaaatcaa | ctccaacgtt | agagtaagtt | atctattcag | 360 |
| ccttggaaaa | catgtctttt | ctagacaaga | taagcataat | caaagccttt | tttagcttta | 420 |
| aactgttatc | ctctaatttt | tcaagaacag | gagagtctgg | gaataatcct | aaagagtttt | 480 |
| ctatttgttg | aagcagtcct | agaattagtg | agacactttt | atggtagagt | tctaagggag | 540 |
| aatttaagaa | agttacttt t | ccttgtttta | ctcgtatttt | taggtctaat | tcggggaaat | 600 |

<210> SEQ ID NO 49
<211> LENGTH: 600
<212> TYPE: DNA
<213> ORGANISM: Chlamydia

<400> SEQUENCE: 49

| | | | | | |
|---|---|---|---|---|---|
| gatccgaatt | cggcacgaga | tgcttctatt | acaattggtt | tggatgcgga | aaaagcttac | 60 |
| cagcttattc | tagaaaagtt | gggagatcaa | attcttggtg | gaattgctga | tactattgtt | 120 |
| gatagtacag | tccaagatat | tttagacaaa | atcacaacag | acccttctct | aggtttgttg | 180 |
| aaagctttta | acaactttcc | aatcactaat | aaaattcaat | gcaacgggtt | attcactccc | 240 |
| aggaacattg | aaactttatt | aggaggaact | gaaataggaa | aattcacagt | cacacccaaa | 300 |
| agctctggga | gcatgttctt | agtctcagca | gatattattg | catcaagaat | ggaaggcggc | 360 |
| gttgttctag | ctttggtacg | agaaggtgat | tctaagccct | acgcgattag | ttatggatac | 420 |
| tcatcaggcg | ttcctaattt | atgtagtcta | agaaccagaa | ttattaatac | aggattgact | 480 |
| ccgacaacgt | attcattacg | tgtaggcggt | ttagaaagcg | gtgtggtatg | ggttaatgcc | 540 |
| ctttctaatg | gcaatgatat | tttaggaata | acaaatactt | ctaatgtatc | tttttt ggag | 600 |

<210> SEQ ID NO 50
<211> LENGTH: 406
<212> TYPE: DNA
<213> ORGANISM: Chlamydia

<400> SEQUENCE: 50

| | | | | | |
|---|---|---|---|---|---|
| gatccgaatt | cggcacgagt | tcttagcttg | cttaattacg | taattaacca | aactaaaggg | 60 |
| gctatcaaat | agcttattca | gtctttcatt | agttaaacga | tcttttctag | ccatgactca | 120 |
| tcctatgttc | ttcagctata | aaaatacttc | ttaaaacttg | atatgctgta | atcaaatcat | 180 |
| cattaaccac | aacataatca | aattcgctag | cggcagcaat | ttcgacagcg | ctatgctcta | 240 |
| atctttcttt | cttctggaaa | tctttctctg | aatcccgagc | attcaaacgg | cgctcaagtt | 300 |
| cttcttgaga | gggagcttga | ataaaaatgt | gactgccggc | atttgcttct | tcagagccaa | 360 |
| agctccttgt | acatcaatca | cggctatgca | gtctcgtgcc | gaattc | | 406 |

```
<210> SEQ ID NO 51
<211> LENGTH: 602
<212> TYPE: DNA
<213> ORGANISM: Chlamydia

<400> SEQUENCE: 51
gatccgaatt cggcacgaga tattttagac aaaatcacaa cagacccttc tctaggtttg      60
ttgaaagctt ttaacaactt tccaatcact aataaaattc aatgcaacgg gttattcact     120
cccaggaaca ttgaaacttt attaggagga actgaaatag gaaaattcac agtcacaccc     180
aaaagctctg ggagcatgtt cttagtctca gcagatatta ttgcatcaag aatggaaggc     240
ggcgttgttc tagctttggt acgagaaggt gattctaagc cctacgcgat tagttatgga     300
tactcatcag gcgttcctaa tttatgtagt ctaagaacca gaattattaa tacaggattg     360
actccgacaa cgtattcatt acgtgtaggc ggtttagaaa gcggtgtggt atgggttaat     420
gcccttteta atggcaatga tattttagga ataacaaata cttctaatgt atcttttttg     480
gaggtaatac ctcaaacaaa cgcttaaaca attttttattg gattttttctt ataggtttta    540
tatttagaga aaaagttcg aattacgggg tttgttatgc aaaataaact cgtgccgaat      600
tc                                                                   602

<210> SEQ ID NO 52
<211> LENGTH: 145
<212> TYPE: DNA
<213> ORGANISM: Chlamydia

<400> SEQUENCE: 52
gatccgaatt cggcacgagc tcgtgccgat gtgttcaaca gcatccatag gatgggcagt      60
caaatatact ccaagtaatt cttttttctct tttcaacaac tccttaggag agcgttggat    120
aacattttca gctcgtgccg aattc                                          145

<210> SEQ ID NO 53
<211> LENGTH: 450
<212> TYPE: DNA
<213> ORGANISM: Chlamydia

<400> SEQUENCE: 53
gatccgaatt cggcacgagg taatcggcac cgcactgctg acactcatct cctcgagctc      60
gatcaaaccc acacttggga caagtaccta caacataacg gtccgctaaa aacttccctt    120
cttcctcaga atacagctgt tcggtcacct gattctctac cagtccgcgt tcctgcaagt    180
ttcgatagaa atcttgcaca atagcaggat gataagcgtt cgtagttctg gaaaagaaat    240
ctacagaaat tcccaatttc ttgaaggtat ctttatgaag cttatgatac atgtcgacat    300
attcttgata ccccatgcct gccaactctg cattaagggt aattgcgatt ccgtattcat    360
cagaaccaca aatatacaaa acctctttgc cttgtagtct ctgaaaacgc gcataaacat    420
ctgcaggcaa ataagcctcg tgccgaattc                                    450

<210> SEQ ID NO 54
<211> LENGTH: 716
<212> TYPE: DNA
<213> ORGANISM: Chlamydia

<400> SEQUENCE: 54
gatcgaaatt cggcacgagc ggcacgagtt ttctgatagc gatttacaat cctttattca      60
acttttgcct agagaggcac actatactaa gaagtttctt gggtgtgtgg cacagtcctg    120
```

-continued

```
tcgtcagggg attctgctag aggggtaggg gaaaaaaccc ttattactat gaccatgcgc    180
atgtggaatt acattccata gactttcgca tcattcccaa catttacaca gctctacacc    240
tcttaagaag aggtgacgtg gattgggtgg ggcagccttg gcaccaaggg attccttttg    300
agcttcggac tacctctgct ctctacaccc attaccctgt agatggcaca ttctggctta    360
ttcttaatcc caaagatcct gtactttcct ctctatctaa tcgtcagcga ttgattgctg    420
ccatccaaaa ggaaaaactg gtgaagcaag ctttaggaac acaatatcga gtagctgaaa    480
gctctccatc tccagaggga atcatagctc atcaagaagc ttctactcct tttcctggga    540
aaattacttt gatatatccc aataatatta cgcgctgtca gcgtttggcc gaggtatcca    600
aaaaatgatc gacaaggagc acgctaaatt tgtacatacc ccaaaatcaa tcagccatct    660
aggcaaatgg aatatcaaag taaacagtat acaactgggg atctcgtgcc gaattc        716
```

<210> SEQ ID NO 55
<211> LENGTH: 463
<212> TYPE: DNA
<213> ORGANISM: Chlamydia trachomatis

<400> SEQUENCE: 55

```
tctcaaatcc ttgctttgaa taatccagat atttcaaaaa ccatgttcga taaattcacc     60
cgacaaggac tccgtttcgt actagaagcc tctgtatcaa atattgagga tataggagat    120
cgcgttcggt taactatcaa tgggaatgtc gaagaatacg attacgttct cgtatctata    180
ggacgccgtt tgaatacaga aaatattggc ttggataaag ctggtgttat ttgtgatgaa    240
cgcggagtca tccctaccga tgccacaatg cgcacaaacg tacctaacat ttatgctatt    300
ggagatatca caggaaaatg gcaacttgcc catgtagctt ctcatcaagg aatcattgca    360
gcacggaata taggtggcca taagaggaa atcgattact ctgctgtccc ttctgtgatc    420
tttaccttcc ctgaagtcgc ttcagtaggc ctctccccaa cag                      463
```

<210> SEQ ID NO 56
<211> LENGTH: 829
<212> TYPE: DNA
<213> ORGANISM: Chlamydia trachomatis

<400> SEQUENCE: 56

```
gtactatggg atcattagtt ggaagacagg ctccggattt ttctggtaaa gccgttgttt     60
gtggagaaga gaaagaaatc tctctagcag actttcgtgg taagtatgta gtgctcttct    120
tttatcctaa agattttacc tatgtttgtc ctacagaatt acatgctttt caagatagat    180
tggtagattt tgaagagcat ggtgcagtcg tccttggttg ctccgttgac gacattgaga    240
cacattctcg ttggctcact gtagcgagag atgcaggagg gatagaggga acagaatatc    300
ctctgttagc agaccctct tttaaaatat cagaagcttt tggtgttttg aatcctgaag    360
gatcgctcgc tttaagagct actttcctta tcgataaaca tggggttatt cgtcatgcgg    420
ttatcaatga tcttccttta gggcgttcca ttgacgagga attgcgtatt ttagattcat    480
tgatcttctt tgagaaccac ggaatggttt gtccagctaa ctggcgttct ggagagcgtg    540
gaatggtgcc ttctgaagag ggattaaaag aatacttcca gacgatggat taagcatctt    600
tgaaagtaag aaagtcgtac agatcttgat ctgaaaagag aagaaggctt tttaattttc    660
tgcagagagc cagcgaggct tcaataatgt tgaagtctcc gacaccaggc aatgctaagg    720
cgacgatatt agttagtgaa gtctgagtat taaggaaatg aaggccaaag aaatagctat    780
caataaagaa gccttcttcc ttgactctaa agaatagtat gtcgtatcc                829
```

<210> SEQ ID NO 57
<211> LENGTH: 1537
<212> TYPE: DNA
<213> ORGANISM: Chlamydia trachomatis

<400> SEQUENCE: 57

| | | | | | |
|---|---|---|---|---|---|
| acatcaagaa | atagcggact | cgcctttagt | gaaaaaagct | gaggagcaga | ttaatcaagc | 60 |
| acaacaagat | attcaaacga | tcacacctag | tggtttggat | attcctatcg | ttggtccgag | 120 |
| tgggtcagct | gcttccgcag | gaagtgcggc | aggagcgttg | aaatcctcta | acaattcagg | 180 |
| aagaatttcc | ttgttgcttg | atgatgtaga | caatgaaatg | gcagcgattg | caatgcaagg | 240 |
| ttttcgatct | atgatcgaac | aatttaatgt | aaacaatcct | gcaacagcta | aagagctaca | 300 |
| agctatggag | gctcagctga | ctgcgatgtc | agatcaactg | gttggtgcgg | atggcgagct | 360 |
| cccagccgaa | atacaagcaa | tcaaagatgc | tcttgcgcaa | gctttgaaac | aaccatcagc | 420 |
| agatggttta | gctacagcta | tgggacaagt | ggcttttgca | gctgccaagg | ttggaggagg | 480 |
| ctccgcagga | acagctggca | ctgtccagat | gaatgtaaaa | cagctttaca | agacagcgtt | 540 |
| ttcttcgact | tcttccagct | cttatgcagc | agcactttcc | gatggatatt | ctgcttacaa | 600 |
| aacactgaac | tctttatatt | ccgaaagcag | aagcggcgtg | cagtcagcta | ttagtcaaac | 660 |
| tgcaaatccc | gcgctttcca | gaagcgtttc | tcgttctggc | atagaaagtc | aaggacgcag | 720 |
| tgcagatgct | agccaaagag | cagcagaaac | tattgtcaga | gatagccaaa | cgttaggtga | 780 |
| tgtatatagc | cgcttacagg | ttctggattc | tttgatgtct | acgattgtga | gcaatccgca | 840 |
| agcaaatcaa | gaagagatta | tgcagaagct | cacggcatct | attagcaaag | ctccacaatt | 900 |
| tgggtatcct | gctgttcaga | attctgtgga | tagcttgcag | aagtttgctg | cacaattgga | 960 |
| aagagagttt | gttgatgggg | aacgtagtct | cgcagaatct | caagagaatg | cgtttagaaa | 1020 |
| acagcccgct | ttcattcaac | aggtgttggt | aaacattgct | tctctattct | ctggttatct | 1080 |
| ttcttaacgt | gtgattgaag | tttgtgaatt | gaggggagc | caaaaagaa | tttcttttt | 1140 |
| ggctcttttt | tcttttcaaa | ggaatctcgt | gtctacagaa | gtcttttcaa | taataagttc | 1200 |
| ttagttccaa | aagaagaaaa | tatataaaag | aaaaaactcc | taattcattt | aaaaagtgct | 1260 |
| cggcagactt | cgtggaaaat | gtctgtaaag | ctggagggga | atcagcagaa | agatgcaaga | 1320 |
| tatccgagaa | aaaaggctca | ggctcgtgcc | gaattcggca | cgagactacg | aaagaaaggt | 1380 |
| ctttctttc | ggaatctgtc | attggatctg | cgtaagactt | aaagttcggc | aacacaggct | 1440 |
| ctgtcttctc | tttaggtttc | ttgcgcgaga | aaaattttct | caagtaacaa | gaagatttct | 1500 |
| ttttacagcc | ggcatccggc | ttctcgcgaa | gtataac | | | 1537 |

<210> SEQ ID NO 58
<211> LENGTH: 463
<212> TYPE: DNA
<213> ORGANISM: Chlamydia trachomatis

<400> SEQUENCE: 58

| | | | | | |
|---|---|---|---|---|---|
| tctcaaatcc | ttgctttgaa | taatccagat | atttcaaaaa | ccatgttcga | taaattcacc | 60 |
| cgacaaggac | tccgtttcgt | actagaagcc | tctgtatcaa | atattgagga | tataggagat | 120 |
| cgcgttcggt | taactatcaa | tgggaatgtc | gaagaatacg | attacgttct | cgtatctata | 180 |
| ggacgccgtt | tgaatacaga | aaatattggc | ttggataaag | ctggtgttat | ttgtgatgaa | 240 |
| cgcggagtca | tccctaccga | tgccacaatg | cgcacaaacg | tacctaacat | ttatgctatt | 300 |

-continued

| | | |
|---|---|---|
| ggagatatca caggaaaatg gcaacttgcc catgtagctt ctcatcaagg aatcattgca | 360 | |
| gcacggaata taggtggcca taaagaggaa atcgattact ctgctgtccc ttctgtgatc | 420 | |
| tttaccttcc ctgaagtcgc ttcagtaggc ctctccccaa cag | 463 | |

<210> SEQ ID NO 59
<211> LENGTH: 552
<212> TYPE: DNA
<213> ORGANISM: Chlamydia trachomatis

<400> SEQUENCE: 59

| | |
|---|---|
| acattcctcc tgctcctcgc ggccatccac aaattgaggt aaccttcgat attgatgcca | 60 |
| acggaatttt acacgtttct gctaaagatg ctgctagtgg acgcgaacaa aaaatccgta | 120 |
| ttgaagcaag ctctggatta aagaagatg aaattcaaca aatgatccgc gatgcagagc | 180 |
| ttcataaaga ggaagacaaa caacgaaaag aagcttctga tgtgaaaaat gaagccgatg | 240 |
| gaatgatctt tagagccgaa aaagctgtga agattacca cgacaaaatt cctgcagaac | 300 |
| ttgttaaaga aattgaagag catattgaga agtacgccca agcaatcaaa gaagatgctt | 360 |
| ccacaacagc tatcaaagca gcttctgatg agttgagtac tcgtatgcaa aaaatcggag | 420 |
| aagctatgca ggctcaatcc gcatccgcag cagcatcttc tgcagcgaat gctcaaggag | 480 |
| ggccaaacat taactccgaa gatctgaaaa acatagtttt cagcacacga cctccagcag | 540 |
| gaggaagcgc ct | 552 |

<210> SEQ ID NO 60
<211> LENGTH: 1180
<212> TYPE: DNA
<213> ORGANISM: Chlamydia trachomatis

<400> SEQUENCE: 60

| | |
|---|---|
| atcctagcgg taaaactgct tactggtcag ataaaatcca tacagaagca acacgtactt | 60 |
| cttttaggag aaaaaatcta taatgctaga aaaatcctga gtaaggatca cttctcctca | 120 |
| acaactttt catcttggat agagttagtt tttagaacta agtcttctgc ttacaatgct | 180 |
| cttgcatatt acgagctttt tataaacctc cccaaccaaa ctctacaaaa agagtttcaa | 240 |
| tcgatcccct ataaatccgc atatattttg gccgctagaa aaggcgattt aaaaaccaag | 300 |
| gtcgatgtga tagggaaagt atgtggaatc tcgtgccgaa ttcggcacga gcggcacgag | 360 |
| gatgtagagt aattagttaa agagctgcat aattatgaca aagcatggaa aacgcattcg | 420 |
| tggtatccaa gagacttacg atttagctaa gtcgtattct ttgggtgaag cgatagatat | 480 |
| tttaaaacag tgtcctactg tgcgtttcga tcaaacggtt gatgtgtctg ttaaattagg | 540 |
| gatcgatcca agaaagagtg atcagcaaat tcgtggttcg gtttctttac ctcacggtac | 600 |
| aggtaaagtt ttgcgaattt tagttttttgc tgctggagat aaggctgcag aggctattga | 660 |
| agcaggagcg gactttgttg gtagcgacga cttggtagaa aaaatcaaag gtggatgggt | 720 |
| tgacttcgat gttgcggttg ccactcccga tatgatgaga gaggtcggaa agctaggaaa | 780 |
| agttttaggt ccaagaaacc ttatgcctac gcctaaagcc ggaactgtaa caacagatgt | 840 |
| ggttaaaact attgcggaac tgcgaaaagg taaaattgaa tttaaagctg atcgagctgg | 900 |
| tgtatgcaac gtcggagttg cgaagctttc tttcgatagt gcgcaaatca agaaaatgt | 960 |
| tgaagcgttg tgtgcagcct tagttaaagc taagcccgca actgctaaag gacaatattt | 1020 |
| agttaatttc actatttcct cgaccatggg gccaggggtt accgtggata ctaggagtt | 1080 |
| gattgcgtta taattctaag tttaaagagg aaaaatgaaa gaagagaaaa agttgctgct | 1140 |

```
tcgcgaggtt gaagaaaaga taaccgcttc tcggcacgag                 1180
```

<210> SEQ ID NO 61
<211> LENGTH: 1215
<212> TYPE: DNA
<213> ORGANISM: Chlamydia trachomatis

<400> SEQUENCE: 61

```
attacagcgt gtgcaggtaa cgacatcatt gcatgatgct tttgatggca ttgatgcggc    60
attccttata gggtcagttc ctagaggccc aggaatggag agaagagatc ttctaaagaa   120
aaatggggag attgttgcta cgcaaggaaa agctttgaac acaacagcca agcgggatgc   180
aaagattttt gttgttggga accctgtgaa taccaattgc tggatagcaa tgaatcatgc   240
tcccagatta ttgagaaaga actttcatgc gatgctacga ttggaccaga atcgtatgca   300
tagcatgtta tcgcatagag cagaagtacc tttatcggct gtatcacaag ttgtggtttg   360
gggaaatcac tccgccaaac aagtgcctga ttttacgcaa gctctgatta atgaccgtcc   420
tatcgcagag acgatagcgg atcgtgattg gttagagaat attatggtgc cttctgtaca   480
gagtcgtggt agtgcagtaa ttgaagcacg agggaagtct tcggcagctt ctgcagcacg   540
agctttagca gaggctgctc gatcaatata tcagccaaaa gaaggactcg tgccgaattc   600
ggcacgagta tcgaaattgc aggcatttct agtgaatggt cgtatgctta taaactacgt   660
ggtacagact tgagctctca aaagtttgct acagattctt acatcgcaga cccttattct   720
aagaatatct actcccctca actatttgga tcccctaaac aagaaaagga ttacgcattt   780
agttacctga aatatgagga ttttgactgg gaaggcgaca ctcctttgca ccttccaaaa   840
gaaaattact tcatttatga aatgcatgtt cggtcattca cccgagatcc gtcttcccag   900
gtttcccatc ctggaacttt ccttggtatc atcgaaaaaa tagaccacct caaacaacta   960
ggcgttcatg cagttgaact ccttcctatt tcgaattcg atgaaaccgt ccatccattt   1020
aaaaatcagg acttccccca cctgtgtaac tattgggggt attcttcggt gaatttttc   1080
tgcccctctc gccgttatac ttatggggca gacccttgcg ctccggcccg agagttcaag  1140
actcttgtca aagcgttaca ccgtgcggga atcgaagtca ttctcgatgt cgttttcaat  1200
catacaggct ttgaa                                                   1215
```

<210> SEQ ID NO 62
<211> LENGTH: 688
<212> TYPE: DNA
<213> ORGANISM: Chlamydia trachomatis

<400> SEQUENCE: 62

```
gtggatccaa aaagaatct aaaaagccat acaaagattg cgttacttct tgcgatgcct    60
ctaacacttt atcagcgtca tctttgagaa gcatctcaat gagcgctttt tcttctctag   120
catgccgcac atccgcttct tcatgttctg tgaaatatgc atagtcttca ggattggaaa   180
atccaaagta ctcagtcaat ccacgaattt tctctctagc gatacgtgga atttgactct   240
cataagaata caaagcagcc actcctgcag ctaaagaatc tcctgtacac caccgcatga   300
aagtagctac tttcgctttt gctgcttcac taggctcatg agcctctaac tcttctggag   360
taactcctag agcaaacaca aactgcttcc acaaatcaat atgattaggg taaccgttct   420
cttcatccat caagttatct aacaataact acgcgcctc taaatcatcg caacgactat   480
gaatcgcaga taaatattta ggaaaggctt tgatatgtaa ataatagtct ttggcacgag   540
```

```
cctgtaattg ctctttagta agctccccct tcgaccattt cacataaaac gtgtgttcta    600
gcatatgctt attttgaata attaaatcta actgatctaa aaaattcata aacacctcca    660
tcatttcttt tcttgactcc acgtaacc                                       688
```

<210> SEQ ID NO 63
<211> LENGTH: 269
<212> TYPE: DNA
<213> ORGANISM: Chlamydia trachomatis

<400> SEQUENCE: 63

```
atgttgaaat cacacaagct gttcctaaat atgctacggt aggatctccc tatcctgttg     60
aaattactgc tacaggtaaa agggattgtg ttgatgttat cattactcag caattaccat    120
gtgaagcaga gttcgtacgc agtgatccag cgacaactcc tactgctgat ggtaagctag    180
tttggaaaat tgaccgctta ggacaaggcg aaaagagtaa aattactgta tgggtaaaac    240
ctcttaaaga aggttgctgc tttacagct                                      269
```

<210> SEQ ID NO 64
<211> LENGTH: 1339
<212> TYPE: DNA
<213> ORGANISM: Chlamydia trachomatis

<400> SEQUENCE: 64

```
cttttattat ggcttctggg gatgatgtca acgatatcga cctgctatct cgaggagatt     60
ttaaaattgt tatacagacg gctccagagg agatgcatgg attagcggac ttttttggctc   120 ccccggcgaa ggatcttggt attctctccg cctgggaagc tggtgagctg cgttacaaac    180
agctagttaa tccttaggaa acatttctgg acctatgccc atcacattgg ctccgtgatc    240
cacatagaga gtttctcccg taattgcgct agctagggga gagactaaga aggctgctgc    300
tgcgcctact tgctcagctt ccattggaga aggtagtgga gcccagtctt ggtagtaatc    360
caccattctc tcaataaatc caatagcttt tcctgcacgg ctagctaatg ccctgccga    420 gatagtattc actcggactc cccaacgtcg gccggcttcc caagccagta cttttgtatc    480
actttctaaa gcagcttttg ctgcgttcat tcctccgcca taccctggaa cagcacgcat    540
ggaagcaaga taagttagag agatggtgct agctcctgca ttcataattg gccaaaatg    600 agagagaagg ctgataaagg agtagctgga tgtacttaag gcggcaagat agcctttacg    660
agaggtatca agtaatggtt tagcaatttc cggactgttt gctaaagagt gaacaagaat    720
atcaatgtgt ccaaaatctt ttttcacctg ttctacaact tcggatacag tgtacccaga    780
aagatctttg taacgtttat tttccaaaat ttcctgagga atatcttctg gggtgtcgaa    840
actggcatcc atgggataga ttttagcgaa agttagcaat tctccattgg agagttcacg    900
agatgcattg aattttccta actcccaaga ttgagagaaa attttataga taggaaccca    960
ggtccccaca agtatggttg cgcctgcttc tgctaacatt ttggcaatgc cccagccata   1020
cccgttatca tcgcctatgc cggctatgaa agcaattttt cctgttaaat caattttcaa   1080
catgagctaa ccccattttg tcttcttgag agaggagagt agcagattct ttattattga   1140
gaaacgggcc tcataataca taaggagtag attcactggc tggatccagg tttctagagt   1200
aaagagtttc cttgtcaaat tcttatatgg gtagagttaa tcaactgttt tcaagtgatt   1260
tatgtttatt ttaaaataat ttgttttaac aactgtttaa tagttttaat ttttaaagtg   1320
tgaaaaacag gtttttatat                                              1339
```

```
<210> SEQ ID NO 65
<211> LENGTH: 195
<212> TYPE: PRT
<213> ORGANISM: Chlamydia trachomatis

<400> SEQUENCE: 65

Met Gly Ser Leu Val Gly Arg Gln Ala Pro Asp Phe Ser Lys Ala
 1               5                  10                  15

Val Val Cys Gly Glu Lys Glu Ile Ser Leu Ala Asp Phe Arg Gly
                20                  25                  30

Lys Tyr Val Val Leu Phe Phe Tyr Pro Lys Asp Phe Thr Tyr Val Cys
             35                  40                  45

Pro Thr Glu Leu His Ala Phe Gln Asp Arg Leu Val Asp Phe Glu Glu
     50                  55                  60

His Gly Ala Val Val Leu Gly Cys Ser Val Asp Asp Ile Glu Thr His
 65                  70                  75                  80

Ser Arg Trp Leu Thr Val Ala Arg Asp Ala Gly Ile Glu Gly Thr
                85                  90                  95

Glu Tyr Pro Leu Leu Ala Asp Pro Ser Phe Lys Ile Ser Glu Ala Phe
                100                 105                 110

Gly Val Leu Asn Pro Glu Gly Ser Leu Ala Leu Arg Ala Thr Phe Leu
            115                 120                 125

Ile Asp Lys His Gly Val Ile Arg His Ala Val Ile Asn Asp Leu Pro
130                 135                 140

Leu Gly Arg Ser Ile Asp Glu Glu Leu Arg Ile Leu Asp Ser Leu Ile
145                 150                 155                 160

Phe Phe Glu Asn His Gly Met Val Cys Pro Ala Asn Trp Arg Ser Gly
                165                 170                 175

Glu Arg Gly Met Val Pro Ser Glu Glu Gly Leu Lys Glu Tyr Phe Gln
            180                 185                 190

Thr Met Asp
        195

<210> SEQ ID NO 66
<211> LENGTH: 520
<212> TYPE: DNA
<213> ORGANISM: Chlamydia

<400> SEQUENCE: 66
gatccgaatt cggcacgagg aggaatggaa gggccctccg attttaaatc tgctaccatg      60
ccattcacta gaaactccat aacagcggtt ttctctgatg gcgagtaaga agcaagcatt     120
tgatgtaaat tagcgcaatt agagggggat gaggttactt ggaaatataa ggagcgaagc     180
gatgaaggag atgtatttgc tctggaagca aaggtttctg aagctaacag aacattgcgt     240
cctccaacaa tcgcctgagg attctggctc atcagttgat gctttgcctg aatgagagcg     300
gacttaagtt tcccatcaga gggagctatt tgaattagat aatcaagagc tagatccttt     360
attgtgggat cagaaaattt acttgtgagc gcatcgagaa tttcgtcaga agaagaatca     420
tcatcgaacg aattttttcaa tcctcgaaaa tcttctccag agacttcgga aagatcttct     480
gtgaaacgat cttcaagagg agtatcgcct ttttcctctg                           520

<210> SEQ ID NO 67
<211> LENGTH: 276
<212> TYPE: DNA
<213> ORGANISM: Chlamydia

<400> SEQUENCE: 67
```

```
gatccgaatt cggcacgagg tattgaagga aaggatctg actcgatcta tgaaatcatg    60
atgcctatct atgaagttat gaatatggat ctagaaacac gaagatcttt tgcggtacag   120
caagggcact atcaggaccc aagagcttca gattatgacc tcccacgtgc tagcgactat   180
gatttgccta gaagcccata tcctactcca cctttgcctt ctagatatca gctacagaat   240
atggatgtag aagcagggtt ccgtgaggca gtttat                             276
```

<210> SEQ ID NO 68
<211> LENGTH: 248
<212> TYPE: DNA
<213> ORGANISM: Chlamydia

<400> SEQUENCE: 68

```
gatccgaatt cggcacgagg tgttcaagaa tatgtccttc aagaatgggt taaattgaaa    60
gatctaccgg tagaagagtt gctagaaaaa cgatatcaga aattccgaac gataggtcta   120
tatgaaactt cttctgaaag cgattctgag cataagaag catttagttt tattcggttt    180
ttctctttta tccatattag ggctaacgat aacgtctcaa gcagaaattt tttctctagg   240
tcttattg                                                            248
```

<210> SEQ ID NO 69
<211> LENGTH: 715
<212> TYPE: DNA
<213> ORGANISM: Chlamydia
<220> FEATURE:
<221> NAME/KEY: unsure
<222> LOCATION: (34)
<223> OTHER INFORMATION: n=A,T,C or G

<400> SEQUENCE: 69

```
gatccgaatt cggcacgaga aggtagatcc gatntcagca aaagtgctcc taaaggaaga    60
ttccttcggt atcctgcagc aaataaggtg gcacactcca tctcggacag tttgagcttt   120
attttcatat agttttcgac ggaactcttt attaaactcc caaaaccgaa tgttagtcgt   180
gtgggtgatg cctatatggt aagggaggtt tttggcttcg agaatattgg tgatcatttt   240
ttgtacgaca aaattagcta atgcaggag ctctgggggg aagtatgcat ctgatgttcc   300
atcttttcgg atgctagcaa caggacaaa ataatctcct atttggtagt gggatcttaa   360
gcctccgcac atgcccaaca tgatcgctgc tgtagcattg ggaaggaaag aacacagatc   420
tacggtaaga gctgctcctg gagagcctaa tttaaaatcg atgattgagg tgtgaatttg   480
aggcgcatgc gctgccgaaa acatggatcc tcgagaaaca gggacctgat agatttcagc   540
gaaaacatcc acggtaatac ccmaaattag taagaaggag atagggctgg aactcttgaa   600
tggtagagcc ggtatagcgc tctagcatgt cacaggcgat tgtttcttcg ctgattttt    660 tatgttgatg ggtcataaat cacagatatt ataatggtta gagaatcttt ttttc         715
```

<210> SEQ ID NO 70
<211> LENGTH: 323
<212> TYPE: DNA
<213> ORGANISM: Chlamydia

<400> SEQUENCE: 70

```
gatccgaatt cggcacgagc agaacgtaaa cagcacactt aaaccgtgta tgaggtttaa    60
cactgtttgg caagcaaaca accattcctc tttccacatc gttcttacca atacctctga   120
ggagcaatcc aacattctct cctgcacgac cttctgggag ttcttttctg aacatttcaa   180
```

-continued

```
ccccagtaac aatcgtttct ttagtatctc taagaccgac caactgaact ttatcggaaa    240
ctttaacaat tccacgctca atacgtccag ttactacagt tcctcgtccg gagatagaga    300
acacgtcctc aatgggcatt aag                                            323
```

<210> SEQ ID NO 71
<211> LENGTH: 715
<212> TYPE: DNA
<213> ORGANISM: Chlamydia

<400> SEQUENCE: 71

```
gatccgaatt cggcacgagg aaaaaaagat tctctaacca ttataatatc tgtgatttat    60
gacccatcaa cataaaaaaa tcagcgaaga aacaatcgcc tgtgacatgc tagagcggct    120
ataccggctc taccattcaa gagttccagc cctatctcct tcttactaat tttgggtatt    180
acgtggatgt tttcgctgaa atctatcagg tccctgtttc tcgaggatcc atgttttcgg    240
gcagcgcatg cgcctcaaat tcacacctca atcatcgatt ttaaattagg ctctccagga    300
gcagctctta ccgtagatct gtgttctttc cttcccaatg ctacagcagc gatcatgttg    360
ggcatgtgcg gaggcttaag atcccactac caaataggag attattttgt ccctgttgct    420
agcatccgaa aagatggaac atcagatgca tacttccccc cagaggtccc tgcattagct    480
aattttgtcg tacaaaaaat gatcaccaat attctcgaag ccaaaaacct cccttaccat    540
ataggcatca cccacacgac taacattcgg ttttgggagt ttaataaaga gttccgtcga    600
aaactatatg aaaataaagc tcaaactgtc gagatggagt gtgccacctt atttgctgca    660
ggataccgaa ggaatcttcc tttaggagca cttttgctga tatcggatct acctt        715
```

<210> SEQ ID NO 72
<211> LENGTH: 641
<212> TYPE: DNA
<213> ORGANISM: Chlamydia
<220> FEATURE:
<221> NAME/KEY: unsure
<222> LOCATION: (550)
<223> OTHER INFORMATION: n=A,T,C or G
<221> NAME/KEY: unsure
<222> LOCATION: (559)
<223> OTHER INFORMATION: n=A,T,C or G
<221> NAME/KEY: unsure
<222> LOCATION: (575)
<223> OTHER INFORMATION: n=A,T,C or G
<221> NAME/KEY: unsure
<222> LOCATION: (583)
<223> OTHER INFORMATION: n=A,T,C or G
<221> NAME/KEY: unsure
<222> LOCATION: (634)
<223> OTHER INFORMATION: n=A,T,C or G
<221> NAME/KEY: unsure
<222> LOCATION: (638)
<223> OTHER INFORMATION: n=A,T,C or G

<400> SEQUENCE: 72

```
gatccgaatt cggcacgaga tctcctcgag ctcgatcaaa cccacacttg ggacaagtac    60
ctacaacata acgtccgct aaaaacttcc cttcttcctc agaatacagc tgttcggtca     120
cctgattctc taccagtccg cgttcctgca gtttcgata gaaatcttgc acaatagcag     180
gatgataagc gttcgtagtt ctggaaaaga aatctacaga aattcccaat ttcttgaagg    240
tatctttatg aagcttatga tacatgtcga catattcttg ataccccatg cctgccaact    300
ctgcattaag ggtaattgcg attccgtatt catcagaacc acaaatatac aaaacctctt    360
tgccttgtag tctctgaaaa cgcgcataaa catctgcagg caaataagca ccgtaatat     420
```

```
gtccaaaatg caaaggacca tttgcgtaag gcaacgcaga agtaataaga atacgggaag    480
attccactat ttcacgtcgc tccagttgta cagagaagga tcttttcttc tggatgttcc    540
gaaaccttgn tctcttcgnc tctctcctgt agcanacaaa tgnctctctc gacatctctt    600
tcagcgtatt cggactgatg ccctaaagat cccnggangt t                        641
```

<210> SEQ ID NO 73
<211> LENGTH: 584
<212> TYPE: DNA
<213> ORGANISM: Chlamydia
<220> FEATURE:
<221> NAME/KEY: unsure
<222> LOCATION: (460)
<223> OTHER INFORMATION: n=A,T,C or G
<221> NAME/KEY: unsure
<222> LOCATION: (523)
<223> OTHER INFORMATION: n=A,T,C or G
<221> NAME/KEY: unsure
<222> LOCATION: (541)
<223> OTHER INFORMATION: n=A,T,C or G
<221> NAME/KEY: unsure
<222> LOCATION: (546)
<223> OTHER INFORMATION: n=A,T,C or G

<400> SEQUENCE: 73

```
gaattcggca cgagacattt ctagaatgga accggcaaca acaaaaact ttgtatctga     60 agatgacttt aagcaatctt tagatgggaa agattttttg gaatgggtct ttttatttgg   120
gacttattac ggaacgagta aggcggagat ttctagagtt ctgcaaaagg gtaagcactg   180
catagccgtg attgatgtac aaggagcttt ggctctgaag aagcaaatgc cggcagtcac   240
tatttttatt caagctccct ctcaagaaga acttgagcgc cgtttgaatg ctcgggattc   300
agagaaagat ttccagaaga aagaaagatt agagcatagc gctgtcgaaa ttgctgccgc   360
tagcgaattt gattatgttg tggttaatga tgatttgatt acagcatatc aagttttaag   420
aagtattttt atagctgaag aacataggat gagtcatggn tagaaaagat cgtttaacta   480
atgaaagact gaataagcta tttgatagcc cctttagttt ggntaattac gtaattaagc   540
nagctnagaa caaaattgct agaggagatg ttcgttcttc taac                    584
```

<210> SEQ ID NO 74
<211> LENGTH: 465
<212> TYPE: DNA
<213> ORGANISM: Chlamydia

<400> SEQUENCE: 74

```
gatccgaatt cggcacgagc tcgtgccgtt tgggatcgtg taatcgcatc ggagaatggt    60
taagaaatta ttttcgagtg aaagagctag gcgtaatcat tacagatagc catactactc   120
caatgcggcg tggagtactg ggtatcgggc tgtgttggta tggattttct ccattacaca   180
actatatagg atcgctagat tgtttcggtc gtcccttaca gatgacgcaa agtaatcttg   240
tagatgcctt agcagttgcg gctgttgttt gtatgggaga ggggaatgag caaacaccgt   300
tagcggtgat agagcaggca cctaatatgg tctaccattc atatcctact tctcgagaag   360
agtattgttc tttgcgcata gatgaaacag aggacttata cggacctttt ttgcaagcgg   420
ttaccgtgga gtcaagaaaa gaaatgatgg aggtgtttat gaatt                   465
```

<210> SEQ ID NO 75
<211> LENGTH: 545
<212> TYPE: DNA
<213> ORGANISM: Chlamydia

<400> SEQUENCE: 75

```
gaattcggca cgagatgaaa agttagcgtc acagggatt ctcctaccaa agaattccga      60
aaagttttct tccaaaaacc tcttcctctc ttgattagtg atccctctgc aactacttta     120
ctatatgttc tgtgaaatat gcatagtctt caggattgga aaatccaaag tactcagtca    180
atccacgaat tttctctcta gcgatacgtg gaatttgact ctcataagaa tacaaagcag    240
ccactcctgc agctaaagaa tctcctgtac accaccgcat gaaagtagct actttcgctt    300
ttgctgcttc actaggctca tgagcctcta actcttctgg agtaactcct agagcaaaca    360
caaactgctt ccacaaatca atatgattag ggtaaccgtt ctcttcatcc atcaagttat    420
ctaacaataa cttacgcgcc tctaaatcat cgcaacgact atgaatcgca gataaatatt    480
taggaaaggc tttgatatgt aaataatagt ctttggcata cgcctgtaat tgctctttag    540
taagc                                                                545
```

<210> SEQ ID NO 76
<211> LENGTH: 797
<212> TYPE: DNA
<213> ORGANISM: Chlamydia
<220> FEATURE:
<221> NAME/KEY: unsure
<222> LOCATION: (788)
<223> OTHER INFORMATION: n=A,T,C or G
<221> NAME/KEY: unsure
<222> LOCATION: (789)
<223> OTHER INFORMATION: n=A,T,C or G

<400> SEQUENCE: 76

```
gatccgaatt cggcacgaga tacgctagat gcgataaatg cggataatga ggattatcct     60
aaaccaggtg acttcccacg atcttccttc tctagtacgc ctcctcatgc tccagtacct    120
caatctgaga ttccaacgtc acctacctca acacagcctc catcaccta acttgtaaaa    180
actgtaataa aaagagcgcg cttcctttat gcaaaatcaa tttgaacaac tccttactga    240
attagggact caaatcaaca gccctcttac tcctgattcc aataatgcct gtatagttcg    300
ctttggatac aacaatgttg ctgtacaaat tgaagaggat ggtaattcag gattttttagt    360
tgctggagtc atgcttggaa aacttccaga gaatacccttt agacaaaaaa ttttcaaagc   420
tgctttgtct atcaatggat ctccgcaatc taatattaaa ggcactctag gatacggtga    480
aatctctaac caactctatc tctgtgatcg gcttaacatg acctatctaa atggagaaaa    540
gctcgcccgt tacttagttc tttttttcgca gcatgccaat atctggatgc aatctatctc   600
aaaaggagaa cttccagatt tacatgctct aggtatgtat cacctgtaaa ttatgccgtc    660
attatcccaa tcccgacgta tcatccagca atcttccatt cgaaagattt ggaatcagat    720
agatacttct cctaagcatg ggggtatgcg taccggttat ttttctcttc atactcaaaa    780
aaagttgnng gggaata                                                   797
```

<210> SEQ ID NO 77
<211> LENGTH: 399
<212> TYPE: DNA
<213> ORGANISM: Chlamydia

<400> SEQUENCE: 77

```
catatgcatc accatcacca tcacatgcca cgcatcattg gaattgatat tcctgcaaag     60
aaaaagttaa aaataagtct gacatatatt tatggaatag gatcagctcg ttctgatgaa    120
atcattaaaa agttgaagtt agatcctgag gcaagagcct ctgaattaac tgaagaagaa    180
```

```
gtaggacgac tgaactctct gctacaatca gaatataccg tagaagggga tttgcgacgt    240
cgtgttcaat cggatatcaa aagattgatc gccatccatt cttatcgagg tcagagacat    300
agactttctt taccagtaag aggacaacgt acaaaaacta attctcgtac tcgaaaaggt    360
aaaagaaaaa cagtcgcagg taagaagaaa taagaattc                           399
```

<210> SEQ ID NO 78
<211> LENGTH: 285
<212> TYPE: DNA
<213> ORGANISM: Chlamydia

<400> SEQUENCE: 78

```
atgcatcacc atcaccatca catgagtcaa aaaataaaa actctgcttt tatgcatccc     60
gtgaatattt ccacagattt agcagttata gttggcaagg gacctatgcc cagaaccgaa   120
attgtaaaga aagtttggga atacattaaa aaacacaact gtcaggatca aaaaaataaa   180
cgtaatatcc ttcccgatgc gaatcttgcc aaagtctttg gctctagtga tcctatcgac   240
atgttccaaa tgaccaaagc cctttccaaa catattgtaa aataa                    285
```

<210> SEQ ID NO 79
<211> LENGTH: 950
<212> TYPE: DNA
<213> ORGANISM: Chlamydia

<400> SEQUENCE: 79

```
aaattaactc gagcacaaat tacggcaatt gctgagcaaa agatgaagga catggatgtc     60
gttcttttag agtccgccga gagaatggtt gaagggactg cccgaagcat gggtgtagat   120
gtagagtaat tagttaaaga gctgcataat tatgacaaag catggaaaac gcattcgtgg   180
tatccaagag acttacgatt tagctaagtc gtattctttg ggtgaagcga tagatatttt   240
aaaacagtgt cctactgtgc gtttcgatca aacggttgat gtgtctgtta aattagggat   300
cgatccaaga aagagtgatc agcaaattcg tggttcggtt tctttacctc acggtacagg   360 taagttttg cgaattttag ttttttgctgc tggagataag gctgcagagg ctattgaagc   420
aggagcggac tttgttggta gcgacgactt ggtagaaaaa atcaaaggtg atgggttga   480 cttcgatgtt gcggttgcca ctcccgatat gatgagagag tcggaaagc taggaaaagt    540 tttaggtcca agaaacctta tgcctacgcc taaagccgga actgtaacaa cagatgtggt   600
taaaactatt gcggaactgc gaaaaggtaa aattgaattt aaagctgatc gagctggtgt   660
atgcaacgtc ggagttgcga agctttcttt cgatagtgcg caaatcaaag aaaatgttga   720
agcgttgtgt gcagccttag ttaaagctaa gcccgcaact gctaaaggac aatatttagt   780
taatttcact atttcctcga ccatggggcc aggggttacc gtggatacta gggagttgat   840
tgcgttataa ttctaagttt aaagaggaaa atgaaagaa gagaaaaagt tgctgcttcg    900
cgaggttgaa gaaaagataa ccgcttctca aggttttatt ttgttgagat                950
```

<210> SEQ ID NO 80
<211> LENGTH: 395
<212> TYPE: DNA
<213> ORGANISM: Chlamydia

<400> SEQUENCE: 80

```
tttcaaggat tttgttttcc cgatcatctt actaaatgca gctccaacaa tcacatcatg     60
ggctggttta gcatctaagg caacagaagc tcctctgctg taataagtga attcttcaga   120
agtaggtgtt cctacttgcg atagcatcgt tcctagtcct gatatccaca ggttgttata   180
```

-continued

| | |
|---|---|
| gctaacttca tcaaagcgag ctagattcat tttatcgttg agcaagcctt gtttgactgt | 240 |
| gaccattgac atttgagatc ccagaatcga gttcgcatag aaatgattgt ctctaggtac | 300 |
| ataagcccat tgtctataag agtcaaattt ccagagcgct gagatcgttc cattttgtag | 360 |
| ttgatcagga tccagagtga gtgttcctgt atatc | 395 |

<210> SEQ ID NO 81
<211> LENGTH: 2085
<212> TYPE: DNA
<213> ORGANISM: Chlamydia

<400> SEQUENCE: 81

| | |
|---|---|
| atttggcgaa ggagtttggg ctacggctat aataaaatca ttcgtgttcg ctgcctccaa | 60 |
| gaccagattg tgtactttct tatgaagaat ctcctattga gcaaatgttg cgttggggag | 120 |
| agtctcagtt agaacaattt gctcaagtag gtttagatac aagttggcaa gttgttttcg | 180 |
| atccaggaat aggatttggg aagactcccg ttcagtcgat gttattgatg gatggagtaa | 240 |
| agcagtttaa acgtgtttta gagtgtcctg tattaatagg ccattctaga aaatcgtgtt | 300 |
| tgagtatgtt gggccgattt aatagtgacg atcgtgattg ggaaacgatc ggctgttctg | 360 |
| tatctcttca tgatcgagga gttgattatc tacgtgtgca tcaggttgaa ggtaacagac | 420 |
| gtgccttagc cgctgctgct tgggctggta tgtttgtatg atccaagcaa caggtatcgt | 480 |
| tgctattgat cccagaggag tgatgggagc tttaggcaag ctcccttgga gttatcccga | 540 |
| agatctacgt ttttttgcag aaaccattcg aaatcatccc atcattatgg gacgaaagac | 600 |
| ttgggagtct cttccagaca agtataagca tgggcgggat atcgttgtct tttctcgcag | 660 |
| gatgcatcca ccacaatgca taggagtttc ttcctttgca gagtatggga cactatcttt | 720 |
| gaatcatccg ttttttaattg ggggagcgga gctctttgaa agtttttttcc aacaaaaacct | 780 |
| tctgaaagct tgttttgtca cacatatcaa aaagaaatat tggggcgata ctttcttccc | 840 |
| tatcacgcga ttatcaggat ggaagaagga atgtatttgt aatacagagg atttcagtat | 900 |
| ttattattat gaaaataact ccgatcaaaa cacgtaaagt atttgcacat gattcgcttc | 960 |
| aagagatctt gcaagaggct ttgccgcctc tgcaagaacg gagtgtggta gttgtctctt | 1020 |
| caaagattgt gagtttatgt gaaggcgctg tcgctgatgc aagaatgtgc aaagcagagt | 1080 |
| tgataaaaaa agaagcggat gcttatttgt tttgtgagaa aagcgggata tatctaacga | 1140 |
| aaaaagaagg tattttgatt ccttctgcag ggattgatga atcgaatacg gaccagcctt | 1200 |
| ttgtttttata tcctaaagat attttgggat cgtgtaatcg catcggagaa tggttaagaa | 1260 |
| attattttcg agtgaaagag ctaggcgtaa tcattacaga tagccatact actccaatgc | 1320 |
| ggcgtggagt actgggtatc gggctgtgtt ggtatggatt ttctccatta cacaactata | 1380 |
| taggatcgct agattgtttc ggtcgtccct tacagatgac gcaaagtaat cttgtagatg | 1440 |
| ccttagcagt tgcggctgtt gtttgtatgg gagagggggaa tgagcaaaca ccgttagcgg | 1500 |
| tgatagagca ggcacctaat atggtctacc attcatatcc tacttctcga aagagtatt | 1560 |
| gttctttgcg catagatgaa acagaggact tatacggacc ttttttgcaa gcggttacgt | 1620 |
| ggagtcaaga aaagaaatga tggaggtgtt tatgaatttt ttagatcagt tagatttaat | 1680 |
| tattcaaaat aagcatatgc tagaacacac gttttatgtg aaatggtcga agggggagct | 1740 |
| tactaaagag caattacagg cgtatgccaa agactattat ttacatatca aagccttttcc | 1800 |
| taaatatttta tctgcgattc atagtcgttg cgatgattta gaggcgcgta agttattgtt | 1860 |

-continued

```
agataacttg atggatgaag agaacggtta ccctaatcat attgatttgt ggaagcagtt    1920
tgtgtttgct ctaggagtta ctccagaaga gttagaggct catgagccta gtgaagcagc    1980
aaaagcgaaa gtagctactt tcatgcggtg gtgtacagga gattctttag ctgcaggagt    2040
ggctgctttg tattcttatg agagtcaaat tccacgtatc gcctc                    2085

<210> SEQ ID NO 82
<211> LENGTH: 405
<212> TYPE: DNA
<213> ORGANISM: Chlamydia

<400> SEQUENCE: 82
ttcatcggtc tagttcgcta ttctactctc caatggttcc gcattttttgg gcagagcttc     60 gcaatcatta tgcaacgagt ggtttgaaaa gcgggtacaa tattgggagt accgatgggt    120
ttctccctgt cattgggcct gttatatggg agtcggaggg tcttttccgc gcttatattt    180
cttcggtgac tgatggggat ggtaagagcc ataaagtagg atttctaaga attcctacat    240
atagttggca ggacatggaa gattttgatc cttcaggacc gcctcctttgg gaagaattgt    300 attggctcca taagggagg agaaaacttc gatatagggg atcgtatcaa ggtgaaagta    360
gcaaaaaata aattagctcc tccattccga actgcagaat tgat                      405

<210> SEQ ID NO 83
<211> LENGTH: 379
<212> TYPE: DNA
<213> ORGANISM: Chlamydia

<400> SEQUENCE: 83
tataccattc gtttgaaagt gcctttgacg ggagaaagtg ttttttgaaga tcaatgcaaa     60 ggtcgtgtcg ttttcccttg ggcagatgtt gacgatcaag ttttggttaa atcagacggg    120
ttccctacgt atcactttgc taatgtagtt gatgatcatt tgatggggat tacccatgtg    180
ttgcgagggg aagagtggtt aagttctaca cctaaacacc ttcttcttta caaagctttt    240
gggtgggagc ctccgcagtt tttccatatg ccgcttcttc taaatcctga tggaagtaag    300 cttttccaaga gaaagaatcc tacttctatt ttttactatc gggatgctgg atacaaaaaa    360
gaagcgttca tgaatttcc                                                  379

<210> SEQ ID NO 84
<211> LENGTH: 715
<212> TYPE: DNA
<213> ORGANISM: Chlamydia

<400> SEQUENCE: 84
tcaatcctgt attaataatt ctggttctta gactacataa attaggaacg cctgatgagt     60
atccataact aatcgcgtag ggcttagaat caccttctcg taccaaagct agaacaacgc    120
cgccttccat tcttgatgca ataatatctg ctgagactaa gaacatgctc ccagagcttt    180
tgggtgtgac tgtgaatttt cctatttcag ttcctcctaa taaagtttca atgttcctgg    240
gagtgaataa cccgttgcat tgaatttttat tagtgattgg aaagttgtta aaagctttca    300
acaaacctag agaagggtct gttgtgattt tgtctaaaat atcttggact gtactatcaa    360
caatagtatc agcaattcca ccaagaattt gatctcccaa cttttctaga ataagctggt    420
aagctttttc cgcatccaaa ccaattgtaa tagaagcatt ggttgatgga ttattggaga    480
ctgttaaaga tattccatca gaagctgtca ttttggctgc acaggtgttt gatgttgtcc    540
caaggattat ttgctggtcc ttgagcggct ctgtcatttg cccaactttg atattatcag    600
```

| | |
|---|---|
| caaagacgca gttttgagtg ttatacaaat aaaaaccaga atttcccatt ttaaaactct | 660 |
| tttttatttt gagctttaaa taaattaggt ttttagtttc aagtttgcta ttaat | 715 |

<210> SEQ ID NO 85
<211> LENGTH: 476
<212> TYPE: DNA
<213> ORGANISM: Chlamydia

<400> SEQUENCE: 85

| | |
|---|---|
| ctcgtgccgc tcgtgccgct cgtgccggtc ttttagaaga gcgtgaagct ttaaataatt | 60 |
| cgattacgtt tatcatggat aagcgtaatt ggatagaaac cgagtctgaa caggtacaag | 120 |
| tggttttcag atatagtaca gcttgcttag gaggaggcgc tattgcagct caagaaattg | 180 |
| tttctattca gaacaatcag gctgggattt ccttcgaggg aggtaaggct agtttcggag | 240 |
| gaggtattgc gtgtggatct ttttcttccg caggcggtgc ttctgtttta gggactattg | 300 |
| atatttcgaa gaatttaggc gcgatttcgt tctctcgtac tttatgtacg acctcagatt | 360 |
| taggacaaat ggagtaccag ggaggaggag ctctatttgg tgaaaatatt tctctttctg | 420 |
| agaatgctgg tgtgctcacc tttaaagaca acattgtgaa gacttttgct tcgaat | 476 |

<210> SEQ ID NO 86
<211> LENGTH: 1551
<212> TYPE: DNA
<213> ORGANISM: Chlamydia

<400> SEQUENCE: 86

| | |
|---|---|
| gcgtatcgat atttcttctg ttacattctt tatagggatt ctgttggctg ttaatgcgct | 60 |
| aacctactct catgtattac gggatttatc tgtgagtatg gatgcgctgt tttctcgtaa | 120 |
| cacgcttgct gttcttttag gtttagtctc tagcgtttta gataatgtgc cattagtcgc | 180 |
| tgcaacaata ggtatgtatg acttacctat gaacgatcct ctttggaaac tcattgccta | 240 |
| tacagcaggc acaggggaa gtattctcat cattggatcc gctgcaggtg ttgcctacat | 300 |
| gggaatggaa aaagtgagtt tcggctggta tgtcaaacac gcttcttgga ttgctttagc | 360 |
| cagttatttt ggaggtctag cagtctattt tctaatggaa aattgtgtga atttgttcgt | 420 |
| ttgaggtagt cagtatggca gagtttcttt aaaaattctt ttaataaaag ggttctctgc | 480 |
| ctattctagg ccccttttg aatggaaaaa tgggttttg gagaacatcg attatgaaaa | 540 |
| tgaataggat ttggctatta ctgcttacct tttcttctgc catacattct cctgtacgag | 600 |
| gagaaagctt ggtttgcaag aatgctcttc aagatttgag ttttttagag catttattac | 660 |
| aggttaaata tgctcctaaa acatggaaag agcaatactt aggatgggat cttgttcaaa | 720 |
| gctccgtttc tgcacagcag aagcttcgta cacaagaaaa tccatcaaca gttttttgcc | 780 |
| agcaggtcct tgctgatttt atcggaggat taaatgactt tcacgctgga gtaactttct | 840 |
| ttgcgataga aagtgcttac cttccttata ccgtacaaaa agtagtgac ggccgtttct | 900 |
| actttgtaga tatcatgact ttttcttcag agatccgtgt tggagatgag ttgctagagg | 960 |
| tggatggggc gcctgtccaa gatgtgctcg ctactctata tggaagcaat cacaaaggga | 1020 |
| ctgcagctga agagtcggct gctttaagaa cactatttc tcgcatggcc tctttagggc | 1080 |
| acaaagtacc ttctgggcgc actactttaa agattcgtcg tccttttggt actacgagag | 1140 |
| aagttcgtgt gaaatggcgt tatgttcctg aaggtgtagg agatttggct accatagctc | 1200 |
| cttctatcag ggctccacag ttacagaaat cgatgagaag cttttcccct aagaaagatg | 1260 |

```
atgcgtttca tcggtctagt tcgctattct actctccaat ggttccgcat ttttgggcag   1320
agcttcgcaa tcattatgca acgagtggtt tgaaaagcgg gtacaatatt gggagtaccg   1380
atgggtttct ccctgtcatt gggcctgtta tatgggagtc ggagggtctt ttccgcgctt   1440
atatttcttc ggtgactgat ggggatggta agagccataa agtaggattt ctaagaattc   1500
ctacatatag ttggcaggac atggaagatt ttgatccttc aggaccgcct c            1551

<210> SEQ ID NO 87
<211> LENGTH: 3031
<212> TYPE: DNA
<213> ORGANISM: Chlamydia

<400> SEQUENCE: 87
atgtaggccc tcaagcggtt ttattgttag accaaattcg agatctattc gttgggtcta     60
aagatagtca ggctgaagga cagtataggt taattgtagg agatccaagt tctttccaag    120
agaaagatgc agatactctt cccgggaagg tagagcaaag tactttgttc tcagtaacca    180
atcccgtggt tttccaaggt gtggaccaac aggatcaagt ctcttcccaa gggttaatttt  240 gtagttttac gagcagcaac cttgattctc cccgtgacgg agaatctttt ttaggtattg    300
cttttgttgg ggatagtagt aaggctggaa tcacattaac tgacgtgaaa gcttcttttgt  360 ctggagcggc tttatattct acagaagatc ttatctttga aaagattaag ggtggattgg    420
aatttgcatc atgttcttct ctagaacagg ggggagcttg tgcagctcaa gtattttga    480 ttcatgattg tcaaggattg caggttaaac actgtactac agccgtgaat gctgaggggt    540
ctagtgcgaa tgatcatctt ggatttggag gaggcgcttt cttgttacg ggttctcttt    600 ctggagagaa aagtctctat atgcctgcag gagatatggt agttgcgaat tgtgatgggg   660
ctatatcttt tgaaggaaac agcgcgaact ttgctaatgg aggagcgatt gctgcctctg    720
ggaaagtgct ttttgtcgct aatgataaaa agacttcttt tatagagaac cgagctttgt   780
ctggaggagc gattgcagcc tcttctgata ttgccttttca aaactgcgca gaactagttt   840
tcaaaggcaa ttgtgcaatt ggaacagagg ataaaggttc tttaggtgga ggggctatat    900
cttctctagg caccgttctt ttgcaaggga atcacgggat aacttgtgat aataatgagt    960
ctgcttcgca aggaggcgcc attttttggca aaaattgtca gatttctgac aacgagggc   1020 cagtggtttt cagagatagt acagcttgct taggaggagg cgctattgca gctcaagaaa   1080
ttgtttctat tcagaacaat caggctggga tttccttcga gggaggtaag gctagtttcg   1140
gaggaggtat tgcgtgtgga tcttttttctt ccgcaggcgg tgcttctgtt ttagggacta   1200
ttgatatttc gaagaattta ggcgcgattt cgttctctcg tactttatgt acgacctcag   1260
atttaggaca aatggagtac cagggaggag gagctctatt tggtgaaaat atttctcttt   1320
ctgagaatgc tggtgtgctc acctttaaag caacattgt gaagacttttt gcttcgaatg   1380 ggaaaattct gggaggagga gcgattttag ctactggtaa ggtggaaatt accaataatt   1440
ccggaggaat ttcttttaca ggaaatgcga gagctccaca agctcttcca actcaagagg   1500
agtttccttt attcagcaaa aaagaagggc gaccactctc ttcaggatat tctggggag    1560 gagcgatttt aggaagagaa gtagctattc tccacaacgc tgcagtagta tttgagcaaa   1620
atcgtttgca gtgcagcgaa aagaagcga cattattagg ttgttgtgga ggaggcgctg    1680
ttcatgggat ggatagcact tcgattgttg gcaactcttc agtaagattt ggtaataatt   1740
acgcaatggg acaaggagtc tcaggaggag ctctttttatc taaaacagtg cagttagctg    1800
gaaatggaag cgtcgatttt tctcgaaata ttgctagttt gggaggacgc aatgttctgt   1860
```

```
tagcttcaga aacctttgct tccagagcaa atacatctcc ttcatcgctt cgctccttat   1920
atttccaagt aacctcatcc ccctctaatt gcgctaattt acatcaaatg cttgcttctt   1980
actcgccatc agagaaaacc gctgttatgg agtttctagt gaatggcatg gtagcagatt   2040
taaaatcgga gggcccttcc attcctcctg caaaattgca agtatatatg acggaactaa   2100
gcaatctcca agccttacac tctgtagata gcttttttga tagaaatatt gggaacttgg   2160
aaaatagctt aaagcatgaa ggacatgccc ctattccatc cttaacgaca ggaaatttaa   2220
ctaaaacctt cttacaatta gtagaagata aattcccttc ctcttccaaa gctcaaaagg   2280
cattaaatga actggtaggc ccagatactg gtcctcaaac tgaagtttta aacttattct   2340
tccgcgctct taatggctgt tcgcctagaa tattctctgg agctgaaaaa aaacagcagc   2400
tggcatcggt tatcacaaat acgctagatg cgataaatgc ggataatgag gattatccta   2460
aaccaggtga cttcccacga tcttccttct ctagtacgcc tcctcatgct ccagtacctc   2520
aatctgagat tccaacgtca cctacctcaa cacagcctcc atcaccctaa cttgtaaaaa   2580
ctgtaataaa aagagcgcgc ttcctttatg caaaatcaat ttgaacaact ccttactgaa   2640
ttagggactc aaatcaacag ccctcttact cctgattcca ataatgcctg tatagttcgc   2700
tttggataca acaatgttgc tgtacaaatt gaagaggatg gtaattcagg attttttagtt  2760 gctggagtca tgcttggaaa acttccagag aatacccttta gacaaaaaat tttcaaagct   2820
gctttgtcta tcaatggatc tccgcaatct aatattaaag gcactctagg atacggtgaa   2880
atctctaacc aactctatct ctgtgatcgg cttaacatga cctatctaaa tggagaaaag   2940
ctcgcccgtt acttagttct ttttttcgcag catgccaata tctggatgca atctatctca   3000
aaaggagaac ttccagattt acatgctcta g                                  3031

<210> SEQ ID NO 88
<211> LENGTH: 976
<212> TYPE: DNA
<213> ORGANISM: Chlamydia

<400> SEQUENCE: 88
aggtggatgg ggcgcctgtc caagatgtgc tcgctactct atatggaagc aatcacaaag    60
ggactgcagc tgaagagtcg gctgctttaa gaacactatt ttctcgcatg gcctctttag   120
ggcacaaagt accttctggg cgcactactt taaagattcg tcgtcctttt ggtactacga   180
gagaagttcg tgtgaaatgg cgttatgttc ctgaaggtgt aggagatttg gctaccatag   240
ctccttctat cagggctcca cagttacaga atcgatgag aagcttttc cctaagaaag   300 atgatgcgtt tcatcggtct agttcgctat tctactctcc aatggttccg cattttttggg   360 cagagcttcg caatcattat gcaacgagtg gtttgaaaag cgggtacaat attgggagta   420
ccgatgggtt tctccctgtc attgggcctg ttatatggga gtcggagggt cttttccgcg   480
cttatatttc ttcggtgact gatggggatg gtaagagcca taagtagga tttctaagaa   540 ttcctacata tagttggcag acatggaag atttttgatcc ttcaggaccg cctccttggg   600
aagaatttgc taagattatt caagtatttt cttctaatac agaagctttg attatcgacc   660
aaacgaacaa cccaggtggt agtgtccttt atctttatgc actgctttcc atgttgacag   720
accgtccttt agaacttcct aaacatagaa tgattctgac tcaggatgaa gtggttgatg   780
cttttagatt gttaaccctg ttggaaaacg tagacacaaa cgtggagtct cgccttgctc   840
tgggagacaa catggaagga tatactgtgg atctacaggt tgccgagtat ttaaaaagct   900
```

```
ttggacgtca agtattgaat tgttggagta aagggatat cgagttatca acacctattc        960 ctcttttgg ttttga                                                         976
```

<210> SEQ ID NO 89
<211> LENGTH: 94
<212> TYPE: PRT
<213> ORGANISM: Chlamydia

<400> SEQUENCE: 89

```
Met His His His His His Met Ser Gln Lys Asn Lys Asn Ser Ala
                  5                  10                  15

Phe Met His Pro Val Asn Ile Ser Thr Asp Leu Ala Val Ile Val Gly
                 20                  25                  30

Lys Gly Pro Met Pro Arg Thr Glu Ile Val Lys Lys Val Trp Glu Tyr
             35                  40                  45

Ile Lys Lys His Asn Cys Gln Asp Gln Lys Asn Lys Arg Asn Ile Leu
 50                  55                  60

Pro Asp Ala Asn Leu Ala Lys Val Phe Gly Ser Ser Asp Pro Ile Asp
 65                  70                  75                  80

Met Phe Gln Met Thr Lys Ala Leu Ser Lys His Ile Val Lys
                 85                  90
```

<210> SEQ ID NO 90
<211> LENGTH: 474
<212> TYPE: PRT
<213> ORGANISM: Chlamydia

<400> SEQUENCE: 90

```
Met Ala Ser His His His His His His Met Asn Glu Ala Phe Asp Cys
                  5                  10                  15

Val Val Ile Gly Ala Gly Pro Gly Gly Tyr Val Ala Ala Ile Thr Ala
                 20                  25                  30

Ala Gln Ala Gly Leu Lys Thr Ala Leu Ile Glu Lys Arg Glu Ala Gly
             35                  40                  45

Gly Thr Cys Leu Asn Arg Gly Cys Ile Pro Ser Lys Ala Leu Leu Ala
 50                  55                  60

Gly Ala Glu Val Val Thr Gln Ile Arg His Ala Asp Gln Phe Gly Ile
 65                  70                  75                  80

His Val Glu Gly Phe Ser Ile Asn Tyr Pro Ala Met Val Gln Arg Lys
                 85                  90                  95

Asp Ser Val Val Arg Ser Ile Arg Asp Gly Leu Asn Gly Leu Ile Arg
                100                 105                 110

Ser Asn Lys Ile Thr Val Phe Ser Gly Arg Gly Ser Leu Ile Ser Ser
            115                 120                 125

Thr Glu Val Lys Ile Leu Gly Glu Asn Pro Ser Val Ile Lys Ala His
130                 135                 140

Ser Ile Ile Leu Ala Thr Gly Ser Glu Pro Arg Ala Phe Pro Gly Ile
145                 150                 155                 160

Pro Phe Ser Ala Glu Ser Pro Arg Ile Leu Cys Ser Thr Gly Val Leu
                165                 170                 175

Asn Leu Lys Glu Ile Pro Gln Lys Met Ala Ile Ile Gly Gly Gly Val
                180                 185                 190

Ile Gly Cys Glu Phe Ala Ser Leu Phe His Thr Leu Gly Ser Glu Val
            195                 200                 205

Ser Val Ile Glu Ala Ser Ser Gln Ile Leu Ala Leu Asn Asn Pro Asp
210                 215                 220
```

```
Ile Ser Lys Thr Met Phe Asp Lys Phe Thr Arg Gln Gly Leu Arg Phe
225                 230                 235                 240

Val Leu Glu Ala Ser Val Ser Asn Ile Glu Asp Ile Gly Asp Arg Val
            245                 250                 255

Arg Leu Thr Ile Asn Gly Asn Val Glu Glu Tyr Asp Tyr Val Leu Val
            260                 265                 270

Ser Ile Gly Arg Arg Leu Asn Thr Glu Asn Ile Gly Leu Asp Lys Ala
            275                 280                 285

Gly Val Ile Cys Asp Glu Arg Gly Val Ile Pro Thr Asp Ala Thr Met
        290                 295                 300

Arg Thr Asn Val Pro Asn Ile Tyr Ala Ile Gly Asp Ile Thr Gly Lys
305                 310                 315                 320

Trp Gln Leu Ala His Val Ala Ser His Gln Gly Ile Ile Ala Ala Arg
                325                 330                 335

Asn Ile Gly Gly His Lys Glu Gly Ile Asp Tyr Ser Ala Val Pro Ser
                340                 345                 350

Val Ile Phe Thr Phe Pro Glu Val Ala Ser Val Gly Leu Ser Pro Thr
            355                 360                 365

Ala Ala Gln Gln Gln Lys Ile Pro Val Lys Val Thr Lys Phe Pro Phe
370                 375                 380

Arg Ala Ile Gly Lys Ala Val Ala Met Gly Glu Ala Asp Gly Phe Ala
385                 390                 395                 400

Ala Ile Ile Ser His Glu Thr Thr Gln Gln Ile Leu Gly Ala Tyr Val
                405                 410                 415

Ile Gly Pro His Ala Ser Ser Leu Ile Ser Glu Ile Thr Leu Ala Val
                420                 425                 430

Arg Asn Glu Leu Thr Leu Pro Cys Ile Tyr Glu Thr Ile His Ala His
            435                 440                 445

Pro Thr Leu Ala Glu Val Trp Ala Glu Ser Ala Leu Leu Ala Val Asp
            450                 455                 460

Thr Pro Leu His Met Pro Pro Ala Lys Lys
465                 470

<210> SEQ ID NO 91
<211> LENGTH: 129
<212> TYPE: PRT
<213> ORGANISM: Chlamydia

<400> SEQUENCE: 91

Met His His His His His Met Pro Arg Ile Ile Gly Ile Asp Ile
                5                  10                  15

Pro Ala Lys Lys Lys Leu Lys Ile Ser Leu Thr Tyr Ile Tyr Gly Ile
                20                  25                  30

Gly Ser Ala Arg Ser Asp Glu Ile Ile Lys Lys Leu Lys Leu Asp Pro
            35                  40                  45

Glu Ala Arg Ala Ser Glu Leu Thr Glu Glu Val Gly Arg Leu Asn
        50                  55                  60

Ser Leu Leu Gln Ser Glu Tyr Thr Val Glu Gly Asp Leu Arg Arg
65                  70                  75                  80

Val Gln Ser Asp Ile Lys Arg Leu Ile Ala Ile His Ser Tyr Arg Gly
                85                  90                  95

Gln Arg His Arg Leu Ser Leu Pro Val Arg Gly Gln Arg Thr Lys Thr
            100                 105                 110
```

Asn Ser Arg Thr Arg Lys Gly Lys Arg Thr Val Ala Gly Lys Lys
            115                 120                 125

Lys

<210> SEQ ID NO 92
<211> LENGTH: 202
<212> TYPE: PRT
<213> ORGANISM: Chlamydia

<400> SEQUENCE: 92

Met His His His His His His Met Gly Ser Leu Val Gly Arg Gln Ala
                  5                  10                  15

Pro Asp Phe Ser Gly Lys Ala Val Val Cys Gly Glu Glu Lys Glu Ile
             20                  25                  30

Ser Leu Ala Asp Phe Arg Gly Lys Tyr Val Val Leu Phe Phe Tyr Pro
         35                  40                  45

Lys Asp Phe Thr Tyr Val Cys Pro Thr Glu Leu His Ala Phe Gln Asp
     50                  55                  60

Arg Leu Val Asp Phe Glu Glu His Gly Ala Val Val Leu Gly Cys Ser
 65                  70                  75                  80

Val Asp Asp Ile Glu Thr His Ser Arg Trp Leu Thr Val Ala Arg Asp
                 85                  90                  95

Ala Gly Gly Ile Glu Gly Thr Glu Tyr Pro Leu Leu Ala Asp Pro Ser
            100                 105                 110

Phe Lys Ile Ser Glu Ala Phe Gly Val Leu Asn Pro Glu Gly Ser Leu
        115                 120                 125

Ala Leu Arg Ala Thr Phe Leu Ile Asp Lys His Gly Val Ile Arg His
    130                 135                 140

Ala Val Ile Asn Asp Leu Pro Leu Gly Arg Ser Ile Asp Glu Glu Leu
145                 150                 155                 160

Arg Ile Leu Asp Ser Leu Ile Phe Phe Glu Asn His Gly Met Val Cys
                165                 170                 175

Pro Ala Asn Trp Arg Ser Gly Glu Arg Gly Met Val Pro Ser Glu Glu
            180                 185                 190

Gly Leu Lys Glu Tyr Phe Gln Thr Met Asp
        195                 200

<210> SEQ ID NO 93
<211> LENGTH: 19
<212> TYPE: PRT
<213> ORGANISM: Artificial Sequence
<220> FEATURE:
<223> OTHER INFORMATION: made in a lab

<400> SEQUENCE: 93

Glu Asn Ser Leu Gln Asp Pro Thr Asn Lys Arg Asn Ile Asn Pro Asp
 1               5                  10                  15

Asp Lys Leu

<210> SEQ ID NO 94
<211> LENGTH: 20
<212> TYPE: PRT
<213> ORGANISM: Artificial Sequence
<220> FEATURE:
<223> OTHER INFORMATION: Made in a lab

<400> SEQUENCE: 94

Asp Pro Thr Asn Lys Arg Asn Ile Asn Pro Asp Asp Lys Leu Ala Lys
 1               5                  10                  15

Val Phe Gly Thr
            20

<210> SEQ ID NO 95
<211> LENGTH: 20
<212> TYPE: PRT
<213> ORGANISM: Artificial Sequence
<220> FEATURE:
<223> OTHER INFORMATION: Made in a lab

<400> SEQUENCE: 95

Lys Arg Asn Ile Asn Pro Asp Asp Lys Leu Ala Lys Val Phe Gly Thr
 1               5                  10                  15

Glu Lys Pro Ile
            20

<210> SEQ ID NO 96
<211> LENGTH: 20
<212> TYPE: PRT
<213> ORGANISM: Artificial Sequence
<220> FEATURE:
<223> OTHER INFORMATION: Made in a lab

<400> SEQUENCE: 96

Asp Asp Lys Leu Ala Lys Val Phe Gly Thr Glu Lys Pro Ile Asp Met
 1               5                  10                  15

Phe Gln Met Thr
            20

<210> SEQ ID NO 97
<211> LENGTH: 20
<212> TYPE: PRT
<213> ORGANISM: Artificial Sequence
<220> FEATURE:
<223> OTHER INFORMATION: Made in a lab

<400> SEQUENCE: 97

Lys Val Phe Gly Thr Glu Lys Pro Ile Asp Met Phe Gln Met Thr Lys
 1               5                  10                  15

Met Val Ser Gln
            20

<210> SEQ ID NO 98
<211> LENGTH: 20
<212> TYPE: PRT
<213> ORGANISM: Artificial Sequence
<220> FEATURE:
<223> OTHER INFORMATION: Made in a lab

<400> SEQUENCE: 98

Asn Lys Arg Asn Ile Asn Pro Asp Asp Lys Leu Ala Lys Val Phe Gly
 1               5                  10                  15

Thr Glu Lys Pro
            20

<210> SEQ ID NO 99
<211> LENGTH: 16
<212> TYPE: PRT
<213> ORGANISM: Artificial Sequence
<220> FEATURE:
<223> OTHER INFORMATION: Made in a lab

<400> SEQUENCE: 99

Asn Lys Arg Asn Ile Leu Pro Asp Ala Asn Leu Ala Lys Val Phe Gly

<210> SEQ ID NO 100
<211> LENGTH: 15
<212> TYPE: PRT
<213> ORGANISM: Artificial Sequence
<220> FEATURE:
<223> OTHER INFORMATION: Made in a lab

<400> SEQUENCE: 100

Lys Met Trp Asp Tyr Ile Lys Glu Asn Ser Leu Gln Asp Pro Thr
1               5                   10                  15

<210> SEQ ID NO 101
<211> LENGTH: 20
<212> TYPE: PRT
<213> ORGANISM: Artificial Sequence
<220> FEATURE:
<223> OTHER INFORMATION: Made in a lab

<400> SEQUENCE: 101

Thr Glu Ile Val Lys Lys Val Trp Glu Tyr Ile Lys Lys His Asn Cys
1               5                   10                  15

Gln Asp Gln Lys
            20

<210> SEQ ID NO 102
<211> LENGTH: 20
<212> TYPE: PRT
<213> ORGANISM: Artificial Sequence
<220> FEATURE:
<223> OTHER INFORMATION: Made in a lab

<400> SEQUENCE: 102

Lys Val Trp Glu Tyr Ile Lys Lys His Asn Cys Gln Asp Gln Lys Asn
1               5                   10                  15

Lys Arg Asn Ile
            20

<210> SEQ ID NO 103
<211> LENGTH: 15
<212> TYPE: PRT
<213> ORGANISM: Artificial Sequence
<220> FEATURE:
<223> OTHER INFORMATION: Made in a lab

<400> SEQUENCE: 103

Lys Val Trp Glu Tyr Ile Lys Lys His Asn Cys Gln Asp Gln Lys
1               5                   10                  15

<210> SEQ ID NO 104
<211> LENGTH: 20
<212> TYPE: PRT
<213> ORGANISM: Artificial Sequence
<220> FEATURE:
<223> OTHER INFORMATION: Made in a lab

<400> SEQUENCE: 104

Ala Glu Leu Thr Glu Glu Glu Val Gly Arg Leu Asn Ala Leu Leu Gln
1               5                   10                  15

Ser Asp Tyr Val
            20

<210> SEQ ID NO 105
<211> LENGTH: 21

```
<212> TYPE: PRT
<213> ORGANISM: Artificial Sequence
<220> FEATURE:
<223> OTHER INFORMATION: Made in a lab

<400> SEQUENCE: 105

Leu Gln Ser Asp Tyr Val Val Glu Gly Asp Leu Arg Arg Val Gln
 1               5                  10                  15

Ser Asp Ile Lys Arg
            20

<210> SEQ ID NO 106
<211> LENGTH: 20
<212> TYPE: PRT
<213> ORGANISM: Artificial Sequence
<220> FEATURE:
<223> OTHER INFORMATION: Made in a lab

<400> SEQUENCE: 106

Met Pro Arg Ile Ile Gly Ile Asp Ile Pro Ala Lys Lys Leu Lys
 1               5                  10                  15

Ile Ser Leu Thr
            20

<210> SEQ ID NO 107
<211> LENGTH: 20
<212> TYPE: PRT
<213> ORGANISM: Artificial Sequence
<220> FEATURE:
<223> OTHER INFORMATION: Made in a lab

<400> SEQUENCE: 107

Ala Glu Leu Thr Glu Glu Val Gly Arg Leu Asn Ala Leu Leu Gln
 1               5                  10                  15

Ser Asp Tyr Val
            20

<210> SEQ ID NO 108
<211> LENGTH: 20
<212> TYPE: PRT
<213> ORGANISM: Artificial Sequence
<220> FEATURE:
<223> OTHER INFORMATION: Made in a lab

<400> SEQUENCE: 108

Leu Asn Ala Leu Leu Gln Ser Asp Tyr Val Val Glu Gly Asp Leu Arg
 1               5                  10                  15

Arg Arg Val Gln
            20

<210> SEQ ID NO 109
<211> LENGTH: 20
<212> TYPE: PRT
<213> ORGANISM: Artificial Sequence
<220> FEATURE:
<223> OTHER INFORMATION: Made in a lab

<400> SEQUENCE: 109

Leu Asn Ser Leu Leu Gln Ser Glu Tyr Thr Val Glu Gly Asp Leu Arg
 1               5                  10                  15

Arg Arg Val Gln
            20

<210> SEQ ID NO 110
```

<211> LENGTH: 1461
<212> TYPE: DNA
<213> ORGANISM: Chlamydia

<400> SEQUENCE: 110

```
ctatctatga agttatgaat atggatctag aaacacgaag atcttttgcg gtacagcaag      60
ggcactatca ggacccaaga gcttcagatt atgacctccc acgtgctagc gactatgatt     120
tgcctagaag cccatatcct actccacctt tgccttctag atatcagcta cagaatatgg     180
atgtagaagc agggttccgt gaggcagttt atgcttcttt tgtagcagga atgtacaatt     240
atgtagtgac acagccgcaa gagcgtattc ccaatagtca gcaggtggaa gggattctgc     300
gtgatatgct taccaacggg tcacagacat ttagcaacct gatgcagcgt tgggatagag     360
aagtcgatag ggaataaact ggtatctacc ataggtttgt atcaaaaaac taagcccacc     420
aagaagaaat tctctttggt gggcttcttt ttttattcaa aaaagaaagc cctcttcaag     480
attatctcgt gccgctcgtg ccgaattcgg cacgagcggc acgaggagct gtaagtaagt     540
attgccaaga gttggaagaa aaatattag atttgtgtaa gcgtcatgcc gcaacaattt     600
gctccattga ggaggatgct aaacaagaaa ttcgtcatca gacagaaagg tttaaacagc     660
ggttgcaaca aaatcagaac acttgcagtc aattaacagc agagttgtgt aaattgagat     720
ctgagaataa ggcattatcg gagcggctgc aggtgcaggc atcccgtcgt aaaaaataat     780
taaagactcc tcagatattg catctgagag ttaggggttc cttttgctta cggcgcttta     840
gttctgcatg ttgcggattt atagtgattt gcgagtaaag cgccgttctg atacagtttt     900
tccgctttaa aaataaaaag gtggaaaaat gagtactact attagcggag acgcttcttc     960
tttaccgttg ccaacagctt cctgcgtaga gacaaaatct acttcgtctt caacaaaagg    1020
gaatacttgt tccaaaattt tggatatagc tttagctatc gtaggcgctt tagttgttgt    1080
cgctggggta ttagctttgg ttttgtgcgc tagcaatgtc atatttactg taataggtat    1140
tcctgcatta attattggat ctgcttgtgt gggtgcggga atatctcgtc ttatgtatcg    1200
atcctcttat gctagcttag aagcaaaaaa tgttttggct gagcaacgtt tgcgtaatct    1260
ttcagaagag aaggacgctt tggcctccgt ctctttcatt aataagatgt tctgcgcagg    1320
tcttacggac gatctccaag cttggaagc taaggtaatg gaatttgaga ttgattgttt    1380
ggacagatta gagaaaaatg agcaagcttt attgtccgat gtgcgcttag ttttatctag    1440
ctacacaaga tggttggata g                                              1461
```

<210> SEQ ID NO 111
<211> LENGTH: 267
<212> TYPE: DNA
<213> ORGANISM: Chlamydia

<400> SEQUENCE: 111

```
gtcctcttct tattatagca gaagacattg aaggcgaagc tttagctact ttggtcgtga      60
acagaattcg tggaggattc cgggtttgcg cagttaaagc tccaggcttt ggagatagaa     120
gaaaagctat gttggaagac atcgctatct taactggcgg tcaactcatt agcgaagagt     180
tgggcatgaa attagaaaac gctaacttag ctatgttagg taaagctaaa aaagttatcg     240
tttctaaaga agacacgacc atcgtcg                                         267
```

<210> SEQ ID NO 112
<211> LENGTH: 698
<212> TYPE: DNA
<213> ORGANISM: Chlamydia

<400> SEQUENCE: 112

```
tgataagcaa gcaaccgctc aactagcagc tctaactatt aaaaaaatcc tctgttttga      60
tgaaaattcc tacgagaagg agctggcatg cttagaaaag aaacgcagta gcgtacaaaa     120
agatctgagc caactgaaaa aatacacagt tctctacatc aagaagctgc tcgaaaccta     180
cagacaactc gggcatcgaa agacaaaaat tgcaaaattt gatgacctac ctaccgagag     240
agtctccgct cataagaaag caaagaact cgctgcgctc gatcaagaag agaacttcta     300
aaacgtgact cggcccttga gatccttaaa ctctcgggcc aaaagacta cagtcttctc     360
gagaagaaaa acggtgttag aaaatacgcg cgctaagact ttctctaaca atgactcaaa     420
aagctgtaaa cgtatacgtt taccgctctt ccataatttc taggctgact ttcacattat     480
ctcgacttgc tacggaaacc aataaagtac ggatagcctt aatagtgcgt ccttctttac     540
cgataatttt accgatatct cccttagcaa cagtcaattc gtagataatc gtattggttc     600
cctgcacctc tttcagatgc acttcctctg cttatcaac aagatttttt acaatgtacg     660
ctaaaaactc tttcatgcga agcaaatcct acacaagc                            698
```

<210> SEQ ID NO 113
<211> LENGTH: 1142
<212> TYPE: DNA
<213> ORGANISM: Chlamydia

<400> SEQUENCE: 113

```
ctcttcaaag attgtgagtt tatgtgaagg cgctgtcgct gatgcaagaa tgtgcaaagc      60
agagttgata aaaaagaag cggatgctta tttgttttgt gagaaaagcg ggatatatct     120
aacgaaaaaa gaaggtattt tgattccttc tgcagggatt gatgaatcga atacggacca     180
gcctttgtt ttatatccta agatattttt gggatcgtgt aatcgcatcg gagaatggtt     240
aagaaattat tttcgagtga aagagctagg cgtaatcatt acagatagcc atactactcc     300
aatgcggcgt ggagtactgg gtatcgggct gtgttggtat ggattttctc cattacacaa     360
ctatatagga tcgctagatt gtttcggtcg tcccttacag atgacgcaaa gtaatcttgt     420
agatgcctta gcagttgcgg ctgttgtttg tatgggagag gggaatgagc aaacaccgtt     480
agcggtgata gagcaggcac ctaatatggt ctaccattca tatcctactt ctcgagaaga     540
gtattgttct ttgcgcatag atgaaacaga ggacttatac ggaccttttt tgcaagcggt     600
tacgtggagt caagaaaaga aatgatggag gtgtttatga attttttaga tcagttagat     660
ttaattattc aaaataagca tatgctagaa cacacgtttt atgtgaaatg gtcgaagggg     720
gagcttacta aagagcaatt acaggcgtat gccaaagact attatttaca tatcaaagcc     780
tttcctaaat atttatctgc gattcatagt cgttgcgatg atttagaggc gcgtaagtta     840
ttgttagata acttgatgga tgaagagaac ggttaccta atcatattga tttgtggaag     900
cagtttgtgt ttgctctagg agttactcca gaagagttag aggctcatga gcctagtgaa     960
gcagcaaaag cgaaagtagc tactttcatg cggtggtgta caggagattc tttagctgca    1020
ggagtggctg ctttgtattc ttatgagagt caaattccac gtatcgctag agagaaaatt    1080
cgtggattga ctgagtactt tggattttcc aatcctgaag actatgcata tttcacagaa    1140
ca                                                                  1142
```

<210> SEQ ID NO 114
<211> LENGTH: 976
<212> TYPE: DNA

<213> ORGANISM: Chlamydia

<400> SEQUENCE: 114

```
aggtggatgg ggcgcctgtc caagatgtgc tcgctactct atatggaagc aatcacaaag      60
ggactgcagc tgaagagtcg gctgctttaa gaacactatt ttctcgcatg gcctctttag     120
ggcacaaagt accttctggg cgcactactt taaagattcg tcgtcctttt ggtactacga     180
gagaagttcg tgtgaaatgg cgttatgttc ctgaaggtgt aggagatttg gctaccatag     240
ctccttctat cagggctcca cagttacaga atcgatgag aagcttttc cctaagaaag       300
atgatgcgtt tcatcggtct agttcgctat tctactctcc aatggttccg catttttggg     360
cagagcttcg caatcattat gcaacgagtg gtttgaaaag cgggtacaat attgggagta     420
ccgatgggtt tctccctgtc attgggcctg ttatatggga gtcggagggt cttttccgcg     480
cttatatttc ttcggtgact gatggggatg gtaagagcca taagtagga tttctaagaa      540
ttcctacata tagttggcag acatggaag atttgatcc ttcaggaccg cctccttggg        600
aagaatttgc taagattatt caagtatttt cttctaatac agaagctttg attatcgacc     660
aaacgaacaa cccaggtggt agtgtccttt atctttatgc actgctttcc atgttgacag     720
accgtccttt agaacttcct aaacatagaa tgattctgac tcaggatgaa gtggttgatg     780
ctttagattg gttaaccctg ttggaaaacg tagacacaaa cgtggagtct cgccttgctc     840
tgggagacaa catggaagga tatactgtgg atctacaggt tgccgagtat ttaaaaagct     900
ttggacgtca agtattgaat tgttggagta aggggatat cgagttatca acacctattc      960
ctcttttggg ttttga                                                     976
```

<210> SEQ ID NO 115
<211> LENGTH: 995
<212> TYPE: DNA
<213> ORGANISM: Chlamydia

<400> SEQUENCE: 115

```
ttatcctaga aatttggtgt tcaatatgag cgaaaaaaga agtctaaca aaattattgg       60
tatcgaccta gggacgacca actcttgcgt ctctgttatg gaaggtggcc aacctaaagt     120
tattgcctct tctgaaggaa ctcgtactac tccttctatc gttgctttta aaggtggcga     180
aactcttgtt ggaattcctg caaaacgtca ggcagtaacc aatcctgaaa aaacattggc     240
ttctactaag cgattcatcg gtagaaaatt ctctgaagtc gaatctgaaa ttaaaacagt     300
cccctacaaa gttgctccta actcgaaagg agatgcggtc tttgatgtgg aacaaaaact     360
gtacactcca gaagaaatcg gcgctcagat cctcatgaag atgaaggaaa ctgctgaggc     420
ttatctcgga gaaacagtaa cggaagcagt cattaccgta ccagcttact ttaacgattc     480
tcaaagagct tctacaaaag atgctggacg tatcgcagga ttagatgtta aacgcattat     540
tcctgaacca acagcggccg ctcttgctta tggtattgat aaggaaggag ataaaaaat      600
cgccgtcttc gacttaggag gaggaacttt cgatatttct atcttggaaa tcggtgacgg     660
agtttttgaa gttctctcaa ccaacgggga tactcacttg ggaggagacg acttcgacgg     720
agtcatcatc aactggatgc ttgatgaatt caaaaaacaa gaaggcattg atctaagcaa     780
agataacatg gctttgcaaa gattgaaaga tgctgctgaa aaagcaaaaa tagaattgtc     840
tggtgtatcg tctactgaaa tcaatcagcc attcatcact atcgacgcta atggacctaa     900
acatttggct ttaactctaa ctcgcgctca attcgaacac ctagcttcct ctctcattga     960
gcgaaccaaa caaccttgtg ctcaggcttt aaaag                                995
```

<210> SEQ ID NO 116
<211> LENGTH: 437
<212> TYPE: DNA
<213> ORGANISM: Chlamydia

<400> SEQUENCE: 116

```
gtcacagcta aaggcggtgg gctttatact gataagaatc tttcgattac taacatcaca      60
ggaattatcg aaattgcaaa taacaaagcg acagatgttg gaggtggtgc ttacgtaaaa     120
ggaacccttc cttgtaaaaa ctctcaccgt ctacaatttt tgaaaaactc ttccgataaa     180
caaggtggag gaatctacgg agaagacaac atcaccctat ctaatttgac agggaagact     240
ctattccaag agaatactgc caaaaaagag gcggtggac tcttcataaa aggtacagat      300
aaagctctta caatgacagg actggatagt ttctgtttaa ttaataacac atcagaaaaa     360
catggtggtg gagcctttgt taccaaagaa atctctcaga cttacacctc tgatgtggaa     420
acaattccag gaatcac                                                    437
```

<210> SEQ ID NO 117
<211> LENGTH: 446
<212> TYPE: DNA
<213> ORGANISM: Chlamydia

<400> SEQUENCE: 117

```
aagtttacct agaccaaact gaagatgacg aaggaaaagt tgttttatcc agagaaaaag      60
caacaagaca cgacaatgg gaatacattc ttgctcactg cgaggaaggt tctattgtta     120
agggacaaat tacccgaaaa gttaagggtg gtttgatcgt agatattggt atggaagcct     180
tccttccagg atcccaaata gacaataaga agatcaagaa cttagatgat tacgtaggca     240
aggtttgtga gttcaaaatt ctcaaaatca acgtggatcg tcggaacgtt gttgtatcta     300
gaagagaact tctcgaagct gaacgcattt ctaagaaagc agagttgatc gagcaaatca     360
ctatcggtga acgtcgcaaa ggtatcgtta agaatatcac agatttcgga gtattcttgg     420
atcttgatgg cattgacggc ctactc                                          446
```

<210> SEQ ID NO 118
<211> LENGTH: 951
<212> TYPE: DNA
<213> ORGANISM: Chlamydia

<400> SEQUENCE: 118

```
agtattgcga aatattactg tgagaagcaa tgctgagagc ggttctagta aaagtgaggg      60
gagagctgtc agaagggatc gctcaggaag cgagacaacg tgtggctgat ttattaggaa     120
gattccctct ttatcctgaa atcgatctgg aaacgctagt ttagtgggag actctatgcc     180
tgaagggaa atgatgcata agttgcaaga tgtcatagat agaaagttgt tggattctcg     240
tcgtatttc ttctccgaac ctgtaacgga gaaagtgct gcagaagcca tcaaaaagct      300
ttggtatttg gaactcacca atcctgggca gccaattgta tttgtcatta atagccctgg     360
aggtctgtt gatgctgggt tgctgtttg ggaccaaatt aaaatgatct cttctccttt      420
gactacagtt gttacaggtt tagcagcatc tatgggatct gtattgagtt tgtgtgctgt     480
tccaggaaga cgttttgcta cgcctcatgc gcgcattatg attccagc cttctattgg      540
aggaaccatt actggtcaag ccacggactt ggatattcat gctcgtgaaa tttttaaaaac     600
aaaagcacgc attattgatg tgtatgtcga ggcaactgga caatctccag aggtgataga     660
```

| | |
|---|---|
| gaaagctatc gatcgagata tgtggatgag tgcaaatgaa gcaatggagt ttggactgtt | 720 |
| agatgggatt ctcttctctt ttaacgactt gtagatatct tttatattct ggagcaggaa | 780 |
| acagtttcat tttgggagaa tcgatgcctt ctccttgagga tgttctgttt ttatgccagg | 840 |
| aagagatggt tgatgggttt ttatgtgtag agtcttctga aatagcagat gctaaactca | 900 |
| ctgtttttaa tagtgatgga tctatcgcgt ctatgtgcgg aatgggttg c | 951 |

<210> SEQ ID NO 119
<211> LENGTH: 953
<212> TYPE: DNA
<213> ORGANISM: Chlamydia

<400> SEQUENCE: 119

| | |
|---|---|
| atatcaaagt tgggcaaatg acagagccgc tcaaggacca gcaaataatc cttgggacaa | 60 |
| catcaacacc tgtcgcagcc aaaatgacag cttctgatgg aatatcttta acagtctcca | 120 |
| ataatccatc aaccaatgct tctattacaa ttggttttgga tgcggaaaaa gcttaccagc | 180 |
| ttattctaga aaagttggga gatcaaattc ttggtggaat tgctgatact attgttgata | 240 |
| gtacagtcca agatatttta gacaaaatca caacagaccc ttctctaggt ttgttgaaag | 300 |
| cttttaacaa ctttccaatc actaataaaa ttcaatgcaa cgggttattc actcccagga | 360 |
| acattgaaac tttattagga ggaactgaaa taggaaaatt cacagtcaca cccaaaagct | 420 |
| ctgggagcat gttcttagtc tcagcagata ttattgcatc aagaatggaa ggcggcgttg | 480 |
| ttctagcttt ggtacgagaa ggtgattcta agccctacgc gattagttat ggatactcat | 540 |
| caggcgttcc taatttatgt agtctaagaa ccagaattat taatacagga ttgactccga | 600 |
| caacgtattc attacgtgta ggcggtttag aaagcgtgt ggtatgggtt aatgcccttt | 660 |
| ctaatggcaa tgatattta ggaataacaa atacttctaa tgtatctttt tggaggtaa | 720 |
| tacctcaaac aaacgcttaa acaatttta ttggatttt cttataggtt ttatatttag | 780 |
| agaaaaagt tcgaattacg gggtttgtta tgcaaaataa aagcaaagtg agggacgatt | 840 |
| ttattaaaat tgttaaagat tcctggtatc ggtctgcgat tccgactcgt ccaacatcaa | 900 |
| tacaacctat taatttcccc tcgtcaaaaa taaggttatc aagtgagaaa tca | 953 |

<210> SEQ ID NO 120
<211> LENGTH: 897
<212> TYPE: DNA
<213> ORGANISM: Chlamydia

<400> SEQUENCE: 120

| | |
|---|---|
| atggcttcta tatgcggacg tttagggtct ggtacaggga atgctctaaa agctttttt | 60 |
| acacagccca gcaataaaat ggcaagggta gtaaataaga cgaagggaat ggataagact | 120 |
| gttaaggtcg ccaagtctgc tgccgaattg accgcaaata ttttggaaca agctggaggc | 180 |
| gcgggctctt ccgcacacat tacagcttcc caagtgtcca aggattagg ggatgcgaga | 240 |
| actgttctcg ctttagggaa tgcctttaac ggagcgttgc caggaacagt tcaaagtgcg | 300 |
| caaagcttct tctcttacat gaaagctgct agtcagaaac cgcaagaagg ggatgagggg | 360 |
| ctcgtagcag atctttgtgt gtctcataag cgcanagcgg ctgcggctgt ctgtagcttc | 420 |
| atcggaggaa ttacctacct cgcgacattc ggagctatcc gtccgattct gtttgtcaac | 480 |
| aaaatgctgg cgcaaccgtt tctttcttcc caaattaaag caaatatggg atcttctgtt | 540 |
| agctatatta tggcggctaa ccatgcagcg tttgtggtgg ttctggact cgctatcagt | 600 |
| gcggaaagag cagattgcga agcccgctgc gctcgtattg cgagagaaga gtcgtcactc | 660 |

```
gaattgtcgg gagaggaaaa tgcttgcgag aggagagtcg ctggagagaa agccaagacg    720
ttcacgcgca tcaagtatgc actcctcact atgctcgaga gttttttgga atgcgttgcc    780
gacgttttca aattggtgcc gttgcctatt acaatgggta ttcgtgcaat tgtggctgcg    840
ggatgtacgt tcacttctgc agttattgga ttgtggactt tctgcgccag agcataa      897
```

<210> SEQ ID NO 121
<211> LENGTH: 298
<212> TYPE: PRT
<213> ORGANISM: Chlamydia

<400> SEQUENCE: 121

```
Met Ala Ser Ile Cys Gly Arg Leu Gly Ser Gly Thr Gly Asn Ala Leu
  1               5                  10                  15

Lys Ala Phe Phe Thr Gln Pro Ser Asn Lys Met Ala Arg Val Val Asn
             20                  25                  30

Lys Thr Lys Gly Met Asp Lys Thr Val Lys Val Ala Lys Ser Ala Ala
         35                  40                  45

Glu Leu Thr Ala Asn Ile Leu Glu Gln Ala Gly Ala Gly Ser Ser
     50                  55                  60

Ala His Ile Thr Ala Ser Gln Val Ser Lys Gly Leu Gly Asp Ala Arg
 65                  70                  75                  80

Thr Val Leu Ala Leu Gly Asn Ala Phe Asn Gly Ala Leu Pro Gly Thr
                 85                  90                  95

Val Gln Ser Ala Gln Ser Phe Phe Ser Tyr Met Lys Ala Ala Ser Gln
            100                 105                 110

Lys Pro Gln Glu Gly Asp Glu Gly Leu Val Ala Asp Leu Cys Val Ser
        115                 120                 125

His Lys Arg Arg Ala Ala Ala Val Cys Ser Phe Ile Gly Gly Ile
    130                 135                 140

Thr Tyr Leu Ala Thr Phe Gly Ala Ile Arg Pro Ile Leu Phe Val Asn
145                 150                 155                 160

Lys Met Leu Ala Gln Pro Phe Leu Ser Ser Gln Ile Lys Ala Asn Met
                165                 170                 175

Gly Ser Ser Val Ser Tyr Ile Met Ala Ala Asn His Ala Ala Phe Val
            180                 185                 190

Val Gly Ser Gly Leu Ala Ile Ser Ala Glu Arg Ala Asp Cys Glu Ala
        195                 200                 205

Arg Cys Ala Arg Ile Ala Arg Glu Glu Ser Ser Leu Glu Leu Ser Gly
    210                 215                 220

Glu Glu Asn Ala Cys Glu Arg Arg Val Ala Gly Glu Lys Ala Lys Thr
225                 230                 235                 240

Phe Thr Arg Ile Lys Tyr Ala Leu Leu Thr Met Leu Glu Lys Phe Leu
                245                 250                 255

Glu Cys Val Ala Asp Val Phe Lys Leu Val Pro Leu Pro Ile Thr Met
            260                 265                 270

Gly Ile Arg Ala Ile Val Ala Gly Cys Thr Phe Thr Ser Ala Val
        275                 280                 285

Ile Gly Leu Trp Thr Phe Cys Ala Arg Ala
    290                 295
```

<210> SEQ ID NO 122
<211> LENGTH: 897
<212> TYPE: DNA
<213> ORGANISM: Chlamydia

-continued

```
<400> SEQUENCE: 122
atggcttcta tatgcggacg tttagggtct ggtacaggga atgctctaaa agcttttttt      60
acacagccca gcaataaaat ggcaagggta gtaaataaga cgaagggaat ggataagact     120
gttaaggtcg ccaagtctgc tgccgaattg accgcaaata ttttggaaca agctggaggc     180
gcgggctctt ccgcacacat tacagcttcc caagtgtcca aaggattagg ggatacgaga     240
actgttgtcg ctttagggaa tgcctttaac ggagcgttgc caggaacagt tcaaagtgcg     300
caaagcttct tctctcacat gaaagctgct agtcagaaaa cgcaagaagg ggatgagggg     360
ctcacagcag atctttgtgt gtctcataag cgcagagcgg ctgcggctgt ctgtggcttc     420
atcggaggaa ttacctacct cgcgacattc ggagttatcc gtccgattct gtttgtcaac     480
aaaatgctgg tgaacccgtt tctttcttcc caaactaaag caaatatggg atcttctgtt     540
agctatatta tggcggctaa ccatgcagcg tctgtggtgg gtgctggact cgctatcagt     600
gcggaaagag cagattgcga agcccgctgc gctcgtattg cgagagaaga gtcgttactc     660
gaagtgtcgg gagaggaaaa tgcttgcgag aagagagtcg ctgagagaa agccaagacg      720
ttcacgcgca tcaagtatgc actcctcact atgctcgaga gttttttgga atgcgttgcc     780
gacgttttca aattggtgcc gctgcctatt acaatgggta ttcgtgcgat tgtggctgct     840
ggatgtacgt tcacttctgc aattattgga ttgtgcactt tctgcgccag agcataa        897

<210> SEQ ID NO 123
<211> LENGTH: 298
<212> TYPE: PRT
<213> ORGANISM: Chlamydia

<400> SEQUENCE: 123

Met Ala Ser Ile Cys Gly Arg Leu Gly Ser Gly Thr Gly Asn Ala Leu
  1               5                  10                  15

Lys Ala Phe Phe Thr Gln Pro Ser Asn Lys Met Ala Arg Val Val Asn
             20                  25                  30

Lys Thr Lys Gly Met Asp Lys Thr Val Lys Val Ala Lys Ser Ala Ala
         35                  40                  45

Glu Leu Thr Ala Asn Ile Leu Glu Gln Ala Gly Ala Gly Ser Ser
     50                  55                  60

Ala His Ile Thr Ala Ser Gln Val Ser Lys Gly Leu Gly Asp Thr Arg
 65                  70                  75                  80

Thr Val Val Ala Leu Gly Asn Ala Phe Asn Gly Ala Leu Pro Gly Thr
                 85                  90                  95

Val Gln Ser Ala Gln Ser Phe Ser His Met Lys Ala Ala Ser Gln
            100                 105                 110

Lys Thr Gln Glu Gly Asp Glu Gly Leu Thr Ala Asp Leu Cys Val Ser
        115                 120                 125

His Lys Arg Arg Ala Ala Ala Val Cys Gly Phe Ile Gly Gly Ile
    130                 135                 140

Thr Tyr Leu Ala Thr Phe Gly Val Ile Arg Pro Ile Leu Phe Val Asn
145                 150                 155                 160

Lys Met Leu Val Asn Pro Phe Leu Ser Ser Gln Thr Lys Ala Asn Met
                165                 170                 175

Gly Ser Ser Val Ser Tyr Ile Met Ala Ala Asn His Ala Ala Ser Val
            180                 185                 190

Val Gly Ala Gly Leu Ala Ile Ser Ala Glu Arg Ala Asp Cys Glu Ala
        195                 200                 205
```

```
Arg Cys Ala Arg Ile Ala Arg Glu Glu Ser Leu Leu Glu Val Ser Gly
        210                 215                 220

Glu Glu Asn Ala Cys Glu Lys Arg Val Ala Gly Glu Lys Ala Lys Thr
225                 230                 235                 240

Phe Thr Arg Ile Lys Tyr Ala Leu Leu Thr Met Leu Glu Lys Phe Leu
            245                 250                 255

Glu Cys Val Ala Asp Val Phe Lys Leu Val Pro Leu Pro Ile Thr Met
            260                 265                 270

Gly Ile Arg Ala Ile Val Ala Ala Gly Cys Thr Phe Thr Ser Ala Ile
            275                 280                 285

Ile Gly Leu Cys Thr Phe Cys Ala Arg Ala
        290                 295

<210> SEQ ID NO 124
<211> LENGTH: 897
<212> TYPE: DNA
<213> ORGANISM: Chlamydia

<400> SEQUENCE: 124
atggcttcta tatgcggacg tttagggtct ggtacaggga atgctctaaa agctttttt     60
acacagccca acaataaaat ggcaagggta gtaaataaga cgaagggaat ggataagact   120
attaaggttg ccaagtctgc tgccgaattg accgcaaata ttttggaaca agctggaggc   180
gcgggctctt ccgcacacat tacagcttcc caagtgtcca aaggattagg ggatgcgaga   240
actgttgtcg ctttagggaa tgcctttaac ggagcgttgc caggaacagt tcaaagtgcg   300
caaagcttct tctctcacat gaaagctgct agtcagaaaa cgcaagaagg ggatgagggg   360
ctcacagcag atctttgtgt gtctcataag cgcagagcgg ctgcggctgt ctgtagcatc   420
atcggaggaa ttacctacct cgcgacattc ggagctatcc gtccgattct gtttgtcaac   480
aaaatgctgg caaaaccgtt tctttcttcc caaactaaag caaatatggg atcttctgtt   540
agctatatta tggcggctaa ccatgcagcg tctgtggtgg gtgctggact cgctatcagt   600
gcggaaagag cagattgcga agcccgctgc gctcgtattg cgagagaaga gtcgttactc   660
gaagtgccgg gagaggaaaa tgcttgcgag aagaaagtcg ctggagagaa agccaagacg   720
ttcacgcgca tcaagtatgc actcctcact atgctcgaga gttttttgga atgcgttgcc   780
gacgttttca aattggtgcc gctgcctatt acaatgggta ttcgtgcgat tgtggctgct   840
ggatgtacgt tcacttctgc aattattgga ttgtgcactt tctgcgccag agcataa     897

<210> SEQ ID NO 125
<211> LENGTH: 298
<212> TYPE: PRT
<213> ORGANISM: Chlamydia

<400> SEQUENCE: 125

Met Ala Ser Ile Cys Gly Arg Leu Gly Ser Gly Thr Gly Asn Ala Leu
1               5                   10                  15

Lys Ala Phe Phe Thr Gln Pro Asn Asn Lys Met Ala Arg Val Val Asn
            20                  25                  30

Lys Thr Lys Gly Met Asp Lys Thr Ile Lys Val Ala Lys Ser Ala Ala
        35                  40                  45

Glu Leu Thr Ala Asn Ile Leu Glu Gln Ala Gly Gly Ala Gly Ser Ser
    50                  55                  60

Ala His Ile Thr Ala Ser Gln Val Ser Lys Gly Leu Gly Asp Ala Arg
65                  70                  75                  80
```

```
Thr Val Val Ala Leu Gly Asn Ala Phe Asn Gly Ala Leu Pro Gly Thr
                85                  90                  95

Val Gln Ser Ala Gln Ser Phe Phe Ser His Met Lys Ala Ala Ser Gln
            100                 105                 110

Lys Thr Gln Glu Gly Asp Glu Gly Leu Thr Ala Asp Leu Cys Val Ser
        115                 120                 125

His Lys Arg Ala Ala Ala Val Cys Ser Ile Ile Gly Gly Ile
    130                 135                 140

Thr Tyr Leu Ala Thr Phe Gly Ala Ile Arg Pro Ile Leu Phe Val Asn
145                 150                 155                 160

Lys Met Leu Ala Lys Pro Phe Leu Ser Ser Gln Thr Lys Ala Asn Met
                165                 170                 175

Gly Ser Ser Val Ser Tyr Ile Met Ala Ala Asn His Ala Ala Ser Val
                180                 185                 190

Val Gly Ala Gly Leu Ala Ile Ser Ala Glu Arg Ala Asp Cys Glu Ala
            195                 200                 205

Arg Cys Ala Arg Ile Ala Arg Glu Glu Ser Leu Leu Glu Val Pro Gly
    210                 215                 220

Glu Glu Asn Ala Cys Glu Lys Lys Val Ala Gly Glu Lys Ala Lys Thr
225                 230                 235                 240

Phe Thr Arg Ile Lys Tyr Ala Leu Leu Thr Met Leu Glu Lys Phe Leu
                245                 250                 255

Glu Cys Val Ala Asp Val Phe Lys Leu Val Pro Leu Pro Ile Thr Met
            260                 265                 270

Gly Ile Arg Ala Ile Val Ala Ala Gly Cys Thr Phe Thr Ser Ala Ile
        275                 280                 285

Ile Gly Leu Cys Thr Phe Cys Ala Arg Ala
290                 295
```

<210> SEQ ID NO 126
<211> LENGTH: 897
<212> TYPE: DNA
<213> ORGANISM: Chlamydia

<400> SEQUENCE: 126

```
atggcttcta tatgcggacg tttagggtct ggtacaggga atgctctaaa agctttttt    60
acacagccca acaataaaat ggcaagggta gtaaataaga cgaagggaat ggataagact   120
attaaggttg ccaagtctgc tgccgaattg accgcaaata ttttggaaca agctggaggc   180
gcgggctctt ccgcacacat tacagcttcc caagtgtcca aaggattagg ggatgcgaga   240
actgttgtcg ctttagggaa tgcctttaac ggagcgttgc caggaacagt tcaaagtgcg   300
caaagcttct tctctcacat gaaagctgct agtcagaaaa cgcaagaagg ggatgagggg   360
ctcacagcag atctttgtgt gtctcataag cgcagagcgg ctgcggctgt ctgtagcatc   420
atcggaggaa ttacctacct cgcgacattc ggagctatcc gtccgattct gtttgtcaac   480
aaaatgctgg caaaccgtt tctttcttcc caaactaaag caaatatggg atcttctgtt   540
agctatatta tggcggctaa ccatgcagcg tctgtggtgg gtgctggact cgctatcagt   600
gcggaaagag cagattgcga agcccgctgc gctcgtattg cgagagaaga gtcgttactc   660
gaagtgccgg gagaggaaaa tgcttgcgag aagaaagtcg ctggagagaa agccaagacg   720
ttcacgcgca tcaagtatgc actcctcact atgctcgaga gttttttgga atgcgttgcc   780
gacgttttca aattggtgcc gctgcctatt acaatgggta ttcgtgcgat tgtggctgct   840
```
ggatgtacgt tcacttctgc aattattgga ttgtgcactt tctgcgccag agcataa 897

<210> SEQ ID NO 127
<211> LENGTH: 298
<212> TYPE: PRT
<213> ORGANISM: Chlamydia

<400> SEQUENCE: 127

Met Ala Ser Ile Cys Gly Arg Leu Gly Ser Gly Thr Gly Asn Ala Leu
1               5                   10                  15

Lys Ala Phe Phe Thr Gln Pro Asn Asn Lys Met Ala Arg Val Val Asn
            20                  25                  30

Lys Thr Lys Gly Met Asp Lys Thr Ile Lys Val Ala Lys Ser Ala Ala
        35                  40                  45

Glu Leu Thr Ala Asn Ile Leu Glu Gln Ala Gly Gly Ala Gly Ser Ser
    50                  55                  60

Ala His Ile Thr Ala Ser Gln Val Ser Lys Gly Leu Gly Asp Ala Arg
65                  70                  75                  80

Thr Val Val Ala Leu Gly Asn Ala Phe Asn Gly Ala Leu Pro Gly Thr
                85                  90                  95

Val Gln Ser Ala Gln Ser Phe Phe Ser His Met Lys Ala Ala Ser Gln
            100                 105                 110

Lys Thr Gln Glu Gly Asp Glu Gly Leu Thr Ala Asp Leu Cys Val Ser
        115                 120                 125

His Lys Arg Ala Ala Ala Ala Val Cys Ser Ile Ile Gly Gly Ile
    130                 135                 140

Thr Tyr Leu Ala Thr Phe Gly Ala Ile Arg Pro Ile Leu Phe Val Asn
145                 150                 155                 160

Lys Met Leu Ala Lys Pro Phe Leu Ser Ser Gln Thr Lys Ala Asn Met
                165                 170                 175

Gly Ser Ser Val Ser Tyr Ile Met Ala Ala Asn His Ala Ala Ser Val
            180                 185                 190

Val Gly Ala Gly Leu Ala Ile Ser Ala Glu Arg Ala Asp Cys Glu Ala
        195                 200                 205

Arg Cys Ala Arg Ile Ala Arg Glu Glu Ser Leu Leu Glu Val Pro Gly
    210                 215                 220

Glu Glu Asn Ala Cys Glu Lys Lys Val Ala Gly Glu Lys Ala Lys Thr
225                 230                 235                 240

Phe Thr Arg Ile Lys Tyr Ala Leu Leu Thr Met Leu Glu Lys Phe Leu
                245                 250                 255

Glu Cys Val Ala Asp Val Phe Lys Leu Val Pro Leu Pro Ile Thr Met
            260                 265                 270

Gly Ile Arg Ala Ile Val Ala Ala Gly Cys Thr Phe Thr Ser Ala Ile
        275                 280                 285

Ile Gly Leu Cys Thr Phe Cys Ala Arg Ala
    290                 295

<210> SEQ ID NO 128
<211> LENGTH: 897
<212> TYPE: DNA
<213> ORGANISM: Chlamydia

<400> SEQUENCE: 128
atggcttcta tatgtggacg tttagggtct ggtacaggga atgctctaaa agctttttt     60 acacagccca gcaataaaat ggcaagggta gtaaataaga cgaagggaat ggataagact   120

-continued

| | |
|---|---|
| gttaaggtcg ccaagtctgc tgccgaattg accgcaaata ttttggaaca agctggaggc | 180 |
| gcgggctctt ccgcacacat tacagcttcc caagtgtcca aaggattagg ggatacgaga | 240 |
| actgttgtcg ctttagggaa tgcctttaac ggagcgttgc caggaacagt tcaaagtgcg | 300 |
| caaagcttct tctctcacat gaaagctgct agtcagaaaa cgcaagaagg ggatgagggg | 360 |
| ctcacagcag atctttgtgt gtctcataag cgcagagcgg ctgcggctgt ctgtggcttc | 420 |
| atcggaggaa ttacctacct cgcgacattc ggagttatcc gtccgattct gtttgtcaac | 480 |
| aaaatgctgg tgaacccgtt tctttcttcc caaactaaag caaatatggg atcttctgtt | 540 |
| agctatatta tggcggctaa ccatgcagcg tctgtggtgg gtgctggact cgctatcagt | 600 |
| gcggaaagag cagattgcga agcccgctgc gctcgtattg cgagagaaga gtcgttactc | 660 |
| gaagtgtcgg gagaggaaaa tgcttgcgag aagagagtcg ctggagagaa agccaagacg | 720 |
| ttcacgcgca tcaagtatgc actcctcact atgctcgaga agttttttgga atgcgttgcc | 780 |
| gacgttttca aattggtgcc gctgcctatt acaatgggta ttcgtgcgat tgtggctgct | 840 |
| ggatgtacgt tcacttctgc aattattgga ttgtgcactt tctgcgccag agcataa | 897 |

<210> SEQ ID NO 129
<211> LENGTH: 298
<212> TYPE: PRT
<213> ORGANISM: Chlamydia

<400> SEQUENCE: 129

Met Ala Ser Ile Cys Gly Arg Leu Gly Ser Gly Thr Gly Asn Ala Leu
1               5                   10                  15

Lys Ala Phe Phe Thr Gln Pro Ser Asn Lys Met Ala Arg Val Val Asn
            20                  25                  30

Lys Thr Lys Gly Met Asp Lys Thr Val Lys Val Ala Lys Ser Ala Ala
        35                  40                  45

Glu Leu Thr Ala Asn Ile Leu Glu Gln Ala Gly Ala Gly Ser Ser
    50                  55                  60

Ala His Ile Thr Ala Ser Gln Val Ser Lys Gly Leu Gly Asp Thr Arg
65                  70                  75                  80

Thr Val Val Ala Leu Gly Asn Ala Phe Asn Gly Ala Leu Pro Gly Thr
                85                  90                  95

Val Gln Ser Ala Gln Ser Phe Phe Ser His Met Lys Ala Ala Ser Gln
            100                 105                 110

Lys Thr Gln Glu Gly Asp Glu Gly Leu Thr Ala Asp Leu Cys Val Ser
        115                 120                 125

His Lys Arg Arg Ala Ala Ala Val Cys Gly Phe Ile Gly Gly Ile
    130                 135                 140

Thr Tyr Leu Ala Thr Phe Gly Val Ile Arg Pro Ile Leu Phe Val Asn
145                 150                 155                 160

Lys Met Leu Val Asn Pro Phe Leu Ser Ser Gln Thr Lys Ala Asn Met
                165                 170                 175

Gly Ser Ser Val Ser Tyr Ile Met Ala Ala Asn His Ala Ala Ser Val
            180                 185                 190

Val Gly Ala Gly Leu Ala Ile Ser Ala Glu Arg Ala Asp Cys Glu Ala
        195                 200                 205

Arg Cys Ala Arg Ile Ala Arg Glu Glu Ser Leu Leu Glu Val Ser Gly
    210                 215                 220

Glu Glu Asn Ala Cys Glu Lys Val Ala Gly Glu Lys Ala Lys Thr
225                 230                 235                 240

```
Phe Thr Arg Ile Lys Tyr Ala Leu Leu Thr Met Leu Glu Lys Phe Leu
                245                 250                 255

Glu Cys Val Ala Asp Val Phe Lys Leu Val Pro Leu Pro Ile Thr Met
            260                 265                 270

Gly Ile Arg Ala Ile Val Ala Ala Gly Cys Thr Phe Thr Ser Ala Ile
        275                 280                 285

Ile Gly Leu Cys Thr Phe Cys Ala Arg Ala
    290                 295
```

<210> SEQ ID NO 130
<211> LENGTH: 897
<212> TYPE: DNA
<213> ORGANISM: Chlamydia

<400> SEQUENCE: 130

```
atggctgcta tatgtggacg tttagggtct ggtacaggga atgctctaaa agctttttt     60
acacagccca gcaataaaat ggcaagggta gtaaataaga cgaagggaat ggataagact    120
gttaaggtcg ccaagtctgc tgccgaattg accgcaaata ttttggaaca agctggaggc    180
gcgggctctt ccgcacacat tacagcttcc caagtgtcca aggattagg ggatgcgaga     240
actgttctcg ctttagggaa tgcctttaac ggagcgttgc caggaacagt tcaaagtgcg    300
caaagcttct tctcttacat gaaagctgct agtcagaaac gcaagaagg ggatgagggg     360
ctcgtagcag atctttgtgt gtctcataag cgcagagcgg ctgcggctgt ctgtagcttc    420
atcggaggaa ttacctacct cgcgacattc ggagctatcc gtccgattct gtttgtcaac    480
aaaatgctgg cgcaaccgtt tctttcttcc caaactaaag caaatatggg atcttctgtt    540
agctatatta tggcggctaa ccatgcagcg tttgtggtgg ttctggact cgctatcagt     600
gcggaaagag cagattgcga agcccgctgc gctcgtattg cgagagaaga gtcgtcactc    660
gaattgtcgg gagaggaaaa tgcttgcgag aggggagtcg ctggagagaa agccaagacg    720
ttcacgcgca tcaagtatgc actcctcact atgctcgaga gttttttgga atgcgttgcc    780
gacgttttca aattggtgcc gttgcctatt acaatggta ttcgtgcaat tgtggctgcg     840
ggatgtacgt tcacttctgc agttattgga ttgtggactt tctgcaacag agtataa      897
```

<210> SEQ ID NO 131
<211> LENGTH: 298
<212> TYPE: PRT
<213> ORGANISM: Chlamydia

<400> SEQUENCE: 131

```
Met Ala Ala Ile Cys Gly Arg Leu Gly Ser Gly Thr Gly Asn Ala Leu
  1               5                  10                  15

Lys Ala Phe Phe Thr Gln Pro Ser Asn Lys Met Ala Arg Val Val Asn
                20                  25                  30

Lys Thr Lys Gly Met Asp Lys Thr Val Lys Val Ala Lys Ser Ala Ala
            35                  40                  45

Glu Leu Thr Ala Asn Ile Leu Glu Gln Ala Gly Ala Gly Ser Ser
         50                  55                  60

Ala His Ile Thr Ala Ser Gln Val Ser Lys Gly Leu Gly Asp Ala Arg
 65                  70                  75                  80

Thr Val Leu Ala Leu Gly Asn Ala Phe Asn Gly Ala Leu Pro Gly Thr
                 85                  90                  95

Val Gln Ser Ala Gln Ser Phe Phe Ser Tyr Met Lys Ala Ala Ser Gln
                100                 105                 110
```

```
Lys Pro Gln Glu Gly Asp Glu Gly Leu Val Ala Asp Leu Cys Val Ser
        115                 120                 125
His Lys Arg Arg Ala Ala Ala Val Cys Ser Phe Ile Gly Gly Ile
        130                 135                 140
Thr Tyr Leu Ala Thr Phe Gly Ala Ile Arg Pro Ile Leu Phe Val Asn
145                 150                 155                 160
Lys Met Leu Ala Gln Pro Phe Leu Ser Ser Gln Thr Lys Ala Asn Met
                165                 170                 175
Gly Ser Ser Val Ser Tyr Ile Met Ala Ala Asn His Ala Ala Phe Val
            180                 185                 190
Val Gly Ser Gly Leu Ala Ile Ser Ala Glu Arg Ala Asp Cys Glu Ala
        195                 200                 205
Arg Cys Ala Arg Ile Ala Arg Glu Glu Ser Ser Leu Glu Leu Ser Gly
    210                 215                 220
Glu Glu Asn Ala Cys Glu Arg Gly Val Ala Gly Glu Lys Ala Lys Thr
225                 230                 235                 240
Phe Thr Arg Ile Lys Tyr Ala Leu Leu Thr Met Leu Glu Lys Phe Leu
                245                 250                 255
Glu Cys Val Ala Asp Val Phe Lys Leu Val Pro Leu Pro Ile Thr Met
            260                 265                 270
Gly Ile Arg Ala Ile Val Ala Ala Gly Cys Thr Phe Thr Ser Ala Val
        275                 280                 285
Ile Gly Leu Trp Thr Phe Cys Asn Arg Val
    290                 295

<210> SEQ ID NO 132
<211> LENGTH: 897
<212> TYPE: DNA
<213> ORGANISM: Chlamydia

<400> SEQUENCE: 132
atggctgcta tatgcggacg tttagggtct ggtacaggga atgctctaaa agcttttttt      60
acacagccca gcaataaaat ggcaagggta gtaaataaga cgaagggaat ggataagact     120
gttaaggtcg ccaagtctgc tgccgaattg accgcaaata ttttggaaca agctggaggc     180
gcgggctctt ccgcacacat tacagcttcc caagtgtcca aaggattagg ggatgcgaga     240
actgttctcg ctttagggaa tgcctttaac ggagcgttgc aggaacagt tcaaagtgcg      300
caaagcttct tctcttacat gaaagctgct agtcagaaac gcaagaagg ggatgagggg      360
ctcgtagcag atctttgtgt gtctcataag cgcagagcgg ctgcggctgt ctgtagcttc     420
atcggaggaa ttacctacct cgcgacattc ggagctatcc gtccgattct gtttgtcaac     480
aaaatgctgg cgcaaccgtt tctttcttcc caaactaaag caaatatggg atcttctgtt     540
agctatatta tggcggctaa ccatgcagcg tttgtggtgg ttctggact cgctatcagt      600
gcggaaagag cagattgcga agcccgctgc gctcgtattg cgagagaaga gtcgtcactc     660
gaattgtcgg gagaggaaaa tgcttgtgag aggagagtcg ctggagagaa agccaagacg     720
ttcacgcgca tcaagtatgc actcctcact atgctcgaga gttttttgga atgcgttgcc     780
gacgttttca aattggtgcc gttgcctatt acaatgggta ttcgtgcaat tgtggctgcg     840
ggatgtacgt tcacttctgc agttattgga ttgtggactt ctgcaacag agtataa        897

<210> SEQ ID NO 133
<211> LENGTH: 298
<212> TYPE: PRT
<213> ORGANISM: Chlamydia
```

-continued

```
<400> SEQUENCE: 133

Met Ala Ala Ile Cys Gly Arg Leu Gly Ser Gly Thr Gly Asn Ala Leu
 1               5                  10                  15
Lys Ala Phe Phe Thr Gln Pro Ser Asn Lys Met Ala Arg Val Val Asn
            20                  25                  30
Lys Thr Lys Gly Met Asp Lys Thr Val Lys Val Ala Lys Ser Ala Ala
        35                  40                  45
Glu Leu Thr Ala Asn Ile Leu Glu Gln Ala Gly Ala Gly Ser Ser
 50                  55                  60
Ala His Ile Thr Ala Ser Gln Val Ser Lys Gly Leu Gly Asp Ala Arg
 65                  70                  75                  80
Thr Val Leu Ala Leu Gly Asn Ala Phe Asn Gly Ala Leu Pro Gly Thr
                85                  90                  95
Val Gln Ser Ala Gln Ser Phe Phe Ser Tyr Met Lys Ala Ala Ser Gln
            100                 105                 110
Lys Pro Gln Glu Gly Asp Glu Gly Leu Val Ala Asp Leu Cys Val Ser
        115                 120                 125
His Lys Arg Arg Ala Ala Ala Val Cys Ser Phe Ile Gly Gly Ile
130                 135                 140
Thr Tyr Leu Ala Thr Phe Gly Ala Ile Arg Pro Ile Leu Phe Val Asn
145                 150                 155                 160
Lys Met Leu Ala Gln Pro Phe Leu Ser Ser Gln Thr Lys Ala Asn Met
                165                 170                 175
Gly Ser Ser Val Ser Tyr Ile Met Ala Ala Asn His Ala Ala Phe Val
            180                 185                 190
Val Gly Ser Gly Leu Ala Ile Ser Ala Glu Arg Ala Asp Cys Glu Ala
        195                 200                 205
Arg Cys Ala Arg Ile Ala Arg Glu Glu Ser Ser Leu Glu Leu Ser Gly
210                 215                 220
Glu Glu Asn Ala Cys Glu Arg Arg Val Ala Gly Glu Lys Ala Lys Thr
225                 230                 235                 240
Phe Thr Arg Ile Lys Tyr Ala Leu Leu Thr Met Leu Glu Lys Phe Leu
                245                 250                 255
Glu Cys Val Ala Asp Val Phe Lys Leu Val Pro Leu Pro Ile Thr Met
            260                 265                 270
Gly Ile Arg Ala Ile Val Ala Ala Gly Cys Thr Phe Thr Ser Ala Val
        275                 280                 285
Ile Gly Leu Trp Thr Phe Cys Asn Arg Val
290                 295

<210> SEQ ID NO 134
<211> LENGTH: 897
<212> TYPE: DNA
<213> ORGANISM: Chlamydia

<400> SEQUENCE: 134
atggcttcta tatgcggacg tttagggtct ggtacaggga atgctctaaa agcttttttt     60
acacagccca acaataaaat ggcaagggta gtaaataaga cgaagggaat ggataagact    120
attaaggttg ccaagtctgc tgccgaattg accgcaaata ttttggaaca agctggaggc    180
gcgggctctt ccgcacacat tacagcttcc caagtgtcca aaggattagg ggatgcgaga    240
actgttgtcg ctttagggaa tgcctttaac ggagcgttgc caggaacagt tcaaagtgcg    300
caaagcttct ctctctcacat gaaagctgct agtcagaaaa cgcaagaagg ggatgagggg    360
```

```
ctcacagcag atctttgtgt gtctcataag cgcagagcgg ctgcggctgt ctgtagcatc    420
atcggaggaa ttacctacct cgcgacattc ggagctatcc gtccgattct gtttgtcaac    480
aaaatgctgg caaaaccgtt tctttcttcc caaactaaag caaatatggg atcttctgtt    540
agctatatta tggcggctaa ccatgcagcg tctgtggtgg gtgctggact cgctatcagt    600
gcggaaagag cagattgcga agcccgctgc gctcgtattg cgagagaaga gtcgttactc    660
gaaatgccgg gagaggaaaa tgcttgcgag aagaaagtcg ctggagagaa agccaagacg    720
ttcacgcgca tcaagtatgc actcctcact atgctcgaga gttttttgga atgcgttgcc    780
gacgttttca aattggtgcc gctgcctatt acaatgggta ttcgtgcgat tgtggctgct    840
ggatgtacgt tcacttctgc aattattgga ttgtgcactt tctgcgccag agcataa      897
```

<210> SEQ ID NO 135
<211> LENGTH: 298
<212> TYPE: PRT
<213> ORGANISM: Chlamydia

<400> SEQUENCE: 135

```
Met Ala Ser Ile Cys Gly Arg Leu Gly Ser Gly Thr Gly Asn Ala Leu
 1               5                  10                  15

Lys Ala Phe Phe Thr Gln Pro Asn Asn Lys Met Ala Arg Val Val Asn
                20                  25                  30

Lys Thr Lys Gly Met Asp Lys Thr Ile Lys Val Ala Lys Ser Ala Ala
            35                  40                  45

Glu Leu Thr Ala Asn Ile Leu Glu Gln Ala Gly Gly Ala Gly Ser Ser
        50                  55                  60

Ala His Ile Thr Ala Ser Gln Val Ser Lys Gly Leu Gly Asp Ala Arg
 65                  70                  75                  80

Thr Val Val Ala Leu Gly Asn Ala Phe Asn Gly Ala Leu Pro Gly Thr
                85                  90                  95

Val Gln Ser Ala Gln Ser Phe Phe Ser His Met Lys Ala Ala Ser Gln
            100                 105                 110

Lys Thr Gln Glu Gly Asp Glu Gly Leu Thr Ala Asp Leu Cys Val Ser
        115                 120                 125

His Lys Arg Arg Ala Ala Ala Val Cys Ser Ile Ile Gly Gly Ile
    130                 135                 140

Thr Tyr Leu Ala Thr Phe Gly Ala Ile Arg Pro Ile Leu Phe Val Asn
145                 150                 155                 160

Lys Met Leu Ala Lys Pro Phe Leu Ser Ser Gln Thr Lys Ala Asn Met
                165                 170                 175

Gly Ser Ser Val Ser Tyr Ile Met Ala Ala Asn His Ala Ala Ser Val
            180                 185                 190

Val Gly Ala Gly Leu Ala Ile Ser Ala Glu Arg Ala Asp Cys Glu Ala
        195                 200                 205

Arg Cys Ala Arg Ile Ala Arg Glu Glu Ser Leu Leu Glu Met Pro Gly
    210                 215                 220

Glu Glu Asn Ala Cys Glu Lys Lys Val Ala Gly Lys Ala Lys Thr
225                 230                 235                 240

Phe Thr Arg Ile Lys Tyr Ala Leu Leu Thr Met Leu Glu Lys Phe Leu
                245                 250                 255

Glu Cys Val Ala Asp Val Phe Lys Leu Val Pro Leu Pro Ile Thr Met
            260                 265                 270

Gly Ile Arg Ala Ile Val Ala Ala Gly Cys Thr Phe Thr Ser Ala Ile
```

```
                275                 280                 285
Ile Gly Leu Cys Thr Phe Cys Ala Arg Ala
    290                 295
```

<210> SEQ ID NO 136
<211> LENGTH: 882
<212> TYPE: DNA
<213> ORGANISM: Chlamydia

<400> SEQUENCE: 136

```
atggcttctg tatgtgggcg attaagtgct ggggtgggga acagatttaa cgcattttc      60
acgcgtcccg gtaacaagct atcacggttt gtaaatagcg caaaggatt agacagatca    120
ataaggttg ggaagtctgc tgctgaatta acggcgagta ttttagagca aactgggggg    180
gcagggactg atgcacatgt tacggcggcc aaggtgtcta agcacttgg ggacgcgcga    240
acagtaatgg ctctagggaa tgtcttcaat gggtctgtgc cagcaaccat tcaaagtgcg    300
cgaagctgtc tcgcccattt acgagcggcc ggcaaagaag aagaaacatg ctccaaggtg    360
aaagatctct gtgtttctca tagacgaaga gctgcggctg aggcttgtaa tgttattgga    420
ggagcaactt atattacaac tttcggagcg attcgtccga cattactcgt taacaagctt    480
cttgccaaac cattcctttc ctcccaagcc aaagaagggt tgggagcttc tgttggttat    540
atcatggcag cgaaccatgc ggcatctgtg cttgggtctg ctttaagtat tagcgcagaa    600
agagcagact gtgaagagcg tgtgatcgc attcgatgta gtgaggatgg tgaaatttgc    660
gaaggcaata aattaacagc tatttcggaa gagaaggcta gatcatggac tctcattaag    720
tacagattcc ttactatgat agaaaaacta tttgagatgg tggcggatat cttcaagtta    780
attcctttgc caatttcgca tggaattcgt gctattgttg ctgcgggatg tacgttgact    840
tctgcagtta ttggcttagg tactttttgg tctagagcat aa                        882
```

<210> SEQ ID NO 137
<211> LENGTH: 293
<212> TYPE: PRT
<213> ORGANISM: Chlamydia

<400> SEQUENCE: 137

```
Met Ala Ser Val Cys Gly Arg Leu Ser Ala Gly Val Gly Asn Arg Phe
  1               5                  10                  15

Asn Ala Phe Phe Thr Arg Pro Gly Asn Lys Leu Ser Arg Phe Val Asn
                 20                  25                  30

Ser Ala Lys Gly Leu Asp Arg Ser Ile Lys Val Gly Lys Ser Ala Ala
             35                  40                  45

Glu Leu Thr Ala Ser Ile Leu Glu Gln Thr Gly Gly Ala Gly Thr Asp
         50                  55                  60

Ala His Val Thr Ala Ala Lys Val Ser Lys Ala Leu Gly Asp Ala Arg
 65                  70                  75                  80

Thr Val Met Ala Leu Gly Asn Val Phe Asn Gly Ser Val Pro Ala Thr
                 85                  90                  95

Ile Gln Ser Ala Arg Ser Cys Leu Ala His Leu Arg Ala Ala Gly Lys
            100                 105                 110

Glu Glu Thr Cys Ser Lys Val Lys Asp Leu Cys Val Ser His Arg
            115                 120                 125

Arg Arg Ala Ala Ala Glu Ala Cys Asn Val Ile Gly Gly Ala Thr Tyr
        130                 135                 140

Ile Thr Thr Phe Gly Ala Ile Arg Pro Thr Leu Leu Val Asn Lys Leu
```

-continued

```
            145                 150                 155                 160
Leu Ala Lys Pro Phe Leu Ser Ser Gln Ala Lys Glu Gly Leu Gly Ala
                    165                 170                 175

Ser Val Gly Tyr Ile Met Ala Ala Asn His Ala Ala Ser Val Leu Gly
                180                 185                 190

Ser Ala Leu Ser Ile Ser Ala Glu Arg Ala Asp Cys Glu Glu Arg Cys
            195                 200                 205

Asp Arg Ile Arg Cys Ser Glu Asp Gly Glu Ile Cys Glu Gly Asn Lys
        210                 215                 220

Leu Thr Ala Ile Ser Glu Glu Lys Ala Arg Ser Trp Thr Leu Ile Lys
225                 230                 235                 240

Tyr Arg Phe Leu Thr Met Ile Glu Lys Leu Phe Glu Met Val Ala Asp
                    245                 250                 255

Ile Phe Lys Leu Ile Pro Leu Pro Ile Ser His Gly Ile Arg Ala Ile
                260                 265                 270

Val Ala Ala Gly Cys Thr Leu Thr Ser Ala Val Ile Gly Leu Gly Thr
            275                 280                 285

Phe Trp Ser Arg Ala
        290

<210> SEQ ID NO 138
<211> LENGTH: 16
<212> TYPE: PRT
<213> ORGANISM: Artificial Sequence
<220> FEATURE:
<223> OTHER INFORMATION: Made in a lab

<400> SEQUENCE: 138

Asp Leu Cys Val Ser His Lys Arg Arg Ala Ala Ala Val Cys Ser
1               5                   10                  15

<210> SEQ ID NO 139
<211> LENGTH: 16
<212> TYPE: PRT
<213> ORGANISM: Artificial Sequence
<220> FEATURE:
<223> OTHER INFORMATION: Made in a lab

<400> SEQUENCE: 139

Arg Ala Ala Ala Ala Val Cys Ser Phe Ile Gly Gly Ile Thr Tyr Leu
1               5                   10                  15

<210> SEQ ID NO 140
<211> LENGTH: 18
<212> TYPE: PRT
<213> ORGANISM: Artificial Sequence
<220> FEATURE:
<223> OTHER INFORMATION: Made in a lab

<400> SEQUENCE: 140

Cys Ser Phe Ile Gly Gly Ile Thr Tyr Leu Ala Thr Phe Gly Ala Ile
1               5                   10                  15

Arg Pro

<210> SEQ ID NO 141
<211> LENGTH: 18
<212> TYPE: PRT
<213> ORGANISM: Artificial Sequence
<220> FEATURE:
<223> OTHER INFORMATION: Made in a lab

<400> SEQUENCE: 141
```

```
Tyr Leu Ala Thr Phe Gly Ala Ile Arg Pro Ile Leu Phe Val Asn Lys
1               5                   10                  15

Met Leu

<210> SEQ ID NO 142
<211> LENGTH: 18
<212> TYPE: PRT
<213> ORGANISM: Artificial Sequence
<220> FEATURE:
<223> OTHER INFORMATION: Made in a lab

<400> SEQUENCE: 142

Arg Pro Ile Leu Phe Val Asn Lys Met Leu Ala Gln Pro Phe Leu Ser
1               5                   10                  15

Ser Gln

<210> SEQ ID NO 143
<211> LENGTH: 17
<212> TYPE: PRT
<213> ORGANISM: Artificial Sequence
<220> FEATURE:
<223> OTHER INFORMATION: Made in a lab

<400> SEQUENCE: 143

Met Leu Ala Gln Pro Phe Leu Ser Ser Gln Thr Lys Ala Asn Met Gly
1               5                   10                  15

Ser

<210> SEQ ID NO 144
<211> LENGTH: 10
<212> TYPE: PRT
<213> ORGANISM: Artificial Sequence
<220> FEATURE:
<223> OTHER INFORMATION: Made in a lab

<400> SEQUENCE: 144

Cys Ser Phe Ile Gly Gly Ile Thr Tyr Leu
1               5                   10

<210> SEQ ID NO 145
<211> LENGTH: 9
<212> TYPE: PRT
<213> ORGANISM: Artificial Sequence
<220> FEATURE:
<223> OTHER INFORMATION: Made in a lab

<400> SEQUENCE: 145

Ser Phe Ile Gly Gly Ile Thr Tyr Leu
1               5

<210> SEQ ID NO 146
<211> LENGTH: 8
<212> TYPE: PRT
<213> ORGANISM: Artificial Sequence
<220> FEATURE:
<223> OTHER INFORMATION: Made in a lab

<400> SEQUENCE: 146

Phe Ile Gly Gly Ile Thr Tyr Leu
1               5

<210> SEQ ID NO 147
<211> LENGTH: 9
<212> TYPE: PRT
```

```
<213> ORGANISM: Artificial Sequence
<220> FEATURE:
<223> OTHER INFORMATION: Made in a lab

<400> SEQUENCE: 147

Cys Ser Phe Ile Gly Gly Ile Thr Tyr
1               5

<210> SEQ ID NO 148
<211> LENGTH: 8
<212> TYPE: PRT
<213> ORGANISM: Artificial Sequence
<220> FEATURE:
<223> OTHER INFORMATION: Made in a lab

<400> SEQUENCE: 148

Cys Ser Phe Ile Gly Gly Ile Thr
1               5

<210> SEQ ID NO 149
<211> LENGTH: 10
<212> TYPE: PRT
<213> ORGANISM: Artificial Sequence
<220> FEATURE:
<223> OTHER INFORMATION: Made in a lab

<400> SEQUENCE: 149

Cys Ser Ile Ile Gly Gly Ile Thr Tyr Leu
1               5                   10

<210> SEQ ID NO 150
<211> LENGTH: 10
<212> TYPE: PRT
<213> ORGANISM: Artificial Sequence
<220> FEATURE:
<223> OTHER INFORMATION: Made in a lab

<400> SEQUENCE: 150

Cys Gly Phe Ile Gly Gly Ile Thr Tyr Leu
1               5                   10

<210> SEQ ID NO 151
<211> LENGTH: 9
<212> TYPE: PRT
<213> ORGANISM: Artificial Sequence
<220> FEATURE:
<223> OTHER INFORMATION: Made in a lab

<400> SEQUENCE: 151

Gly Phe Ile Gly Gly Ile Thr Tyr Leu
1               5

<210> SEQ ID NO 152
<211> LENGTH: 20
<212> TYPE: PRT
<213> ORGANISM: Artificial Sequence
<220> FEATURE:
<223> OTHER INFORMATION: Made in a lab

<400> SEQUENCE: 152

Gln Ile Phe Val Cys Leu Ile Ser Ala Glu Arg Leu Arg Leu Arg Leu
1               5                   10                  15

Ser Val Ala Ser
            20

<210> SEQ ID NO 153
```

```
<211> LENGTH: 20
<212> TYPE: PRT
<213> ORGANISM: Artificial Sequence
<220> FEATURE:
<223> OTHER INFORMATION: Made in a lab

<400> SEQUENCE: 153

Glu Arg Leu Arg Leu Arg Leu Ser Val Ala Ser Ser Glu Glu Leu Pro
 1               5                  10                  15

Thr Ser Arg His
         20

<210> SEQ ID NO 154
<211> LENGTH: 20
<212> TYPE: PRT
<213> ORGANISM: Artificial Sequence
<220> FEATURE:
<223> OTHER INFORMATION: Made in a lab

<400> SEQUENCE: 154

Ala Ser Ser Glu Glu Leu Pro Thr Ser Arg His Ser Glu Leu Ser Val
 1               5                  10                  15

Arg Phe Cys Leu
         20

<210> SEQ ID NO 155
<211> LENGTH: 20
<212> TYPE: PRT
<213> ORGANISM: Artificial Sequence
<220> FEATURE:
<223> OTHER INFORMATION: Made in a lab

<400> SEQUENCE: 155

Arg His Ser Glu Leu Ser Val Arg Phe Cys Leu Ser Thr Lys Cys Trp
 1               5                  10                  15

Arg Asn Arg Phe
         20

<210> SEQ ID NO 156
<211> LENGTH: 20
<212> TYPE: PRT
<213> ORGANISM: Artificial Sequence
<220> FEATURE:
<223> OTHER INFORMATION: Made in a lab

<400> SEQUENCE: 156

Leu Ser Thr Lys Cys Trp Arg Asn Arg Phe Phe Leu Pro Lys Leu Lys
 1               5                  10                  15

Gln Ile Trp Asp
         20

<210> SEQ ID NO 157
<211> LENGTH: 53
<212> TYPE: PRT
<213> ORGANISM: Artificial Sequence
<220> FEATURE:
<223> OTHER INFORMATION: Made in a lab

<400> SEQUENCE: 157

Ile Phe Val Cys Leu Ile Ser Ala Glu Arg Leu Arg Leu Ser Val Ala
 1               5                  10                  15

Ser Ser Glu Glu Leu Pro Thr Ser Arg His Ser Glu Leu Ser Val Arg
             20                  25                  30

Phe Cys Leu Ser Thr Lys Cys Trp Arg Asn Arg Phe Phe Leu Pro Lys
```

```
              35                  40                  45

Leu Lys Gln Ile Trp
     50

<210> SEQ ID NO 158
<211> LENGTH: 52
<212> TYPE: PRT
<213> ORGANISM: Artificial Sequence
<220> FEATURE:
<223> OTHER INFORMATION: Made in a lab

<400> SEQUENCE: 158

Leu Cys Val Ser His Lys Arg Ala Ala Ala Val Cys Ser Phe
 1               5                  10                  15

Ile Gly Gly Ile Thr Tyr Leu Ala Thr Phe Gly Ala Ile Arg Pro Ile
                 20                  25                  30

Leu Phe Val Asn Lys Met Leu Ala Gln Pro Phe Leu Ser Ser Gln Ile
                 35                  40                  45

Lys Ala Asn Met
     50

<210> SEQ ID NO 159
<211> LENGTH: 24
<212> TYPE: DNA
<213> ORGANISM: Chlamydia

<400> SEQUENCE: 159
ttttgaagca ggtaggtgaa tatg                                       24

<210> SEQ ID NO 160
<211> LENGTH: 24
<212> TYPE: DNA
<213> ORGANISM: Chlamydia

<400> SEQUENCE: 160
ttaagaaatt taaaaaatcc ctta                                       24

<210> SEQ ID NO 161
<211> LENGTH: 24
<212> TYPE: DNA
<213> ORGANISM: Chlamydia

<400> SEQUENCE: 161
ggtataatat ctctctaaat tttg                                       24

<210> SEQ ID NO 162
<211> LENGTH: 19
<212> TYPE: DNA
<213> ORGANISM: Chlamydia

<400> SEQUENCE: 162
agataaaaaa ggctgtttc                                             19

<210> SEQ ID NO 163
<211> LENGTH: 24
<212> TYPE: DNA
<213> ORGANISM: Chlamydia

<400> SEQUENCE: 163
ttttgaagca ggtaggtgaa tatg                                       24

<210> SEQ ID NO 164
```

```
<211> LENGTH: 29
<212> TYPE: DNA
<213> ORGANISM: Chlamydia

<400> SEQUENCE: 164
tttacaataa gaaaagctaa gcactttgt                                  29

<210> SEQ ID NO 165
<211> LENGTH: 20
<212> TYPE: DNA
<213> ORGANISM: Chlamydia

<400> SEQUENCE: 165
ccttacacag tcctgctgac                                            20

<210> SEQ ID NO 166
<211> LENGTH: 20
<212> TYPE: DNA
<213> ORGANISM: Chlamydia

<400> SEQUENCE: 166
gtttccgggc cctcacattg                                            20

<210> SEQ ID NO 167
<211> LENGTH: 9
<212> TYPE: PRT
<213> ORGANISM: Artificial Sequence
<220> FEATURE:
<223> OTHER INFORMATION: Made in a lab

<400> SEQUENCE: 167

Ser Phe Ile Gly Gly Ile Thr Tyr Leu
 1               5

<210> SEQ ID NO 168
<211> LENGTH: 9
<212> TYPE: PRT
<213> ORGANISM: Artificial Sequence
<220> FEATURE:
<223> OTHER INFORMATION: Made in a lab

<400> SEQUENCE: 168

Ser Ile Ile Gly Gly Ile Thr Tyr Leu
 1               5

<210> SEQ ID NO 169
<211> LENGTH: 2643
<212> TYPE: DNA
<213> ORGANISM: Chlamydia

<400> SEQUENCE: 169
gcaatcatgc gacctgatca tatgaacttc tgttgtctat gtgctgctat tttgtcatcc    60
acagcggtcc tctttggcca ggatccctta ggtgaaaccg ccctcctcac taaaaatcct   120
aatcatgtcg tctgtacatt ttttgaggac tgtaccatgg agagcctctt tcctgctctt   180
tgtgctcatg catcacaaga cgatcctttg tatgtacttg gaaattccta ctgttggttc   240
gtatctaaac tccatatcac ggaccccaaa gaggctcttt ttaaagaaaa aggagatctt   300
tccattcaaa actttcgctt cctttccttc acagattgct cttccaagga aagctctcct   360
tctattattc atcaaaagaa tggtcagtta tccttgcgca ataatggtag catgagtttc   420
tgtcgaaatc atgctgaagg ctctggagga gccatctctg cggatgcctt ttctctacag   480
cacaactatc ttttcacagc ttttgaagag aattcttcta aaggaaatgg cggagccatt   540
```

```
caggctcaaa ccttctcttt atctagaaat gtgtcgccta tttctttcgc ccgtaatcgt    600
gcggatttaa atggcggcgc tatttgctgt agtaatctta tttgttcagg aatgtaaac    660 cctctctttt tcactggaaa ctccgccacg aatggaggcg ctatttgttg tatcagcgat    720
ctaaacacct cagaaaaagg ctctctctct cttgcttgta accaagaaac gctatttgca    780
agcaattctg ctaaagaaaa aggcgggggct atttatgcca agcacatggt attgcgttat    840
aacggtcctg tttccttcat taacaacagc gctaaaatag gtggagctat cgccatccag    900
tccggaggga gtctctctat ccttgcaggt gaaggatctg ttctgttcca gaataactcc    960
caacgcacct ccgaccaagg tctagtaaga aacgccatct acttaragaa agatgcgatt   1020
ctttcttcct tagaagctcg caacggagat attcttttct ttgatcctat tgtacaagaa   1080
agtagcagca aagaatcgcc tcttccctcc tctttgcaag ccagcgtgac ttctcccacc   1140
ccagccaccg catctccttt agttattcag acaagtgcaa accgttcagt gattttctcg   1200
agcgaacgtc tttctgaaga agaaaaaact cctgataacc tcacttccca actacagcag   1260
cctatcgaac tgaaatccgg acgcttagtt ttaaaagatc gcgctgtcct ttccgcgcct   1320
tctctctctc aggatcctca agctctcctc attatggaag cgggaacttc tttaaaaact   1380
tcctctgatt tgaagttagc tacgctaagt attccccttc attccttaga tactgaaaaa   1440
agcgtaacta tccacgcccc taatctttct atccaaaaga tcttcctctc taactctgga   1500
gatgagaatt tttatgaaaa tgtagagctt ctcagtaaag agcaaaacaa tattcctctc   1560
cttactctcc ctaaagagca atctcattta catcttcctg atgggaacct ctcttctcac   1620
tttggatatc aaggagattg gacttttttct tggaaagatt ctgatgaagg gcattctctg   1680
attgctaatt ggacgcctaa aaactatgtg cctcatccag aacgtcaatc tacactcgtt   1740
gcgaacactc tttggaacac ctattccgat atgcaagctg tgcagtcgat gattaataca   1800
acagcgcacg gaggagccta tctatttgga acgtggggat ctgctgtttc taatttattc   1860
tatgttcacg acagctctgg gaaacctatc gataattggc atcatagaag ccttggctac   1920
ctattcggta tcagtactca cagtttagat gaccattctt tctgcttggc tgcaggacaa   1980
ttactcggga aatcgtccga ttcctttatt acgtctacag aaacgacctc ctatatagct   2040
actgtacaag cgcaactcgc tacctctcta atgaaaatct ctgcacaggc atgctacaat   2100
gaaagtatcc atgagctaaa aacaaaatat cgctccttct ctaaagaagg attcggatcc   2160
tggcatagcg ttgcagtatc cggagaagtg tgcgcatcga ttcctattgt atccaatggt   2220
tccggactgt tcagctcctt ctctattttc tctaaactgc aaggattttc aggaacacag   2280
gacggttttg aggagagttc gggagagatt cggtcctttt ctgccagctc tttcagaaat   2340
atttcacttc ctataggaat aacatttgaa aaaaatccc aaaaaacacg aacctactat   2400
tactttctag gagcctacat ccaagacctg aaacgtgatg tggaatcggg acctgtagtg   2460
ttactcaaaa atgccgtctc ctgggatgct cctatggcga acttggattc acgagcctac   2520
atgttccggc ttacgaatca aagagctcta cacagacttc agacgctgtt aaatgtgtct   2580
tgtgtgctgc gtgggcaaag ccatagttac tccctggatc tggggaccac ttacaggttc   2640
tag                                                                 2643

<210> SEQ ID NO 170
<211> LENGTH: 2949
<212> TYPE: DNA
<213> ORGANISM: Chlamydia
```

```
<400> SEQUENCE: 170
atgattcctc aaggaatttta cgatggggag acgttaactg tatcatttcc ctatactgtt      60
ataggagatc cgagtgggac tactgttttt tctgcaggag agttaacatt aaaaaatctt     120
gacaattcta ttgcagcttt gcctttaagt tgttttggga acttattagg gagttttact     180
gttttaggga gaggacactc gttgactttc gagaacatac ggacttctac aaatggggca     240
gctctaagta atagcgctgc tgatggactg tttactattg agggttttaa agaattatcc     300
ttttccaatt gcaattcatt acttgccgta ctgcctgctg caacgactaa taagggtagc     360
cagactccga cgacaacatc tacaccgtct aatggtacta tttattctaa aacagatctt     420
ttgttactca ataatgagaa gttctcattc tatagtaatt tagtctctgg agatggggga     480
gctatagatg ctaagagctt aacggttcaa ggaattagca agctttgtgt cttccaagaa     540
aatactgctc aagctgatgg gggagcttgt caagtagtca ccagtttctc tgctatggct     600
aacgaggctc ctattgcctt tgtagcgaat gttgcaggag taagagggg agggattgct     660
gctgttcagg atgggcagca gggagtgtca tcatctactt caacagaaga tccagtagta     720
agttttttcca gaaatactgc ggtagagttt gatgggaacg tagcccgagt aggaggaggg     780
atttactcct acgggaacgt tgctttcctg aataatggaa aaaccttgtt tctcaacaat     840
gttgcttctc ctgtttacat tgctgctaag caaccaacaa gtggacaggc ttctaatacg     900
agtaataatt acgagatgg aggagctatc ttctgtaaga atggtgcgca agcaggatcc     960
aataactctg gatcagtttc ctttgatgga gagggagtag ttttctttag tagcaatgta    1020
gctgctggga aaggggagc tatttatgcc aaaaagctct cggttgctaa ctgtggccct    1080
gtacaatttt taaggaatat cgctaatgat ggtgagcga tttatttagg agaatctgga    1140
gagctcagtt tatctgctga ttatggagat attattttcg atgggaatct aaaagaaca    1200
gccaaagaga atgctgccga tgttaatggc gtaactgtgt cctcacaagc catttcgatg    1260
ggatcgggag ggaaaataac gacattaaga gctaaagcag gcatcagat tctctttaat    1320
gatcccatcg agatggcaaa cggaaataac cagccgcgc agtcttccaa acttctaaaa    1380
attaacgatg gtgaaggata cacagggat attgttttg ctaatggaag cagtactttg    1440
taccaaaatg ttacgataga gcaaggaagg attgttcttc gtgaaaaggc aaaattatca    1500
gtgaattctc taagtcagac aggtgggagt ctgtatatgg aagctgggag tacattggat    1560
tttgtaactc cacaaccacc acaacagcct cctgccgcta atcagttgat cacgcttcc    1620
aatctgcatt tgtctctttc ttctttgtta gcaaacaatg cagttacgaa tcctcctacc    1680
aatcctccag cgcaagattc tcatcctgca gtcattggta gcacaactgc tggttctgtt    1740
acaattagtg ggcctatctt ttttgaggat ttggatgata cagcttatga taggtatgat    1800
tggctaggtt ctaatcaaaa aatcaatgtc ctgaaattac agttagggac taagcccca    1860
gctaatgccc catcagattt gactctaggg aatgagatgc ctaagtatgg ctatcaagga    1920
agctggaagc ttgcgtggga tcctaataca gcaaataatg gtccttatac tctgaaagct    1980
acatggacta aaactgggta taatcctggg cctgagcgag tagcttcttt ggttccaaat    2040
agtttatggg gatccatttt agatatacga tctgcgcatt cagcaattca agcaagtgtg    2100
gatgggcgct cttattgtcg aggattatgg gtttctggag tttcgaattt cttctatcat    2160
gaccgcgatg ctttaggtca gggatatcgg tatattagtg ggggttattc cttaggagca    2220
aactcctact ttggatcatc gatgtttggt ctagcattta ccgaagtatt tggtagatct    2280
aaagattatg tagtgtgtcg ttccaatcat catgcttgca taggatccgt ttatctatct    2340
```

```
acccaacaag ctttatgtgg atcctatttg ttcggagatg cgtttatccg tgctagctac      2400
gggtttggga atcagcatat gaaaacctca tatacatttg cagaggagag cgatgttcgt      2460
tgggataata actgtctggc tggagagatt ggagcgggat taccgattgt gattactcca      2520
tctaagctct atttgaatga gttgcgtcct ttcgtgcaag ctgagttttc ttatgccgat      2580
catgaatctt ttacagagga aggcgatcaa gctcgggcat tcaagagcgg acatctccta      2640
aatctatcag ttcctgttgg agtgaagttt gatcgatgtt ctagtacaca tcctaataaa      2700
tatagcttta tggcggctta tatctgtgat gcttatcgca ccatctctgg tactgagaca      2760
acgctcctat cccatcaaga gacatggaca acagatgcct ttcatttagc aagacatgga      2820
gttgtggtta gaggatctat gtatgcttct ctaacaagta atatagaagt atatggccat      2880
ggaagatatg agtatcgaga tgcttctcga ggctatggtt tgagtgcagg magtaaagtc      2940 yggttctaa                                                              2949

<210> SEQ ID NO 171
<211> LENGTH: 2895
<212> TYPE: DNA
<213> ORGANISM: Chlamydia

<400> SEQUENCE: 171
atgaaaaaag cgttttcctt tttccttatc ggaaactccc tatcaggact agctagagag        60
gttccttcta gaatctttct tatgcccaac tcagttccag atcctacgaa agagtcgcta       120
tcaaataaaa ttagtttgac aggagacact cacaatctca ctaactgcta tctcgataac       180
ctacgctaca tactggctat tctacaaaaa actcccaatg aaggagctgc tgtcacaata       240
acagattacc taagcttttt tgatacacaa aaagaaggta tttatttgc aaaaaatctc        300 accccctgaaa gtggtggtgc gattggttat gcgagtccca attctcctac cgtggagatt       360
cgtgatacaa taggtcctgt aatctttgaa ataatactt gttgcagact atttacatgg        420
agaaatcctt atgctgctga taaaataaga gaaggcggag ccattcatgc tcaaaatctt       480
tacataaatc ataatcatga tgtggtcgga tttatgaaga acttttctta tgtccaagga       540
ggagccatta gtaccgctaa taccttttgtt gtgagcgaga atcagtcttg ttttctcttt       600
atggacaaca tctgtattca aactaataca gcaggaaaag gtggcgctat ctatgctgga       660
acgagcaatt cttttgagag taataactgc gatctcttct tcatcaataa cgcctgttgt       720
gcaggaggag cgatcttctc ccctatctgt tctctaacag gaaatcgtgg taacatcgtt       780
ttctataaca atcgctgctt taaaaatgta gaaacagctt cttcagaagc ttctgatgga       840
ggagcaatta agtaactac tcgcctagat gttacaggca atcgtggtag gatctttttt        900
agtgacaata tcacaaaaaa ttatggcgga gctatttacg ctcctgtagt taccctagtg       960
gataatggcc ctacctactt tataaacaat atcgccaata taaggggggg cgctatctat      1020
atagacggaa ccagtaactc caaaatttct gccgaccgcc atgctattat ttttaatgaa      1080 atattgtga ctaatgtaac taatgcaaat ggtaccagta cgtcagctaa tcctcctaga       1140
agaaatgcaa taacagtagc aagctcctct ggtgaaattc tattaggagc agggagtagc      1200
caaaatttaa ttttttatga tcctattgaa gttagcaatg caggggtctc tgtgtccttc      1260
aataaggaag ctgatcaaac aggctctgta gtattttcag gagctactgt taattctgca      1320
gattttcatc aacgcaattt acaaacaaaa acacctgcac cccttactct cagtaatggt      1380
tttctatgta tcgaagatca tgctcagctt acagtgaatc gattcacaca aactgggggt      1440
```

-continued

```
gttgtttctc ttgggaatgg agcagttctg agttgctata aaaatggtac aggagattct    1500
gctagcaatg cctctataac actgaagcat attggattga atctttcttc cattctgaaa    1560
agtggtgctg agattccttt attgtgggta gagcctacaa ataacagcaa taactataca    1620
gcagatactg cagctacctt ttcattaagt gatgtaaaac tctcactcat tgatgactac    1680
gggaactctc cttatgaatc cacagatctg acccatgctc tgtcatcaca gcctatgcta    1740
tctatttctg aagctagcga taaccagcta caatcagaaa atatagattt tcgggacta     1800 aatgtccctc attatggatg gcaaggactt tggacttggg gctgggcaaa aactcaagat    1860
ccagaaccag catcttcagc aacaatcact gatccacaaa aagccaatag atttcataga    1920
accttactac taacatggct tcctgccggg tatgttccta gcccaaaaca cagaagtccc    1980
ctcatagcta acacttatg ggggaatatg ctgcttgcaa cagaaagctt aaaaaatagt    2040
gcagagctga cacctagtgg tcatcctttc tggggaatta caggaggagg actaggcatg    2100
atggtttacc aagatcctcg agaaaatcat cctggattcc atatgcgctc ttccggatac    2160
tctgcgggga tgatagcagg gcagacacac accttctcat tgaaattcag tcagacctac    2220
accaaactca atgagcgtta cgcaaaaaac aacgtatctt ctaaaaatta ctcatgccaa    2280
ggagaaatgc tcttctcatt gcaagaaggt ttccttgctga ctaaattagt tgggctttac    2340
agctatggag accataactg tcaccatttc tatactcaag agaaaatct aacatctcaa     2400 gggacgttcc gcagtcaaac gatgggaggt gctgtctttt ttgatctccc tatgaaaccc    2460
tttggatcaa cgcatatact gacagctccc ttttaggtg ctcttggtat ttattctagc     2520
ctgtctcact ttactgaggt gggagcctat ccgcgaagct tttctacaaa gactcctttg    2580
atcaatgtcc tagtccctat tggagttaaa ggtagcttta tgaatgctac ccacagacct    2640
caagcctgga ctgtagaatt ggcataccaa cccgttctgt atagacaaga accagggatc    2700
gcgacccagc tcctagccag taaggtatt tggtttggta gtggaagccc ctcatcgcgt     2760
catgccatgt cctataaaat ctcacagcaa acacaacctt tgagttggtt aactctccat    2820
ttccagtatc atggattcta ctcctcttca accttctgta attatctcaa tggggaaatt    2880
gctctgcgat tctag                                                      2895
```

<210> SEQ ID NO 172
<211> LENGTH: 4593
<212> TYPE: DNA
<213> ORGANISM: Chlamydia

<400> SEQUENCE: 172

```
atgagttccg agaaagatat aaaaagcacc tgttctaagt tttctttgtc tgtagtagca      60
gctatccttg cctctgttag cgggttagct agttgcgtag atcttcatgc tggaggacag     120
tctgtaaatg agctggtata tgtaggccct caagcggttt tattgttaga ccaaattcga     180
gatctattcg ttgggtctaa agatagtcag gctgaaggac agtataggtt aattgtagga     240
gatccaagtt cttttccaaga gaaagatgca gatactcttc ccgggaaggt agagcaaagt    300 acttttgttct cagtaaccaa tcccgtggtt ttccaaggtg tggaccaaca ggatcaagtc    360
tcttcccaag ggttaatttg tagttttacg agcagcaacc ttgattctcc ccgtgacgga    420
gaatcttttt taggtattgc ttttgttggg gatagtagta aggctggaat cacattaact    480
gacgtgaaag cttctttgtc tggagcggct ttatattcta cagaagatct tatctttgaa    540
aagattaagg gtggattgga atttgcatca tgttcttctc tagaacaggg gggagcttgt   600
gcagctcaaa gtatttttga tcatgattgt caaggattgc aggttaaaca ctgtactaca    660
```

```
gccgtgaatg ctgaggggtc tagtgcgaat gatcatcttg gatttggagg aggcgctttc     720
tttgttacgg gttctctttc tggagagaaa agtctctata tgcctgcagg agatatggta     780
gttgcgaatt gtgatgggc tatatctttt gaaggaaaca gcgcgaactt tgctaatgga     840
ggagcgattg ctgcctctgg gaaagtgctt tttgtcgcta atgataaaaa gacttctttt     900
atagagaacc gagctttgtc tggaggagcg attgcagcct cttctgatat tgcctttcaa     960
aactgcgcag aactagtttt caaaggcaat tgtgcaattg aacagagga taaaggttct     1020 ttaggtggag gggctatatc ttctctaggc accgttcttt tgcaagggaa tcacgggata     1080
acttgtgata agaatgagtc tgcttcgcaa ggaggcgcca ttttggcaa aaattgtcag     1140 atttctgaca acgaggggcc agtggttttc agagatagta cagcttgctt aggaggaggc     1200
gctattgcag ctcaagaaat tgtttctatt cagaacaatc aggctgggat tccttcgag     1260 ggaggtaagg ctagtttcgg aggaggtatt gcgtgtggat ctttttcttc cgcaggcggt     1320
gcttctgttt tagggactat tgatatttcg aagaatttag gcgcgatttc gttctctcgt     1380
actttatgta cgacctcaga tttaggacaa atggagtacc aggaggagg agctctattt     1440 ggtgaaaata tttctctttc tgagaatgct ggtgtgctca cctttaaaga caacattgtg     1500
aagacttttg cttcgaatgg gaaaattctg ggaggaggag cgattttagc tactggtaag     1560
gtggaaatta ccaataattc cggaggaatt tcttttacag gaaatgcgag agctccacaa     1620
gctcttccaa ctcaagagga gttttccttta ttcagcaaaa agaagggcg accactctct     1680 tcaggatatt ctggggagg agcgattta ggaagagaag tagctattct ccacaacgct     1740
gcagtagtat ttgagcaaaa tcgtttgcag tgcagcgaag aagaagcgac attattaggt     1800
tgttgtggag gaggcgctgt tcatgggatg gatagcactt cgattgttgg caactcttca     1860 gtaagattg gtaataatta cgcaatggga caaggagtct caggaggagc tcttttatct     1920
aaaacagtgc agttagctgg aaatggaagc gtcgattttt ctcgaaatat tgctagtttg     1980
ggaggaggag ctcttcaagc ttctgaagga aattgtgagc tagttgataa cggctatgtg     2040
ctattcagag ataatcgagg gagggtttat gggggtgcta tttcttgctt acgtggagat     2100
gtagtcattt ctggaaacaa gggtagagtt gaatttaaag acaacatagc aacacgtctt     2160
tatgtggaag aaactgtaga aaaggttgaa gaggtagagc cagctcctga gcaaaaagac     2220
aataatgagc tttctttctt agggagtgta gaacagagtt ttattactgc agctaatcaa     2280
gctcttttcg catctgaaga tggggattta tcacctgagt catccatttc ttctgaagaa     2340
cttgcgaaaa gaagagagtg tgctggagga gctatttttg caaaacggt tcgtattgta     2400 gataaccaag aggccgttgt attctcgaat aacttctctg atatttatgg cggcgccatt     2460
tttacaggtt ctcttcgaga agaggataag ttagatgggc aaatccctga agtcttgatc     2520
tcaggcaatg caggggatgt tgttttttcc ggaaattcct cgaagcgtga tgagcatctt     2580
cctcatacag gtgggggagc catttgtact caaaatttga cgatttctca gaatacaggg     2640
aatgttctgt tttataacaa cgtggcctgt tcgggaggag ctgttcgtat agaggatcat     2700
ggtaatgttc ttttagaagc ttttggagga gatattgttt taaaggaaa ttcttctttc     2760 agagcacaag gatccgatgc tatctatttt gcagtaaagg aatcgcatat tacagccctg     2820
aatgctacgg aaggacatgc tattgttttc cacgacgcat tagttttga aaatctaaaa     2880 gaaaggaaat ctgctgaagt attgttaatc aatagtcgag aaaatccagg ttacactgga     2940
tctattcgat ttttagaagc agaaagtaaa gttcctcaat gtattcatgt acaacaagga     3000
```

-continued

| | |
|---|---|
| agccttgagt tgctaaatgg agctacatta tgtagttatg gttttaaaca agatgctgga | 3060 |
| gctaagttgg tattggctgc tggatctaaa ctgaagattt tagattcagg aactcctgta | 3120 |
| caagggcatg ctatcagtaa acctgaagca gaaatcgagt catcttctga accagagggt | 3180 |
| gcacattctc tttggattgc gaagaatgct caaacaacag ttcctatggt tgatatccat | 3240 |
| actatttctg tagatttagc ctccttctct tctagtcaac aggaggggac agtagaagct | 3300 |
| cctcaggtta ttgttcctgg aggaagttat gttcgatctg gagagcttaa tttggagtta | 3360 |
| gttaacacaa caggtactgg ttatgaaaat catgctttgt tgaagaatga ggctaaagtt | 3420 |
| ccattgatgt ctttcgttgc ttctagtgat gaagcttcag ccgaaatcag taacttgtcg | 3480 |
| gtttctgatt tacagattca tgtagcaact ccagagattg aagaagacac atacggccat | 3540 |
| atgggagatt ggtctgaggc taaaattcaa gatggaactc ttgtcattaa ttggaatcct | 3600 |
| actggatatc gattagatcc tcaaaaagca ggggctttag tatttaatgc attatgggaa | 3660 |
| gaagggctg tcttgtctgc tctgaaaaat gcacgctttg ctcataatct cactgctcag | 3720 |
| cgtatggaat tcgattattc tacaaatgtg tggggattcg cctttggtgg tttccgaact | 3780 |
| ctatctgcag agaatctggt tgctattgat ggatacaaag gagcttatgg tggtgcttct | 3840 |
| gctggagtcg atattcaatt gatggaagat tttgttctag gagttagtgg agctgctttc | 3900 |
| ctaggtaaaa tggatagtca gaagtttgat gcggaggttt ctcggaaggg agttgttggt | 3960 |
| tctgtatata caggatttt agctggatcc tggttcttca aaggacaata tagccttgga | 4020 |
| gaaacacaga acgatatgaa aacgcgttat ggagtactag gagagtcgag tgcttcttgg | 4080 |
| acatctcgag gagtactggc agatgcttta gttgaatacc gaagtttagt tggtcctgtg | 4140 |
| agacctactt tttatgcttt gcatttcaat ccttatgtcg aagtatctta tgcttctatg | 4200 |
| aaattccctg gctttacaga acaaggaaga gaagcgcgtt cttttgaaga cgcttccctt | 4260 |
| accaatatca ccattccttt agggatgaag tttgaattgg cgttcataaa aggacagttt | 4320 |
| tcagaggtga actctttggg aataagttat gcatgggaag cttatcgaaa agtagaagga | 4380 |
| ggcgcggtgc agcttttaga agctgggttt gattgggagg gagctccaat ggatcttcct | 4440 |
| agacaggagc tgcgtgtcgc tctggaaaat aatacggaat ggagttctta cttcagcaca | 4500 |
| gtcttaggat taacagcttt ttgtggagga tttacttcta cagatagtaa actaggatat | 4560 |
| gaggcgaata ctggattgcg attgatcttt taa | 4593 |

<210> SEQ ID NO 173
<211> LENGTH: 5331
<212> TYPE: DNA
<213> ORGANISM: Chlamydia

<400> SEQUENCE: 173

| | |
|---|---|
| gcaatcatga aatttatgtc agctactgct gtatttgctg cagtactctc ctccgttact | 60 |
| gaggcgagct cgatccaaga tcaaataaag aataccgact gcaatgttag caaagtagga | 120 |
| tattcaactt ctcaagcatt tactgatatg atgctagcag acaacacaga gtatcgagct | 180 |
| gctgatagtg tttcattcta tgacttttcg acatcttccg gattacctag aaaacatctt | 240 |
| agtagtagta gtgaagcttc tccaacgaca gaaggagtgt cttcatcttc atctggagaa | 300 |
| aatactgaga attcacaaga ttcagctccc tcttctggag aaactgataa gaaaacagaa | 360 |
| gaagaactag acaatggcgg aatcatttat gctagagaga aactaactat ctcagaatct | 420 |
| caggactctc tctctaatcc aagcatagaa ctccatgaca atagttttt cttcggagaa | 480 |
| ggtgaagtta tctttgatca cagagttgcc ctcaaaaacg gaggagctat ttatggagag | 540 |

-continued

```
aaagaggtag tctttgaaaa cataaaatct ctactagtag aagtaaatat ctcggtcgag    600 aaaggggta gcgtctatgc aaaagaacga gtatctttag aaaatgttac cgaagcaacc    660
ttctcctcca atggtgggga acaaggtggt ggtggaatct attcagaaca agatatgtta    720
atcagtgatt gcaacaatgt acatttccaa gggaatgctg caggagcaac agcagtaaaa    780
caatgtctgg atgaagaaat gatcgtattg ctcacagaat gcgttgatag cttatccgaa    840
gatacactgg atagcactcc agaaacggaa cagactaagt caaatggaaa tcaagatggt    900
tcgtctgaaa caaaagatac acaagtatca gaatcaccag aatcaactcc tagccccgac    960
gatgttttag gtaaaggtgg tggtatctat acagaaaaat ctttgaccat cactggaatt   1020
acagggacta tagattttgt cagtaacata gctaccgatt ctggagcagg tgtattcact   1080
aaagaaaact tgtcttgcac caacacgaat agcctacagt ttttgaaaaa ctcggcaggt   1140
caacatggag gaggagccta cgttactcaa accatgtctg ttactaatac aactagtgaa   1200
agtataacta ctcccccctct cgtaggagaa gtgattttct ctgaaaatac agctaaaggg   1260
cacggtggtg gtatctgcac taacaaactt tctttatcta atttaaaaac ggtgactctc   1320
actaaaaact ctgcaaagga gtctggagga gctatttta cagatctagc gtctatacca   1380
acaacagata ccccagagtc ttctacccccc tcttcctcct cgcctgcaag cactcccgaa   1440
gtagttgctt ctgctaaaat aaatcgattc tttgcctcta cggcagaacc ggcagcccct   1500
tctctaacag aggctgagtc tgatcaaacg gatcaaacag aaacttctga tactaatagc   1560
gatatagacg tgtcgattga aacatttttg aatgtcgcta tcaatcaaaa cacttctgcg   1620
aaaaaaggag gggctatttta cgggaaaaaa gctaaacttt cccgtattaa caatcttgaa   1680
ctttcaggga attcatccca ggatgtagga ggaggtctct gtttaactga aagcgtagaa   1740
tttgatgcaa ttggatcgct cttatcccac tataactctg ctgctaaaga aggtggggtt   1800
attcattcta aaacggttac tctatctaac ctcaagtcta ccttcacttt tgcagataac   1860
actgttaaag caatagtaga aagcactcct gaagctccag aagagattcc tccagtagaa   1920
ggagaagagt ctacagcaac agaaaatccg aattctaata cagaaggaag ttcggctaac   1980
actaaccttg aaggatctca agggatact gctgatacag ggactggtgt tgttaacaat   2040
gagtctcaag acacatcaga tactggaaac gctgaatctg gagaacaact acaagattct   2100
acacaatcta atgaagaaaa tacccttccc aatagtagta ttgatcaatc taacgaaaac   2160
acagacgaat catctgatag ccacactgag gaaataactg acgagagtgt ctcatcgtcc   2220
tctaaaagtg gatcatctac tcctcaagat ggaggagcag cttcttcagg ggctccctca   2280
ggagatcaat ctatctctgc aaacgcttgt ttagctaaaa gctatgctgc gagtactgat   2340
agctcccctg tatctaattc ttcaggttca gacgttactg catcttctga taatccagac   2400
tcttcctcat ctggagatag cgctggagac tctgaaggac cgactgagcc agaagctggt   2460
tctacaacag aaactcctac tttaatagga ggaggtgcta tctatggaga aactgttaag   2520
attgagaact tctctggcca aggaatattt tctggaaaca aagctatcga taacaccaca   2580
gaaggctcct cttccaaatc taacgtcctc ggaggtgcgg tctatgctaa acattgttt   2640 aatctcgata gcgggagctc tagacgaact gtcaccttct ccgggaatac tgtctcttct   2700
caatctacaa caggtcaggt tgctggagga gctatctact ctcctactgt aaccattgct   2760
actcctgtag tattttctaa aaactctgca acaaacaatg ctaataacgc tacagatact   2820
cagagaaaag acacctttgg aggagctatc ggagctactt ctgctgtttc tctatcagga   2880
```

-continued

```
ggggctcatt tcttagaaaa cgttgctgac ctcggatctg ctattgggtt ggtgccagac    2940
acacaaaata cagaaacagt gaaattagag tctggctcct actactttga aaaaaataaa    3000
gctttaaaac gagctactat ttacgcacct gtcgtttcca ttaaagccta tactgcgaca    3060
tttaaccaaa acagatctct agaagaagga agcgcgattt actttacaaa agaagcatct    3120
attgagtctt taggctctgt tctcttcaca ggaaacttag taaccccaac gctaagcaca    3180
actacagaag gcacaccagc cacaacctca ggagatgtaa caaaatatgg tgctgctatc    3240
tttggacaaa tagcaagctc aaacggatct cagacggata accttcccct gaaactcatt    3300
gcttcaggag gaaatatttg tttccgaaac aatgaatacc gtcctacttc ttctgatacc    3360
ggaacctcta ctttctgtag tattgcggga gatgttaaat taaccatgca agctgcaaaa    3420
gggaaaacga tcagtttctt tgatgcaatc cggacctcta ctaagaaaac aggtacacag    3480
gcaactgcct acgatactct cgatattaat aaatctgagg attcagaaac tgtaaactct    3540
gcgtttacag gaacgattct gttctcctct gaattacatg aaaataaatc ctatattcca    3600
caaaacgtag ttctacacag tggatctctt gtattgaagc caaataccga gcttcatgtc    3660 atttctttg agcagaaaga aggctcttct ctcgttatga cacctggatc tgttctttcg    3720
aaccagactg ttgctgatgg agctttggtc ataaataaca tgaccattga tttatccagc    3780
gtagagaaaa atggtattgc tgaaggaaat atctttactc ctccagaatt gagaatcata    3840
gacactacta caagtggaag cggtggaacc ccatctacag atagtgaaag taaccagaat    3900
agtgatgata ccaaggagca aaataataat gacgcctcga atcaaggaga aagcgcgaat    3960
ggatcgtctt ctcctgcagt agctgctgca cacacatctc gtacaagaaa ctttgccgct    4020
gcagctacag ccacacctac gacaacacca acggctacaa ctacaacaag caaccaagta    4080
atcctaggag gagaaatcaa actcatcgat cctaatggga ccttcttcca gaaccctgca    4140
ttaagatccg accaacaaat ctccttgtta gtgctcccta cagactcatc aaaaatgcaa    4200
gctcagaaaa tagtactgac gggtgatatt gctcctcaga aaggatatac aggaacactc    4260
actctggatc ctgatcaact acaaaatgga acgatctcag cgctctggaa atttgactct    4320
tatagacaat gggcttatgt acctagagac aatcatttct atgcgaactc gattctggga    4380
tctcaaatgt caatggtcac agtcaaacaa ggcttgctca acgataaaat gaatctagct    4440
cgctttgatg aagttagcta taacaacctg tggatatcag gactaggaac gatgctatcg    4500
caagtaggaa cacctacttc tgaagaattc acttattaca gcagaggagc ttctgttgcc    4560
ttagatgcta accagcccca tgatgtgatt gttggagctg catttagtaa gatgatcggg    4620
aaaacaaaat ccttgaaaag agagaataac tacactcaca aaggatccga atattcttac    4680
caagcatcgg tatacggagg caaaccattc cactttgtaa tcaataaaaa aacggaaaaa    4740
tcgctaccgc tattgttaca aggagtcatc tcttacggat atatcaaaca tgatacagtg    4800
actcactatc caacgatccg tgaacgaaac caaggagaat gggaagactt aggatggctg    4860
acagctctcc gtgtctcctc tgtcttaaga actcctgcac aagggatac taaacgtatc    4920 actgtttacg gagaattgga atactccagt atccgtcaga aacaattcac agaaacagaa    4980
tacgatcctc gttacttcga caactgcacc tatagaaact agcaattcc tatgggtta     5040 gcattcgaag gagagctctc tggtaacgat attttgatgt acaacagatt ctctgtagca    5100
tacatgccat caatctatcg aaattctcca acatgcaaat accaagtgct ctcttcagga    5160
gaaggcggag aaattatttg tggagtaccg acaagaaact cagctcgcgg agaatacagc    5220
acgcagctgt acccgggacc tttgtggact ctgtatggat cctacacgat agaagcagac    5280
```

```
gcacatacac tagctcatat gatgaactgc ggtgctcgta tgacattcta a          5331

<210> SEQ ID NO 174
<211> LENGTH: 5265
<212> TYPE: DNA
<213> ORGANISM: Chlamydia

<400> SEQUENCE: 174
gcaatcatga aatggctgtc agctactgcg gtgtttgctg ctgttctccc ctcagtttca    60
gggttttgct tcccagaacc taagaattaa aatttctctc gcgtagaaac ttcttcctct   120
accactttta ctgaaacaat tggagaagct ggggcagaat atatcgtctc tggtaacgca   180
tctttcacaa aatttaccaa cattcctact accgatacaa caactcccac gaactcaaac   240
tcctctagct ctagcggaga aactgcttcc gtttctgagg atagtgactc tacaacaacg   300
actcctgatc ctaaaggtgg cggcgccttt tataacgcgc actccggagt tttgtccttt   360
atgacacgat caggaacaga aggttcctta actctgtctg agataaaaat gactggtgaa   420
ggcggtgcta tcttctctca aggagagctg ctatttacag atctgacaag tctaaccatc   480
caaaataact tatcccagct atccggagga gcgattttg gaggatctac aatctcccta    540
tcagggatta ctaaagcgac tttctcctgc aactctgcag aagttcctgc tcctgttaag   600
aaacctacag aacctaaagc tcaaacagca agcgaaacgt cgggttctag tagttctagc   660
ggaaatgatt cggtgtcttc ccccagttcc agtagagctg aacccgcagc agctaatctt   720
caaagtcact ttatttgtgc tacagctact cctgctgctc aaaccgatac agaaacatca   780
actccctctc ataagccagg atctggggga gctatctatg ctaaaggcga ccttactatc   840
gcagactctc aagaggtact attctcaata aataaagcta ctaaagatgg aggagcgatc   900
tttgctgaga aagatgtttc tttcgagaat attacatcat taaagtaca aactaacggt    960
gctgaagaaa agggaggagc tatctatgct aaaggtgacc tctcaattca atcttctaaa  1020
cagagtcttt ttaattctaa ctacagtaaa caaggtgggg gggctctata tgttgaagga  1080
ggtataaact tccaagatct tgaagaaatt cgcattaagt acaataaagc tggaacgttc  1140
gaaacaaaaa aaatcacttt accttcttta aaagctcaag catctgcagg aaatgcagat  1200
gcttgggcct cttcctctcc tcaatctggt tctggagcaa ctacagtctc cgactcagga  1260
gactctagct ctggctcaga ctcggatacc tcagaaacag ttccagtcac agctaaaggc  1320
ggtgggcttt atactgataa gaatctttcg attactaaca tcacaggaat tatcgaaatt  1380
gcaaataaca aagcgacaga tgttggaggt ggtgcttacg taaaaggaac ccttacttgt  1440
gaaaactctc accgtctaca atttttgaaa aactcttccg ataaacaagg tggaggaatc  1500
tacggagaag acaacatcac cctatctaat ttgacaggga agactctatt ccaagagaat  1560
actgccaaag aagagggcgg tggactcttc ataaaaggta cagataaagc tcttacaatg  1620
acaggactgg atagtttctg tttaattaat aacacatcag aaaaacatgg tggtggagcc  1680
tttgttacca aagaaatctc tcagacttac acctctgatg tggaaacaat tccaggaatc  1740
acgcctgtac atggtgaaac agtcattact ggcaataaat ctacaggagg taatggtgga  1800
ggcgtgtgta caaaacgtct tgccttatct aaccttcaaa gcatttctat atccgggaat  1860
tctgcagcag aaaatggtgg tggagcccac acatgcccag atagcttccc aacggcggat  1920
actgcagaac agcccgcagc agcttctgcc gcgacgtcta ctcccaaatc tgccccggtc  1980
tcaactgctc taagcacacc ttcatcttct accgtctctt cattaacctt actagcagcc  2040
```

```
tcttcacaag cctctcctgc aacctctaat aaggaaactc aagatcctaa tgctgataca    2100
gacttattga tcgattatgt agttgatacg actatcagca aaaacactgc taagaaaggc    2160
ggtggaatct atgctaaaaa agccaagatg tcccgcatag accaactgaa tatctctgag    2220
aactccgcta cagagatagg tggaggtatc tgctgtaaag aatctttaga actagatgct    2280
ctagtctcct tatctgtaac agagaacctt gttgggaaaa aggtggagg cttacatgct    2340 aaaactgtaa atatttctaa tctgaaatca ggcttctctt tctcgaacaa caaagcaaac    2400
tcctcatcca caggagtcgc aacaacagct tcagcacctg ctgcagctgc tgcttcccta    2460
caagcagccg cagcagccgc accatcatct ccagcaacac caacttattc aggtgtagta    2520
ggaggagcta tctatggaga aaaggttaca ttctctcaat gtagcgggac ttgtcagttc    2580
tctgggaacc aagctatcga taacaatccc tcccaatcat cgttgaacgt acaaggagga    2640
gccatctatg ccaaaacctc tttgtctatt ggatcttccg atgctggaac ctcctatatt    2700
ttctcgggga acagtgtctc cactgggaaa tctcaaacaa cagggcaaat agcgggagga    2760
gcgatctact cccctactgt tacattgaat tgtcctgcga cattctctaa caatacagcc    2820
tctatagcta caccgaagac ttcttctgaa gatggatcct caggaaattc tattaaagat    2880
accattggag gagccattgc agggacagcc attaccctat ctggagtctc tcgattttca    2940
gggaatacgg ctgatttagg agctgcaata ggaactctag ctaatgcaaa tacacccagt    3000
gcaactagcg gatctcaaaa tagcattaca gaaaaaatta cttttagaaaa cggttctttt    3060 attttgaaa gaaaccaagc taataaacgt ggagcgattt actctcctag cgtttccatt    3120
aaagggaata atattacctt caatcaaaat acatccactc atgatggaag cgctatctac    3180
tttacaaaag atgctacgat tgagtcttta ggatctgttc tttttacagg aaataacgtt    3240
acagctacac aagctagttc tgcaacatct ggacaaaata caaatactgc caactatggg    3300
gcagccatct ttggagatcc aggaaccact caatcgtctc aaacagatgc cattttaacc    3360
cttcttgctt cttctggaaa cattactttt agcaacaaca gtttacagaa taaccaaggt    3420
gatactcccg ctagcaagtt ttgtagtatt gcaggatacg tcaaactctc tctacaagcc    3480
gctaaaggga agactattag ctttttcgat tgtgtgcaca cctctaccaa aaaacaggt    3540 tcaacacaaa acgtttatga aactttagat attaataaag aagagaacag taatccatat    3600
acaggaacta ttgtgttctc ttctgaatta catgaaaaca aatcttacat cccacagaat    3660
gcaatccttc acaacggaac tttagttctt aaagagaaaa cagaactcca cgtagtctct    3720
tttgagcaga aagaagggtc taaattaatt atggaacccg gagctgtgtt atctaaccaa    3780
aacatagcta acggagctct agctatcaat gggttaacga ttgatctttc cagtatgggg    3840
actcctcaag caggggaaat cttctctcct ccagaattac gtatcgttgc cacgacctct    3900
agtgcatccg gaggaagcgg ggtcagcagt agtataccaa caatcctaa aaggatttct    3960 gcagcagtgc cttcaggttc tgccgcaact actccaacta tgagcgagaa caaagttttc    4020
ctaacaggag accttacttt aatagatcct aatgaaaact tttaccaaaa ccctatgtta    4080
ggaagcgatc tagatgtacc actaattaag cttccgacta acacaagtga cgtccaagtc    4140
tatgatttaa ctttatctgg ggatcttttc cctcagaaag ggtacatggg aacctggaca    4200
ttagattcta atccacaaac agggaaactt caagccagat ggacattcga tacctatcgt    4260
cgctgggtat acatacctag ggataatcat tttatgcga actctatctt aggctcccaa    4320
aactcaatga ttgttgtgaa gcaagggctt atcaacaaca tgttgaataa tgcccgcttc    4380
gatgatatcg cttacaataa cttctgggtt tcaggagtag gaactttctt agctcaacaa    4440
```

```
ggaactcctc tttccgaaga attcagttac tacagccgcg gaacttcagt tgccatcgat    4500
gccaaaccta gacaagattt tatcctagga gctgcattta gtaagatagt ggggaaaacc    4560
aaagccatca aaaaaatgca taattacttc cataagggct ctgagtactc ttaccaagct    4620
tctgtctatg gaggtaaatt cctgtatttc ttgctcaata agcaacatgg ttgggcactt    4680
cctttcctaa tacaaggagt cgtgtcctat ggacatatta acatgatac aacaacactt    4740 taccettcta tccatgaaag aaataaagga gattgggaag atttaggatg gttagcggat    4800
cttcgtatct ctatggatct taagaacct tctaaagatt cttctaaacg gatcactgtc    4860
tatggggaac tcgagtattc cagcattcgc cagaaacagt tcacagaaat cgattacgat    4920
ccaagacact tcgatgattg tgcttacaga aatctgtcgc ttcctgtggg atgcgctgtc    4980
gaaggagcta tcatgaactg taatattctt atgtataata agcttgcatt agcctacatg    5040
ccttctatct acagaaataa tcctgtctgt aaatatcggg tattgtcttc gaatgaagct    5100
ggtcaagtta tctgcggagt gccaactaga acctctgcta gagcagaata cagtactcaa    5160
ctatatcttg gtcccttctg gactctctac ggaaactata ctatcgatgt aggcatgtat    5220
acgctatcgc aaatgactag ctgcggtgct cgcatgatct tctaa    5265
```

<210> SEQ ID NO 175
<211> LENGTH: 880
<212> TYPE: PRT
<213> ORGANISM: Chlamydia
<220> FEATURE:
<221> NAME/KEY: VARIANT
<222> LOCATION: (1)...(880)
<223> OTHER INFORMATION: Xaa = Any Amino Acid

<400> SEQUENCE: 175

```
Ala Ile Met Arg Pro Asp His Met Asn Phe Cys Cys Leu Cys Ala Ala
 1               5                  10                  15

Ile Leu Ser Ser Thr Ala Val Leu Phe Gly Gln Asp Pro Leu Gly Glu
            20                  25                  30

Thr Ala Leu Leu Thr Lys Asn Pro Asn His Val Val Cys Thr Phe Phe
        35                  40                  45

Glu Asp Cys Thr Met Glu Ser Leu Phe Pro Ala Leu Cys Ala His Ala
    50                  55                  60

Ser Gln Asp Asp Pro Leu Tyr Val Leu Gly Asn Ser Tyr Cys Trp Phe
65                  70                  75                  80

Val Ser Lys Leu His Ile Thr Asp Pro Lys Glu Ala Leu Phe Lys Glu
                85                  90                  95

Lys Gly Asp Leu Ser Ile Gln Asn Phe Arg Phe Leu Ser Phe Thr Asp
            100                 105                 110

Cys Ser Ser Lys Glu Ser Ser Pro Ser Ile Ile His Gln Lys Asn Gly
        115                 120                 125

Gln Leu Ser Leu Arg Asn Asn Gly Ser Met Ser Phe Cys Arg Asn His
    130                 135                 140

Ala Glu Gly Ser Gly Gly Ala Ile Ser Ala Ala Phe Ser Leu Gln
145                 150                 155                 160

His Asn Tyr Leu Phe Thr Ala Phe Glu Glu Asn Ser Ser Lys Gly Asn
                165                 170                 175

Gly Gly Ala Ile Gln Ala Gln Thr Phe Ser Leu Ser Arg Asn Val Ser
            180                 185                 190

Pro Ile Ser Phe Ala Arg Asn Arg Ala Asp Leu Asn Gly Gly Ala Ile
        195                 200                 205
```

-continued

```
Cys Cys Ser Asn Leu Ile Cys Ser Gly Asn Val Asn Pro Leu Phe Phe
    210                 215                 220
Thr Gly Asn Ser Ala Thr Asn Gly Gly Ala Ile Cys Cys Ile Ser Asp
225                 230                 235                 240
Leu Asn Thr Ser Glu Lys Gly Ser Leu Ser Leu Ala Cys Asn Gln Glu
                245                 250                 255
Thr Leu Phe Ala Ser Asn Ser Ala Lys Glu Lys Gly Gly Ala Ile Tyr
                260                 265                 270
Ala Lys His Met Val Leu Arg Tyr Asn Gly Pro Val Ser Phe Ile Asn
                275                 280                 285
Asn Ser Ala Lys Ile Gly Gly Ala Ile Ala Ile Gln Ser Gly Gly Ser
290                 295                 300
Leu Ser Ile Leu Ala Gly Glu Gly Ser Val Leu Phe Gln Asn Asn Ser
305                 310                 315                 320
Gln Arg Thr Ser Asp Gln Gly Leu Val Arg Asn Ala Ile Tyr Leu Xaa
                325                 330                 335
Lys Asp Ala Ile Leu Ser Ser Leu Glu Ala Arg Asn Gly Asp Ile Leu
                340                 345                 350
Phe Phe Asp Pro Ile Val Gln Glu Ser Ser Lys Glu Ser Pro Leu
                355                 360                 365
Pro Ser Ser Leu Gln Ala Ser Val Thr Ser Pro Thr Pro Ala Thr Ala
370                 375                 380
Ser Pro Leu Val Ile Gln Thr Ser Ala Asn Arg Ser Val Ile Phe Ser
385                 390                 395                 400
Ser Glu Arg Leu Ser Glu Glu Lys Thr Pro Asp Asn Leu Thr Ser
                405                 410                 415
Gln Leu Gln Gln Pro Ile Glu Leu Lys Ser Gly Arg Leu Val Leu Lys
                420                 425                 430
Asp Arg Ala Val Leu Ser Ala Pro Ser Leu Ser Gln Asp Pro Gln Ala
                435                 440                 445
Leu Leu Ile Met Glu Ala Gly Thr Ser Leu Lys Thr Ser Ser Asp Leu
                450                 455                 460
Lys Leu Ala Thr Leu Ser Ile Pro Leu His Ser Leu Asp Thr Glu Lys
465                 470                 475                 480
Ser Val Thr Ile His Ala Pro Asn Leu Ser Ile Gln Lys Ile Phe Leu
                485                 490                 495
Ser Asn Ser Gly Asp Glu Asn Phe Tyr Glu Asn Val Glu Leu Leu Ser
                500                 505                 510
Lys Glu Gln Asn Asn Ile Pro Leu Leu Thr Leu Pro Lys Glu Gln Ser
                515                 520                 525
His Leu His Leu Pro Asp Gly Asn Leu Ser Ser His Phe Gly Tyr Gln
                530                 535                 540
Gly Asp Trp Thr Phe Ser Trp Lys Asp Ser Asp Glu Gly His Ser Leu
545                 550                 555                 560
Ile Ala Asn Trp Thr Pro Lys Asn Tyr Val Pro His Pro Glu Arg Gln
                565                 570                 575
Ser Thr Leu Val Ala Asn Thr Leu Trp Asn Thr Tyr Ser Asp Met Gln
                580                 585                 590
Ala Val Gln Ser Met Ile Asn Thr Thr Ala His Gly Gly Ala Tyr Leu
                595                 600                 605
Phe Gly Thr Trp Gly Ser Ala Val Ser Asn Leu Phe Tyr Val His Asp
610                 615                 620
```

```
Ser Ser Gly Lys Pro Ile Asp Asn Trp His His Arg Ser Leu Gly Tyr
625                 630                 635                 640

Leu Phe Gly Ile Ser Thr His Ser Leu Asp Asp His Ser Phe Cys Leu
                645                 650                 655

Ala Ala Gly Gln Leu Leu Gly Lys Ser Ser Asp Ser Phe Ile Thr Ser
                660                 665                 670

Thr Glu Thr Thr Ser Tyr Ile Ala Thr Val Gln Ala Gln Leu Ala Thr
            675                 680                 685

Ser Leu Met Lys Ile Ser Ala Gln Ala Cys Tyr Asn Glu Ser Ile His
            690                 695                 700

Glu Leu Lys Thr Lys Tyr Arg Ser Phe Ser Lys Glu Gly Phe Gly Ser
705                 710                 715                 720

Trp His Ser Val Ala Val Ser Gly Glu Val Cys Ala Ser Ile Pro Ile
                725                 730                 735

Val Ser Asn Gly Ser Gly Leu Phe Ser Ser Phe Ser Ile Phe Ser Lys
                740                 745                 750

Leu Gln Gly Phe Ser Gly Thr Gln Asp Gly Phe Glu Glu Ser Ser Gly
                755                 760                 765

Glu Ile Arg Ser Phe Ser Ala Ser Ser Phe Arg Asn Ile Ser Leu Pro
770                 775                 780

Ile Gly Ile Thr Phe Glu Lys Lys Ser Gln Lys Thr Arg Thr Tyr Tyr
785                 790                 795                 800

Tyr Phe Leu Gly Ala Tyr Ile Gln Asp Leu Lys Arg Asp Val Glu Ser
                805                 810                 815

Gly Pro Val Val Leu Leu Lys Asn Ala Val Ser Trp Asp Ala Pro Met
                820                 825                 830

Ala Asn Leu Asp Ser Arg Ala Tyr Met Phe Arg Leu Thr Asn Gln Arg
                835                 840                 845

Ala Leu His Arg Leu Gln Thr Leu Leu Asn Val Ser Cys Val Leu Arg
                850                 855                 860

Gly Gln Ser His Ser Tyr Ser Leu Asp Leu Gly Thr Thr Tyr Arg Phe
865                 870                 875                 880
```

<210> SEQ ID NO 176
<211> LENGTH: 982
<212> TYPE: PRT
<213> ORGANISM: Chlamydia
<220> FEATURE:
<221> NAME/KEY: VARIANT
<222> LOCATION: (1)...(982)
<223> OTHER INFORMATION: Xaa = Any Amino Acid

<400> SEQUENCE: 176

```
Met Ile Pro Gln Gly Ile Tyr Asp Gly Glu Thr Leu Thr Val Ser Phe
1               5                   10                  15

Pro Tyr Thr Val Ile Gly Asp Pro Ser Gly Thr Thr Val Phe Ser Ala
                20                  25                  30

Gly Glu Leu Thr Leu Lys Asn Leu Asp Asn Ser Ile Ala Ala Leu Pro
                35                  40                  45

Leu Ser Cys Phe Gly Asn Leu Leu Gly Ser Phe Thr Val Leu Gly Arg
            50                  55                  60

Gly His Ser Leu Thr Phe Glu Asn Ile Arg Thr Ser Thr Asn Gly Ala
65                  70                  75                  80

Ala Leu Ser Asn Ser Ala Ala Asp Gly Leu Phe Thr Ile Glu Gly Phe
                85                  90                  95

Lys Glu Leu Ser Phe Ser Asn Cys Asn Ser Leu Leu Ala Val Leu Pro
```

-continued

```
                  100                 105                 110
Ala Ala Thr Thr Asn Lys Gly Ser Gln Thr Pro Thr Thr Ser Thr
            115                 120                 125
Pro Ser Asn Gly Thr Ile Tyr Ser Lys Thr Asp Leu Leu Leu Asn
130                 135                 140
Asn Glu Lys Phe Ser Phe Tyr Ser Asn Leu Val Ser Gly Asp Gly
145                 150                 155                 160
Ala Ile Asp Ala Lys Ser Leu Thr Val Gln Gly Ile Ser Lys Leu Cys
            165                 170                 175
Val Phe Gln Glu Asn Thr Ala Gln Ala Asp Gly Gly Ala Cys Gln Val
                180                 185                 190
Val Thr Ser Phe Ser Ala Met Ala Asn Glu Ala Pro Ile Ala Phe Val
            195                 200                 205
Ala Asn Val Ala Gly Val Arg Gly Gly Gly Ile Ala Ala Val Gln Asp
            210                 215                 220
Gly Gln Gln Gly Val Ser Ser Thr Ser Thr Glu Asp Pro Val Val
225                 230                 235                 240
Ser Phe Ser Arg Asn Thr Ala Val Glu Phe Asp Gly Asn Val Ala Arg
                245                 250                 255
Val Gly Gly Gly Ile Tyr Ser Tyr Gly Asn Val Ala Phe Leu Asn Asn
            260                 265                 270
Gly Lys Thr Leu Phe Leu Asn Asn Val Ala Ser Pro Val Tyr Ile Ala
            275                 280                 285
Ala Lys Gln Pro Thr Ser Gly Gln Ala Ser Asn Thr Ser Asn Asn Tyr
            290                 295                 300
Gly Asp Gly Gly Ala Ile Phe Cys Lys Asn Gly Ala Gln Ala Gly Ser
305                 310                 315                 320
Asn Asn Ser Gly Ser Val Ser Phe Asp Gly Glu Gly Val Val Phe Phe
                325                 330                 335
Ser Ser Asn Val Ala Ala Gly Lys Gly Gly Ala Ile Tyr Ala Lys Lys
                340                 345                 350
Leu Ser Val Ala Asn Cys Gly Pro Val Gln Phe Leu Arg Asn Ile Ala
            355                 360                 365
Asn Asp Gly Gly Ala Ile Tyr Leu Gly Glu Ser Gly Glu Leu Ser Leu
370                 375                 380
Ser Ala Asp Tyr Gly Asp Ile Ile Phe Asp Gly Asn Leu Lys Arg Thr
385                 390                 395                 400
Ala Lys Glu Asn Ala Ala Asp Val Asn Gly Val Thr Val Ser Ser Gln
                405                 410                 415
Ala Ile Ser Met Gly Ser Gly Gly Lys Ile Thr Thr Leu Arg Ala Lys
            420                 425                 430
Ala Gly His Gln Ile Leu Phe Asn Asp Pro Ile Glu Met Ala Asn Gly
            435                 440                 445
Asn Asn Gln Pro Ala Gln Ser Ser Lys Leu Leu Lys Ile Asn Asp Gly
            450                 455                 460
Glu Gly Tyr Thr Gly Asp Ile Val Phe Ala Asn Gly Ser Ser Thr Leu
465                 470                 475                 480
Tyr Gln Asn Val Thr Ile Glu Gln Gly Arg Ile Val Leu Arg Glu Lys
                485                 490                 495
Ala Lys Leu Ser Val Asn Ser Leu Ser Gln Thr Gly Gly Ser Leu Tyr
            500                 505                 510
Met Glu Ala Gly Ser Thr Leu Asp Phe Val Thr Pro Gln Pro Gln
515                 520                 525
```

```
Gln Pro Pro Ala Ala Asn Gln Leu Ile Thr Leu Ser Asn Leu His Leu
    530                 535                 540

Ser Leu Ser Ser Leu Leu Ala Asn Asn Ala Val Thr Asn Pro Pro Thr
545                 550                 555                 560

Asn Pro Pro Ala Gln Asp Ser His Pro Ala Val Ile Gly Ser Thr Thr
                565                 570                 575

Ala Gly Ser Val Thr Ile Ser Gly Pro Ile Phe Phe Glu Asp Leu Asp
            580                 585                 590

Asp Thr Ala Tyr Asp Arg Tyr Asp Trp Leu Gly Ser Asn Gln Lys Ile
        595                 600                 605

Asn Val Leu Lys Leu Gln Leu Gly Thr Lys Pro Pro Ala Asn Ala Pro
    610                 615                 620

Ser Asp Leu Thr Leu Gly Asn Glu Met Pro Lys Tyr Gly Tyr Gln Gly
625                 630                 635                 640

Ser Trp Lys Leu Ala Trp Asp Pro Asn Thr Ala Asn Asn Gly Pro Tyr
                645                 650                 655

Thr Leu Lys Ala Thr Trp Thr Lys Thr Gly Tyr Asn Pro Gly Pro Glu
            660                 665                 670

Arg Val Ala Ser Leu Val Pro Asn Ser Leu Trp Gly Ser Ile Leu Asp
        675                 680                 685

Ile Arg Ser Ala His Ser Ala Ile Gln Ala Ser Val Asp Gly Arg Ser
    690                 695                 700

Tyr Cys Arg Gly Leu Trp Val Ser Gly Val Ser Asn Phe Phe Tyr His
705                 710                 715                 720

Asp Arg Asp Ala Leu Gly Gln Gly Tyr Arg Tyr Ile Ser Gly Gly Tyr
                725                 730                 735

Ser Leu Gly Ala Asn Ser Tyr Phe Gly Ser Ser Met Phe Gly Leu Ala
            740                 745                 750

Phe Thr Glu Val Phe Gly Arg Ser Lys Asp Tyr Val Val Cys Arg Ser
        755                 760                 765

Asn His His Ala Cys Ile Gly Ser Val Tyr Leu Ser Thr Gln Gln Ala
    770                 775                 780

Leu Cys Gly Ser Tyr Leu Phe Gly Asp Ala Phe Ile Arg Ala Ser Tyr
785                 790                 795                 800

Gly Phe Gly Asn Gln His Met Lys Thr Ser Tyr Thr Phe Ala Glu Glu
                805                 810                 815

Ser Asp Val Arg Trp Asp Asn Asn Cys Leu Ala Gly Glu Ile Gly Ala
            820                 825                 830

Gly Leu Pro Ile Val Ile Thr Pro Ser Lys Leu Tyr Leu Asn Glu Leu
        835                 840                 845

Arg Pro Phe Val Gln Ala Glu Phe Ser Tyr Ala Asp His Glu Ser Phe
    850                 855                 860

Thr Glu Glu Gly Asp Gln Ala Arg Ala Phe Lys Ser Gly His Leu Leu
865                 870                 875                 880

Asn Leu Ser Val Pro Val Gly Val Lys Phe Asp Arg Cys Ser Ser Thr
                885                 890                 895

His Pro Asn Lys Tyr Ser Phe Met Ala Ala Tyr Ile Cys Asp Ala Tyr
            900                 905                 910

Arg Thr Ile Ser Gly Thr Glu Thr Leu Leu Ser His Gln Glu Thr
        915                 920                 925

Trp Thr Thr Asp Ala Phe His Leu Ala Arg His Gly Val Val Val Arg
930                 935                 940
```

```
Gly Ser Met Tyr Ala Ser Leu Thr Ser Asn Ile Glu Val Tyr Gly His
945                 950                 955                 960

Gly Arg Tyr Glu Tyr Arg Asp Ala Ser Arg Gly Tyr Gly Leu Ser Ala
                965                 970                 975

Gly Ser Lys Val Xaa Phe
                980

<210> SEQ ID NO 177
<211> LENGTH: 964
<212> TYPE: PRT
<213> ORGANISM: Chlamydia

<400> SEQUENCE: 177

Met Lys Lys Ala Phe Phe Phe Leu Ile Gly Asn Ser Leu Ser Gly
  1               5                  10                  15

Leu Ala Arg Glu Val Pro Ser Arg Ile Phe Leu Met Pro Asn Ser Val
                 20                  25                  30

Pro Asp Pro Thr Lys Glu Ser Leu Ser Asn Lys Ile Ser Leu Thr Gly
                 35                  40                  45

Asp Thr His Asn Leu Thr Asn Cys Tyr Leu Asp Asn Leu Arg Tyr Ile
 50                  55                  60

Leu Ala Ile Leu Gln Lys Thr Pro Asn Glu Gly Ala Val Thr Ile
 65                  70                  75                  80

Thr Asp Tyr Leu Ser Phe Phe Asp Thr Gln Lys Glu Gly Ile Tyr Phe
                 85                  90                  95

Ala Lys Asn Leu Thr Pro Glu Ser Gly Ala Ile Gly Tyr Ala Ser
                100                 105                 110

Pro Asn Ser Pro Thr Val Glu Ile Arg Asp Thr Ile Gly Pro Val Ile
                115                 120                 125

Phe Glu Asn Asn Thr Cys Cys Arg Leu Phe Thr Trp Arg Asn Pro Tyr
130                 135                 140

Ala Ala Asp Lys Ile Arg Glu Gly Gly Ala Ile His Ala Gln Asn Leu
145                 150                 155                 160

Tyr Ile Asn His Asn His Asp Val Val Gly Phe Met Lys Asn Phe Ser
                165                 170                 175

Tyr Val Gln Gly Gly Ala Ile Ser Thr Ala Asn Thr Phe Val Val Ser
                180                 185                 190

Glu Asn Gln Ser Cys Phe Leu Phe Met Asp Asn Ile Cys Ile Gln Thr
                195                 200                 205

Asn Thr Ala Gly Lys Gly Ala Ile Tyr Ala Gly Thr Ser Asn Ser
210                 215                 220

Phe Glu Ser Asn Asn Cys Asp Leu Phe Phe Ile Asn Asn Ala Cys Cys
225                 230                 235                 240

Ala Gly Gly Ala Ile Phe Ser Pro Ile Cys Ser Leu Thr Gly Asn Arg
                245                 250                 255

Gly Asn Ile Val Phe Tyr Asn Asn Arg Cys Phe Lys Asn Val Glu Thr
                260                 265                 270

Ala Ser Ser Glu Ala Ser Asp Gly Gly Ala Ile Lys Val Thr Thr Arg
                275                 280                 285

Leu Asp Val Thr Gly Asn Arg Gly Arg Ile Phe Phe Ser Asp Asn Ile
                290                 295                 300

Thr Lys Asn Tyr Gly Gly Ala Ile Tyr Ala Pro Val Val Thr Leu Val
305                 310                 315                 320

Asp Asn Gly Pro Thr Tyr Phe Ile Asn Asn Ile Ala Asn Asn Lys Gly
                325                 330                 335
```

-continued

```
Gly Ala Ile Tyr Ile Asp Gly Thr Ser Asn Ser Lys Ile Ser Ala Asp
            340                 345                 350
Arg His Ala Ile Ile Phe Asn Glu Asn Ile Val Thr Asn Val Thr Asn
            355                 360                 365
Ala Asn Gly Thr Ser Thr Ser Ala Asn Pro Pro Arg Arg Asn Ala Ile
            370                 375                 380
Thr Val Ala Ser Ser Ser Gly Glu Ile Leu Leu Gly Ala Gly Ser Ser
385                 390                 395                 400
Gln Asn Leu Ile Phe Tyr Asp Pro Ile Glu Val Ser Asn Ala Gly Val
            405                 410                 415
Ser Val Ser Phe Asn Lys Glu Ala Asp Gln Thr Gly Ser Val Val Phe
            420                 425                 430
Ser Gly Ala Thr Val Asn Ser Ala Asp Phe His Gln Arg Asn Leu Gln
            435                 440                 445
Thr Lys Thr Pro Ala Pro Leu Thr Leu Ser Asn Gly Phe Leu Cys Ile
            450                 455                 460
Glu Asp His Ala Gln Leu Thr Val Asn Arg Phe Thr Gln Thr Gly Gly
465                 470                 475                 480
Val Val Ser Leu Gly Asn Gly Ala Val Leu Ser Cys Tyr Lys Asn Gly
            485                 490                 495
Thr Gly Asp Ser Ala Ser Asn Ala Ser Ile Thr Leu Lys His Ile Gly
            500                 505                 510
Leu Asn Leu Ser Ser Ile Leu Lys Ser Gly Ala Glu Ile Pro Leu Leu
            515                 520                 525
Trp Val Glu Pro Thr Asn Asn Ser Asn Asn Tyr Thr Ala Asp Thr Ala
            530                 535                 540
Ala Thr Phe Ser Leu Ser Asp Val Lys Leu Ser Leu Ile Asp Asp Tyr
545                 550                 555                 560
Gly Asn Ser Pro Tyr Glu Ser Thr Asp Leu Thr His Ala Leu Ser Ser
            565                 570                 575
Gln Pro Met Leu Ser Ile Ser Glu Ala Ser Asp Asn Gln Leu Gln Ser
            580                 585                 590
Glu Asn Ile Asp Phe Ser Gly Leu Asn Val Pro His Tyr Gly Trp Gln
            595                 600                 605
Gly Leu Trp Thr Trp Gly Trp Ala Lys Thr Gln Asp Pro Glu Pro Ala
            610                 615                 620
Ser Ser Ala Thr Ile Thr Asp Pro Gln Lys Ala Asn Arg Phe His Arg
625                 630                 635                 640
Thr Leu Leu Leu Thr Trp Leu Pro Ala Gly Tyr Val Pro Ser Pro Lys
            645                 650                 655
His Arg Ser Pro Leu Ile Ala Asn Thr Leu Trp Gly Asn Met Leu Leu
            660                 665                 670
Ala Thr Glu Ser Leu Lys Asn Ser Ala Glu Leu Thr Pro Ser Gly His
            675                 680                 685
Pro Phe Trp Gly Ile Thr Gly Gly Leu Gly Met Met Val Tyr Gln
            690                 695                 700
Asp Pro Arg Glu Asn His Pro Gly Phe His Met Arg Ser Ser Gly Tyr
705                 710                 715                 720
Ser Ala Gly Met Ile Ala Gly Gln Thr His Thr Phe Ser Leu Lys Phe
            725                 730                 735
Ser Gln Thr Tyr Thr Lys Leu Asn Glu Arg Tyr Ala Lys Asn Asn Val
            740                 745                 750
```

```
Ser Ser Lys Asn Tyr Ser Cys Gln Gly Glu Met Leu Phe Ser Leu Gln
        755                 760                 765

Glu Gly Phe Leu Leu Thr Lys Leu Val Gly Leu Tyr Ser Tyr Gly Asp
    770                 775                 780

His Asn Cys His His Phe Tyr Thr Gln Gly Glu Asn Leu Thr Ser Gln
785                 790                 795                 800

Gly Thr Phe Arg Ser Gln Thr Met Gly Gly Ala Val Phe Phe Asp Leu
                805                 810                 815

Pro Met Lys Pro Phe Gly Ser Thr His Ile Leu Thr Ala Pro Phe Leu
                820                 825                 830

Gly Ala Leu Gly Ile Tyr Ser Ser Leu Ser His Phe Thr Glu Val Gly
            835                 840                 845

Ala Tyr Pro Arg Ser Phe Ser Thr Lys Thr Pro Leu Ile Asn Val Leu
    850                 855                 860

Val Pro Ile Gly Val Lys Gly Ser Phe Met Asn Ala Thr His Arg Pro
865                 870                 875                 880

Gln Ala Trp Thr Val Glu Leu Ala Tyr Gln Pro Val Leu Tyr Arg Gln
                885                 890                 895

Glu Pro Gly Ile Ala Thr Gln Leu Leu Ala Ser Lys Gly Ile Trp Phe
                900                 905                 910

Gly Ser Gly Ser Pro Ser Arg His Ala Met Ser Tyr Lys Ile Ser
            915                 920                 925

Gln Gln Thr Gln Pro Leu Ser Trp Leu Thr Leu His Phe Gln Tyr His
    930                 935                 940

Gly Phe Tyr Ser Ser Ser Thr Phe Cys Asn Tyr Leu Asn Gly Glu Ile
945                 950                 955                 960

Ala Leu Arg Phe

<210> SEQ ID NO 178
<211> LENGTH: 1530
<212> TYPE: PRT
<213> ORGANISM: Chlamydia

<400> SEQUENCE: 178

Met Ser Ser Glu Lys Asp Ile Lys Ser Thr Cys Ser Lys Phe Ser Leu
1               5                   10                  15

Ser Val Val Ala Ala Ile Leu Ala Ser Val Ser Gly Leu Ala Ser Cys
            20                  25                  30

Val Asp Leu His Ala Gly Gly Gln Ser Val Asn Glu Leu Val Tyr Val
        35                  40                  45

Gly Pro Gln Ala Val Leu Leu Leu Asp Gln Ile Arg Asp Leu Phe Val
    50                  55                  60

Gly Ser Lys Asp Ser Gln Ala Glu Gly Gln Tyr Arg Leu Ile Val Gly
65                  70                  75                  80

Asp Pro Ser Ser Phe Gln Glu Lys Asp Ala Asp Thr Leu Pro Gly Lys
                85                  90                  95

Val Glu Gln Ser Thr Leu Phe Ser Val Thr Asn Pro Val Val Phe Gln
            100                 105                 110

Gly Val Asp Gln Gln Asp Gln Val Ser Ser Gln Gly Leu Ile Cys Ser
        115                 120                 125

Phe Thr Ser Ser Asn Leu Asp Ser Pro Arg Asp Gly Glu Ser Phe Leu
    130                 135                 140

Gly Ile Ala Phe Val Gly Asp Ser Ser Lys Ala Gly Ile Thr Leu Thr
145                 150                 155                 160
```

-continued

```
Asp Val Lys Ala Ser Leu Ser Gly Ala Ala Leu Tyr Ser Thr Glu Asp
            165                 170                 175

Leu Ile Phe Glu Lys Ile Lys Gly Gly Leu Glu Phe Ala Ser Cys Ser
        180                 185                 190

Ser Leu Glu Gln Gly Gly Ala Cys Ala Ala Gln Ser Ile Leu Ile His
    195                 200                 205

Asp Cys Gln Gly Leu Gln Val Lys His Cys Thr Thr Ala Val Asn Ala
210                 215                 220

Glu Gly Ser Ser Ala Asn Asp His Leu Gly Phe Gly Gly Ala Phe
225                 230                 235                 240

Phe Val Thr Gly Ser Leu Ser Gly Glu Lys Ser Leu Tyr Met Pro Ala
                245                 250                 255

Gly Asp Met Val Val Ala Asn Cys Asp Gly Ala Ile Ser Phe Glu Gly
            260                 265                 270

Asn Ser Ala Asn Phe Ala Asn Gly Gly Ala Ile Ala Ala Ser Gly Lys
        275                 280                 285

Val Leu Phe Val Ala Asn Asp Lys Lys Thr Ser Phe Ile Glu Asn Arg
    290                 295                 300

Ala Leu Ser Gly Gly Ala Ile Ala Ala Ser Ser Asp Ile Ala Phe Gln
305                 310                 315                 320

Asn Cys Ala Glu Leu Val Phe Lys Gly Asn Cys Ala Ile Gly Thr Glu
                325                 330                 335

Asp Lys Gly Ser Leu Gly Gly Ala Ile Ser Ser Leu Gly Thr Val
            340                 345                 350

Leu Leu Gln Gly Asn His Gly Ile Thr Cys Asp Lys Asn Glu Ser Ala
        355                 360                 365

Ser Gln Gly Gly Ala Ile Phe Gly Lys Asn Cys Gln Ile Ser Asp Asn
    370                 375                 380

Glu Gly Pro Val Val Phe Arg Asp Ser Thr Ala Cys Leu Gly Gly
385                 390                 395                 400

Ala Ile Ala Ala Gln Glu Ile Val Ser Ile Gln Asn Asn Gln Ala Gly
                405                 410                 415

Ile Ser Phe Glu Gly Gly Lys Ala Ser Phe Gly Gly Gly Ile Ala Cys
            420                 425                 430

Gly Ser Phe Ser Ser Ala Gly Ala Ser Val Leu Gly Thr Ile Asp
        435                 440                 445

Ile Ser Lys Asn Leu Gly Ala Ile Ser Phe Ser Arg Thr Leu Cys Thr
    450                 455                 460

Thr Ser Asp Leu Gly Gln Met Glu Tyr Gln Gly Gly Ala Leu Phe
465                 470                 475                 480

Gly Glu Asn Ile Ser Leu Ser Glu Asn Ala Gly Val Leu Thr Phe Lys
                485                 490                 495

Asp Asn Ile Val Lys Thr Phe Ala Ser Asn Gly Lys Ile Leu Gly Gly
            500                 505                 510

Gly Ala Ile Leu Ala Thr Gly Lys Val Glu Ile Thr Asn Asn Ser Gly
        515                 520                 525

Gly Ile Ser Phe Thr Gly Asn Ala Arg Ala Pro Gln Ala Leu Pro Thr
    530                 535                 540

Gln Glu Glu Phe Pro Leu Phe Ser Lys Lys Gly Arg Pro Leu Ser
545                 550                 555                 560

Ser Gly Tyr Ser Gly Gly Ala Ile Leu Gly Arg Glu Val Ala Ile
                565                 570                 575

Leu His Asn Ala Ala Val Val Phe Glu Gln Asn Arg Leu Gln Cys Ser
```

```
                580                 585                 590
Glu Glu Glu Ala Thr Leu Leu Gly Cys Cys Gly Gly Ala Val His
            595                 600                 605
Gly Met Asp Ser Thr Ser Ile Val Gly Asn Ser Val Arg Phe Gly
    610                 615                 620
Asn Asn Tyr Ala Met Gly Gln Gly Val Ser Gly Gly Ala Leu Leu Ser
625                 630                 635                 640
Lys Thr Val Gln Leu Ala Gly Asn Gly Ser Val Asp Phe Ser Arg Asn
                645                 650                 655
Ile Ala Ser Leu Gly Gly Ala Leu Gln Ala Ser Glu Gly Asn Cys
                660                 665                 670
Glu Leu Val Asp Asn Gly Tyr Val Leu Phe Arg Asp Asn Arg Gly Arg
                675                 680                 685
Val Tyr Gly Gly Ala Ile Ser Cys Leu Arg Gly Asp Val Val Ile Ser
    690                 695                 700
Gly Asn Lys Gly Arg Val Glu Phe Lys Asp Asn Ile Ala Thr Arg Leu
705                 710                 715                 720
Tyr Val Glu Glu Thr Val Glu Lys Val Glu Val Glu Pro Ala Pro
                725                 730                 735
Glu Gln Lys Asp Asn Asn Glu Leu Ser Phe Leu Gly Ser Val Glu Gln
                740                 745                 750
Ser Phe Ile Thr Ala Ala Asn Gln Ala Leu Phe Ala Ser Glu Asp Gly
        755                 760                 765
Asp Leu Ser Pro Glu Ser Ser Ile Ser Ser Glu Glu Leu Ala Lys Arg
        770                 775                 780
Arg Glu Cys Ala Gly Gly Ala Ile Phe Ala Lys Arg Val Arg Ile Val
785                 790                 795                 800
Asp Asn Gln Glu Ala Val Val Phe Ser Asn Asn Phe Ser Asp Ile Tyr
                805                 810                 815
Gly Gly Ala Ile Phe Thr Gly Ser Leu Arg Glu Glu Asp Lys Leu Asp
                820                 825                 830
Gly Gln Ile Pro Glu Val Leu Ile Ser Gly Asn Ala Gly Asp Val Val
            835                 840                 845
Phe Ser Gly Asn Ser Ser Lys Arg Asp Glu His Leu Pro His Thr Gly
850                 855                 860
Gly Gly Ala Ile Cys Thr Gln Asn Leu Thr Ile Ser Gln Asn Thr Gly
865                 870                 875                 880
Asn Val Leu Phe Tyr Asn Asn Val Ala Cys Ser Gly Gly Ala Val Arg
                885                 890                 895
Ile Glu Asp His Gly Asn Val Leu Leu Glu Ala Phe Gly Asp Ile
            900                 905                 910
Val Phe Lys Gly Asn Ser Ser Phe Arg Ala Gln Gly Ser Asp Ala Ile
        915                 920                 925
Tyr Phe Ala Gly Lys Glu Ser His Ile Thr Ala Leu Asn Ala Thr Glu
    930                 935                 940
Gly His Ala Ile Val Phe His Asp Ala Leu Val Phe Glu Asn Leu Lys
945                 950                 955                 960
Glu Arg Lys Ser Ala Glu Val Leu Leu Ile Asn Ser Arg Glu Asn Pro
                965                 970                 975
Gly Tyr Thr Gly Ser Ile Arg Phe Leu Glu Ala Glu Ser Lys Val Pro
            980                 985                 990
Gln Cys Ile His Val Gln Gln Gly Ser Leu Glu Leu Leu Asn Gly Ala
        995                 1000                1005
```

-continued

```
Thr Leu Cys Ser Tyr Gly Phe Lys Gln Asp Ala Gly Ala Lys Leu Val
    1010                1015                1020
Leu Ala Ala Gly Ser Lys Leu Lys Ile Leu Asp Ser Gly Thr Pro Val
1025                1030                1035                1040
Gln Gly His Ala Ile Ser Lys Pro Glu Ala Glu Ile Glu Ser Ser Ser
                1045                1050                1055
Glu Pro Glu Gly Ala His Ser Leu Trp Ile Ala Lys Asn Ala Gln Thr
                1060                1065                1070
Thr Val Pro Met Val Asp Ile His Thr Ile Ser Val Asp Leu Ala Ser
            1075                1080                1085
Phe Ser Ser Ser Gln Gln Glu Gly Thr Val Glu Ala Pro Gln Val Ile
    1090                1095                1100
Val Pro Gly Gly Ser Tyr Val Arg Ser Gly Glu Leu Asn Leu Glu Leu
1105                1110                1115                1120
Val Asn Thr Thr Gly Thr Gly Tyr Glu Asn His Ala Leu Leu Lys Asn
                1125                1130                1135
Glu Ala Lys Val Pro Leu Met Ser Phe Val Ala Ser Ser Asp Glu Ala
            1140                1145                1150
Ser Ala Glu Ile Ser Asn Leu Ser Val Ser Asp Leu Gln Ile His Val
    1155                1160                1165
Ala Thr Pro Glu Ile Glu Glu Asp Thr Tyr Gly His Met Gly Asp Trp
    1170                1175                1180
Ser Glu Ala Lys Ile Gln Asp Gly Thr Leu Val Ile Asn Trp Asn Pro
1185                1190                1195                1200
Thr Gly Tyr Arg Leu Asp Pro Gln Lys Ala Gly Ala Leu Val Phe Asn
                1205                1210                1215
Ala Leu Trp Glu Glu Gly Ala Val Leu Ser Ala Leu Lys Asn Ala Arg
            1220                1225                1230
Phe Ala His Asn Leu Thr Ala Gln Arg Met Glu Phe Asp Tyr Ser Thr
    1235                1240                1245
Asn Val Trp Gly Phe Ala Phe Gly Gly Phe Arg Thr Leu Ser Ala Glu
    1250                1255                1260
Asn Leu Val Ala Ile Asp Gly Tyr Lys Gly Ala Tyr Gly Gly Ala Ser
1265                1270                1275                1280
Ala Gly Val Asp Ile Gln Leu Met Glu Asp Phe Val Leu Gly Val Ser
                1285                1290                1295
Gly Ala Ala Phe Leu Gly Lys Met Asp Ser Gln Lys Phe Asp Ala Glu
            1300                1305                1310
Val Ser Arg Lys Gly Val Val Gly Ser Val Tyr Thr Gly Phe Leu Ala
    1315                1320                1325
Gly Ser Trp Phe Phe Lys Gly Gln Tyr Ser Leu Gly Glu Thr Gln Asn
    1330                1335                1340
Asp Met Lys Thr Arg Tyr Gly Val Leu Gly Glu Ser Ser Ala Ser Trp
1345                1350                1355                1360
Thr Ser Arg Gly Val Leu Ala Asp Ala Leu Val Glu Tyr Arg Ser Leu
                1365                1370                1375
Val Gly Pro Val Arg Pro Thr Phe Tyr Ala Leu His Phe Asn Pro Tyr
            1380                1385                1390
Val Glu Val Ser Tyr Ala Ser Met Lys Phe Pro Gly Phe Thr Glu Gln
    1395                1400                1405
Gly Arg Glu Ala Arg Ser Phe Glu Asp Ala Ser Leu Thr Asn Ile Thr
    1410                1415                1420
```

-continued

```
Ile Pro Leu Gly Met Lys Phe Glu Leu Ala Phe Ile Lys Gly Gln Phe
1425                1430                1435                1440

Ser Glu Val Asn Ser Leu Gly Ile Ser Tyr Ala Trp Glu Ala Tyr Arg
            1445                1450                1455

Lys Val Glu Gly Gly Ala Val Gln Leu Leu Glu Ala Gly Phe Asp Trp
                1460                1465                1470

Glu Gly Ala Pro Met Asp Leu Pro Arg Gln Glu Leu Arg Val Ala Leu
        1475                1480                1485

Glu Asn Asn Thr Glu Trp Ser Ser Tyr Phe Ser Thr Val Leu Gly Leu
    1490                1495                1500

Thr Ala Phe Cys Gly Gly Phe Thr Ser Thr Asp Ser Lys Leu Gly Tyr
1505                1510                1515                1520

Glu Ala Asn Thr Gly Leu Arg Leu Ile Phe
                1525                1530

<210> SEQ ID NO 179
<211> LENGTH: 1776
<212> TYPE: PRT
<213> ORGANISM: Chlamydia

<400> SEQUENCE: 179

Ala Ile Met Lys Phe Met Ser Ala Thr Ala Val Phe Ala Ala Val Leu
1               5                   10                  15

Ser Ser Val Thr Glu Ala Ser Ser Ile Gln Asp Gln Ile Lys Asn Thr
            20                  25                  30

Asp Cys Asn Val Ser Lys Val Gly Tyr Ser Thr Ser Gln Ala Phe Thr
        35                  40                  45

Asp Met Met Leu Ala Asp Asn Thr Glu Tyr Arg Ala Ala Asp Ser Val
    50                  55                  60

Ser Phe Tyr Asp Phe Ser Thr Ser Gly Leu Pro Arg Lys His Leu
65                  70                  75                  80

Ser Ser Ser Ser Glu Ala Ser Pro Thr Thr Glu Gly Val Ser Ser Ser
                85                  90                  95

Ser Ser Gly Glu Asn Thr Glu Asn Ser Gln Asp Ser Ala Pro Ser Ser
            100                 105                 110

Gly Glu Thr Asp Lys Lys Thr Glu Glu Glu Leu Asp Asn Gly Gly Ile
        115                 120                 125

Ile Tyr Ala Arg Glu Lys Leu Thr Ile Ser Glu Ser Gln Asp Ser Leu
    130                 135                 140

Ser Asn Pro Ser Ile Glu Leu His Asp Asn Ser Phe Phe Phe Gly Glu
145                 150                 155                 160

Gly Glu Val Ile Phe Asp His Arg Val Ala Leu Lys Asn Gly Gly Ala
                165                 170                 175

Ile Tyr Gly Glu Lys Glu Val Val Phe Glu Asn Ile Lys Ser Leu Leu
            180                 185                 190

Val Glu Val Asn Ile Ser Val Glu Lys Gly Gly Ser Val Tyr Ala Lys
        195                 200                 205

Glu Arg Val Ser Leu Glu Asn Val Thr Glu Ala Thr Phe Ser Ser Asn
    210                 215                 220

Gly Gly Glu Gln Gly Gly Gly Ile Tyr Ser Glu Gln Asp Met Leu
225                 230                 235                 240

Ile Ser Asp Cys Asn Asn Val His Phe Gln Gly Asn Ala Ala Gly Ala
                245                 250                 255

Thr Ala Val Lys Gln Cys Leu Asp Glu Glu Met Ile Val Leu Leu Thr
            260                 265                 270
```

-continued

```
Glu Cys Val Asp Ser Leu Ser Glu Asp Thr Leu Asp Ser Thr Pro Glu
            275                 280                 285

Thr Glu Gln Thr Lys Ser Asn Gly Asn Gln Asp Gly Ser Ser Glu Thr
        290                 295                 300

Lys Asp Thr Gln Val Ser Glu Ser Pro Glu Ser Thr Pro Ser Pro Asp
305                 310                 315                 320

Asp Val Leu Gly Lys Gly Gly Gly Ile Tyr Thr Glu Lys Ser Leu Thr
                    325                 330                 335

Ile Thr Gly Ile Thr Gly Thr Ile Asp Phe Val Ser Asn Ile Ala Thr
            340                 345                 350

Asp Ser Gly Ala Gly Val Phe Thr Lys Glu Asn Leu Ser Cys Thr Asn
            355                 360                 365

Thr Asn Ser Leu Gln Phe Leu Lys Asn Ser Ala Gly Gln His Gly Gly
        370                 375                 380

Gly Ala Tyr Val Thr Gln Thr Met Ser Val Thr Asn Thr Thr Ser Glu
385                 390                 395                 400

Ser Ile Thr Thr Pro Pro Leu Val Gly Glu Val Ile Phe Ser Glu Asn
                    405                 410                 415

Thr Ala Lys Gly His Gly Gly Gly Ile Cys Thr Asn Lys Leu Ser Leu
            420                 425                 430

Ser Asn Leu Lys Thr Val Thr Leu Thr Lys Asn Ser Ala Lys Glu Ser
            435                 440                 445

Gly Gly Ala Ile Phe Thr Asp Leu Ala Ser Ile Pro Thr Thr Asp Thr
        450                 455                 460

Pro Glu Ser Ser Thr Pro Ser Ser Ser Pro Ala Ser Thr Pro Glu
465                 470                 475                 480

Val Val Ala Ser Ala Lys Ile Asn Arg Phe Phe Ala Ser Thr Ala Glu
                    485                 490                 495

Pro Ala Ala Pro Ser Leu Thr Glu Ala Glu Ser Asp Gln Thr Asp Gln
                500                 505                 510

Thr Glu Thr Ser Asp Thr Asn Ser Asp Ile Asp Val Ser Ile Glu Asn
            515                 520                 525

Ile Leu Asn Val Ala Ile Asn Gln Asn Thr Ser Ala Lys Lys Gly Gly
        530                 535                 540

Ala Ile Tyr Gly Lys Lys Ala Lys Leu Ser Arg Ile Asn Asn Leu Glu
545                 550                 555                 560

Leu Ser Gly Asn Ser Ser Gln Asp Val Gly Gly Leu Cys Leu Thr
                    565                 570                 575

Glu Ser Val Glu Phe Asp Ala Ile Gly Ser Leu Leu Ser His Tyr Asn
                580                 585                 590

Ser Ala Ala Lys Glu Gly Gly Val Ile His Ser Lys Thr Val Thr Leu
            595                 600                 605

Ser Asn Leu Lys Ser Thr Phe Thr Phe Ala Asp Asn Thr Val Lys Ala
            610                 615                 620

Ile Val Glu Ser Thr Pro Glu Ala Pro Glu Glu Ile Pro Pro Val Glu
625                 630                 635                 640

Gly Glu Glu Ser Thr Ala Thr Glu Asn Pro Asn Ser Asn Thr Glu Gly
                    645                 650                 655

Ser Ser Ala Asn Thr Asn Leu Glu Gly Ser Gln Gly Asp Thr Ala Asp
                660                 665                 670

Thr Gly Thr Gly Val Val Asn Asn Glu Ser Gln Asp Thr Ser Asp Thr
            675                 680                 685
```

```
Gly Asn Ala Glu Ser Gly Glu Gln Leu Gln Asp Ser Thr Gln Ser Asn
    690                 695                 700
Glu Glu Asn Thr Leu Pro Asn Ser Ser Ile Asp Gln Ser Asn Glu Asn
705                 710                 715                 720
Thr Asp Glu Ser Ser Asp Ser His Thr Glu Ile Thr Asp Glu Ser
                725                 730                 735
Val Ser Ser Ser Lys Ser Gly Ser Ser Thr Pro Gln Asp Gly Gly
                740                 745                 750
Ala Ala Ser Ser Gly Ala Pro Ser Gly Asp Gln Ser Ile Ser Ala Asn
        755                 760                 765
Ala Cys Leu Ala Lys Ser Tyr Ala Ala Ser Thr Asp Ser Ser Pro Val
    770                 775                 780
Ser Asn Ser Ser Gly Ser Asp Val Thr Ala Ser Ser Asp Asn Pro Asp
785                 790                 795                 800
Ser Ser Ser Ser Gly Asp Ser Ala Gly Asp Ser Glu Gly Pro Thr Glu
                805                 810                 815
Pro Glu Ala Gly Ser Thr Thr Glu Thr Pro Thr Leu Ile Gly Gly Gly
            820                 825                 830
Ala Ile Tyr Gly Glu Thr Val Lys Ile Glu Asn Phe Ser Gly Gln Gly
        835                 840                 845
Ile Phe Ser Gly Asn Lys Ala Ile Asp Asn Thr Thr Glu Gly Ser Ser
    850                 855                 860
Ser Lys Ser Asn Val Leu Gly Gly Ala Val Tyr Ala Lys Thr Leu Phe
865                 870                 875                 880
Asn Leu Asp Ser Gly Ser Ser Arg Arg Thr Val Thr Phe Ser Gly Asn
                885                 890                 895
Thr Val Ser Ser Gln Ser Thr Thr Gly Gln Val Ala Gly Gly Ala Ile
                900                 905                 910
Tyr Ser Pro Thr Val Thr Ile Ala Thr Pro Val Val Phe Ser Lys Asn
        915                 920                 925
Ser Ala Thr Asn Asn Ala Asn Asn Ala Thr Asp Thr Gln Arg Lys Asp
    930                 935                 940
Thr Phe Gly Gly Ala Ile Gly Ala Thr Ser Ala Val Ser Leu Ser Gly
945                 950                 955                 960
Gly Ala His Phe Leu Glu Asn Val Ala Asp Leu Gly Ser Ala Ile Gly
                965                 970                 975
Leu Val Pro Asp Thr Gln Asn Thr Glu Thr Val Lys Leu Glu Ser Gly
                980                 985                 990
Ser Tyr Tyr Phe Glu Lys Asn Lys Ala Leu Lys Arg Ala Thr Ile Tyr
        995                 1000                1005
Ala Pro Val Val Ser Ile Lys Ala Tyr Thr Ala Thr Phe Asn Gln Asn
    1010                1015                1020
Arg Ser Leu Glu Glu Gly Ser Ala Ile Tyr Phe Thr Lys Glu Ala Ser
1025                1030                1035                1040
Ile Glu Ser Leu Gly Ser Val Leu Phe Thr Gly Asn Leu Val Thr Pro
                1045                1050                1055
Thr Leu Ser Thr Thr Thr Glu Gly Thr Pro Ala Thr Thr Ser Gly Asp
            1060                1065                1070
Val Thr Lys Tyr Gly Ala Ala Ile Phe Gly Gln Ile Ala Ser Ser Asn
        1075                1080                1085
Gly Ser Gln Thr Asp Asn Leu Pro Leu Lys Leu Ile Ala Ser Gly Gly
    1090                1095                1100
Asn Ile Cys Phe Arg Asn Asn Glu Tyr Arg Pro Thr Ser Ser Asp Thr
```

-continued

```
              1105                1110                1115                1120
Gly Thr Ser Thr Phe Cys Ser Ile Ala Gly Asp Val Lys Leu Thr Met
                    1125                1130                1135
Gln Ala Ala Lys Gly Lys Thr Ile Ser Phe Phe Asp Ala Ile Arg Thr
                    1140                1145                1150
Ser Thr Lys Lys Thr Gly Thr Gln Ala Thr Ala Tyr Asp Thr Leu Asp
                    1155                1160                1165
Ile Asn Lys Ser Glu Asp Ser Glu Thr Val Asn Ser Ala Phe Thr Gly
              1170                1175                1180
Thr Ile Leu Phe Ser Ser Glu Leu His Glu Asn Lys Ser Tyr Ile Pro
1185                1190                1195                1200
Gln Asn Val Val Leu His Ser Gly Ser Leu Val Leu Lys Pro Asn Thr
                    1205                1210                1215
Glu Leu His Val Ile Ser Phe Glu Gln Lys Glu Gly Ser Ser Leu Val
                    1220                1225                1230
Met Thr Pro Gly Ser Val Leu Ser Asn Gln Thr Val Ala Asp Gly Ala
                    1235                1240                1245
Leu Val Ile Asn Asn Met Thr Ile Asp Leu Ser Ser Val Glu Lys Asn
              1250                1255                1260
Gly Ile Ala Glu Gly Asn Ile Phe Thr Pro Pro Glu Leu Arg Ile Ile
1265                1270                1275                1280
Asp Thr Thr Thr Ser Gly Ser Gly Thr Pro Ser Thr Asp Ser Glu
                    1285                1290                1295
Ser Asn Gln Asn Ser Asp Asp Thr Lys Glu Gln Asn Asn Asn Asp Ala
                    1300                1305                1310
Ser Asn Gln Gly Glu Ser Ala Asn Gly Ser Ser Ser Pro Ala Val Ala
                    1315                1320                1325
Ala Ala His Thr Ser Arg Thr Arg Asn Phe Ala Ala Ala Ala Thr Ala
              1330                1335                1340
Thr Pro Thr Thr Thr Pro Thr Ala Thr Thr Thr Thr Ser Asn Gln Val
1345                1350                1355                1360
Ile Leu Gly Gly Glu Ile Lys Leu Ile Asp Pro Asn Gly Thr Phe Phe
                    1365                1370                1375
Gln Asn Pro Ala Leu Arg Ser Asp Gln Gln Ile Ser Leu Leu Val Leu
                    1380                1385                1390
Pro Thr Asp Ser Ser Lys Met Gln Ala Gln Lys Ile Val Leu Thr Gly
                    1395                1400                1405
Asp Ile Ala Pro Gln Lys Gly Tyr Thr Gly Thr Leu Thr Leu Asp Pro
              1410                1415                1420
Asp Gln Leu Gln Asn Gly Thr Ile Ser Ala Leu Trp Lys Phe Asp Ser
1425                1430                1435                1440
Tyr Arg Gln Trp Ala Tyr Val Pro Arg Asp Asn His Phe Tyr Ala Asn
                    1445                1450                1455
Ser Ile Leu Gly Ser Gln Met Ser Met Val Thr Val Lys Gln Gly Leu
                    1460                1465                1470
Leu Asn Asp Lys Met Asn Leu Ala Arg Phe Asp Glu Val Ser Tyr Asn
                    1475                1480                1485
Asn Leu Trp Ile Ser Gly Leu Gly Thr Met Leu Ser Gln Val Gly Thr
              1490                1495                1500
Pro Thr Ser Glu Glu Phe Thr Tyr Tyr Ser Arg Gly Ala Ser Val Ala
1505                1510                1515                1520
Leu Asp Ala Lys Pro Ala His Asp Val Ile Val Gly Ala Ala Phe Ser
                    1525                1530                1535
```

```
Lys Met Ile Gly Lys Thr Lys Ser Leu Lys Arg Glu Asn Asn Tyr Thr
            1540            1545                1550

His Lys Gly Ser Glu Tyr Ser Tyr Gln Ala Ser Val Tyr Gly Gly Lys
            1555            1560                1565

Pro Phe His Phe Val Ile Asn Lys Lys Thr Glu Lys Ser Leu Pro Leu
            1570            1575                1580

Leu Leu Gln Gly Val Ile Ser Tyr Gly Tyr Ile Lys His Asp Thr Val
1585            1590            1595                1600

Thr His Tyr Pro Thr Ile Arg Glu Arg Asn Gln Gly Glu Trp Glu Asp
            1605            1610                1615

Leu Gly Trp Leu Thr Ala Leu Arg Val Ser Ser Val Leu Arg Thr Pro
            1620            1625                1630

Ala Gln Gly Asp Thr Lys Arg Ile Thr Val Tyr Gly Glu Leu Glu Tyr
            1635            1640                1645

Ser Ser Ile Arg Gln Lys Gln Phe Thr Glu Thr Glu Tyr Asp Pro Arg
            1650            1655                1660

Tyr Phe Asp Asn Cys Thr Tyr Arg Asn Leu Ala Ile Pro Met Gly Leu
1665            1670            1675                1680

Ala Phe Glu Gly Glu Leu Ser Gly Asn Asp Ile Leu Met Tyr Asn Arg
            1685            1690                1695

Phe Ser Val Ala Tyr Met Pro Ser Ile Tyr Arg Asn Ser Pro Thr Cys
            1700            1705                1710

Lys Tyr Gln Val Leu Ser Ser Gly Glu Gly Glu Ile Ile Cys Gly
            1715            1720                1725

Val Pro Thr Arg Asn Ser Ala Arg Gly Glu Tyr Ser Thr Gln Leu Tyr
            1730            1735                1740

Pro Gly Pro Leu Trp Thr Leu Tyr Gly Ser Tyr Thr Ile Glu Ala Asp
1745            1750            1755                1760

Ala His Thr Leu Ala His Met Met Asn Cys Gly Ala Arg Met Thr Phe
            1765            1770                1775

<210> SEQ ID NO 180
<211> LENGTH: 1752
<212> TYPE: PRT
<213> ORGANISM: Chlamydia

<400> SEQUENCE: 180

Met Lys Trp Leu Ser Ala Thr Ala Val Phe Ala Ala Val Leu Pro Ser
  1              5                  10                  15

Val Ser Gly Phe Cys Phe Pro Glu Pro Lys Glu Leu Asn Phe Ser Arg
             20                  25                  30

Val Glu Thr Ser Ser Ser Thr Thr Phe Thr Glu Thr Ile Gly Glu Ala
         35                  40                  45

Gly Ala Glu Tyr Ile Val Ser Gly Asn Ala Ser Phe Thr Lys Phe Thr
     50                  55                  60

Asn Ile Pro Thr Thr Asp Thr Thr Pro Thr Asn Ser Asn Ser Ser
 65                  70                  75                  80

Ser Ser Ser Gly Glu Thr Ala Ser Val Ser Glu Asp Ser Asp Ser Thr
             85                  90                  95

Thr Thr Thr Pro Asp Pro Lys Gly Gly Ala Phe Tyr Asn Ala His
            100                 105                 110

Ser Gly Val Leu Ser Phe Met Thr Arg Ser Gly Thr Glu Gly Ser Leu
            115                 120                 125

Thr Leu Ser Glu Ile Lys Met Thr Gly Glu Gly Gly Ala Ile Phe Ser
```

-continued

```
            130                 135                 140
Gln Gly Glu Leu Leu Phe Thr Asp Leu Thr Ser Leu Thr Ile Gln Asn
145                 150                 155                 160
Asn Leu Ser Gln Leu Ser Gly Gly Ala Ile Phe Gly Gly Ser Thr Ile
                165                 170                 175
Ser Leu Ser Gly Ile Thr Lys Ala Thr Phe Ser Cys Asn Ser Ala Glu
                180                 185                 190
Val Pro Ala Pro Val Lys Lys Pro Thr Glu Pro Lys Ala Gln Thr Ala
                195                 200                 205
Ser Glu Thr Ser Gly Ser Ser Ser Ser Gly Asn Asp Ser Val Ser
210                 215                 220
Ser Pro Ser Ser Ser Arg Ala Glu Pro Ala Ala Ala Asn Leu Gln Ser
225                 230                 235                 240
His Phe Ile Cys Ala Thr Ala Thr Pro Ala Ala Gln Thr Asp Thr Glu
                245                 250                 255
Thr Ser Thr Pro Ser His Lys Pro Gly Ser Gly Gly Ala Ile Tyr Ala
                260                 265                 270
Lys Gly Asp Leu Thr Ile Ala Asp Ser Gln Glu Val Leu Phe Ser Ile
                275                 280                 285
Asn Lys Ala Thr Lys Asp Gly Gly Ala Ile Phe Ala Glu Lys Asp Val
                290                 295                 300
Ser Phe Glu Asn Ile Thr Ser Leu Lys Val Gln Thr Asn Gly Ala Glu
305                 310                 315                 320
Glu Lys Gly Gly Ala Ile Tyr Ala Lys Gly Asp Leu Ser Ile Gln Ser
                325                 330                 335
Ser Lys Gln Ser Leu Phe Asn Ser Asn Tyr Ser Lys Gln Gly Gly Gly
                340                 345                 350
Ala Leu Tyr Val Glu Gly Gly Ile Asn Phe Gln Asp Leu Glu Glu Ile
                355                 360                 365
Arg Ile Lys Tyr Asn Lys Ala Gly Thr Phe Glu Thr Lys Lys Ile Thr
                370                 375                 380
Leu Pro Ser Leu Lys Ala Gln Ala Ser Ala Gly Asn Ala Asp Ala Trp
385                 390                 395                 400
Ala Ser Ser Ser Pro Gln Ser Gly Ser Gly Ala Thr Thr Val Ser Asp
                405                 410                 415
Ser Gly Asp Ser Ser Ser Gly Ser Asp Ser Asp Thr Ser Glu Thr Val
                420                 425                 430
Pro Val Thr Ala Lys Gly Gly Leu Tyr Thr Asp Lys Asn Leu Ser
                435                 440                 445
Ile Thr Asn Ile Thr Gly Ile Ile Glu Ile Ala Asn Asn Lys Ala Thr
450                 455                 460
Asp Val Gly Gly Gly Ala Tyr Val Lys Gly Thr Leu Thr Cys Glu Asn
465                 470                 475                 480
Ser His Arg Leu Gln Phe Leu Lys Asn Ser Ser Asp Lys Gln Gly Gly
                485                 490                 495
Gly Ile Tyr Gly Glu Asp Asn Ile Thr Leu Ser Asn Leu Thr Gly Lys
                500                 505                 510
Thr Leu Phe Gln Glu Asn Thr Ala Lys Glu Glu Gly Gly Leu Phe
                515                 520                 525
Ile Lys Gly Thr Asp Lys Ala Leu Thr Met Thr Gly Leu Asp Ser Phe
                530                 535                 540
Cys Leu Ile Asn Asn Thr Ser Glu Lys His Gly Gly Ala Phe Val
545                 550                 555                 560
```

```
Thr Lys Glu Ile Ser Gln Thr Tyr Thr Ser Asp Val Glu Thr Ile Pro
            565                 570                 575
Gly Ile Thr Pro Val His Gly Glu Thr Val Ile Thr Gly Asn Lys Ser
        580                 585                 590
Thr Gly Gly Asn Gly Gly Val Cys Thr Lys Arg Leu Ala Leu Ser
    595                 600                 605
Asn Leu Gln Ser Ile Ser Ile Ser Gly Asn Ser Ala Ala Glu Asn Gly
        610                 615                 620
Gly Gly Ala His Thr Cys Pro Asp Ser Phe Pro Thr Ala Asp Thr Ala
625                 630                 635                 640
Glu Gln Pro Ala Ala Ser Ala Ala Thr Ser Thr Pro Lys Ser Ala
            645                 650                 655
Pro Val Ser Thr Ala Leu Ser Thr Pro Ser Ser Ser Thr Val Ser Ser
            660                 665                 670
Leu Thr Leu Leu Ala Ala Ser Ser Gln Ala Ser Pro Ala Thr Ser Asn
            675                 680                 685
Lys Glu Thr Gln Asp Pro Asn Ala Asp Thr Asp Leu Leu Ile Asp Tyr
        690                 695                 700
Val Val Asp Thr Thr Ile Ser Lys Asn Thr Ala Lys Lys Gly Gly
705                 710                 715                 720
Ile Tyr Ala Lys Lys Ala Lys Met Ser Arg Ile Asp Gln Leu Asn Ile
                725                 730                 735
Ser Glu Asn Ser Ala Thr Glu Ile Gly Gly Ile Cys Cys Lys Glu
            740                 745                 750
Ser Leu Glu Leu Asp Ala Leu Val Ser Leu Ser Val Thr Glu Asn Leu
            755                 760                 765
Val Gly Lys Glu Gly Gly Leu His Ala Lys Thr Val Asn Ile Ser
    770                 775                 780
Asn Leu Lys Ser Gly Phe Ser Phe Ser Asn Asn Lys Ala Asn Ser Ser
785                 790                 795                 800
Ser Thr Gly Val Ala Thr Thr Ala Ser Ala Pro Ala Ala Ala Ala
            805                 810                 815
Ser Leu Gln Ala Ala Ala Ala Ala Pro Ser Ser Pro Ala Thr Pro
            820                 825                 830
Thr Tyr Ser Gly Val Val Gly Gly Ala Ile Tyr Gly Glu Lys Val Thr
        835                 840                 845
Phe Ser Gln Cys Ser Gly Thr Cys Gln Phe Ser Gly Asn Gln Ala Ile
    850                 855                 860
Asp Asn Asn Pro Ser Gln Ser Ser Leu Asn Val Gln Gly Gly Ala Ile
865                 870                 875                 880
Tyr Ala Lys Thr Ser Leu Ser Ile Gly Ser Ser Asp Ala Gly Thr Ser
                885                 890                 895
Tyr Ile Phe Ser Gly Asn Ser Val Ser Thr Gly Lys Ser Gln Thr Thr
            900                 905                 910
Gly Gln Ile Ala Gly Gly Ile Tyr Ser Pro Thr Val Thr Leu Asn
        915                 920                 925
Cys Pro Ala Thr Phe Ser Asn Asn Thr Ala Ser Ile Ala Thr Pro Lys
    930                 935                 940
Thr Ser Ser Glu Asp Gly Ser Ser Gly Asn Ser Ile Lys Asp Thr Ile
945                 950                 955                 960
Gly Gly Ala Ile Ala Gly Thr Ala Ile Thr Leu Ser Gly Val Ser Arg
                965                 970                 975
```

-continued

```
Phe Ser Gly Asn Thr Ala Asp Leu Gly Ala Ala Ile Gly Thr Leu Ala
            980                 985                 990

Asn Ala Asn Thr Pro Ser Ala Thr Ser Gly Ser Gln Asn Ser Ile Thr
            995                 1000                1005

Glu Lys Ile Thr Leu Glu Asn Gly Ser Phe Ile Phe Glu Arg Asn Gln
            1010                1015                1020

Ala Asn Lys Arg Gly Ala Ile Tyr Ser Pro Ser Val Ser Ile Lys Gly
1025                1030                1035                1040

Asn Asn Ile Thr Phe Asn Gln Asn Thr Ser Thr His Asp Gly Ser Ala
            1045                1050                1055

Ile Tyr Phe Thr Lys Asp Ala Thr Ile Glu Ser Leu Gly Ser Val Leu
            1060                1065                1070

Phe Thr Gly Asn Asn Val Thr Ala Thr Gln Ala Ser Ser Ala Thr Ser
            1075                1080                1085

Gly Gln Asn Thr Asn Thr Ala Asn Tyr Gly Ala Ala Ile Phe Gly Asp
            1090                1095                1100

Pro Gly Thr Thr Gln Ser Ser Gln Thr Asp Ala Ile Leu Thr Leu Leu
1105                1110                1115                1120

Ala Ser Ser Gly Asn Ile Thr Phe Ser Asn Asn Ser Leu Gln Asn Asn
            1125                1130                1135

Gln Gly Asp Thr Pro Ala Ser Lys Phe Cys Ser Ile Ala Gly Tyr Val
            1140                1145                1150

Lys Leu Ser Leu Gln Ala Ala Lys Gly Lys Thr Ile Ser Phe Phe Asp
            1155                1160                1165

Cys Val His Thr Ser Thr Lys Lys Thr Gly Ser Thr Gln Asn Val Tyr
            1170                1175                1180

Glu Thr Leu Asp Ile Asn Lys Glu Glu Asn Ser Asn Pro Tyr Thr Gly
1185                1190                1195                1200

Thr Ile Val Phe Ser Ser Glu Leu His Glu Asn Lys Ser Tyr Ile Pro
            1205                1210                1215

Gln Asn Ala Ile Leu His Asn Gly Thr Leu Val Leu Lys Glu Lys Thr
            1220                1225                1230

Glu Leu His Val Val Ser Phe Glu Gln Lys Glu Gly Ser Lys Leu Ile
            1235                1240                1245

Met Glu Pro Gly Ala Val Leu Ser Asn Gln Asn Ile Ala Asn Gly Ala
            1250                1255                1260

Leu Ala Ile Asn Gly Leu Thr Ile Asp Leu Ser Ser Met Gly Thr Pro
1265                1270                1275                1280

Gln Ala Gly Glu Ile Phe Ser Pro Pro Glu Leu Arg Ile Val Ala Thr
            1285                1290                1295

Thr Ser Ser Ala Ser Gly Gly Ser Gly Val Ser Ser Ile Pro Thr
            1300                1305                1310

Asn Pro Lys Arg Ile Ser Ala Ala Val Pro Ser Gly Ser Ala Ala Thr
            1315                1320                1325

Thr Pro Thr Met Ser Glu Asn Lys Val Phe Leu Thr Gly Asp Leu Thr
            1330                1335                1340

Leu Ile Asp Pro Asn Gly Asn Phe Tyr Gln Asn Pro Met Leu Gly Ser
1345                1350                1355                1360

Asp Leu Asp Val Pro Leu Ile Lys Leu Pro Thr Asn Thr Ser Asp Val
            1365                1370                1375

Gln Val Tyr Asp Leu Thr Leu Ser Gly Asp Leu Phe Pro Gln Lys Gly
            1380                1385                1390

Tyr Met Gly Thr Trp Thr Leu Asp Ser Asn Pro Gln Thr Gly Lys Leu
```

```
                1395                1400                1405
Gln Ala Arg Trp Thr Phe Asp Thr Tyr Arg Arg Trp Val Tyr Ile Pro
                1410                1415                1420

Arg Asp Asn His Phe Tyr Ala Asn Ser Ile Leu Gly Ser Gln Asn Ser
1425                1430                1435                1440

Met Ile Val Val Lys Gln Gly Leu Ile Asn Asn Met Leu Asn Asn Ala
                1445                1450                1455

Arg Phe Asp Asp Ile Ala Tyr Asn Asn Phe Trp Val Ser Gly Val Gly
                1460                1465                1470

Thr Phe Leu Ala Gln Gln Gly Thr Pro Leu Ser Glu Glu Phe Ser Tyr
                1475                1480                1485

Tyr Ser Arg Gly Thr Ser Val Ala Ile Asp Ala Lys Pro Arg Gln Asp
                1490                1495                1500

Phe Ile Leu Gly Ala Ala Phe Ser Lys Ile Val Gly Lys Thr Lys Ala
1505                1510                1515                1520

Ile Lys Lys Met His Asn Tyr Phe His Lys Gly Ser Glu Tyr Ser Tyr
                1525                1530                1535

Gln Ala Ser Val Tyr Gly Gly Lys Phe Leu Tyr Phe Leu Leu Asn Lys
                1540                1545                1550

Gln His Gly Trp Ala Leu Pro Phe Leu Ile Gln Gly Val Val Ser Tyr
                1555                1560                1565

Gly His Ile Lys His Asp Thr Thr Thr Leu Tyr Pro Ser Ile His Glu
                1570                1575                1580

Arg Asn Lys Gly Asp Trp Glu Asp Leu Gly Trp Leu Ala Asp Leu Arg
1585                1590                1595                1600

Ile Ser Met Asp Leu Lys Glu Pro Ser Lys Asp Ser Ser Lys Arg Ile
                1605                1610                1615

Thr Val Tyr Gly Glu Leu Glu Tyr Ser Ser Ile Arg Gln Lys Gln Phe
                1620                1625                1630

Thr Glu Ile Asp Tyr Asp Pro Arg His Phe Asp Asp Cys Ala Tyr Arg
                1635                1640                1645

Asn Leu Ser Leu Pro Val Gly Cys Ala Val Glu Gly Ala Ile Met Asn
                1650                1655                1660

Cys Asn Ile Leu Met Tyr Asn Lys Leu Ala Leu Ala Tyr Met Pro Ser
1665                1670                1675                1680

Ile Tyr Arg Asn Asn Pro Val Cys Lys Tyr Arg Val Leu Ser Ser Asn
                1685                1690                1695

Glu Ala Gly Gln Val Ile Cys Gly Val Pro Thr Arg Thr Ser Ala Arg
                1700                1705                1710

Ala Glu Tyr Ser Thr Gln Leu Tyr Leu Gly Pro Phe Trp Thr Leu Tyr
                1715                1720                1725

Gly Asn Tyr Thr Ile Asp Val Gly Met Tyr Thr Leu Ser Gln Met Thr
                1730                1735                1740

Ser Cys Gly Ala Arg Met Ile Phe
1745                1750

<210> SEQ ID NO 181
<211> LENGTH: 2601
<212> TYPE: DNA
<213> ORGANISM: Chlamydia

<400> SEQUENCE: 181
atggctagcc atcaccatca ccatcacctc tttggccagg atcccttagg tgaaaccgcc      60
ctcctcacta aaaatcctaa tcatgtcgtc tgtacatttt ttgaggactg taccatggag     120
```

```
agcctctttc ctgctctttg tgctcatgca tcacaagacg atcctttgta tgtacttgga    180
aattcctact gttggttcgt atctaaactc catatcacgg accccaaaga ggctcttttt    240
aaagaaaaag gagatctttc cattcaaaac tttcgcttcc tttccttcac agattgctct    300
tccaaggaaa gctctccttc tattattcat caaaagaatg gtcagttatc cttgcgcaat    360
aatggtagca tgagtttctg tcgaaatcat gctgaaggct ctggaggagc catctctgcg    420
gatgcctttt ctctacagca caactatctt ttcacagctt ttgaagagaa ttcttctaaa    480
ggaaatggcg gagccattca ggctcaaacc ttctctttat ctagaaatgt gtcgcctatt    540
tctttcgccc gtaatcgtgc ggatttaaat ggcggcgcta tttgctgtag taatcttatt    600
tgttcaggga atgtaaaccc tctcttttc actggaaact ccgccacraa tggaggcsct    660
atttgttgta tcagcgatct aaacacctca gaaaaggct ctctctctct tgcttgtaac    720
caaraaacgc tatttgcaag caattctgct aaagaaaaag gcgggctat ttatgccaag    780
cacatggtat tgcgttataa cggtcctgtt tccttcatta acaacagcgc taaaataggt    840
ggagctatcg ccatccagtc cggagggagt ctctctatcc ttgcaggtga aggatctgtt    900
ctgttccaga ataactccca acgcacctcc gaccaaggtc tagtaagaaa cgccatctac    960
ttagagaaag atgcgattct ttcttcctta gaagctcgca acgagatat tcttttcttt    1020
gatcctattg tacaagaaag tagcagcaaa gaatcgcctc ttccctcctc tttgcaagcc    1080
agcgtgactt ctcccacccc agccaccgca tctcctttag ttattcagac aagtgcaaac    1140
cgttcagtga ttttctcgag cgaacgtctt tctgaagaag aaaaaactcc tgataacctc    1200
acttcccaac tacagcagcc tatcgaactg aaatccggac gcttagtttt aaaagatcgc    1260
gctgtccttt ccgsgccttc tctctctcag gatcctcaag ctctcctcat tatggaagcg    1320
ggaacttctt taaaaacttc ctytgatttg aagttagsta cgstaagtat tccccttcat    1380
tccttagata ctgaaaaaag cgtaactatc cacgcccta atctttctat ccaaaagatc    1440
ttcctctcta actctggaga tgagaatttt tatgaaaatg tagagcttct cagtaaagag    1500
caaaacaata ttcctctcct tactctccct aaagagcaat ctcatttaca tcttcctgat    1560
gggaacctct cttctcactt tggatatcaa ggagattgga cttttttcttg gaaagattct    1620
gatgaagggc attctctgat tgctaattgg acgcctaaaa actatgtgcc tcatccagaa    1680
cgtcaatcta cactcgttgc gaacactctt tggaacacct attccgatat gcaagctgtg    1740
cagtcgatga ttaatacaac agcgcacgga ggagcctatc tatttggaac gtggggatct    1800
gctgttttcta atttattcta tgttcacgac agctctggga aacctatcga taattggcat    1860
catagaagcc ttggctacct attcggtatc agtactcaca gtttagatga ccattctttc    1920
tgcttggctg caggacaatt actcgggaaa tcgtccgatt cctttattac gtctacagaa    1980
acgacctcct atatagctac tgtacaagcg caactcgcta cctctctaat gaaaatctct    2040
gcacaggcat gctacaatga agtatccat gagctaaaaa caaaatatcg ctccttctct    2100
aaagaaggat tcggatcctg gcatagcgtt gcagtatccg gagaagtgtg cgcatcgatt    2160
cctattgtat ccaatggttc cggactgttc agctccttct ctattttctc taaactgcaa    2220
ggattttcag gaacacagga cggttttgag gagagttcgg gagagattcg gtccttttct    2280
gccagctctt tcagaaatat ttcacttcct ataggaataa catttgaaaa aaaatcccaa    2340
aaaacacgaa cctactatta ctttctagga gcctacatcc aagacctgaa acgtgatgtg    2400
gaatcgggac ctgtagtgtt actcaaaaat gccgtctcct gggatgctcc tatggcgaac    2460
```

-continued

| | |
|---|---|
| ttggattcac gagcctacat gttccggctt acgaatcaaa gagctctaca cagacttcag | 2520 |
| acgctgttaa atgtgtcttg tgtgctgcgt gggcaaagcc atagttactc cctggatctg | 2580 |
| gggaccactt acaggttcta g | 2601 |

<210> SEQ ID NO 182
<211> LENGTH: 3021
<212> TYPE: DNA
<213> ORGANISM: Chlamydia

<400> SEQUENCE: 182

| | |
|---|---|
| atggctagca tgactggtgg acagcaaatg ggtcgggatt caagcttggt accgcatcac | 60 |
| catcaccatc acatgattcc tcaaggaatt tacgatgggg agacgttaac tgtatcattt | 120 |
| ccctatactg ttataggaga tccgagtggg actactgttt tttctgcagg agagttaaca | 180 |
| ttaaaaaatc ttgacaattc tattgcagct ttgcctttaa gttgttttgg gaacttatta | 240 |
| gggagtttta ctgttttagg gagaggacac tcgttgactt tcgagaacat acggacttct | 300 |
| acaaatgggg cagctctaag taatagcgct gctgatggac tgtttactat tgagggtttt | 360 |
| aaagaattat cctttccaa ttgcaattca ttacttgccg tactgcctgc tgcaacgact | 420 |
| aataagggta gccagactcc gacgacaaca tctacaccgt ctaatggtac tatttattct | 480 |
| aaaacagatc ttttgttact caataatgag aagttctcat tctatagtaa tttagtctct | 540 |
| ggagatgggg gagctataga tgctaagagc ttaacggttc aaggaattag caagctttgt | 600 |
| gtcttccaag aaaatactgc tcaagctgat ggggagctt gtcaagtagt caccagtttc | 660 |
| tctgctatgg ctaacgaggc tcctattgcc tttgtagcga atgttgcagg agtaagaggg | 720 |
| ggagggattg ctgctgttca ggatgggcag cagggagtgt catcatctac ttcaacagaa | 780 |
| gatccagtag taagtttttc cagaaatact gcggtagagt ttgatgggaa cgtagcccga | 840 |
| gtaggaggag ggatttactc ctacgggaac gttgctttcc tgaataatgg aaaaaccttg | 900 |
| tttctcaaca atgttgcttc tcctgtttac attgctgcta agcaaccaac aagtggacag | 960 |
| gcttctaata cgagtaataa ttacggagat ggaggagcta tcttctgtaa gatggtgcg | 1020 |
| caagcaggat ccataactc tggatcagtt cctttgatg agagggagt agttttcttt | 1080 |
| agtagcaatg tagctgctgg gaagggggga gctatttatg ccaaaaagct ctcggttgct | 1140 |
| aactgtggcc ctgtacaatt ttaaggaat atcgctaatg atggtggagc gatttattta | 1200 |
| ggagaatctg gagagctcag tttatctgct gattatggag atattatttt cgatgggaat | 1260 |
| cttaaaagaa cagccaaaga gaatgctgcc gatgttaatg gcgtaactgt gtcctcacaa | 1320 |
| gccatttcga tgggatcggg agggaaaata acgacattaa gagctaaagc agggcatcag | 1380 |
| attctctttta atgatcccat cgagatggca aacggaaata accagccagc gcagtcttcc | 1440 |
| aaacttctaa aaattaacga tggtgaagga tacacagggg atattgtttt tgctaatgga | 1500 |
| agcagtactt tgtaccaaaa tgttacgata gagcaaggaa ggattgttct tcgtgaaaag | 1560 |
| gcaaaattat cagtgaattc tctaagtcag acaggtggga gtctgtatat ggaagctggg | 1620 |
| agtacattgg attttgtaac tccacaacca ccacaacagc ctcctgccgc taatcagttg | 1680 |
| atcacgcttt ccaatctgca tttgtctctt tcttctttgt tagcaaacaa tgcagttacg | 1740 |
| aatcctccta ccaatcctcc agcgcaagat tctcatcctg cagtcattgg tagcacaact | 1800 |
| gctggttctg ttacaattag tgggcctatc ttttttgagg attggatga tacagcttat | 1860 |
| gataggtatg attggctagg ttctaatcaa aaaatcaatg tcctgaaatt acagttaggg | 1920 |
| actaagcccc cagctaatgc cccatcagat ttgactctag ggaatgagat gcctaagtat | 1980 |

```
ggctatcaag gaagctggaa gcttgcgtgg gatcctaata cagcaaataa tggtccttat    2040
actctgaaag ctacatggac taaaactggg tataatcctg ggcctgagcg agtagcttct    2100
ttggttccaa atagtttatg gggatccatt ttagatatac gatctgcgca ttcagcaatt    2160
caagcaagtg tggatgggcg ctcttattgt cgaggattat gggtttctgg agtttcgaat    2220
ttcttctatc atgaccgcga tgctttaggt cagggatatc ggtatattag tggggttat     2280 tccttaggag caaactccta ctttggatca tcgatgtttg gtctagcatt taccgaagta    2340
tttggtagat ctaaagatta tgtagtgtgt cgttccaatc atcatgcttg cataggatcc    2400
gtttatctat ctacccaaca agctttatgt ggatcctatt tgttcggaga tgcgtttatc    2460
cgtgctagct acgggtttgg gaatcagcat atgaaaacct catatacatt tgcagaggag    2520
agcgatgttc gttgggataa taactgtctg gctggagaga ttggagcggg attaccgatt    2580
gtgattactc catctaagct ctatttgaat gagttgcgtc ctttcgtgca agctgagttt    2640
tcttatgccg atcatgaatc ttttacagag gaaggcgatc aagctcgggc attcaagagc    2700
ggacatctcc taaatctatc agttcctgtt ggagtgaagt tgatcgatg ttctagtaca     2760 catcctaata aatatagctt tatggcggct tatatctgtg atgcttatcg caccatctct    2820
ggtactgaga caacgctcct atcccatcaa gagacatgga caacagatgc ctttcattta    2880
gcaagacatg gagttgtggt tagaggatct atgtatgctt ctctaacaag taatatagaa    2940
gtatatggcc atgaagata tgagtatcga gatgcttctc gaggctatgg tttgagtgca     3000
ggaagtaaag tccggttcta a                                               3021

<210> SEQ ID NO 183
<211> LENGTH: 2934
<212> TYPE: DNA
<213> ORGANISM: Chlamydia

<400> SEQUENCE: 183
atggctagca tgactggtgg acagcaaatg ggtcgggatt caagcttggt accgagctcg      60
gatccacatc accatcacca tcacggacta gctagagagg ttccttctag aatctttctt     120
atgcccaact cagttccaga tcctacgaaa gagtcgctat caaataaaat tagttttgaca   180 ggagacactc acaatctcac taactgctat ctcgataacc tacgctacat actggctatt    240
ctacaaaaaa ctcccaatga aggagctgct gtcacaataa cagattacct aagctttttt    300
gatacacaaa agaaggtat ttattttgca aaaaatctca ccctgaaag tggtggtgcg      360 attggttatg cgagtcccaa ttctcctacc gtggagattc gtgatacaat aggtcctgta    420
atctttgaaa ataatacttg ttgcagacta tttacatgga gaaatcctta tgctgctgat   480
aaaataagag aaggcggagc cattcatgct caaaatcttt acataaatca taatcatgat    540
gtggtcggat ttatgaagaa ctttttctat gtccaaggag gagccattag taccgctaat    600
acctttgttg tgagcgagaa tcagtcttgt tttctctttta tggacaacat ctgtattcaa     660
actaatacag caggaaaagg tggcgctatc tatgctggaa cgagcaattc ttttgagagt    720
aataactgcg atctcttctt catcaataac gcctgttgtg caggaggagc gatcttctcc    780
cctatctgtt ctctaacagg aaatcgtggt aacatcgttt tctataacaa tcgctgcttt    840 aaaatgtag aaacagcttc ttcagaagct tctgatggag gagcaattaa agtaactact    900
cgcctagatg ttacaggcaa tcgtggtagg atctttttta gtgacaatat cacaaaaaat   960
tatggcggag ctatttacgc tcctgtagtt accctagtgg ataatggccc tacctacttt    1020
```

```
ataaacaata tcgccaataa taagggggc gctatctata tagacggaac cagtaactcc      1080
aaaatttctg ccgaccgcca tgctattatt tttaatgaaa atattgtgac taatgtaact      1140
aatgcaaatg gtaccagtac gtcagctaat cctcctagaa gaaatgcaat aacagtagca      1200
agctcctctg gtgaaattct attaggagca gggagtagcc aaaatttaat ttttttatgat     1260 cctattgaag ttagcaatgc agggtctct gtgtccttca ataaggaagc tgatcaaaca      1320
ggctctgtag tattttcagg agctactgtt aattctgcag attttcatca acgcaattta      1380
caaacaaaaa cacctgcacc ccttactctc agtaatggtt ttctatgtat cgaagatcat      1440
gctcagctta cagtgaatcg attcacacaa actgggggtg ttgtttctct tgggaatgga     1500
gcagttctga gttgctataa aaatggtaca ggagattctg ctagcaatgc ctctataaca      1560
ctgaagcata ttggattgaa tctttcttcc attctgaaaa gtggtgctga gattccttta     1620
ttgtgggtag agcctacaaa taacagcaat aactatacag cagatactgc agctaccttt      1680
tcattaagtg atgtaaaact ctcactcatt gatgactacg ggaactctcc ttatgaatcc      1740
acagatctga cccatgctct gtcatcacag cctatgctat ctatttctga agctagcgat      1800
aaccagctac aatcagaaaa tatagatttt tcgggactaa atgtccctca ttatggatgg      1860
caaggacttt ggacttgggg ctgggcaaaa actcaagatc cagaaccagc atcttcagca      1920
acaatcactg atccacaaaa agccaataga tttcatagaa ccttactact aacatggctt      1980
cctgccgggt atgttcctag cccaaaaacac agaagtcccc tcatagctaa caccttatgg      2040
gggaatatgc tgcttgcaac agaaagctta aaaaatagtg cagagctgac acctagtggt     2100
catcctttct ggggaattac aggaggagga ctaggcatga tggtttacca agatcctcga      2160
gaaaatcatc ctgattcca tatgcgctct tccggatact ctgcggggat gatagcaggg     2220
cagacacaca ccttctcatt gaaattcagt cagacctaca ccaaactcaa tgagcgttac      2280
gcaaaaaaca acgtatcttc taaaaattac tcatgccaag gagaaatgct cttctcattg      2340
caagaaggtt tcttgctgac taaattagtt gggctttaca gctatggaga ccataactgt      2400
caccatttct atactcaagg agaaaatcta acatctcaag ggacgttccg cagtcaaacg      2460
atgggaggtg ctgtcttttt tgatctccct atgaaaccct ttggatcaac gcatatactg      2520
acagctccct ttttaggtgc tcttggtatt tattctagcc tgtctcactt tactgaggtg      2580
ggagcctatc cgcgaagctt ttctacaaag actcctttga tcaatgtcct agtccctatt     2640
ggagttaaag gtagctttat gaatgctacc cacagacctc aagcctggac tgtagaattg     2700
gcataccaac ccgttctgta tagacaagaa ccagggatcg cgacccagct cctagccagt     2760
aaaggtattt ggtttggtag tggaagcccc tcatcgcgtc atgccatgtc ctataaaatc     2820
tcacagcaaa cacaaccttt gagttggtta actctccatt tccagtatca tggattctac     2880
tcctcttcaa ccttctgtaa ttatctcaat ggggaaattg ctctgcgatt ctag           2934
```

<210> SEQ ID NO 184
<211> LENGTH: 2547
<212> TYPE: DNA
<213> ORGANISM: Chlamydia

<400> SEQUENCE: 184

```
atggctagcc atcaccatca ccatcacggt gctatttctt gcttacgtgg agatgtagtc        60
atttctggaa acaagggtag agttgaattt aaagacaaca tagcaacacg tctttatgtg       120
gaagaaactg tagaaaaggt tgaagaggta gagccagctc ctgagcaaaa agacaataat       180
gagctttctt tcttagggag tgtagaacag agttttatta ctgcagctaa tcaagctctt       240
```

```
ttcgcatctg aagatgggga tttatcacct gagtcatcca tttcttctga agaacttgcg    300
aaaagaagag agtgtgctgg aggagctatt tttgcaaaac gggttcgtat tgtagataac    360
caagaggccg ttgtattctc gaataacttc tctgatattt atggcggcgc cattttttaca  420
ggttctcttc gagaagagga taagttagat gggcaaatcc ctgaagtctt gatctcaggc    480
aatgcagggg atgttgtttt ttccggaaat tcctcgaagc gtgatgagca tcttcctcat    540
acaggtgggg gagccatttg tactcaaaat ttgacgattt ctcagaatac agggaatgtt    600
ctgttttata caacgtggc ctgttcggga ggagctgttc gtatagagga tcatggtaat    660
gttcttttag aagcttttgg aggagatatt gtttttaaag gaaattcttc tttcagagca    720
caaggatccg atgctatcta ttttgcaggt aaagaatcgc atattacagc cctgaatgct    780
acggaaggac atgctattgt tttccacgac gcattagttt tgaaaatct aaaagaaagg     840
aaatctgctg aagtattgtt aatcaatagt cgagaaaatc caggttacac tggatctatt    900
cgattttag aagcagaaag taagttcct caatgtattc atgtacaaca aggaagcctt      960
gagttgctaa atggagctac attatgtagt tatggtttta acaagatgc tggagctaag    1020
ttggtattgg ctgctggatc taaactgaag attttagatt caggaactcc tgtacaaggg    1080
catgctatca gtaaacctga agcagaaatc gagtcatctt ctgaaccaga gggtgcacat    1140
tctctttgga ttgcgaagaa tgctcaaaca acagttccta tggttgatat ccatactatt    1200
tctgtagatt tagcctcctt ctcttctagt caacaggagg ggacagtaga agctcctcag    1260
gttattgttc ctggaggaag ttatgttcga tctggagagc ttaatttgga gttagttaac    1320
acaacaggta ctggttatga aaatcatgct tgttgaaga atgaggctaa agttccattg     1380
atgtctttcg ttgcttctag tgatgaagct tcagccgaaa tcagtaactt gtcggtttct    1440
gatttacaga ttcatgtagc aactccagag attgaagaag acacatacgg ccatatggga    1500
gattggtctg aggctaaaat tcaagatgga actcttgtca ttaattggaa tcctactgga    1560
tatcgattag atcctcaaaa agcaggggct ttagtattta atgcattatg ggaagaaggg    1620
gctgtcttgt ctgctctgaa aaatgcacgc tttgctcata atctcactgc tcagcgtatg    1680
gaattcgatt attctacaaa tgtgtgggga ttcgcctttg gtggtttccg aactctatct    1740
gcagagaatc tggttgctat tgatggatac aaaggagctt atggtggtgc ttctgctgga    1800
gtcgatattc aattgatgga agattttgtt ctaggagtta gtggagctgc tttcctaggt    1860
aaaatggata gtcagaagtt tgatgcggag gtttctcgga agggagttgt tggttctgta    1920
tatacaggat ttttagctgg atcctggttc ttcaaaggac aatatagcct tggagaaaca    1980
cagaacgata tgaaaacgcg ttatggagta ctaggagagt cgagtgcttc ttggacatct    2040
cgaggagtac tggcagatgc tttagttgaa taccgaagtt tagttggtcc tgtgagacct    2100
acttttatg ctttgcattt caatccttat gtcgaagtat cttatgcttc tatgaaattc     2160
cctggctta cagaacaagg aagagaagcg cgttctttg aagacgcttc ccttaccaat      2220
atcaccattc ctttagggat gaagtttgaa ttggcgttca taaaggaca gttttcagag    2280
gtgaactctt tgggaataag ttatgcatgg gaagcttatc gaaaagtaga aggaggcgcg    2340
gtgcagcttt tagaagctgg gtttgattgg agggagctc caatggatct tcctagacag    2400
gagctgcgtg tcgctctgga aaataatacg gaatggagtt cttacttcag cacagtctta    2460
ggattaacag cttttttgtgg aggatttact tctacagata gtaaactagg atatgaggcg    2520
aatactggat tgcgattgat cttttaa                                       2547
```

<210> SEQ ID NO 185
<211> LENGTH: 2337
<212> TYPE: DNA
<213> ORGANISM: Chlamydia

<400> SEQUENCE: 185

```
atgcatcacc atcaccatca cgggttagct agttgcgtag atcttcatgc tggaggacag      60
tctgtaaatg agctggtata tgtaggccct caagcggttt tattgttaga ccaaattcga     120
gatctattcg ttgggtctaa agatagtcag gctgaaggac agtataggtt aattgtagga     180
gatccaagtt ctttccaaga gaaagatgca gatactcttc ccgggaaggt agagcaaagt     240
actttgttct cagtaaccaa tcccgtggtt ttccaaggtg tggaccaaca ggatcaagtc     300
tcttcccaag ggttaatttg tagttttacg agcagcaacc ttgattctcc ccgtgacgga     360
gaatcttttt taggtattgc ttttgttggg atagtagta aggctggaat cacattaact     420
gacgtgaaag cttcttttgtc tggagcggct ttatattcta cagaagatct tatctttgaa     480
aagattaagg gtggattgga atttgcatca tgttcttctc tagaacaggg gggagcttgt     540
gcagctcaaa gtattttgat tcatgattgt caaggattgc aggttaaaca ctgtactaca     600
gccgtgaatg ctgaggggtc tagtgcgaat gatcatcttg gatttggagg aggcgctttc     660
tttgttacgg gttctctttc tggagagaaa agtctctata tgcctgcagg agatatggta     720
gttgcgaatt gtgatgggc tatatctttt gaaggaaaca gcgcgaactt tgctaatgga     780
ggagcgattg ctgcctctgg gaaagtgctt tttgtcgcta atgataaaaa gacttctttt     840
atagagaacc gagctttgtc tggaggagcg attgcagcct cttctgatat tgcctttcaa     900
aactgcgcag aactagtttt caaaggcaat gtgcaattg aacagagga taaaggttct     960
ttaggtggag gggctatatc ttctctaggc accgttcttt tgcaagggaa tcacgggata    1020
acttgtgata agaatgagtc tgcttcgcaa ggaggcgcca tttttggcaa aaattgtcag    1080
atttctgaca acgaggggcc agtggttttc agagatagta cagcttgctt aggaggaggc    1140
gctattgcag ctcaagaaat tgtttctatt cagaacaatc aggctgggat ttccttcgag    1200
ggaggtaagg ctagtttcgg aggaggtatt gcgtgtggat ctttttcttc cgcaggcggt    1260
gcttctgttt tagggactat tgatatttcg aagaatttag gcgcgatttc gttctctcgt    1320
actttatgta cgacctcaga tttaggacaa atggagtacc agggaggagg agctctatt    1380
ggtgaaaata tttctctttc tgagaatgct ggtgtgctca cctttaaaga caacattgtg    1440
aagactttg cttcgaatgg gaaaattctg ggaggaggag cgattttagc tactggtaag    1500
gtggaaatta ccataattc cggaggaatt tcttttacag gaaatgcgag agctccacaa    1560
gctcttccaa ctcaagagga gtttcctta ttcagcaaaa agaagggcg accactctct    1620
tcaggatatt ctgggggagg agcgatttta ggaagagaag tagctattct ccacaacgct    1680
gcagtagtat ttgagcaaaa tcgtttgcag tgcagcgaag aagaagcgac attattaggt    1740
tgttgtggag gaggcgctgt tcatgggatg gatagcactt cgattgttgg caactcttca    1800
gtaagatttg gtaataatta cgcaatggga caaggagtct caggaggagc tcttttatct    1860
aaaacagtgc agttagctgg aaatggaagc gtcgattttt ctcgaaatat tgctagtttg    1920
ggaggaggag ctcttcaagc ttctgaagga aattgtgagc tagttgataa cggctatgtg    1980
ctattcagag ataatcgagg gagggttat ggggggtgcta tttcttgctt acgtggagat    2040
gtagtcattt ctgaaacaa gggtagagtt gaatttaaag acaacatagc aacacgtctt    2100
tatgtggaag aaactgtaga aaaggttgaa gaggtagagc cagctcctga gcaaaaagac    2160
```

```
aataatgagc tttctttctt agggagtgta gaacagagtt ttattactgc agctaatcaa    2220
gctcttttcg catctgaaga tggggattta tcacctgagt catccatttc ttctgaagaa    2280
cttgcgaaaa gaagagagtg tgctggagga gctgactcga gcagatccgg ctgctaa      2337

<210> SEQ ID NO 186
<211> LENGTH: 2847
<212> TYPE: DNA
<213> ORGANISM: Chlamydia

<400> SEQUENCE: 186
atggctagca tgcatcacca tcaccatcac gttaagattg agaacttctc tggccaagga      60
atattttctg gaaacaaagc tatcgataac accacagaag gctcctcttc caaatctaac     120
gtcctcggag gtgcggtcta tgctaaaaca ttgtttaatc tcgatagcgg gagctctaga     180
cgaactgtca ccttctccgg gaatactgtc tcttctcaat ctacaacagg tcaggttgct     240
ggaggagcta tctactctcc tactgtaacc attgctactc ctgtagtatt ttctaaaaac     300
tctgcaacaa acaatgctaa taacgctaca gatactcaga gaaagacac ctttggagga     360 gctatcggag ctacttctgc tgtttctcta tcaggagggg ctcatttctt agaaaacgtt     420
gctgacctcg gatctgctat tgggttggtg ccagacacac aaaatacaga aacagtgaaa     480
ttagagtctg gctcctacta ctttgaaaaa aataaagctt taaaacgagc tactatttac     540
gcacctgtcg tttccattaa agcctatact gcgacattta accaaacag atctctagaa     600 gaaggaagcg cgatttactt tacaaaagaa gcatctattg agtctttagg ctctgttctc     660
ttcacaggaa acttagtaac cccaacgcta agcacaacta cagaaggcac accagccaca     720
acctcaggag atgtaacaaa atatggtgct gctatctttg gacaaatagc aagctcaaac     780
ggatctcaga cggataaacct tccctgaaa ctcattgctt caggaggaaa tatttgtttc     840
cgaaacaatg aataccgtcc tacttcttct gataccggaa cctctacttt ctgtagtatt     900
gcgggagatg ttaaattaac catgcaagct gcaaagggaa aaacgatcag tttctttgat     960
gcaatccgga cctctactaa gaaaacaggt acacaggcaa ctgcctacga tactctcgat    1020
attaataaat ctgaggattc agaaactgta aactctgcgt ttacaggaac gattctgttc    1080
tcctctgaat tacatgaaaa taaatcctat attccacaaa acgtagttct acacagtgga    1140
tctcttgtat tgaagccaaa taccgagctt catgtcattt cttttgagca gaaagaaggc    1200
tcttctctcg ttatgacacc tggatctgtt cttttcgaacc agactgttgc tgatggagct    1260
ttggtcataa ataacatgac cattgattta tccagcgtag agaaaaatgg tattgctgaa    1320
ggaaatatct ttactcctcc agaattgaga atcatagaca ctactacaag tggaagcggt    1380
ggaaccccat ctacagatag tgaaagtaac cagaatagtg atgataccaa ggagcaaaat    1440
aataatgacg cctcgaatca aggagaaagc gcgaatggat cgtcttctcc tgcagtagct    1500
gctgcacaca catctcgtac aagaaacttt gccgctgcag ctacagccac acctacgaca    1560
acaccaacgc tacaactac aacaagcaac caagtaatcc taggaggaga atcaaactc    1620 atcgatccta tgggaccctt cttccagaac cctgcattaa gatccgacca acaaatctcc    1680
ttgttagtgc tccctacaga ctcatcaaaa atgcaagctc agaaaatagt actgacgggt    1740
gatattgctc ctcagaaagg atatacagga acactcactc tggatcctga tcaactacaa    1800
aatgaaacga tctcagcgct ctggaaattt gactcttata gacaatgggc ttatgtacct    1860
agagacaatc atttctatgc gaactcgatt ctgggatctc aaatgtcaat ggtcacagtc    1920
```

-continued

| | | | | |
|---|---|---|---|---|
| aaacaaggct | tgctcaacga | taaaatgaat | ctagctcgct | ttgatgaagt | tagctataac | 1980 |
| aacctgtgga | tatcaggact | aggaacgatg | ctatcgcaag | taggaacacc | tacttctgaa | 2040 |
| gaattcactt | attacagcag | aggagcttct | gttgccttag | atgctaaacc | agcccatgat | 2100 |
| gtgattgttg | gagctgcatt | tagtaagatg | atcgggaaaa | caaaatcctt | gaaaagagag | 2160 |
| aataactaca | ctcacaaagg | atccgaatat | tcttaccaag | catcggtata | cggaggcaaa | 2220 |
| ccattccact | ttgtaatcaa | taaaaaaacg | gaaaaatcgc | taccgctatt | gttacaagga | 2280 |
| gtcatctctt | acggatatat | caaacatgat | acagtgactc | actatccaac | gatccgtgaa | 2340 |
| cgaaaccaag | gagaatggga | agacttagga | tggctgacag | ctctccgtgt | ctcctctgtc | 2400 |
| ttaagaactc | ctgcacaagg | ggatactaaa | cgtatcactg | tttacggaga | attggaatac | 2460 |
| tccagtatcc | gtcagaaaca | attcacagaa | acagaatacg | atcctcgtta | cttcgacaac | 2520 |
| tgcacctata | gaaacttagc | aattcctatg | gggttagcat | tcgaaggaga | gctctctggt | 2580 |
| aacgatattt | tgatgtacaa | cagattctct | gtagcataca | tgccatcaat | ctatcgaaat | 2640 |
| tctccaacat | gcaaatacca | agtgctctct | tcaggagaag | gcggagaaat | tatttgtgga | 2700 |
| gtaccgacaa | gaaactcagc | tcgcggagaa | tacagcacgc | agctgtaccc | gggacctttg | 2760 |
| tggactctgt | atggatccta | cacgatagaa | gcagacgcac | atacactagc | tcatatgatg | 2820 |
| aactgcggtg | ctcgtatgac | attctaa | | | | 2847 |

<210> SEQ ID NO 187
<211> LENGTH: 2466
<212> TYPE: DNA
<213> ORGANISM: Chlamydia

<400> SEQUENCE: 187

| | | | | |
|---|---|---|---|---|
| atgcatcacc | atcaccatca | cgaggcgagc | tcgatccaag | atcaaataaa | gaataccgac | 60 |
| tgcaatgtta | gcaaagtagg | atattcaact | tctcaagcat | ttactgatat | gatgctagca | 120 |
| gacaacacag | agtatcgagc | tgctgatagt | gtttcattct | atgactttttc | gacatcttcc | 180 |
| ggattaccta | gaaaacatct | tagtagtagt | agtgaagctc | tccaacgac | agaaggagtg | 240 |
| tcttcatctt | catctggaga | aaatactgag | aattcacaag | attcagctcc | ctcttctgga | 300 |
| gaaactgata | agaaaacaga | agaagaacta | gacaatggcg | gaatcattta | tgctagagag | 360 |
| aaactaacta | tctcagaatc | tcaggactct | ctctctaatc | caagcataga | actccatgac | 420 |
| aatagttttt | tcttcggaga | aggtgaagtt | atctttgatc | acagagttgc | cctcaaaaac | 480 |
| ggaggagcta | tttatggaga | gaaagaggta | gtctttgaaa | acataaaatc | tctactagta | 540 |
| gaagtaaata | tctcggtcga | gaaaggggt | agcgtctatg | caaagaacg | agtatcttta | 600 |
| gaaaatgtta | ccgaagcaac | cttctcctcc | aatggtgggg | aacaaggtgg | tggtggaatc | 660 |
| tattcagaac | aagatatgtt | aatcagtgat | tgcaacaatg | tacatttcca | agggaatgct | 720 |
| gcaggagcaa | cagcagtaaa | acaatgtctg | gatgaagaaa | tgatcgtatt | gctcacagaa | 780 |
| tgcgttgata | gcttatccga | agatacactg | gatagcactc | cagaaacgga | acagactaag | 840 |
| tcaaatggaa | atcaagatgg | ttcgtctgaa | acaaaagata | cacaagtatc | agaatcacca | 900 |
| gaatcaactc | ctagccccga | cgatgtttta | ggtaaaggtg | gtggtatcta | tacagaaaaa | 960 |
| tctttgacca | tcactggaat | tacagggact | atagattttg | tcagtaacat | agctaccgat | 1020 |
| tctggagcag | gtgtattcac | taagaaaaac | ttgtcttgca | ccaacacgaa | tagcctacag | 1080 |
| tttttgaaaa | actcggcagg | tcaacatgga | ggaggagcct | acgttactca | aaccatgtct | 1140 |
| gttactaata | caactagtga | aagtataact | actcccccctc | tcgtaggaga | agtgattttc | 1200 |

```
tctgaaaata cagctaaagg gcacggtggt ggtatctgca ctaacaaact ttctttatct    1260
aatttaaaaa cggtgactct cactaaaaac tctgcaaagg agtctggagg agctattttt    1320
acagatctag cgtctatacc aacaacagat accccagagt cttctacccc ctcttcctcc    1380
tcgcctgcaa gcactcccga agtagttgct tctgctaaaa taaatcgatt ctttgcctct    1440
acggcagaac cggcagcccc ttctctaaca gaggctgagt ctgatcaaac ggatcaaaca    1500
gaaacttctg atactaatag cgatatagac gtgtcgattg agaacatttt gaatgtcgct    1560
atcaatcaaa acacttctgc gaaaaaagga ggggctattt acgggaaaaa agctaaactt    1620
tcccgtatta acaatcttga actttcaggg aattcatccc aggatgtagg aggaggtctc    1680
tgtttaactg aaagcgtaga atttgatgca attggatcgc tcttatccca ctataactct    1740
gctgctaaag aaggtgggt tattcattct aaaacggtta ctctatctaa cctcaagtct    1800
accttcactt ttgcagataa cactgttaaa gcaatagtag aaagcactcc tgaagctcca    1860
gaagagattc ctccagtaga aggagaagag tctacagcaa cagaaaatcc gaattctaat    1920
acagaaggaa gttcggctaa cactaacctt gaaggatctc aagggatac tgctgataca    1980 gggactggtg ttgttaacaa tgagtctcaa gacacatcag atactggaaa cgctgaatct    2040
ggagaacaac tacaagattc tacacaatct aatgaagaaa ataccttcc caatagtagt    2100 attgatcaat ctaacgaaaa cacagacgaa tcatctgata gccacactga ggaaataact    2160
gacgagagtg tctcatcgtc ctctaaaagt ggatcatcta ctcctcaaga tggaggagca    2220
gcttcttcag gggctccctc aggagatcaa tctatctctg caaacgcttg tttagctaaa    2280
agctatgctg cgagtactga tagctcccct gtatctaatt cttcaggttc agacgttact    2340
gcatcttctg ataatccaga ctcttcctca tctggagata gcgctggaga ctctgaagga    2400
ccgactgagc cagaagctgg ttctacaaca gaaactccta cttaatagg aggaggtgct    2460 atctga                                                                2466

<210> SEQ ID NO 188
<211> LENGTH: 1578
<212> TYPE: DNA
<213> ORGANISM: Chlamydia

<400> SEQUENCE: 188
atgcatcacc atcaccatca cacggccgcg tccgataact tccagctgtc ccagggtggg      60
cagggattcg ccattccgat cgggcaggcg atggcgatcg cgggccagat caagcttccc     120
accgttcata tcgggcctac cgccttcctc ggcttgggtg ttgtcgacaa caacggcaac     180
ggcgcacgag tccaacgcgt ggtcgggagc gctccggcgc caagtctcgg catctccacc     240
ggcgacgtga tcaccgcggt cgacggcgct ccgatcaact cggccaccgc gatggcggac     300
gcgcttaacg ggcatcatcc cggtgacgtc atctcggtga cctggcaaac caagtcgggc     360
ggcacgcgta cagggaacgt gacattggcc gagggacccc cggccgaatt cccgctagta     420
cctagaggtt caccgctgcc tgtggggaat ccagctgaac caagtttatt aatcgatggc     480
actatgtggg aaggtgcttc aggagatcct tgcgatcctt gcgctacttg gtgtgacgcc     540
attagcatcc gcgcaggata ctacggagat tatgttttcg atcgtgtatt aaaagttgat     600
gtgaataaaa cttttagcgg catggctgca actcctacgc aggctatagg taacgcaagt     660
aatactaatc agccagaagc aaatggcaga ccgaacatcg cttacggaag gcatatgcaa     720
gatgcagagt ggttttcaaa tgcagccttc ctagccttaa acatttggga tcgcttcgac     780
```

-continued

```
attttctgca ccttaggggc atccaatgga tacttcaaag caagttcggc tgcattcaac      840
ttggttgggt taatagggtt ttcagctgca agctcaatct ctaccgatct tccaatgcaa      900
cttcctaacg taggcattac ccaaggtgtt gtggaatttt atacagacac atcattttct      960
tggagcgtag gtgcacgtgg agctttatgg gaatgtggtt gtgcaacttt aggagctgag     1020
ttccaatacg ctcaatctaa tcctaagatt gagatgctca acgtcacttc aagcccagca     1080
caatttgtga ttcacaaacc aagaggctat aaaggagcta gctcgaattt tcctttacct     1140
ataacggctg gaacaacaga agctacagac accaaatcag ctacaattaa ataccatgaa     1200
tggcaagtag gcctcgccct gtcttacaga ttgaatatgc ttgttccata tattggcgta     1260
aactggtcaa gagcaacttt tgatgctgat actatccgca ttgctcaacc taaattaaaa     1320
tcggagattc ttaacattac tacatggaac ccaagcctta taggatcaac cactgctttg     1380
cccaataata gtggtaagga tgttctatct gatgtcttgc aaattgcttc gattcagatc     1440
aacaaaatga agtctagaaa agcttgtggt gtagctgttg gtgcaacgtt aatcgacgct     1500
gacaaatggt caatcactgg tgaagcacgc ttaatcaatg aaagagctgc tcacatgaat     1560
gcacaattcc gcttctaa                                                   1578
```

<210> SEQ ID NO 189
<211> LENGTH: 866
<212> TYPE: PRT
<213> ORGANISM: Chlamydia
<220> FEATURE:
<221> NAME/KEY: VARIANT
<222> LOCATION: (1)...(866)
<223> OTHER INFORMATION: Xaa = Any Amino Acid

<400> SEQUENCE: 189

```
Met Ala Ser His His His His His His Leu Phe Gly Gln Asp Pro Leu
 1               5                  10                  15

Gly Glu Thr Ala Leu Leu Thr Lys Asn Pro Asn His Val Val Cys Thr
                20                  25                  30

Phe Phe Glu Asp Cys Thr Met Glu Ser Leu Phe Pro Ala Leu Cys Ala
            35                  40                  45

His Ala Ser Gln Asp Asp Pro Leu Tyr Val Leu Gly Asn Ser Tyr Cys
        50                  55                  60

Trp Phe Val Ser Lys Leu His Ile Thr Asp Pro Lys Glu Ala Leu Phe
65                  70                  75                  80

Lys Glu Lys Gly Asp Leu Ser Ile Gln Asn Phe Arg Phe Leu Ser Phe
                85                  90                  95

Thr Asp Cys Ser Ser Lys Glu Ser Ser Pro Ser Ile Ile His Gln Lys
            100                 105                 110

Asn Gly Gln Leu Ser Leu Arg Asn Asn Gly Ser Met Ser Phe Cys Arg
        115                 120                 125

Asn His Ala Glu Gly Ser Gly Ala Ile Ser Ala Asp Ala Phe Ser
    130                 135                 140

Leu Gln His Asn Tyr Leu Phe Thr Ala Phe Glu Glu Asn Ser Ser Lys
145                 150                 155                 160

Gly Asn Gly Gly Ala Ile Gln Ala Gln Thr Phe Ser Leu Ser Arg Asn
                165                 170                 175

Val Ser Pro Ile Ser Phe Ala Arg Asn Arg Ala Asp Leu Asn Gly Gly
            180                 185                 190

Ala Ile Cys Cys Ser Asn Leu Ile Cys Ser Gly Asn Val Asn Pro Leu
        195                 200                 205
```

```
Phe Phe Thr Gly Asn Ser Ala Thr Asn Gly Gly Xaa Ile Cys Cys Ile
    210                 215                 220

Ser Asp Leu Asn Thr Ser Glu Lys Gly Ser Leu Ser Leu Ala Cys Asn
225                 230                 235                 240

Gln Xaa Thr Leu Phe Ala Ser Asn Ser Ala Lys Glu Lys Gly Gly Ala
            245                 250                 255

Ile Tyr Ala Lys His Met Val Leu Arg Tyr Asn Gly Pro Val Ser Phe
            260                 265                 270

Ile Asn Asn Ser Ala Lys Ile Gly Gly Ala Ile Ala Ile Gln Ser Gly
        275                 280                 285

Gly Ser Leu Ser Ile Leu Ala Gly Glu Gly Ser Val Leu Phe Gln Asn
    290                 295                 300

Asn Ser Gln Arg Thr Ser Asp Gln Gly Leu Val Arg Asn Ala Ile Tyr
305                 310                 315                 320

Leu Glu Lys Asp Ala Ile Leu Ser Ser Leu Glu Ala Arg Asn Gly Asp
            325                 330                 335

Ile Leu Phe Phe Asp Pro Ile Val Gln Glu Ser Ser Lys Glu Ser
            340                 345                 350

Pro Leu Pro Ser Ser Leu Gln Ala Ser Val Thr Ser Pro Thr Pro Ala
    355                 360                 365

Thr Ala Ser Pro Leu Val Ile Gln Thr Ser Ala Asn Arg Ser Val Ile
    370                 375                 380

Phe Ser Ser Glu Arg Leu Ser Glu Glu Glu Lys Thr Pro Asp Asn Leu
385                 390                 395                 400

Thr Ser Gln Leu Gln Gln Pro Ile Glu Leu Lys Ser Gly Arg Leu Val
            405                 410                 415

Leu Lys Asp Arg Ala Val Leu Ser Xaa Pro Ser Leu Ser Gln Asp Pro
            420                 425                 430

Gln Ala Leu Leu Ile Met Glu Ala Gly Thr Ser Leu Lys Thr Ser Xaa
        435                 440                 445

Asp Leu Lys Leu Xaa Thr Xaa Ser Ile Pro Leu His Ser Leu Asp Thr
450                 455                 460

Glu Lys Ser Val Thr Ile His Ala Pro Asn Leu Ser Ile Gln Lys Ile
465                 470                 475                 480

Phe Leu Ser Asn Ser Gly Asp Glu Asn Phe Tyr Glu Asn Val Glu Leu
            485                 490                 495

Leu Ser Lys Glu Gln Asn Asn Ile Pro Leu Leu Thr Leu Pro Lys Glu
        500                 505                 510

Gln Ser His Leu His Leu Pro Asp Gly Asn Leu Ser Ser His Phe Gly
    515                 520                 525

Tyr Gln Gly Asp Trp Thr Phe Ser Trp Lys Asp Ser Asp Glu Gly His
    530                 535                 540

Ser Leu Ile Ala Asn Trp Thr Pro Lys Asn Tyr Val Pro His Pro Glu
545                 550                 555                 560

Arg Gln Ser Thr Leu Val Ala Asn Thr Leu Trp Asn Thr Tyr Ser Asp
            565                 570                 575

Met Gln Ala Val Gln Ser Met Ile Asn Thr Thr Ala His Gly Gly Ala
            580                 585                 590

Tyr Leu Phe Gly Thr Trp Gly Ser Ala Val Ser Asn Leu Phe Tyr Val
        595                 600                 605

His Asp Ser Ser Gly Lys Pro Ile Asp Asn Trp His His Arg Ser Leu
610                 615                 620

Gly Tyr Leu Phe Gly Ile Ser Thr His Ser Leu Asp Asp His Ser Phe
```

```
625                 630                 635                 640
Cys Leu Ala Ala Gly Gln Leu Gly Lys Ser Ser Asp Ser Phe Ile
                645                 650                 655
Thr Ser Thr Glu Thr Thr Ser Tyr Ile Ala Thr Val Gln Ala Gln Leu
                660                 665                 670
Ala Thr Ser Leu Met Lys Ile Ser Ala Gln Ala Cys Tyr Asn Glu Ser
                675                 680                 685
Ile His Glu Leu Lys Thr Lys Tyr Arg Ser Phe Ser Lys Glu Gly Phe
                690                 695                 700
Gly Ser Trp His Ser Val Ala Val Ser Gly Glu Val Cys Ala Ser Ile
705                 710                 715                 720
Pro Ile Val Ser Asn Gly Ser Gly Leu Phe Ser Ser Phe Ser Ile Phe
                725                 730                 735
Ser Lys Leu Gln Gly Phe Ser Gly Thr Gln Asp Gly Phe Glu Glu Ser
                740                 745                 750
Ser Gly Glu Ile Arg Ser Phe Ser Ala Ser Ser Phe Arg Asn Ile Ser
                755                 760                 765
Leu Pro Ile Gly Ile Thr Phe Glu Lys Lys Ser Gln Lys Thr Arg Thr
                770                 775                 780
Tyr Tyr Tyr Phe Leu Gly Ala Tyr Ile Gln Asp Leu Lys Arg Asp Val
785                 790                 795                 800
Glu Ser Gly Pro Val Val Leu Leu Lys Asn Ala Val Ser Trp Asp Ala
                805                 810                 815
Pro Met Ala Asn Leu Asp Ser Arg Ala Tyr Met Phe Arg Leu Thr Asn
                820                 825                 830
Gln Arg Ala Leu His Arg Leu Gln Thr Leu Leu Asn Val Ser Cys Val
                835                 840                 845
Leu Arg Gly Gln Ser His Ser Tyr Ser Leu Asp Leu Gly Thr Thr Tyr
                850                 855                 860
Arg Phe
865

<210> SEQ ID NO 190
<211> LENGTH: 1006
<212> TYPE: PRT
<213> ORGANISM: Chlamydia

<400> SEQUENCE: 190

Met Ala Ser Met Thr Gly Gly Gln Gln Met Gly Arg Asp Ser Ser Leu
  1               5                  10                  15
Val Pro His His His His His His Met Ile Pro Gln Gly Ile Tyr Asp
                 20                  25                  30
Gly Glu Thr Leu Thr Val Ser Phe Pro Tyr Thr Val Ile Gly Asp Pro
                 35                  40                  45
Ser Gly Thr Thr Val Phe Ser Ala Gly Glu Leu Thr Leu Lys Asn Leu
 50                  55                  60
Asp Asn Ser Ile Ala Ala Leu Pro Leu Ser Cys Phe Gly Asn Leu Leu
 65                  70                  75                  80
Gly Ser Phe Thr Val Leu Gly Arg Gly His Ser Leu Thr Phe Glu Asn
                 85                  90                  95
Ile Arg Thr Ser Thr Asn Gly Ala Ala Leu Ser Asn Ser Ala Ala Asp
                100                 105                 110
Gly Leu Phe Thr Ile Glu Gly Phe Lys Glu Leu Ser Phe Ser Asn Cys
                115                 120                 125
```

```
Asn Ser Leu Leu Ala Val Leu Pro Ala Ala Thr Thr Asn Lys Gly Ser
    130                 135                 140

Gln Thr Pro Thr Thr Thr Ser Thr Pro Ser Asn Gly Thr Ile Tyr Ser
145                 150                 155                 160

Lys Thr Asp Leu Leu Leu Asn Asn Glu Lys Phe Ser Phe Tyr Ser
                165                 170                 175

Asn Leu Val Ser Gly Asp Gly Ala Ile Asp Ala Lys Ser Leu Thr
            180                 185                 190

Val Gln Gly Ile Ser Lys Leu Cys Val Phe Gln Glu Asn Thr Ala Gln
        195                 200                 205

Ala Asp Gly Gly Ala Cys Gln Val Val Thr Ser Phe Ser Ala Met Ala
    210                 215                 220

Asn Glu Ala Pro Ile Ala Phe Val Ala Asn Val Ala Gly Val Arg Gly
225                 230                 235                 240

Gly Gly Ile Ala Ala Val Gln Asp Gly Gln Gln Gly Val Ser Ser Ser
                245                 250                 255

Thr Ser Thr Glu Asp Pro Val Val Ser Phe Ser Arg Asn Thr Ala Val
            260                 265                 270

Glu Phe Asp Gly Asn Val Ala Arg Val Gly Gly Ile Tyr Ser Tyr
        275                 280                 285

Gly Asn Val Ala Phe Leu Asn Asn Gly Lys Thr Leu Phe Leu Asn Asn
    290                 295                 300

Val Ala Ser Pro Val Tyr Ile Ala Ala Lys Gln Pro Thr Ser Gly Gln
305                 310                 315                 320

Ala Ser Asn Thr Ser Asn Asn Tyr Gly Asp Gly Gly Ala Ile Phe Cys
                325                 330                 335

Lys Asn Gly Ala Gln Ala Gly Ser Asn Asn Ser Gly Ser Val Ser Phe
            340                 345                 350

Asp Gly Glu Gly Val Val Phe Phe Ser Ser Asn Val Ala Ala Gly Lys
        355                 360                 365

Gly Gly Ala Ile Tyr Ala Lys Lys Leu Ser Val Ala Asn Cys Gly Pro
    370                 375                 380

Val Gln Phe Leu Arg Asn Ile Ala Asn Asp Gly Gly Ala Ile Tyr Leu
385                 390                 395                 400

Gly Glu Ser Gly Glu Leu Ser Leu Ser Ala Asp Tyr Gly Asp Ile Ile
                405                 410                 415

Phe Asp Gly Asn Leu Lys Arg Thr Ala Lys Glu Asn Ala Ala Asp Val
            420                 425                 430

Asn Gly Val Thr Val Ser Ser Gln Ala Ile Ser Met Gly Ser Gly Gly
        435                 440                 445

Lys Ile Thr Thr Leu Arg Ala Lys Ala Gly His Gln Ile Leu Phe Asn
    450                 455                 460

Asp Pro Ile Glu Met Ala Asn Gly Asn Gln Pro Ala Gln Ser Ser
465                 470                 475                 480

Lys Leu Leu Lys Ile Asn Asp Gly Glu Gly Tyr Thr Gly Asp Ile Val
                485                 490                 495

Phe Ala Asn Gly Ser Ser Thr Leu Tyr Gln Asn Val Thr Ile Glu Gln
            500                 505                 510

Gly Arg Ile Val Leu Arg Glu Lys Ala Lys Leu Ser Val Asn Ser Leu
        515                 520                 525

Ser Gln Thr Gly Gly Ser Leu Tyr Met Glu Ala Gly Ser Thr Leu Asp
    530                 535                 540

Phe Val Thr Pro Gln Pro Pro Gln Gln Pro Ala Ala Asn Gln Leu
```

-continued

```
545                 550                 555                 560
Ile Thr Leu Ser Asn Leu His Leu Ser Leu Ser Ser Leu Leu Ala Asn
                565                 570                 575

Asn Ala Val Thr Asn Pro Pro Thr Asn Pro Pro Ala Gln Asp Ser His
                580                 585                 590

Pro Ala Val Ile Gly Ser Thr Thr Ala Gly Ser Val Thr Ile Ser Gly
                595                 600                 605

Pro Ile Phe Phe Glu Asp Leu Asp Asp Thr Ala Tyr Asp Arg Tyr Asp
                610                 615                 620

Trp Leu Gly Ser Asn Gln Lys Ile Asn Val Leu Lys Leu Gln Leu Gly
625                 630                 635                 640

Thr Lys Pro Pro Ala Asn Ala Pro Ser Asp Leu Thr Leu Gly Asn Glu
                645                 650                 655

Met Pro Lys Tyr Gly Tyr Gln Gly Ser Trp Lys Leu Ala Trp Asp Pro
                660                 665                 670

Asn Thr Ala Asn Asn Gly Pro Tyr Thr Leu Lys Ala Thr Trp Thr Lys
                675                 680                 685

Thr Gly Tyr Asn Pro Gly Pro Glu Arg Val Ala Ser Leu Val Pro Asn
                690                 695                 700

Ser Leu Trp Gly Ser Ile Leu Asp Ile Arg Ser Ala His Ser Ala Ile
705                 710                 715                 720

Gln Ala Ser Val Asp Gly Arg Ser Tyr Cys Arg Gly Leu Trp Val Ser
                725                 730                 735

Gly Val Ser Asn Phe Phe Tyr His Asp Arg Asp Ala Leu Gly Gln Gly
                740                 745                 750

Tyr Arg Tyr Ile Ser Gly Gly Tyr Ser Leu Gly Ala Asn Ser Tyr Phe
                755                 760                 765

Gly Ser Ser Met Phe Gly Leu Ala Phe Thr Glu Val Phe Gly Arg Ser
770                 775                 780

Lys Asp Tyr Val Val Cys Arg Ser Asn His His Ala Cys Ile Gly Ser
785                 790                 795                 800

Val Tyr Leu Ser Thr Gln Gln Ala Leu Cys Gly Ser Tyr Leu Phe Gly
                805                 810                 815

Asp Ala Phe Ile Arg Ala Ser Tyr Gly Phe Gly Asn Gln His Met Lys
                820                 825                 830

Thr Ser Tyr Thr Phe Ala Glu Glu Ser Asp Val Arg Trp Asp Asn Asn
                835                 840                 845

Cys Leu Ala Gly Glu Ile Gly Ala Gly Leu Pro Ile Val Ile Thr Pro
850                 855                 860

Ser Lys Leu Tyr Leu Asn Glu Leu Arg Pro Phe Val Gln Ala Glu Phe
865                 870                 875                 880

Ser Tyr Ala Asp His Glu Ser Phe Thr Glu Glu Gly Asp Gln Ala Arg
                885                 890                 895

Ala Phe Lys Ser Gly His Leu Leu Asn Leu Ser Val Pro Val Gly Val
                900                 905                 910

Lys Phe Asp Arg Cys Ser Ser Thr His Pro Asn Lys Tyr Ser Phe Met
                915                 920                 925

Ala Ala Tyr Ile Cys Asp Ala Tyr Arg Thr Ile Ser Gly Thr Glu Thr
                930                 935                 940

Thr Leu Leu Ser His Gln Glu Thr Trp Thr Thr Asp Ala Phe His Leu
945                 950                 955                 960

Ala Arg His Gly Val Val Val Arg Gly Ser Met Tyr Ala Ser Leu Thr
                965                 970                 975
```

-continued

Ser Asn Ile Glu Val Tyr Gly His Gly Arg Tyr Glu Tyr Arg Asp Ala
            980                 985                 990

Ser Arg Gly Tyr Gly Leu Ser Ala Gly Ser Lys Val Arg Phe
            995                 1000                1005

<210> SEQ ID NO 191
<211> LENGTH: 977
<212> TYPE: PRT
<213> ORGANISM: Chlamydia

<400> SEQUENCE: 191

Met Ala Ser Met Thr Gly Gly Gln Gln Met Gly Arg Asp Ser Ser Leu
 1               5                  10                  15

Val Pro Ser Ser Asp Pro His His His His Gly Leu Ala Arg
            20                  25                  30

Glu Val Pro Ser Arg Ile Phe Leu Met Pro Asn Ser Val Pro Asp Pro
            35                  40                  45

Thr Lys Glu Ser Leu Ser Asn Lys Ile Ser Leu Thr Gly Asp Thr His
        50                  55                  60

Asn Leu Thr Asn Cys Tyr Leu Asp Asn Leu Arg Tyr Ile Leu Ala Ile
65                  70                  75                  80

Leu Gln Lys Thr Pro Asn Glu Gly Ala Ala Val Thr Ile Thr Asp Tyr
                85                  90                  95

Leu Ser Phe Phe Asp Thr Gln Lys Glu Gly Ile Tyr Phe Ala Lys Asn
            100                 105                 110

Leu Thr Pro Glu Ser Gly Gly Ala Ile Gly Tyr Ala Ser Pro Asn Ser
            115                 120                 125

Pro Thr Val Glu Ile Arg Asp Thr Ile Gly Pro Val Ile Phe Glu Asn
        130                 135                 140

Asn Thr Cys Cys Arg Leu Phe Thr Trp Arg Asn Pro Tyr Ala Ala Asp
145                 150                 155                 160

Lys Ile Arg Glu Gly Gly Ala Ile His Ala Gln Asn Leu Tyr Ile Asn
                165                 170                 175

His Asn His Asp Val Val Gly Phe Met Lys Asn Phe Ser Tyr Val Gln
            180                 185                 190

Gly Gly Ala Ile Ser Thr Ala Asn Thr Phe Val Val Ser Glu Asn Gln
            195                 200                 205

Ser Cys Phe Leu Phe Met Asp Asn Ile Cys Ile Gln Thr Asn Thr Ala
        210                 215                 220

Gly Lys Gly Gly Ala Ile Tyr Ala Gly Thr Ser Asn Ser Phe Glu Ser
225                 230                 235                 240

Asn Asn Cys Asp Leu Phe Ile Asn Asn Ala Cys Cys Ala Gly Gly
                245                 250                 255

Ala Ile Phe Ser Pro Ile Cys Ser Leu Thr Gly Asn Arg Gly Asn Ile
            260                 265                 270

Val Phe Tyr Asn Asn Arg Cys Phe Lys Asn Val Glu Thr Ala Ser Ser
            275                 280                 285

Glu Ala Ser Asp Gly Gly Ala Ile Lys Val Thr Thr Arg Leu Asp Val
        290                 295                 300

Thr Gly Asn Arg Gly Arg Ile Phe Phe Ser Asp Asn Ile Thr Lys Asn
305                 310                 315                 320

Tyr Gly Gly Ala Ile Tyr Ala Pro Val Val Thr Leu Val Asp Asn Gly
                325                 330                 335

Pro Thr Tyr Phe Ile Asn Asn Ile Ala Asn Asn Lys Gly Gly Ala Ile

-continued

```
                    340                 345                 350
Tyr Ile Asp Gly Thr Ser Asn Ser Lys Ile Ser Ala Asp Arg His Ala
        355                 360                 365
Ile Ile Phe Asn Glu Asn Ile Val Thr Asn Val Thr Asn Ala Asn Gly
        370                 375                 380
Thr Ser Thr Ser Ala Asn Pro Pro Arg Arg Asn Ala Ile Thr Val Ala
385                 390                 395                 400
Ser Ser Ser Gly Glu Ile Leu Leu Gly Ala Gly Ser Ser Gln Asn Leu
                    405                 410                 415
Ile Phe Tyr Asp Pro Ile Glu Val Ser Asn Ala Gly Val Ser Val Ser
                420                 425                 430
Phe Asn Lys Glu Ala Asp Gln Thr Gly Ser Val Val Phe Ser Gly Ala
            435                 440                 445
Thr Val Asn Ser Ala Asp Phe His Gln Arg Asn Leu Gln Thr Lys Thr
        450                 455                 460
Pro Ala Pro Leu Thr Leu Ser Asn Gly Phe Leu Cys Ile Glu Asp His
465                 470                 475                 480
Ala Gln Leu Thr Val Asn Arg Phe Thr Gln Thr Gly Gly Val Val Ser
                    485                 490                 495
Leu Gly Asn Gly Ala Val Leu Ser Cys Tyr Lys Asn Gly Thr Gly Asp
                500                 505                 510
Ser Ala Ser Asn Ala Ser Ile Thr Leu Lys His Ile Gly Leu Asn Leu
            515                 520                 525
Ser Ser Ile Leu Lys Ser Gly Ala Glu Ile Pro Leu Leu Trp Val Glu
        530                 535                 540
Pro Thr Asn Asn Ser Asn Asn Tyr Thr Ala Asp Thr Ala Ala Thr Phe
545                 550                 555                 560
Ser Leu Ser Asp Val Lys Leu Ser Leu Ile Asp Asp Tyr Gly Asn Ser
                    565                 570                 575
Pro Tyr Glu Ser Thr Asp Leu Thr His Ala Leu Ser Ser Gln Pro Met
                580                 585                 590
Leu Ser Ile Ser Glu Ala Ser Asp Asn Gln Leu Gln Ser Glu Asn Ile
            595                 600                 605
Asp Phe Ser Gly Leu Asn Val Pro His Tyr Gly Trp Gln Gly Leu Trp
        610                 615                 620
Thr Trp Gly Trp Ala Lys Thr Gln Asp Pro Glu Pro Ala Ser Ser Ala
625                 630                 635                 640
Thr Ile Thr Asp Pro Gln Lys Ala Asn Arg Phe His Arg Thr Leu Leu
                    645                 650                 655
Leu Thr Trp Leu Pro Ala Gly Tyr Val Pro Ser Pro Lys His Arg Ser
                660                 665                 670
Pro Leu Ile Ala Asn Thr Leu Trp Gly Asn Met Leu Leu Ala Thr Glu
            675                 680                 685
Ser Leu Lys Asn Ser Ala Glu Leu Thr Pro Ser Gly His Pro Phe Trp
        690                 695                 700
Gly Ile Thr Gly Gly Gly Leu Gly Met Met Val Tyr Gln Asp Pro Arg
705                 710                 715                 720
Glu Asn His Pro Gly Phe His Met Arg Ser Ser Gly Tyr Ser Ala Gly
                    725                 730                 735
Met Ile Ala Gly Gln Thr His Thr Phe Ser Leu Lys Phe Ser Gln Thr
                740                 745                 750
Tyr Thr Lys Leu Asn Glu Arg Tyr Ala Lys Asn Asn Val Ser Ser Lys
            755                 760                 765
```

```
Asn Tyr Ser Cys Gln Gly Glu Met Leu Phe Ser Leu Gln Glu Gly Phe
        770                 775                 780

Leu Leu Thr Lys Leu Val Gly Leu Tyr Ser Tyr Gly Asp His Asn Cys
785                 790                 795                 800

His His Phe Tyr Thr Gln Gly Glu Asn Leu Thr Ser Gln Gly Thr Phe
                805                 810                 815

Arg Ser Gln Thr Met Gly Gly Ala Val Phe Phe Asp Leu Pro Met Lys
                820                 825                 830

Pro Phe Gly Ser Thr His Ile Leu Thr Ala Pro Phe Leu Gly Ala Leu
                835                 840                 845

Gly Ile Tyr Ser Ser Leu Ser His Phe Thr Glu Val Gly Ala Tyr Pro
        850                 855                 860

Arg Ser Phe Ser Thr Lys Thr Pro Leu Ile Asn Val Leu Val Pro Ile
865                 870                 875                 880

Gly Val Lys Gly Ser Phe Met Asn Ala Thr His Arg Pro Gln Ala Trp
                885                 890                 895

Thr Val Glu Leu Ala Tyr Gln Pro Val Leu Tyr Arg Gln Glu Pro Gly
                900                 905                 910

Ile Ala Thr Gln Leu Leu Ala Ser Lys Gly Ile Trp Phe Gly Ser Gly
                915                 920                 925

Ser Pro Ser Ser Arg His Ala Met Ser Tyr Lys Ile Ser Gln Gln Thr
        930                 935                 940

Gln Pro Leu Ser Trp Leu Thr Leu His Phe Gln Tyr His Gly Phe Tyr
945                 950                 955                 960

Ser Ser Ser Thr Phe Cys Asn Tyr Leu Asn Gly Glu Ile Ala Leu Arg
                965                 970                 975

Phe

<210> SEQ ID NO 192
<211> LENGTH: 848
<212> TYPE: PRT
<213> ORGANISM: Chlamydia

<400> SEQUENCE: 192

Met Ala Ser His His His His His His Gly Ala Ile Ser Cys Leu Arg
1               5                   10                  15

Gly Asp Val Val Ile Ser Gly Asn Lys Gly Arg Val Glu Phe Lys Asp
                20                  25                  30

Asn Ile Ala Thr Arg Leu Tyr Val Glu Glu Thr Val Glu Lys Val Glu
                35                  40                  45

Glu Val Glu Pro Ala Pro Glu Gln Lys Asp Asn Asn Glu Leu Ser Phe
        50                  55                  60

Leu Gly Ser Val Glu Gln Ser Phe Ile Thr Ala Ala Asn Gln Ala Leu
65                  70                  75                  80

Phe Ala Ser Glu Asp Gly Asp Leu Ser Pro Glu Ser Ser Ile Ser Ser
                85                  90                  95

Glu Glu Leu Ala Lys Arg Arg Cys Ala Gly Gly Ala Ile Phe Ala
                100                 105                 110

Lys Arg Val Arg Ile Val Asp Asn Gln Glu Ala Val Phe Ser Asn
        115                 120                 125

Asn Phe Ser Asp Ile Tyr Gly Gly Ala Ile Phe Thr Gly Ser Leu Arg
        130                 135                 140

Glu Glu Asp Lys Leu Asp Gly Gln Ile Pro Glu Val Leu Ile Ser Gly
145                 150                 155                 160
```

-continued

```
Asn Ala Gly Asp Val Val Phe Ser Gly Asn Ser Lys Arg Asp Glu
                165                 170                 175

His Leu Pro His Thr Gly Gly Ala Ile Cys Thr Gln Asn Leu Thr
            180                 185                 190

Ile Ser Gln Asn Thr Gly Asn Val Leu Phe Tyr Asn Asn Val Ala Cys
        195                 200                 205

Ser Gly Gly Ala Val Arg Ile Glu Asp His Gly Asn Val Leu Leu Glu
    210                 215                 220

Ala Phe Gly Gly Asp Ile Val Phe Lys Gly Asn Ser Ser Phe Arg Ala
225                 230                 235                 240

Gln Gly Ser Asp Ala Ile Tyr Phe Ala Gly Lys Glu Ser His Ile Thr
                245                 250                 255

Ala Leu Asn Ala Thr Glu Gly His Ala Ile Val Phe His Asp Ala Leu
            260                 265                 270

Val Phe Glu Asn Leu Lys Glu Arg Lys Ser Ala Glu Val Leu Leu Ile
        275                 280                 285

Asn Ser Arg Glu Asn Pro Gly Tyr Thr Gly Ser Ile Arg Phe Leu Glu
290                 295                 300

Ala Glu Ser Lys Val Pro Gln Cys Ile His Val Gln Gln Gly Ser Leu
305                 310                 315                 320

Glu Leu Leu Asn Gly Ala Thr Leu Cys Ser Tyr Gly Phe Lys Gln Asp
                325                 330                 335

Ala Gly Ala Lys Leu Val Leu Ala Ala Gly Ser Lys Leu Lys Ile Leu
            340                 345                 350

Asp Ser Gly Thr Pro Val Gln Gly His Ala Ile Ser Lys Pro Glu Ala
        355                 360                 365

Glu Ile Glu Ser Ser Ser Glu Pro Glu Gly Ala His Ser Leu Trp Ile
370                 375                 380

Ala Lys Asn Ala Gln Thr Thr Val Pro Met Val Asp Ile His Thr Ile
385                 390                 395                 400

Ser Val Asp Leu Ala Ser Phe Ser Ser Gln Gln Glu Gly Thr Val
                405                 410                 415

Glu Ala Pro Gln Val Ile Val Pro Gly Gly Ser Tyr Val Arg Ser Gly
            420                 425                 430

Glu Leu Asn Leu Glu Leu Val Asn Thr Thr Gly Thr Gly Tyr Glu Asn
        435                 440                 445

His Ala Leu Leu Lys Asn Glu Ala Lys Val Pro Leu Met Ser Phe Val
    450                 455                 460

Ala Ser Ser Asp Glu Ala Ser Ala Glu Ile Ser Asn Leu Ser Val Ser
465                 470                 475                 480

Asp Leu Gln Ile His Val Ala Thr Pro Glu Ile Glu Glu Asp Thr Tyr
                485                 490                 495

Gly His Met Gly Asp Trp Ser Glu Ala Lys Ile Gln Asp Gly Thr Leu
            500                 505                 510

Val Ile Asn Trp Asn Pro Thr Gly Tyr Arg Leu Asp Pro Gln Lys Ala
        515                 520                 525

Gly Ala Leu Val Phe Asn Ala Leu Trp Glu Glu Gly Ala Val Leu Ser
    530                 535                 540

Ala Leu Lys Asn Ala Arg Phe Ala His Asn Leu Thr Ala Gln Arg Met
545                 550                 555                 560

Glu Phe Asp Tyr Ser Thr Asn Val Trp Gly Phe Ala Phe Gly Gly Phe
                565                 570                 575
```

-continued

```
Arg Thr Leu Ser Ala Glu Asn Leu Val Ala Ile Asp Gly Tyr Lys Gly
            580                 585                 590

Ala Tyr Gly Gly Ala Ser Ala Gly Val Asp Ile Gln Leu Met Glu Asp
        595                 600                 605

Phe Val Leu Gly Val Ser Gly Ala Ala Phe Leu Gly Lys Met Asp Ser
    610                 615                 620

Gln Lys Phe Asp Ala Glu Val Ser Arg Lys Gly Val Val Gly Ser Val
625                 630                 635                 640

Tyr Thr Gly Phe Leu Ala Gly Ser Trp Phe Phe Lys Gly Gln Tyr Ser
                645                 650                 655

Leu Gly Glu Thr Gln Asn Asp Met Lys Thr Arg Tyr Gly Val Leu Gly
            660                 665                 670

Glu Ser Ser Ala Ser Trp Thr Ser Arg Gly Val Leu Ala Asp Ala Leu
        675                 680                 685

Val Glu Tyr Arg Ser Leu Val Gly Pro Val Arg Pro Thr Phe Tyr Ala
    690                 695                 700

Leu His Phe Asn Pro Tyr Val Glu Val Ser Tyr Ala Ser Met Lys Phe
705                 710                 715                 720

Pro Gly Phe Thr Glu Gln Gly Arg Glu Ala Arg Ser Phe Glu Asp Ala
                725                 730                 735

Ser Leu Thr Asn Ile Thr Ile Pro Leu Gly Met Lys Phe Glu Leu Ala
            740                 745                 750

Phe Ile Lys Gly Gln Phe Ser Glu Val Asn Ser Leu Gly Ile Ser Tyr
        755                 760                 765

Ala Trp Glu Ala Tyr Arg Lys Val Glu Gly Gly Ala Val Gln Leu Leu
    770                 775                 780

Glu Ala Gly Phe Asp Trp Glu Gly Ala Pro Met Asp Leu Pro Arg Gln
785                 790                 795                 800

Glu Leu Arg Val Ala Leu Glu Asn Asn Thr Glu Trp Ser Ser Tyr Phe
                805                 810                 815

Ser Thr Val Leu Gly Leu Thr Ala Phe Cys Gly Gly Phe Thr Ser Thr
            820                 825                 830

Asp Ser Lys Leu Gly Tyr Glu Ala Asn Thr Gly Leu Arg Leu Ile Phe
        835                 840                 845
```

<210> SEQ ID NO 193
<211> LENGTH: 778
<212> TYPE: PRT
<213> ORGANISM: Chlamydia

<400> SEQUENCE: 193

```
Met His His His His His Gly Leu Ala Ser Cys Val Asp Leu His
 1               5                  10                  15

Ala Gly Gly Gln Ser Val Asn Glu Leu Val Tyr Val Gly Pro Gln Ala
            20                  25                  30

Val Leu Leu Leu Asp Gln Ile Arg Asp Leu Phe Val Gly Ser Lys Asp
        35                  40                  45

Ser Gln Ala Glu Gly Gln Tyr Arg Leu Ile Val Gly Asp Pro Ser Ser
    50                  55                  60

Phe Gln Glu Lys Asp Ala Asp Thr Leu Pro Gly Lys Val Glu Gln Ser
65                  70                  75                  80

Thr Leu Phe Ser Val Thr Asn Pro Val Phe Gln Gly Val Asp Gln
                85                  90                  95

Gln Asp Gln Val Ser Ser Gln Gly Leu Ile Cys Ser Phe Thr Ser Ser
            100                 105                 110
```

```
Asn Leu Asp Ser Pro Arg Asp Gly Glu Ser Phe Leu Gly Ile Ala Phe
            115                 120                 125
Val Gly Asp Ser Ser Lys Ala Gly Ile Thr Leu Thr Asp Val Lys Ala
    130                 135                 140
Ser Leu Ser Gly Ala Ala Leu Tyr Ser Thr Glu Asp Leu Ile Phe Glu
145                 150                 155                 160
Lys Ile Lys Gly Gly Leu Glu Phe Ala Ser Cys Ser Ser Leu Glu Gln
                165                 170                 175
Gly Gly Ala Cys Ala Ala Gln Ser Ile Leu Ile His Asp Cys Gln Gly
                180                 185                 190
Leu Gln Val Lys His Cys Thr Thr Ala Val Asn Ala Glu Gly Ser Ser
            195                 200                 205
Ala Asn Asp His Leu Gly Phe Gly Gly Ala Phe Phe Val Thr Gly
    210                 215                 220
Ser Leu Ser Gly Glu Lys Ser Leu Tyr Met Pro Ala Gly Asp Met Val
225                 230                 235                 240
Val Ala Asn Cys Asp Gly Ala Ile Ser Phe Glu Gly Asn Ser Ala Asn
                245                 250                 255
Phe Ala Asn Gly Gly Ala Ile Ala Ala Ser Gly Lys Val Leu Phe Val
                260                 265                 270
Ala Asn Asp Lys Lys Thr Ser Phe Ile Glu Asn Arg Ala Leu Ser Gly
            275                 280                 285
Gly Ala Ile Ala Ala Ser Ser Asp Ile Ala Phe Gln Asn Cys Ala Glu
            290                 295                 300
Leu Val Phe Lys Gly Asn Cys Ala Ile Gly Thr Glu Asp Lys Gly Ser
305                 310                 315                 320
Leu Gly Gly Gly Ala Ile Ser Ser Leu Gly Thr Val Leu Leu Gln Gly
                325                 330                 335
Asn His Gly Ile Thr Cys Asp Lys Asn Glu Ser Ala Ser Gln Gly Gly
            340                 345                 350
Ala Ile Phe Gly Lys Asn Cys Gln Ile Ser Asp Asn Glu Gly Pro Val
            355                 360                 365
Val Phe Arg Asp Ser Thr Ala Cys Leu Gly Gly Ala Ile Ala Ala
    370                 375                 380
Gln Glu Ile Val Ser Ile Gln Asn Asn Gln Ala Gly Ile Ser Phe Glu
385                 390                 395                 400
Gly Gly Lys Ala Ser Phe Gly Gly Ile Ala Cys Gly Ser Phe Ser
                405                 410                 415
Ser Ala Gly Gly Ala Ser Val Leu Gly Thr Ile Asp Ile Ser Lys Asn
                420                 425                 430
Leu Gly Ala Ile Ser Phe Ser Arg Thr Leu Cys Thr Thr Ser Asp Leu
            435                 440                 445
Gly Gln Met Glu Tyr Gln Gly Gly Ala Leu Phe Gly Glu Asn Ile
    450                 455                 460
Ser Leu Ser Glu Asn Ala Gly Val Leu Thr Phe Lys Asp Asn Ile Val
465                 470                 475                 480
Lys Thr Phe Ala Ser Asn Gly Lys Ile Leu Gly Gly Ala Ile Leu
                485                 490                 495
Ala Thr Gly Lys Val Glu Ile Thr Asn Asn Ser Gly Gly Ile Ser Phe
            500                 505                 510
Thr Gly Asn Ala Arg Ala Pro Gln Ala Leu Pro Thr Gln Glu Glu Phe
            515                 520                 525
```

```
Pro Leu Phe Ser Lys Lys Glu Gly Arg Pro Leu Ser Ser Gly Tyr Ser
    530                 535                 540

Gly Gly Gly Ala Ile Leu Gly Arg Glu Val Ala Ile Leu His Asn Ala
545                 550                 555                 560

Ala Val Val Phe Glu Gln Asn Arg Leu Gln Cys Ser Glu Glu Glu Ala
                565                 570                 575

Thr Leu Leu Gly Cys Cys Gly Gly Ala Val His Gly Met Asp Ser
            580                 585                 590

Thr Ser Ile Val Gly Asn Ser Ser Val Arg Phe Gly Asn Asn Tyr Ala
        595                 600                 605

Met Gly Gln Gly Val Ser Gly Gly Ala Leu Leu Ser Lys Thr Val Gln
    610                 615                 620

Leu Ala Gly Asn Gly Ser Val Asp Phe Ser Arg Asn Ile Ala Ser Leu
625                 630                 635                 640

Gly Gly Gly Ala Leu Gln Ala Ser Glu Gly Asn Cys Glu Leu Val Asp
                645                 650                 655

Asn Gly Tyr Val Leu Phe Arg Asp Asn Arg Gly Arg Val Tyr Gly Gly
            660                 665                 670

Ala Ile Ser Cys Leu Arg Gly Asp Val Val Ile Ser Gly Asn Lys Gly
        675                 680                 685

Arg Val Glu Phe Lys Asp Asn Ile Ala Thr Arg Leu Tyr Val Glu Glu
    690                 695                 700

Thr Val Glu Lys Val Glu Glu Val Glu Pro Ala Pro Glu Gln Lys Asp
705                 710                 715                 720

Asn Asn Glu Leu Ser Phe Leu Gly Ser Val Glu Gln Ser Phe Ile Thr
                725                 730                 735

Ala Ala Asn Gln Ala Leu Phe Ala Ser Glu Asp Gly Asp Leu Ser Pro
            740                 745                 750

Glu Ser Ser Ile Ser Ser Glu Glu Leu Ala Lys Arg Arg Glu Cys Ala
        755                 760                 765

Gly Gly Ala Asp Ser Ser Arg Ser Gly Cys
    770                 775

<210> SEQ ID NO 194
<211> LENGTH: 948
<212> TYPE: PRT
<213> ORGANISM: Chlamydia

<400> SEQUENCE: 194

Met Ala Ser Met His His His His His Val Lys Ile Glu Asn Phe
1               5                   10                  15

Ser Gly Gln Gly Ile Phe Ser Gly Asn Lys Ala Ile Asp Asn Thr Thr
            20                  25                  30

Glu Gly Ser Ser Ser Lys Ser Asn Val Leu Gly Gly Ala Val Tyr Ala
        35                  40                  45

Lys Thr Leu Phe Asn Leu Asp Ser Gly Ser Ser Arg Arg Thr Val Thr
    50                  55                  60

Phe Ser Gly Asn Thr Val Ser Ser Gln Ser Thr Thr Gly Gln Val Ala
65                  70                  75                  80

Gly Gly Ala Ile Tyr Ser Pro Thr Val Thr Ile Ala Thr Pro Val Val
                85                  90                  95

Phe Ser Lys Asn Ser Ala Thr Asn Ala Asn Asn Ala Thr Asp Thr
            100                 105                 110

Gln Arg Lys Asp Thr Phe Gly Gly Ala Ile Gly Ala Thr Ser Ala Val
        115                 120                 125
```

-continued

```
Ser Leu Ser Gly Gly Ala His Phe Leu Glu Asn Val Ala Asp Leu Gly
    130                 135                 140
Ser Ala Ile Gly Leu Val Pro Asp Thr Gln Asn Thr Glu Thr Val Lys
145                 150                 155                 160
Leu Glu Ser Gly Ser Tyr Tyr Phe Glu Lys Asn Lys Ala Leu Lys Arg
                165                 170                 175
Ala Thr Ile Tyr Ala Pro Val Val Ser Ile Lys Ala Tyr Thr Ala Thr
                180                 185                 190
Phe Asn Gln Asn Arg Ser Leu Glu Gly Ser Ala Ile Tyr Phe Thr
                195                 200                 205
Lys Glu Ala Ser Ile Glu Ser Leu Gly Ser Val Leu Phe Thr Gly Asn
    210                 215                 220
Leu Val Thr Pro Thr Leu Ser Thr Thr Thr Glu Gly Thr Pro Ala Thr
225                 230                 235                 240
Thr Ser Gly Asp Val Thr Lys Tyr Gly Ala Ala Ile Phe Gly Gln Ile
                245                 250                 255
Ala Ser Ser Asn Gly Ser Gln Thr Asp Asn Leu Pro Leu Lys Leu Ile
                260                 265                 270
Ala Ser Gly Gly Asn Ile Cys Phe Arg Asn Asn Glu Tyr Arg Pro Thr
                275                 280                 285
Ser Ser Asp Thr Gly Thr Ser Thr Phe Cys Ser Ile Ala Gly Asp Val
    290                 295                 300
Lys Leu Thr Met Gln Ala Ala Lys Gly Lys Thr Ile Ser Phe Phe Asp
305                 310                 315                 320
Ala Ile Arg Thr Ser Thr Lys Lys Thr Gly Thr Gln Ala Thr Ala Tyr
                325                 330                 335
Asp Thr Leu Asp Ile Asn Lys Ser Glu Asp Ser Glu Thr Val Asn Ser
                340                 345                 350
Ala Phe Thr Gly Thr Ile Leu Phe Ser Ser Glu Leu His Glu Asn Lys
                355                 360                 365
Ser Tyr Ile Pro Gln Asn Val Val Leu His Ser Gly Ser Leu Val Leu
    370                 375                 380
Lys Pro Asn Thr Glu Leu His Val Ile Ser Phe Glu Gln Lys Glu Gly
385                 390                 395                 400
Ser Ser Leu Val Met Thr Pro Gly Ser Val Leu Ser Asn Gln Thr Val
                405                 410                 415
Ala Asp Gly Ala Leu Val Ile Asn Asn Met Thr Ile Asp Leu Ser Ser
                420                 425                 430
Val Glu Lys Asn Gly Ile Ala Glu Gly Asn Ile Phe Thr Pro Pro Glu
                435                 440                 445
Leu Arg Ile Ile Asp Thr Thr Thr Ser Gly Ser Gly Gly Thr Pro Ser
    450                 455                 460
Thr Asp Ser Glu Ser Asn Gln Asn Ser Asp Asp Thr Lys Glu Gln Asn
465                 470                 475                 480
Asn Asn Asp Ala Ser Asn Gln Gly Glu Ser Ala Asn Gly Ser Ser Ser
                485                 490                 495
Pro Ala Val Ala Ala Ala His Thr Ser Arg Thr Arg Asn Phe Ala Ala
                500                 505                 510
Ala Ala Thr Ala Thr Pro Thr Thr Thr Pro Thr Ala Thr Thr Thr Thr
                515                 520                 525
Ser Asn Gln Val Ile Leu Gly Gly Glu Ile Lys Leu Ile Asp Pro Asn
    530                 535                 540
```

```
Gly Thr Phe Phe Gln Asn Pro Ala Leu Arg Ser Asp Gln Gln Ile Ser
545                 550                 555                 560

Leu Leu Val Leu Pro Thr Asp Ser Ser Lys Met Gln Ala Gln Lys Ile
            565                 570                 575

Val Leu Thr Gly Asp Ile Ala Pro Gln Lys Gly Tyr Thr Gly Thr Leu
            580                 585                 590

Thr Leu Asp Pro Asp Gln Leu Gln Asn Gly Thr Ile Ser Ala Leu Trp
        595                 600                 605

Lys Phe Asp Ser Tyr Arg Gln Trp Ala Tyr Val Pro Arg Asp Asn His
    610                 615                 620

Phe Tyr Ala Asn Ser Ile Leu Gly Ser Gln Met Ser Met Val Thr Val
625                 630                 635                 640

Lys Gln Gly Leu Leu Asn Asp Lys Met Asn Leu Ala Arg Phe Asp Glu
                645                 650                 655

Val Ser Tyr Asn Asn Leu Trp Ile Ser Gly Leu Gly Thr Met Leu Ser
                660                 665                 670

Gln Val Gly Thr Pro Thr Ser Glu Glu Phe Thr Tyr Tyr Ser Arg Gly
            675                 680                 685

Ala Ser Val Ala Leu Asp Ala Lys Pro Ala His Asp Val Ile Val Gly
690                 695                 700

Ala Ala Phe Ser Lys Met Ile Gly Lys Thr Lys Ser Leu Lys Arg Glu
705                 710                 715                 720

Asn Asn Tyr Thr His Lys Gly Ser Glu Tyr Ser Tyr Gln Ala Ser Val
                725                 730                 735

Tyr Gly Gly Lys Pro Phe His Phe Val Ile Asn Lys Lys Thr Glu Lys
                740                 745                 750

Ser Leu Pro Leu Leu Gln Gly Val Ile Ser Tyr Gly Tyr Ile Lys
            755                 760                 765

His Asp Thr Val Thr His Tyr Pro Thr Ile Arg Glu Arg Asn Gln Gly
    770                 775                 780

Glu Trp Glu Asp Leu Gly Trp Leu Thr Ala Leu Arg Val Ser Ser Val
785                 790                 795                 800

Leu Arg Thr Pro Ala Gln Gly Asp Thr Lys Arg Ile Thr Val Tyr Gly
                805                 810                 815

Glu Leu Glu Tyr Ser Ser Ile Arg Gln Lys Gln Phe Thr Glu Thr Glu
            820                 825                 830

Tyr Asp Pro Arg Tyr Phe Asp Asn Cys Thr Tyr Arg Asn Leu Ala Ile
        835                 840                 845

Pro Met Gly Leu Ala Phe Glu Gly Leu Ser Gly Asn Asp Ile Leu
850                 855                 860

Met Tyr Asn Arg Phe Ser Val Ala Tyr Met Pro Ser Ile Tyr Arg Asn
865                 870                 875                 880

Ser Pro Thr Cys Lys Tyr Gln Val Leu Ser Ser Gly Glu Gly Gly Glu
                885                 890                 895

Ile Ile Cys Gly Val Pro Thr Arg Asn Ser Arg Gly Glu Tyr Ser
                900                 905                 910

Thr Gln Leu Tyr Pro Gly Pro Leu Trp Thr Leu Tyr Gly Ser Tyr Thr
        915                 920                 925

Ile Glu Ala Asp Ala His Thr Leu Ala His Met Met Asn Cys Gly Ala
    930                 935                 940

Arg Met Thr Phe
945
```

<210> SEQ ID NO 195
<211> LENGTH: 821
<212> TYPE: PRT
<213> ORGANISM: Chlamydia

<400> SEQUENCE: 195

```
Met His His His His His Glu Ala Ser Ser Ile Gln Asp Gln Ile
 1               5                  10                  15

Lys Asn Thr Asp Cys Asn Val Ser Lys Val Gly Tyr Ser Thr Ser Gln
             20                  25                  30

Ala Phe Thr Asp Met Met Leu Ala Asp Asn Thr Glu Tyr Arg Ala Ala
         35                  40                  45

Asp Ser Val Ser Phe Tyr Asp Phe Ser Thr Ser Ser Gly Leu Pro Arg
     50                  55                  60

Lys His Leu Ser Ser Ser Ser Glu Ala Ser Pro Thr Thr Glu Gly Val
 65                  70                  75                  80

Ser Ser Ser Ser Ser Gly Glu Asn Thr Glu Asn Ser Gln Asp Ser Ala
                 85                  90                  95

Pro Ser Ser Gly Glu Thr Asp Lys Lys Thr Glu Glu Leu Asp Asn
             100                 105                 110

Gly Gly Ile Ile Tyr Ala Arg Glu Lys Leu Thr Ile Ser Glu Ser Gln
         115                 120                 125

Asp Ser Leu Ser Asn Pro Ser Ile Glu Leu His Asp Asn Ser Phe Phe
    130                 135                 140

Phe Gly Glu Gly Glu Val Ile Phe Asp His Arg Val Ala Leu Lys Asn
145                 150                 155                 160

Gly Gly Ala Ile Tyr Gly Glu Lys Glu Val Val Phe Glu Asn Ile Lys
                165                 170                 175

Ser Leu Leu Val Glu Val Asn Ile Ser Val Glu Lys Gly Gly Ser Val
            180                 185                 190

Tyr Ala Lys Glu Arg Val Ser Leu Glu Asn Val Thr Glu Ala Thr Phe
        195                 200                 205

Ser Ser Asn Gly Gly Glu Gln Gly Gly Gly Ile Tyr Ser Glu Gln
    210                 215                 220

Asp Met Leu Ile Ser Asp Cys Asn Asn Val His Phe Gln Gly Asn Ala
225                 230                 235                 240

Ala Gly Ala Thr Ala Val Lys Gln Cys Leu Asp Glu Met Ile Val
                245                 250                 255

Leu Leu Thr Glu Cys Val Asp Ser Leu Ser Glu Asp Thr Leu Asp Ser
            260                 265                 270

Thr Pro Glu Thr Glu Gln Thr Lys Ser Asn Gly Asn Gln Asp Gly Ser
        275                 280                 285

Ser Glu Thr Lys Asp Thr Gln Val Ser Glu Ser Pro Glu Ser Thr Pro
    290                 295                 300

Ser Pro Asp Asp Val Leu Gly Lys Gly Gly Ile Tyr Thr Glu Lys
305                 310                 315                 320

Ser Leu Thr Ile Thr Gly Ile Thr Gly Thr Ile Asp Phe Val Ser Asn
                325                 330                 335

Ile Ala Thr Asp Ser Gly Ala Gly Val Phe Thr Lys Glu Asn Leu Ser
            340                 345                 350

Cys Thr Asn Thr Asn Ser Leu Gln Phe Leu Lys Asn Ser Ala Gly Gln
        355                 360                 365

His Gly Gly Gly Ala Tyr Val Thr Gln Thr Met Ser Val Thr Asn Thr
    370                 375                 380
```

-continued

```
Thr Ser Glu Ser Ile Thr Thr Pro Pro Leu Val Gly Glu Val Ile Phe
385                 390                 395                 400

Ser Glu Asn Thr Ala Lys Gly His Gly Gly Gly Ile Cys Thr Asn Lys
                405                 410                 415

Leu Ser Leu Ser Asn Leu Lys Thr Val Thr Leu Thr Lys Asn Ser Ala
            420                 425                 430

Lys Glu Ser Gly Gly Ala Ile Phe Thr Asp Leu Ala Ser Ile Pro Thr
        435                 440                 445

Thr Asp Thr Pro Glu Ser Ser Thr Pro Ser Ser Ser Ser Pro Ala Ser
    450                 455                 460

Thr Pro Glu Val Val Ala Ser Ala Lys Ile Asn Arg Phe Phe Ala Ser
465                 470                 475                 480

Thr Ala Glu Pro Ala Ala Pro Ser Leu Thr Glu Ala Glu Ser Asp Gln
                485                 490                 495

Thr Asp Gln Thr Glu Thr Ser Asp Thr Asn Ser Asp Ile Asp Val Ser
            500                 505                 510

Ile Glu Asn Ile Leu Asn Val Ala Ile Asn Gln Asn Thr Ser Ala Lys
        515                 520                 525

Lys Gly Gly Ala Ile Tyr Gly Lys Lys Ala Lys Leu Ser Arg Ile Asn
    530                 535                 540

Asn Leu Glu Leu Ser Gly Asn Ser Ser Gln Asp Val Gly Gly Gly Leu
545                 550                 555                 560

Cys Leu Thr Glu Ser Val Glu Phe Asp Ala Ile Gly Ser Leu Leu Ser
                565                 570                 575

His Tyr Asn Ser Ala Ala Lys Glu Gly Gly Val Ile His Ser Lys Thr
            580                 585                 590

Val Thr Leu Ser Asn Leu Lys Ser Thr Phe Thr Phe Ala Asp Asn Thr
        595                 600                 605

Val Lys Ala Ile Val Glu Ser Thr Pro Glu Ala Pro Glu Glu Ile Pro
    610                 615                 620

Pro Val Glu Gly Glu Glu Ser Thr Ala Thr Glu Asn Pro Asn Ser Asn
625                 630                 635                 640

Thr Glu Gly Ser Ser Ala Asn Thr Asn Leu Glu Gly Ser Gln Gly Asp
                645                 650                 655

Thr Ala Asp Thr Gly Thr Gly Val Val Asn Asn Glu Ser Gln Asp Thr
            660                 665                 670

Ser Asp Thr Gly Asn Ala Glu Ser Gly Glu Gln Leu Gln Asp Ser Thr
        675                 680                 685

Gln Ser Asn Glu Glu Asn Thr Leu Pro Asn Ser Ser Ile Asp Gln Ser
    690                 695                 700

Asn Glu Asn Thr Asp Glu Ser Ser Asp Ser His Thr Glu Glu Ile Thr
705                 710                 715                 720

Asp Glu Ser Val Ser Ser Ser Lys Ser Gly Ser Ser Thr Pro Gln
                725                 730                 735

Asp Gly Gly Ala Ala Ser Ser Gly Ala Pro Ser Gly Asp Gln Ser Ile
            740                 745                 750

Ser Ala Asn Ala Cys Leu Ala Lys Ser Tyr Ala Ala Ser Thr Asp Ser
        755                 760                 765

Ser Pro Val Ser Asn Ser Ser Gly Ser Asp Val Thr Ala Ser Ser Asp
    770                 775                 780

Asn Pro Asp Ser Ser Ser Ser Gly Asp Ser Ala Gly Asp Ser Glu Gly
785                 790                 795                 800

Pro Thr Glu Pro Glu Ala Gly Ser Thr Thr Glu Thr Pro Thr Leu Ile
```

```
                    805                 810                 815

Gly Gly Gly Ala Ile
            820

<210> SEQ ID NO 196
<211> LENGTH: 525
<212> TYPE: PRT
<213> ORGANISM: Chlamydia

<400> SEQUENCE: 196

Met His His His His His His Thr Ala Ala Ser Asp Asn Phe Gln Leu
  1               5                  10                  15

Ser Gln Gly Gly Gln Gly Phe Ala Ile Pro Ile Gly Gln Ala Met Ala
             20                  25                  30

Ile Ala Gly Gln Ile Lys Leu Pro Thr Val His Ile Gly Pro Thr Ala
         35                  40                  45

Phe Leu Gly Leu Gly Val Val Asp Asn Asn Gly Asn Gly Ala Arg Val
 50                  55                  60

Gln Arg Val Val Gly Ser Ala Pro Ala Ser Leu Gly Ile Ser Thr
 65                  70                  75                  80

Gly Asp Val Ile Thr Ala Val Asp Gly Ala Pro Ile Asn Ser Ala Thr
                 85                  90                  95

Ala Met Ala Asp Ala Leu Asn Gly His His Pro Gly Asp Val Ile Ser
            100                 105                 110

Val Thr Trp Gln Thr Lys Ser Gly Gly Thr Arg Thr Gly Asn Val Thr
        115                 120                 125

Leu Ala Glu Gly Pro Pro Ala Glu Phe Pro Leu Val Pro Arg Gly Ser
130                 135                 140

Pro Leu Pro Val Gly Asn Pro Ala Glu Pro Ser Leu Leu Ile Asp Gly
145                 150                 155                 160

Thr Met Trp Glu Gly Ala Ser Gly Asp Pro Cys Asp Pro Cys Ala Thr
                165                 170                 175

Trp Cys Asp Ala Ile Ser Ile Arg Ala Gly Tyr Tyr Gly Asp Tyr Val
            180                 185                 190

Phe Asp Arg Val Leu Lys Val Asp Val Asn Lys Thr Phe Ser Gly Met
        195                 200                 205

Ala Ala Thr Pro Thr Gln Ala Ile Gly Asn Ala Ser Asn Thr Asn Gln
210                 215                 220

Pro Glu Ala Asn Gly Arg Pro Asn Ile Ala Tyr Gly Arg His Met Gln
225                 230                 235                 240

Asp Ala Glu Trp Phe Ser Asn Ala Ala Phe Leu Ala Leu Asn Ile Trp
                245                 250                 255

Asp Arg Phe Asp Ile Phe Cys Thr Leu Gly Ala Ser Asn Gly Tyr Phe
            260                 265                 270

Lys Ala Ser Ser Ala Ala Phe Asn Leu Val Gly Leu Ile Gly Phe Ser
        275                 280                 285

Ala Ala Ser Ser Ile Ser Thr Asp Leu Pro Met Gln Leu Pro Asn Val
290                 295                 300

Gly Ile Thr Gln Gly Val Val Glu Phe Tyr Thr Asp Thr Ser Phe Ser
305                 310                 315                 320

Trp Ser Val Gly Ala Arg Gly Ala Leu Trp Glu Cys Gly Cys Ala Thr
                325                 330                 335

Leu Gly Ala Glu Phe Gln Tyr Ala Gln Ser Asn Pro Lys Ile Glu Met
            340                 345                 350
```

```
Leu Asn Val Thr Ser Ser Pro Ala Gln Phe Val Ile His Lys Pro Arg
            355                 360                 365
Gly Tyr Lys Gly Ala Ser Ser Asn Phe Pro Leu Pro Ile Thr Ala Gly
        370                 375                 380
Thr Thr Glu Ala Thr Asp Thr Lys Ser Ala Thr Ile Lys Tyr His Glu
385                 390                 395                 400
Trp Gln Val Gly Leu Ala Leu Ser Tyr Arg Leu Asn Met Leu Val Pro
                405                 410                 415
Tyr Ile Gly Val Asn Trp Ser Arg Ala Thr Phe Asp Ala Asp Thr Ile
            420                 425                 430
Arg Ile Ala Gln Pro Lys Leu Lys Ser Glu Ile Leu Asn Ile Thr Thr
        435                 440                 445
Trp Asn Pro Ser Leu Ile Gly Ser Thr Thr Ala Leu Pro Asn Asn Ser
    450                 455                 460
Gly Lys Asp Val Leu Ser Asp Val Leu Gln Ile Ala Ser Ile Gln Ile
465                 470                 475                 480
Asn Lys Met Lys Ser Arg Lys Ala Cys Gly Val Ala Val Gly Ala Thr
                485                 490                 495
Leu Ile Asp Ala Asp Lys Trp Ser Ile Thr Gly Glu Ala Arg Leu Ile
            500                 505                 510
Asn Glu Arg Ala Ala His Met Asn Ala Gln Phe Arg Phe
        515                 520                 525

<210> SEQ ID NO 197
<211> LENGTH: 43
<212> TYPE: DNA
<213> ORGANISM: Chlamydia

<400> SEQUENCE: 197
gataggcgcg ccgcaatcat gaaatttatg tcagctactg ctg           43

<210> SEQ ID NO 198
<211> LENGTH: 34
<212> TYPE: DNA
<213> ORGANISM: Chlamydia

<400> SEQUENCE: 198
cagaacgcgt ttagaatgtc atacgagcac cgca                     34

<210> SEQ ID NO 199
<211> LENGTH: 6
<212> TYPE: DNA
<213> ORGANISM: Chlamydia

<400> SEQUENCE: 199 gcaatc                                                    6

<210> SEQ ID NO 200
<211> LENGTH: 34
<212> TYPE: DNA
<213> ORGANISM: Chlamydia

<400> SEQUENCE: 200
tgcaatcatg agttcgcaga aagatataaa aagc                     34

<210> SEQ ID NO 201
<211> LENGTH: 38
<212> TYPE: DNA
<213> ORGANISM: Chlamydia
```

-continued

```
<400> SEQUENCE: 201
cagagctagc ttaaaagatc aatcgcaatc cagtattc                                38

<210> SEQ ID NO 202
<211> LENGTH: 5
<212> TYPE: DNA
<213> ORGANISM: Chlamydia

<400> SEQUENCE: 202 caatc                                                                    5

<210> SEQ ID NO 203
<211> LENGTH: 31
<212> TYPE: DNA
<213> ORGANISM: Chlamydia

<400> SEQUENCE: 203
tgcaatcatg aaaaaagcgt ttttcttttt c                                       31

<210> SEQ ID NO 204
<211> LENGTH: 31
<212> TYPE: DNA
<213> ORGANISM: Chlamydia

<400> SEQUENCE: 204
cagaacgcgt ctagaatcgc agagcaattt c                                       31

<210> SEQ ID NO 205
<211> LENGTH: 30
<212> TYPE: DNA
<213> ORGANISM: Chlamydia

<400> SEQUENCE: 205
gtgcaatcat gattcctcaa ggaatttacg                                         30

<210> SEQ ID NO 206
<211> LENGTH: 31
<212> TYPE: DNA
<213> ORGANISM: Chlamydia

<400> SEQUENCE: 206
cagaacgcgt ttagaaccgg actttacttc c                                       31

<210> SEQ ID NO 207
<211> LENGTH: 50
<212> TYPE: DNA
<213> ORGANISM: Chlamydia

<400> SEQUENCE: 207
cagacatatg catcaccatc accatcacga ggcgagctcg atccaagatc                   50

<210> SEQ ID NO 208
<211> LENGTH: 40
<212> TYPE: DNA
<213> ORGANISM: Chlamydia

<400> SEQUENCE: 208
cagaggtacc tcagatagca ctctctccta ttaaagtagg                              40

<210> SEQ ID NO 209
<211> LENGTH: 55
<212> TYPE: DNA
<213> ORGANISM: Chlamydia
```

<400> SEQUENCE: 209
cagagctagc atgcatcacc atcaccatca cgttaagatt gagaacttct ctggc     55

<210> SEQ ID NO 210
<211> LENGTH: 35
<212> TYPE: DNA
<213> ORGANISM: Chlamydia

<400> SEQUENCE: 210
cagaggtacc ttagaatgtc atacgagcac cgcag     35

<210> SEQ ID NO 211
<211> LENGTH: 36
<212> TYPE: DNA
<213> ORGANISM: Chlamydia

<400> SEQUENCE: 211
cagacatatg catcaccatc accatcacgg gttagc     36

<210> SEQ ID NO 212
<211> LENGTH: 35
<212> TYPE: DNA
<213> ORGANISM: Chlamydia

<400> SEQUENCE: 212
cagaggtacc tcagctcctc cagcacactc tcttc     35

<210> SEQ ID NO 213
<211> LENGTH: 51
<212> TYPE: DNA
<213> ORGANISM: Chlamydia

<400> SEQUENCE: 213
cagagctagc catcaccatc accatcacgg tgctatttct tgcttacgtg g     51

<210> SEQ ID NO 214
<211> LENGTH: 38
<212> TYPE: DNA
<213> ORGANISM: Chlamydia

<400> SEQUENCE: 214
cagaggtact taaaagatca atcgcaatcc agtattcg     38

<210> SEQ ID NO 215
<211> LENGTH: 48
<212> TYPE: DNA
<213> ORGANISM: Chlamydia

<400> SEQUENCE: 215
cagaggatcc acatcaccat caccatcacg gactagctag agaggttc     48

<210> SEQ ID NO 216
<211> LENGTH: 31
<212> TYPE: DNA
<213> ORGANISM: Chlamydia

<400> SEQUENCE: 216
cagagaattc ctagaatcgc agagcaattt c     31

<210> SEQ ID NO 217
<211> LENGTH: 7
<212> TYPE: DNA

```
<213> ORGANISM: Chlamydia

<400> SEQUENCE: 217 tgcaatc                                                              7

<210> SEQ ID NO 218
<211> LENGTH: 22
<212> TYPE: PRT
<213> ORGANISM: Chlamydia

<400> SEQUENCE: 218

Met Ala Ser Met Thr Gly Gly Gln Gln Met Gly Arg Asp Ser Ser Leu
 1               5                  10                  15

Val Pro Ser Ser Asp Pro
            20

<210> SEQ ID NO 219
<211> LENGTH: 51
<212> TYPE: DNA
<213> ORGANISM: Chlamydia

<400> SEQUENCE: 219
cagaggtacc gcatcaccat caccatcaca tgattcctca aggaatttac g             51

<210> SEQ ID NO 220
<211> LENGTH: 33
<212> TYPE: DNA
<213> ORGANISM: Chlamydia

<400> SEQUENCE: 220
cagagcggcc gcttagaacc ggactttact tcc                                 33

<210> SEQ ID NO 221
<211> LENGTH: 24
<212> TYPE: PRT
<213> ORGANISM: Chlamydia

<400> SEQUENCE: 221

Met Ala Ser Met Thr Gly Gly Gln Gln Asn Gly Arg Asp Ser Ser Leu
 1               5                  10                  15

Val Pro His His His His His His
            20

<210> SEQ ID NO 222
<211> LENGTH: 46
<212> TYPE: DNA
<213> ORGANISM: Chlamydia

<400> SEQUENCE: 222
cagagctagc catcaccatc accatcacct ctttggccag gatccc                   6

<210> SEQ ID NO 223
<211> LENGTH: 30
<212> TYPE: DNA
<213> ORGANISM: Chlamydia

<400> SEQUENCE: 223
cagaactagt ctagaacctg taagtggtcc                                     30

<210> SEQ ID NO 224
<211> LENGTH: 20
<212> TYPE: PRT
<213> ORGANISM: Artificial Sequence
```

```
<220> FEATURE:
<223> OTHER INFORMATION: Made in a lab

<400> SEQUENCE: 224

Met Ser Gln Lys Asn Lys Asn Ser Ala Phe Met His Pro Val Asn Ile
 1               5                  10                  15

Ser Thr Asp Leu
            20

<210> SEQ ID NO 225
<211> LENGTH: 20
<212> TYPE: PRT
<213> ORGANISM: Artificial Sequence
<220> FEATURE:
<223> OTHER INFORMATION: Made in a lab

<400> SEQUENCE: 225

Lys Asn Ser Ala Phe Met His Pro Val Asn Ile Ser Thr Asp Leu Ala
 1               5                  10                  15

Val Ile Val Gly
            20

<210> SEQ ID NO 226
<211> LENGTH: 20
<212> TYPE: PRT
<213> ORGANISM: Artificial Sequence
<220> FEATURE:
<223> OTHER INFORMATION: Made in a lab

<400> SEQUENCE: 226

His Pro Val Asn Ile Ser Thr Asp Leu Ala Val Ile Val Gly Lys Gly
 1               5                  10                  15

Pro Met Pro Arg
            20

<210> SEQ ID NO 227
<211> LENGTH: 20
<212> TYPE: PRT
<213> ORGANISM: Artificial Sequence
<220> FEATURE:
<223> OTHER INFORMATION: Made in a lab

<400> SEQUENCE: 227

Ser Thr Asp Leu Ala Val Ile Val Gly Lys Gly Pro Met Pro Arg Thr
 1               5                  10                  15

Glu Ile Val Lys
            20

<210> SEQ ID NO 228
<211> LENGTH: 20
<212> TYPE: PRT
<213> ORGANISM: Artificial Sequence
<220> FEATURE:
<223> OTHER INFORMATION: Made in a lab

<400> SEQUENCE: 228

Val Ile Val Gly Lys Gly Pro Met Pro Arg Thr Glu Ile Val Lys Lys
 1               5                  10                  15

Val Trp Glu Tyr
            20

<210> SEQ ID NO 229
<211> LENGTH: 20
<212> TYPE: PRT
```

```
<213> ORGANISM: Artificial Sequence
<220> FEATURE:
<223> OTHER INFORMATION: Made in a lab

<400> SEQUENCE: 229

Gly Pro Met Pro Arg Thr Glu Ile Val Lys Lys Val Trp Glu Tyr Ile
1               5                   10                  15

Lys Lys His Asn
            20

<210> SEQ ID NO 230
<211> LENGTH: 20
<212> TYPE: PRT
<213> ORGANISM: Artificial Sequence
<220> FEATURE:
<223> OTHER INFORMATION: Made in a lab

<400> SEQUENCE: 230

Ile Lys Lys His Asn Cys Gln Asp Gln Lys Asn Lys Arg Asn Ile Leu
1               5                   10                  15

Pro Asp Ala Asn
            20

<210> SEQ ID NO 231
<211> LENGTH: 20
<212> TYPE: PRT
<213> ORGANISM: Artificial Sequence
<220> FEATURE:
<223> OTHER INFORMATION: Made in a lab

<400> SEQUENCE: 231

Asn Cys Gln Asp Gln Lys Asn Lys Arg Asn Ile Leu Pro Asp Ala Asn
1               5                   10                  15

Leu Ala Lys Val
            20

<210> SEQ ID NO 232
<211> LENGTH: 20
<212> TYPE: PRT
<213> ORGANISM: Artificial Sequence
<220> FEATURE:
<223> OTHER INFORMATION: Made in a lab

<400> SEQUENCE: 232

Lys Asn Lys Arg Asn Ile Leu Pro Asp Ala Asn Leu Ala Lys Val Phe
1               5                   10                  15

Gly Ser Ser Asp
            20

<210> SEQ ID NO 233
<211> LENGTH: 20
<212> TYPE: PRT
<213> ORGANISM: Artificial Sequence
<220> FEATURE:
<223> OTHER INFORMATION: Made in a lab

<400> SEQUENCE: 233

Ile Leu Pro Asp Ala Asn Leu Ala Lys Val Phe Gly Ser Ser Asp Pro
1               5                   10                  15

Ile Asp Met Phe
            20

<210> SEQ ID NO 234
<211> LENGTH: 20
```

```
<212> TYPE: PRT
<213> ORGANISM: Artificial Sequence
<220> FEATURE:
<223> OTHER INFORMATION: Made in a lab

<400> SEQUENCE: 234

Asn Leu Ala Lys Val Phe Gly Ser Ser Asp Pro Ile Asp Met Phe Gln
 1               5                  10                  15

Met Thr Lys Ala
            20

<210> SEQ ID NO 235
<211> LENGTH: 22
<212> TYPE: PRT
<213> ORGANISM: Artificial Sequence
<220> FEATURE:
<223> OTHER INFORMATION: Made in a lab

<400> SEQUENCE: 235

Phe Gly Ser Ser Asp Pro Ile Asp Met Phe Gln Met Thr Lys Ala Leu
 1               5                  10                  15

Ser Lys His Ile Val Lys
            20

<210> SEQ ID NO 236
<211> LENGTH: 20
<212> TYPE: PRT
<213> ORGANISM: Artificial Sequence
<220> FEATURE:
<223> OTHER INFORMATION: Made in a lab

<400> SEQUENCE: 236

Val Glu Ile Thr Gln Ala Val Pro Lys Tyr Ala Thr Val Gly Ser Pro
 1               5                  10                  15

Tyr Pro Val Glu
            20

<210> SEQ ID NO 237
<211> LENGTH: 20
<212> TYPE: PRT
<213> ORGANISM: Artificial Sequence
<220> FEATURE:
<223> OTHER INFORMATION: Made in a lab

<400> SEQUENCE: 237

Ala Val Pro Lys Tyr Ala Thr Val Gly Ser Pro Tyr Pro Val Glu Ile
 1               5                  10                  15

Thr Ala Thr Gly
            20

<210> SEQ ID NO 238
<211> LENGTH: 20
<212> TYPE: PRT
<213> ORGANISM: Artificial Sequence
<220> FEATURE:
<223> OTHER INFORMATION: Made in a lab

<400> SEQUENCE: 238

Ala Thr Val Gly Ser Pro Tyr Pro Val Glu Ile Thr Ala Thr Gly Lys
 1               5                  10                  15

Arg Asp Cys Val
            20

<210> SEQ ID NO 239
```

```
<211> LENGTH: 20
<212> TYPE: PRT
<213> ORGANISM: Artificial Sequence
<220> FEATURE:
<223> OTHER INFORMATION: Made in a lab

<400> SEQUENCE: 239

Pro Tyr Pro Val Glu Ile Thr Ala Thr Gly Lys Arg Asp Cys Val Asp
 1               5                  10                  15

Val Ile Ile Thr
            20

<210> SEQ ID NO 240
<211> LENGTH: 21
<212> TYPE: PRT
<213> ORGANISM: Artificial Sequence
<220> FEATURE:
<223> OTHER INFORMATION: Made in a lab

<400> SEQUENCE: 240

Ile Thr Ala Thr Gly Lys Arg Asp Cys Val Asp Val Ile Ile Thr Gln
 1               5                  10                  15

Gln Leu Pro Cys Glu
            20

<210> SEQ ID NO 241
<211> LENGTH: 20
<212> TYPE: PRT
<213> ORGANISM: Artificial Sequence
<220> FEATURE:
<223> OTHER INFORMATION: Made in a lab

<400> SEQUENCE: 241

Lys Arg Asp Cys Val Asp Val Ile Ile Thr Gln Gln Leu Pro Cys Glu
 1               5                  10                  15

Ala Glu Phe Val
            20

<210> SEQ ID NO 242
<211> LENGTH: 20
<212> TYPE: PRT
<213> ORGANISM: Artificial Sequence
<220> FEATURE:
<223> OTHER INFORMATION: Made in a lab

<400> SEQUENCE: 242

Asp Val Ile Ile Thr Gln Gln Leu Pro Cys Glu Ala Glu Phe Val Arg
 1               5                  10                  15

Ser Asp Pro Ala
            20

<210> SEQ ID NO 243
<211> LENGTH: 20
<212> TYPE: PRT
<213> ORGANISM: Artificial Sequence
<220> FEATURE:
<223> OTHER INFORMATION: Made in a lab

<400> SEQUENCE: 243

Thr Gln Gln Leu Pro Cys Glu Ala Glu Phe Val Arg Ser Asp Pro Ala
 1               5                  10                  15

Thr Thr Pro Thr
            20
```

```
<210> SEQ ID NO 244
<211> LENGTH: 20
<212> TYPE: PRT
<213> ORGANISM: Artificial Sequence
<220> FEATURE:
<223> OTHER INFORMATION: Made in a lab

<400> SEQUENCE: 244

Cys Glu Ala Glu Phe Val Arg Ser Asp Pro Ala Thr Thr Pro Thr Ala
 1               5                  10                  15

Asp Gly Lys Leu
            20

<210> SEQ ID NO 245
<211> LENGTH: 20
<212> TYPE: PRT
<213> ORGANISM: Artificial Sequence
<220> FEATURE:
<223> OTHER INFORMATION: Made in a lab

<400> SEQUENCE: 245

Val Arg Ser Asp Pro Ala Thr Thr Pro Thr Ala Asp Gly Lys Leu Val
 1               5                  10                  15

Trp Lys Ile Asp
            20

<210> SEQ ID NO 246
<211> LENGTH: 20
<212> TYPE: PRT
<213> ORGANISM: Artificial Sequence
<220> FEATURE:
<223> OTHER INFORMATION: Made in a lab

<400> SEQUENCE: 246

Ala Thr Thr Pro Thr Ala Asp Gly Lys Leu Val Trp Lys Ile Asp Arg
 1               5                  10                  15

Leu Gly Gln Gly
            20

<210> SEQ ID NO 247
<211> LENGTH: 20
<212> TYPE: PRT
<213> ORGANISM: Artificial Sequence
<220> FEATURE:
<223> OTHER INFORMATION: Made in a lab

<400> SEQUENCE: 247

Ala Asp Gly Lys Leu Val Trp Lys Ile Asp Arg Leu Gly Gln Gly Glu
 1               5                  10                  15

Lys Ser Lys Ile
            20

<210> SEQ ID NO 248
<211> LENGTH: 20
<212> TYPE: PRT
<213> ORGANISM: Artificial Sequence
<220> FEATURE:
<223> OTHER INFORMATION: Made in a lab

<400> SEQUENCE: 248

Val Trp Lys Ile Asp Arg Leu Gly Gln Gly Glu Lys Ser Lys Ile Thr
 1               5                  10                  15

Val Trp Val Lys
            20
```

<210> SEQ ID NO 249
<211> LENGTH: 20
<212> TYPE: PRT
<213> ORGANISM: Artificial Sequence
<220> FEATURE:
<223> OTHER INFORMATION: Made in a lab

<400> SEQUENCE: 249

Arg Leu Gly Gln Gly Glu Lys Ser Lys Ile Thr Val Trp Val Lys Pro
 1               5                  10                  15

Leu Lys Glu Gly
            20

<210> SEQ ID NO 250
<211> LENGTH: 20
<212> TYPE: PRT
<213> ORGANISM: Artificial Sequence
<220> FEATURE:
<223> OTHER INFORMATION: Made in a lab

<400> SEQUENCE: 250

Gly Glu Lys Ser Lys Ile Thr Val Trp Val Lys Pro Leu Lys Glu Gly
 1               5                  10                  15

Cys Cys Phe Thr
            20

<210> SEQ ID NO 251
<211> LENGTH: 16
<212> TYPE: PRT
<213> ORGANISM: Artificial Sequence
<220> FEATURE:
<223> OTHER INFORMATION: Made in a lab

<400> SEQUENCE: 251

Gly Glu Lys Ser Lys Ile Thr Val Trp Val Lys Pro Leu Lys Glu Gly
 1               5                  10                  15

<210> SEQ ID NO 252
<211> LENGTH: 12
<212> TYPE: PRT
<213> ORGANISM: Artificial Sequence
<220> FEATURE:
<223> OTHER INFORMATION: Made in a lab

<400> SEQUENCE: 252

Lys Ile Thr Val Trp Val Lys Pro Leu Lys Glu Gly
 1               5                  10

<210> SEQ ID NO 253
<211> LENGTH: 16
<212> TYPE: PRT
<213> ORGANISM: Artificial Sequence
<220> FEATURE:
<223> OTHER INFORMATION: Made in a lab

<400> SEQUENCE: 253

Gly Asp Lys Cys Lys Ile Thr Val Trp Val Lys Pro Leu Lys Glu Gly
 1               5                  10                  15

<210> SEQ ID NO 254
<211> LENGTH: 20
<212> TYPE: PRT
<213> ORGANISM: Artificial Sequence
<220> FEATURE:
<223> OTHER INFORMATION: Made in a lab

<400> SEQUENCE: 254

Thr Glu Tyr Pro Leu Leu Ala Asp Pro Ser Phe Lys Ile Ser Glu Ala
1               5                   10                  15
Phe Gly Val Leu
            20

<210> SEQ ID NO 255
<211> LENGTH: 20
<212> TYPE: PRT
<213> ORGANISM: Artificial Sequence
<220> FEATURE:
<223> OTHER INFORMATION: Made in a lab

<400> SEQUENCE: 255

Leu Ala Asp Pro Ser Phe Lys Ile Ser Glu Ala Phe Gly Val Leu Asn
1               5                   10                  15
Pro Glu Gly Ser
            20

<210> SEQ ID NO 256
<211> LENGTH: 20
<212> TYPE: PRT
<213> ORGANISM: Artificial Sequence
<220> FEATURE:
<223> OTHER INFORMATION: Made in a lab

<400> SEQUENCE: 256

Phe Lys Ile Ser Glu Ala Phe Gly Val Leu Asn Pro Glu Gly Ser Leu
1               5                   10                  15
Ala Leu Arg Ala
            20

<210> SEQ ID NO 257
<211> LENGTH: 20
<212> TYPE: PRT
<213> ORGANISM: Artificial Sequence
<220> FEATURE:
<223> OTHER INFORMATION: Made in a lab

<400> SEQUENCE: 257

Ala Phe Gly Val Leu Asn Pro Glu Gly Ser Leu Ala Leu Arg Ala Thr
1               5                   10                  15
Phe Leu Ile Asp
            20

<210> SEQ ID NO 258
<211> LENGTH: 20
<212> TYPE: PRT
<213> ORGANISM: Artificial Sequence
<220> FEATURE:
<223> OTHER INFORMATION: Made in a lab

<400> SEQUENCE: 258

Asn Pro Glu Gly Ser Leu Ala Leu Arg Ala Thr Phe Leu Ile Asp Lys
1               5                   10                  15
His Gly Val Ile
            20

<210> SEQ ID NO 259
<211> LENGTH: 20
<212> TYPE: PRT
<213> ORGANISM: Artificial Sequence
<220> FEATURE:
<223> OTHER INFORMATION: Made in a lab

<400> SEQUENCE: 259

Leu Ala Leu Arg Ala Thr Phe Leu Ile Asp Lys His Gly Val Ile Arg
1               5                   10                  15

His Ala Val Ile
            20

<210> SEQ ID NO 260
<211> LENGTH: 20
<212> TYPE: PRT
<213> ORGANISM: Artificial Sequence
<220> FEATURE:
<223> OTHER INFORMATION: Made in a lab

<400> SEQUENCE: 260

Thr Phe Leu Ile Asp Lys His Gly Val Ile Arg His Ala Val Ile Asn
1               5                   10                  15

Asp Leu Pro Leu
            20

<210> SEQ ID NO 261
<211> LENGTH: 20
<212> TYPE: PRT
<213> ORGANISM: Artificial Sequence
<220> FEATURE:
<223> OTHER INFORMATION: Made in a lab

<400> SEQUENCE: 261

Lys His Gly Val Ile Arg His Ala Val Ile Asn Asp Leu Pro Leu Gly
1               5                   10                  15

Arg Ser Ile Asp
            20

<210> SEQ ID NO 262
<211> LENGTH: 20
<212> TYPE: PRT
<213> ORGANISM: Artificial Sequence
<220> FEATURE:
<223> OTHER INFORMATION: Made in a lab

<400> SEQUENCE: 262

Arg His Ala Val Ile Asn Asp Leu Pro Leu Gly Arg Ser Ile Asp Glu
1               5                   10                  15

Glu Leu Arg Ile
            20

<210> SEQ ID NO 263
<211> LENGTH: 897
<212> TYPE: DNA
<213> ORGANISM: Chlamydia
<220> FEATURE:
<221> NAME/KEY: misc_feature
<222> LOCATION: (1)...(897)
<223> OTHER INFORMATION: n = A,T,C or G

<400> SEQUENCE: 263

```
atggcttcta tatgcggacg tttagggtct ggtacaggga atgctctaaa agcttttttt      60
acacagccca acaataaaat ggcaagggta gtaaataaga cgaagggagt ggataagact     120
attaaggttg ccaagtctgc tgccgaattg accgcaaata ttttggaaca agctggaggc     180
gcgggctctt ccgcacacat tacagcttcc caagtgtcca aaggattagg ggatgcgaga     240
actgttgtcg ctttagggaa tgcctttaac ggagcgttgc caggaacagt tcaaagtgcg     300
```

-continued

```
caaagcttct tctctcacat gaaagctgct agtcagaaaa cgcaagaagg ggatgagggg      360
ctcacagcag atctttgtgt gtctcataag cgcagagcgg ctgcggctgt ctgtagcatc      420
atcggaggaa ttacctacct cgcgacattc ggagctatcc gtccgattct gtttgtcaac      480
aaaatgctgg caaaaccgtt tctttcttcc caaactaaag caaatatggg atcttctgtt      540
agctatatta tggcggctaa ccatgcagcg tctgtggtgg gtgctggact cgctatcagt      600
gcgnaaagag cagattgcga agcccgctgc gctcgtattg cgagagaaga gtcgttactc      660
gaagtgccgg gagaggaaaa tgcttgcgag aagaaagtcg ctggagagaa agccaagacg      720
ttcacgcgca tcaagtatgc actcctcact atgctcgaga gttttttgga atgcgttgcc      780
gacgttttca aattggtgcc gctgcctatt acaatgggta ttcgtgcgat tgtggctgct      840
ggatgtacgt tcacttctgc aattattgga ttgtgcactt tctgcgccag agcataa       897
```

<210> SEQ ID NO 264
<211> LENGTH: 298
<212> TYPE: PRT
<213> ORGANISM: Chlamydia
<220> FEATURE:
<221> NAME/KEY: VARIANT
<222> LOCATION: (1)...(298)
<223> OTHER INFORMATION: Xaa = Any Amino Acid

<400> SEQUENCE: 264

```
Met Ala Ser Ile Cys Gly Arg Leu Gly Ser Gly Thr Gly Asn Ala Leu
 1               5                  10                  15

Lys Ala Phe Phe Thr Gln Pro Asn Asn Lys Met Ala Arg Val Val Asn
             20                  25                  30

Lys Thr Lys Gly Val Asp Lys Thr Ile Lys Val Ala Lys Ser Ala Ala
         35                  40                  45

Glu Leu Thr Ala Asn Ile Leu Glu Gln Ala Gly Gly Ala Gly Ser Ser
     50                  55                  60

Ala His Ile Thr Ala Ser Gln Val Ser Lys Gly Leu Gly Asp Ala Arg
 65                  70                  75                  80

Thr Val Val Ala Leu Gly Asn Ala Phe Asn Gly Ala Leu Pro Gly Thr
                 85                  90                  95

Val Gln Ser Ala Gln Ser Phe Phe Ser His Met Lys Ala Ala Ser Gln
            100                 105                 110

Lys Thr Gln Glu Gly Asp Glu Gly Leu Thr Ala Asp Leu Cys Val Ser
        115                 120                 125

His Lys Arg Arg Ala Ala Ala Val Cys Ser Ile Ile Gly Gly Ile
    130                 135                 140

Thr Tyr Leu Ala Thr Phe Gly Ala Ile Arg Pro Ile Leu Phe Val Asn
145                 150                 155                 160

Lys Met Leu Ala Lys Pro Phe Leu Ser Ser Gln Thr Lys Ala Asn Met
                165                 170                 175

Gly Ser Ser Val Ser Tyr Ile Met Ala Ala Asn His Ala Ala Ser Val
            180                 185                 190

Val Gly Ala Gly Leu Ala Ile Ser Ala Xaa Arg Ala Asp Cys Glu Ala
        195                 200                 205

Arg Cys Ala Arg Ile Ala Arg Glu Glu Ser Leu Leu Glu Val Pro Gly
    210                 215                 220

Glu Glu Asn Ala Cys Glu Lys Lys Val Ala Gly Glu Lys Ala Lys Thr
225                 230                 235                 240

Phe Thr Arg Ile Lys Tyr Ala Leu Leu Thr Met Leu Glu Lys Phe Leu
                245                 250                 255
```

Glu Cys Val Ala Asp Val Phe Lys Leu Val Pro Leu Pro Ile Thr Met
          260                 265                 270

Gly Ile Arg Ala Ile Val Ala Ala Gly Cys Thr Phe Thr Ser Ala Ile
      275                 280                 285

Ile Gly Leu Cys Thr Phe Cys Ala Arg Ala
    290                 295

<210> SEQ ID NO 265
<211> LENGTH: 897
<212> TYPE: DNA
<213> ORGANISM: Chlamydia
<220> FEATURE:
<221> NAME/KEY: misc_feature
<222> LOCATION: (1)...(897)
<223> OTHER INFORMATION: n = A,T,C or G

<400> SEQUENCE: 265

| | | | | | |
|---|---|---|---|---|---|
| atggcttcta | tatgcggacg | tttagggtct | ggtacaggga | atgctctaaa | agcttttttt | 60 |
| acacagccca | acaataaaat | ggcaagggta | gtaaataaga | cgaagggaat | ggataagact | 120 |
| attaaggttg | ccaagtctgc | tgccgaattg | accgcaaata | ttttggaaca | agctggaggc | 180 |
| gcgggctctt | ccgcacacat | tacagcttcc | caagtgtcca | aaggattagg | ggatgcgaga | 240 |
| actgttgtcg | ctttagggaa | tgcctttaac | ggagcgttgc | caggaacagt | tcaaagtgcg | 300 |
| caaagcttct | tctctcacat | gaaagctgct | agtcagaaaa | cgcaagaagg | ggatgagggg | 360 |
| ctcacagcag | atctttgtgt | gtctcataag | cgcagagcgg | ctgcggctgt | ctgtagcatc | 420 |
| atcggaggaa | ttacctacct | cgcgacattc | ggagctatcc | gtccgattct | gtttgtcaac | 480 |
| aaaatgctgg | caaaaccgtt | tctttcttcc | caaactaaag | caaatatggg | atcttctgtt | 540 |
| agctatatta | tggcggctaa | ccatgcagcg | tctgtggtgg | gtgctggact | cgctatcagt | 600 |
| gcgnaaagag | cagattgcga | agcccgctgc | gctcgtattg | cgagagaaga | gtcgttactc | 660 |
| gaagtgccgg | gagaggaaaa | tgcttgcgag | aagaaagtcg | ctggagagaa | agccaagacg | 720 |
| ttcacgcgca | tcaagtatgc | actcctcact | atgctcgaga | agtttttgga | atgcgttgcc | 780 |
| gacgttttca | aattggtgcc | gctgcctatt | acaatgggta | ttcgtgcgat | tgtggctgct | 840 |
| ggatgtacgt | tcacttctgc | aattattgga | ttgtgcactt | tctgcgccag | agcataa | 897 |

<210> SEQ ID NO 266
<211> LENGTH: 298
<212> TYPE: PRT
<213> ORGANISM: Chlamydia
<220> FEATURE:
<221> NAME/KEY: VARIANT
<222> LOCATION: (1)...(298)
<223> OTHER INFORMATION: Xaa = Any Amino Acid

<400> SEQUENCE: 266

Met Ala Ser Ile Cys Gly Arg Leu Gly Ser Gly Thr Gly Asn Ala Leu
1               5                   10                  15

Lys Ala Phe Phe Thr Gln Pro Asn Asn Lys Met Ala Arg Val Val Asn
            20                  25                  30

Lys Thr Lys Gly Met Asp Lys Thr Ile Lys Val Ala Lys Ser Ala Ala
        35                  40                  45

Glu Leu Thr Ala Asn Ile Leu Glu Gln Ala Gly Gly Ala Gly Ser Ser
    50                  55                  60

Ala His Ile Thr Ala Ser Gln Val Ser Gly Leu Gly Asp Ala Arg
65                  70                  75                  80

```
Thr Val Val Ala Leu Gly Asn Ala Phe Asn Gly Ala Leu Pro Gly Thr
                85                  90                  95

Val Gln Ser Ala Gln Ser Phe Phe Ser His Met Lys Ala Ala Ser Gln
            100                 105                 110

Lys Thr Gln Glu Gly Asp Glu Gly Leu Thr Ala Asp Leu Cys Val Ser
        115                 120                 125

His Lys Arg Ala Ala Ala Val Cys Ser Ile Ile Gly Gly Ile
    130                 135                 140

Thr Tyr Leu Ala Thr Phe Gly Ala Ile Arg Pro Ile Leu Phe Val Asn
145                 150                 155                 160

Lys Met Leu Ala Lys Pro Phe Leu Ser Ser Gln Thr Lys Ala Asn Met
                165                 170                 175

Gly Ser Ser Val Ser Tyr Ile Met Ala Ala Asn His Ala Ala Ser Val
            180                 185                 190

Val Gly Ala Gly Leu Ala Ile Ser Ala Xaa Arg Ala Asp Cys Glu Ala
        195                 200                 205

Arg Cys Ala Arg Ile Ala Arg Glu Glu Ser Leu Leu Glu Val Pro Gly
    210                 215                 220

Glu Glu Asn Ala Cys Glu Lys Lys Val Ala Gly Glu Lys Ala Lys Thr
225                 230                 235                 240

Phe Thr Arg Ile Lys Tyr Ala Leu Leu Thr Met Leu Glu Lys Phe Leu
                245                 250                 255

Glu Cys Val Ala Asp Val Phe Lys Leu Val Pro Leu Pro Ile Thr Met
            260                 265                 270

Gly Ile Arg Ala Ile Val Ala Ala Gly Cys Thr Phe Thr Ser Ala Ile
        275                 280                 285

Ile Gly Leu Cys Thr Phe Cys Ala Arg Ala
    290                 295
```

<210> SEQ ID NO 267
<211> LENGTH: 680
<212> TYPE: DNA
<213> ORGANISM: Chlamydia

<400> SEQUENCE: 267

```
tctatatcca tattgatagg aaaaaacgtc gcagaaagat tttagctatg acgtttatcc    60
gagctttagg atattcaaca gatgcagata ttattgaaga gttctttcct gtagaggagc   120
gttccttacg ttcagagaag gattttgtcg cgttagttgg taaagtttta gctgataacg   180
tagttgatgc ggattcttca ttagtttacg ggaaagctgg agagaagcta agtactgcta   240
tgctaaaacg catcttagat acgggagtcc aatctttgaa gattgctgtt ggcgcagatg   300
aaaatcaccc aattattaag atgctcgcaa agatcctac ggattcttac gaagctgctc    360
ttaaagattt ttatcgcaga ttcgaccag gagagcctgc aactttagct aatgctcgat    420
ccacaattat gcgtttattc ttcgatgcta acgttataa tttaggccgc gttggacgtt    480
ataaattaaa taaaaatta ggcttcccat tagacgacga acattatct caagtgactt     540
tgagaaaaga agatgttatc ggcgcgttga aatatttgat tcgtttgcga atgggcgatg   600
agaagacatc tatcgatgat attgaccatt tggcaaaccg acgagttcgc tctgttggag   660
aactaattca gaatcactgt                                               680
```

<210> SEQ ID NO 268
<211> LENGTH: 359
<212> TYPE: DNA
<213> ORGANISM: Chlamydia

<400> SEQUENCE: 268

```
cttatgttct ggagaatgtt gcaacaacat attaatcgaa ccagctcctc ctagtaacat      60
agaaaccaag ccctttgag aaaaaacctg tacttcgcat cctttagcca tttgttgaat     120
agctcctaac aaagagctaa ttttttcctc ttccttgttt ttctgaggcg ctgtggactc    180
taaatatagc aagtgctctt ggaacacctc atcaacaatc gcttgtccta gattaggtat   240
agagactgtc tctccatcaa ttaaatggag tttcaaagta atatcccctt ccgtccctcc   300
atcacaagac tctatgaaag ctatctgatt ccatcgagca gaaatgtatg gggaaatac    359
```

<210> SEQ ID NO 269
<211> LENGTH: 124
<212> TYPE: DNA
<213> ORGANISM: Chlamydia

<400> SEQUENCE: 269

```
gatcgaatca attgagggag ctcattaaca agaatagctg cagtttcttt gcgttcttct    60
ggaataacaa gaaataggta atcggtacca ttgatagaac gaacacgaca aatcgcagaa   120
ggtt                                                                 124
```

<210> SEQ ID NO 270
<211> LENGTH: 219
<212> TYPE: DNA
<213> ORGANISM: Chlamydia

<400> SEQUENCE: 270

```
gatcctgttg ggcctagtaa taatacgttg gatttcccat aactcacttg tttatcctgc    60
ataagagcac ggatacgctt atagtggtta tagacggcaa ccgaaatcgt ttttttcgcg   120
cgctcttgtc caatgacata agagtcgatg tggcgtttga tttctttagg ggttaacact   180
ctcagacttg ttggagagct tgtggaagat gttgcgatc                           219
```

<210> SEQ ID NO 271
<211> LENGTH: 511
<212> TYPE: DNA
<213> ORGANISM: Chlamydia
<220> FEATURE:
<221> NAME/KEY: misc_feature
<222> LOCATION: (1)...(511)
<223> OTHER INFORMATION: n = A,T,C or G

<400> SEQUENCE: 271

```
ggatccgaat tcggcacgag gagaaaatat aggaggttcc akcatcggaa gatctaatag    60
acaaagaggt tttggcatag atggctcctc cttgtacgtt caacgatgat tgggagggat   120
tgttatcgat agcttggttc ccagagaact gacaagtccc gctacattga gagaatgtaa   180
cctgttctcc atagatagct cctcctacta cacctgaata agttggtgtt gctggagatg   240
atggtgcggc tgctgcggct gcttgtaggg aagcagcagc tgcagcaggt gctgaagctg   300
ttgttgcgac tcctgtggat gaggagtttg ctttgttgtt cgagaaagag aagcctgatt   360
tcagattaga aatatttaca gttttagcat gtaagcctcc accttctttc ccaacaaggt   420
tctctgttac agataaggag actagangca tctagtttta aagattttt acagcagata    480
cctccaccta tctctgtagc ggagttctca g                                  511
```

<210> SEQ ID NO 272
<211> LENGTH: 598
<212> TYPE: DNA

<213> ORGANISM: Chlamydia

<400> SEQUENCE: 272

| | | | | | |
|---|---|---|---|---|---|
| ctcttcctct | cctcaatcta | gttctggagc | aactacagtc | tccgactcag | gagactctag | 60 |
| ctctggctca | aactcggata | cctcaaaaac | agttccagtc | acagctaaag | gcggtgggct | 120 |
| ttatactgat | aagaatcttt | cgattactaa | catcacagga | attatcgaaa | ttgcaaataa | 180 |
| caaagcgaca | gatgttggag | gtggtgctta | cgtaaaagga | acccttactt | gtaaaaactc | 240 |
| tcaccgtcta | caattttttga | aaactcttc | cgataaacaa | ggtggaggaa | tctacggaga | 300 |
| agacaacatc | accctatcta | atttgacagg | gaagactcta | ttccaagaga | atactgccaa | 360 |
| aaaagagggc | ggtggactct | tcataaaagg | tacagataaa | gctcttacaa | tgacaggact | 420 |
| ggatagtttc | tgtttaatta | ataacacatc | agaaaaacat | ggtggtggga | gcctttgtta | 480 |
| ccaaagaaat | ctctcagact | tacacctctt | gatgtggaaa | caattccagg | aatcacgcct | 540 |
| gtacatggtg | aaacagtcat | tactggcaat | aaatctacag | gaggtaatgg | tggagggc | 598 |

<210> SEQ ID NO 273
<211> LENGTH: 126
<212> TYPE: DNA
<213> ORGANISM: Chlamydia

<400> SEQUENCE: 273

| | | | | | |
|---|---|---|---|---|---|
| ggatccgaat | tcggcacgag | atgagcctta | tagtttaaca | aaagcttctc | acattccttc | 60 |
| gatagctttt | tattagccgt | ttttagcatc | ctaatgagat | ctcctcgttc | gtaacaaata | 120 |
| cgagag | | | | | | 126 |

<210> SEQ ID NO 274
<211> LENGTH: 264
<212> TYPE: DNA
<213> ORGANISM: Chlamydia

<400> SEQUENCE: 274

| | | | | | |
|---|---|---|---|---|---|
| ggatccgaat | tcggcacgag | ctcttttaaa | tcttaattac | aaaaagacaa | attaattcaa | 60 |
| tttttcaaaa | aagaatttaa | acattaattg | ttgtaaaaaa | acaatatttta | ttctaaaata | 120 |
| ataaccatag | ttacggggga | atctctttca | tggtttatt | tagagctcat | caacctaggc | 180 |
| atacgcctaa | acatttcct | ttgaaagttc | accattcgtt | ctccgataag | catcctcaaa | 240 |
| ttgctaaagc | tatgtggatt | acgg | | | | 264 |

<210> SEQ ID NO 275
<211> LENGTH: 359
<212> TYPE: DNA
<213> ORGANISM: Chlamydia

<400> SEQUENCE: 275

| | | | | | |
|---|---|---|---|---|---|
| ggatccgaat | tcggcacgag | ataaaacctg | aaccacaaca | aagatctaaa | acttcttgat | 60 |
| tttcagctgc | aaattctttt | agataaatat | caaccatttc | ttcagtttca | tatcttggaa | 120 |
| ttaaaacttg | ttctcttaaa | ttaattctag | tatttaagta | ttcaacatag | cccattatta | 180 |
| attgaattgg | ataattttgc | cttaataatt | cacattcttt | ttcagtaatt | ttaggttcta | 240 |
| aaccgtaccg | ctttttttct | aaaattaatg | tttcttcatt | attcatttta | taagccactt | 300 |
| tcctttattt | tttgattttg | ttcttctgtt | agtaatgctt | caataatagt | taataattt | 359 |

<210> SEQ ID NO 276
<211> LENGTH: 357

<212> TYPE: DNA
<213> ORGANISM: Chlamydia

<400> SEQUENCE: 276

| | | | | | |
|---|---|---|---|---|---|
| aaaacaattg | atataatttt | tttttcata | acttccagac | tcctttctag | aaaagtcttt | 60 |
| atgggtagta | gtgactctaa | cgttttttat | tattaagacg | atccccggag | atccttttaa | 120 |
| tgatgaaaac | ggaaacatcc | tttcgccaga | aactttagca | ctattaaaga | atcgttacgg | 180 |
| gttagataag | cctttattca | cccagtatct | tatctatttg | aaatgtctgc | taacactaga | 240 |
| tttcggggaa | tctcttatct | acaaagatcg | aaatctcagc | attattgctg | ccgctcttcc | 300 |
| atcttccgct | attcttggac | ttgaaagctt | gtgtttactc | gtgccgaatt | cggatcc | 357 |

<210> SEQ ID NO 277
<211> LENGTH: 505
<212> TYPE: DNA
<213> ORGANISM: Chlamydia

<400> SEQUENCE: 277

| | | | | | |
|---|---|---|---|---|---|
| ggatccgaat | tcggcacgag | ctcgtgccga | ttgcttgctt | cagtcacccc | atcggtatag | 60 |
| agcactaaaa | gagactcctc | ttcaagaacg | agagtgtaag | cagggtgagg | aggaacttca | 120 |
| ggtaaaaatc | ctaaggccat | accaggatgc | gacaggaaaa | agatatctcc | attaggagct | 180 |
| cggagacacg | ctgggttgtg | gccacaagaa | tagtattcta | gttctcgtgt | tgcgtaatga | 240 |
| taacaataaa | tgcatagtgt | tacaaacatc | ccagattcag | ctgtctgttg | atagaagaga | 300 |
| gcagctgttt | gttgaacggc | ttcttgaata | gaggagagct | cactcaaaaa | ggtatgtaac | 360 |
| atgtttttca | ggaataagga | gtaggcgcac | gcattgactc | ctttcccgga | agcatcagca | 420 |
| acgattagaa | agagtttagc | ttggggacct | tcgcctataa | caaagatatc | aaagaaatct | 480 |
| cctcctaccg | taactgcagg | aatat | | | | 505 |

<210> SEQ ID NO 278
<211> LENGTH: 407
<212> TYPE: DNA
<213> ORGANISM: Chlamydia

<400> SEQUENCE: 278

| | | | | | |
|---|---|---|---|---|---|
| ggatccgaat | tcggcacgag | aactactgag | caaattgggt | atccaacttc | ctctttacga | 60 |
| aagaaaaaca | gaaggcattc | tccataccaa | gatttgttgc | atcgacaata | aaactccaat | 120 |
| cttttggctct | gctaactgga | gcggtgctgg | tatgattaaa | aactttgaag | acctattcat | 180 |
| ccttcgccca | attacagaga | cacagcttca | ggcctttatg | gacgtctggt | ctcttctaga | 240 |
| aacaaatagc | tcctatctgt | ccccagagag | cgtgcttacg | gccctactc | cttcaagtag | 300 |
| acctactcaa | caagatacag | attctgatga | cgaacaaccg | agtaccagcc | agcaagctat | 360 |
| ccgtatgaga | aaataggatt | agggaaacaa | aacgacagca | aaccaca | | 407 |

<210> SEQ ID NO 279
<211> LENGTH: 351
<212> TYPE: DNA
<213> ORGANISM: Chlamydia

<400> SEQUENCE: 279

| | | | | | |
|---|---|---|---|---|---|
| ctcgtgccgc | ttacaggagg | cttgtatcct | ttaaaataga | gttttcttta | tgaccccatg | 60 |
| tggcgatagg | ccgggtctag | cgccgatagt | agaaatatcg | gttggttttt | gtccttgagg | 120 |
| ggatcgtata | cttttcaaa | gtatggtccc | cgtatcgatt | atctggaggc | tcttatgtct | 180 |

-continued

```
tttttttcata ctagaaaata taagcttatc ctcagaggac tcttgtgttt agcaggctgt    240
ttcttaatga acagctgttc ctctagtcga ggaaatcaac ccgctgatga gagcatctat    300
gtcttgtcta tgaatcgcat gatttgtgat tctcgtgccg aattcggatc c             351
```

<210> SEQ ID NO 280
<211> LENGTH: 522
<212> TYPE: DNA
<213> ORGANISM: Chlamydia

<400> SEQUENCE: 280

```
ggatccgaat tcggcacgag cagaggaaaa aggcgatact cctcttgaag atcgtttcac     60
agaagatctt tccgaagtct ctggagaaga ttttcgagga ttgaaaaatt cgttcgatga    120
tgattcttct tctgacgaaa ttctcgatgc gctcacaagt aaattttctg atcccacaat    180
aaaggatcta gctcttgatt atctaattca aatagctccc tctgatggga aacttaagtc    240
cgctctcatt caggcaaagc atcaactgat gagccagaat cctcaggcga ttgttggagg    300
acgcaatgtt ctgttagctt cagaaacctt tgcttccaga gcaaatacat ctccttcatc    360
gcttcgctcc ttatatttcc aagtaacctc atcccctct aattgcgcta atttacatca     420
aatgcttgct tcttactcgc catcagagaa accgctgtt atggagtttc tagtgaatgg     480
catggtagca gatttaaaat cggagggccc ttccattcct cc                      522
```

<210> SEQ ID NO 281
<211> LENGTH: 577
<212> TYPE: DNA
<213> ORGANISM: Chlamydia

<400> SEQUENCE: 281

```
ggatccgaat tcggcacgag atgcttctat tacaattggt ttggatgcgg aaaaagctta     60
ccagcttatt ctagaaaagt tgggagatca aattcttggt ggaattgctg atactattgt    120
tgatagtaca gtccaagata ttttagacaa atcacaaca gacccttctc taggtttgtt     180
gaaagctttt aacaactttc caatcactaa taaaattcaa tgcaacgggt tattcactcc    240
caggaacatt gaaactttat taggaggaac tgaaatagga aaattcacag tcacacccaa    300
aagctctggg agcatgttct tagtctcagc agatattatt gcatcaagaa tggaaggcgg    360
cgttgttcta gctttggtac gagaaggtga ttctaagccc tacgcgatta gttatggata    420
ctcatcaggc gttcctaatt tatgtagtct aagaaccaga attattaata caggattgac    480
tccgacaacg tattcattac gtgtaggcgg tttagaaagc ggtgtggtat gggttaatgc    540
cctttctaat ggcaatgata ttttaggaat aacaaat                              577
```

<210> SEQ ID NO 282
<211> LENGTH: 607
<212> TYPE: DNA
<213> ORGANISM: Chlamydia

<400> SEQUENCE: 282

```
actmatcttc cccgggctcg agtgcggccg caagcttgtc gacggagctc gatacaaaaa     60
tgtgtgcgtg tgaaccgctt cttcaaaagc ttgtcttaaa agatattgtc tcgcttccgg    120
attagttaca tgtttaaaaa ttgctagaac aatattattc ccaaccaagc tctctgcggt    180
gctgaaaaaa cctaaattca aaagaatgac tcgccgctca tcttcagaaa gacgatccga    240
cttccataat tcgatgtctt tccccatggg gatctctgta gggagccagt tatttgcgca    300
gccattcaaa taatgttccc aagcccattt gtacttaata ggaacaagtt ggttgacatc    360
```

```
gacctggttg cagttcacta gacgcttgct atttagatta acgcgtttct gttttccatc    420
taaaatatct gcttgcataa gaaccgttaa ttttattgtt aatttatatg attaattact    480
gacatgcttc acacccttct tccaaagaac agacaggtgc tttcttcgct ctttcaacaa    540
taattcctgc cgaagcagac ttattcttca tccaacgagg ctgaattcct ctcttattaa    600
tatctac                                                              607
```

<210> SEQ ID NO 283
<211> LENGTH: 1077
<212> TYPE: DNA
<213> ORGANISM: Chlamydia

<400> SEQUENCE: 283

```
ggatccgaat tcggcacgag aagttaacga tgacgatttg ttcctttggt agagaaggag     60
caatcgaaac taaatgtgcg agagcatgtg aagactccaa tgcaggaata atcccctcat    120
ttctagtaag caggaaaaaa gctcgtaacg cctcttcatc ggtggctaat gtataaaagg    180
ctcgtcctga ctcatgcatt tcggcatgat ctggcccaac tgaaggataa tctaatccag    240
cggaaatgga gtgagtttgt aatacttgtc catcgtcatc ttgaagaaga tacgaataaa    300
atccgtggaa tactccaggt cgccctgttg caaaacgtgc tgcatgtttt cctgaagaaa    360
tgcccagtcc tcccccttcc actccaatta attggacttt tggattcggg ataaaatgat    420
ggaaaaatcc aatagcgttg gagccaccte cgatacatgc aatcagaata tcaggatctc    480
ttcctgcaac tgcatggatt tgctctttca cttcagcgct tataacagac tgaaaaaatc    540
gaacgatatc gggataaggt aaaggtccta aggccgatcc taagcaatag tgagtaaatg    600
agtgtgttgt tgcccaatct tgtagagctt gattaactgc atctttgagt ccacaagatc    660
cttttgttac agaaacgact tcagcaccta aaaagcgcat tttctctaca tttggtttct    720
gtcgttccac atcttttgct cccatgtata ctacacaatc taatcctaga taagcacacg    780
ctgttgctgt tgctactcca tgttgtcccg cacctgtttc agctacaaca cgtgttttcc    840
caagatattt agcaagcaaa cactgaccaa gagcattatt cagtttatgt gctcctgtat    900
gcaaaagatc ttcgcgttta agaaatactc tagggccatc aatagctcga gcaaaattct    960
taacttcagt cagaggagtt tgtctccccg catagttttt caaaatacaa tctagttcag   1020
ataaaaaact tgctgagtt ttgagaatct cccattccgc ttttagattc tgtatag       1077
```

<210> SEQ ID NO 284
<211> LENGTH: 407
<212> TYPE: DNA
<213> ORGANISM: Chlamydia

<400> SEQUENCE: 284

```
ggatccgaat tcggcacgag aactactgag caaattgggt atccaacttc ctctttacga     60
aagaaaaaca gaaggcattc tccataccaa gatttgttgc atcgacaata aaactccaat    120
ctttggctct gctaactgga gcggtgctgg tatgattaaa aactttgaag acctattcat    180
ccttcgccca attacagaga cacagcttca ggcctttatg gacgtctggt ctcttctaga    240
aacaaatagc tccatctgt ccccagagag cgtgcttacg gcccctactc cttcaagtag    300
acctactcaa caagatacag attctgatga cgaacaaccg agtaccagcc agcaagctat    360
ccgtatgaga aaataggatt agggaaacaa aacgacagca aaccaca                  407
```

<210> SEQ ID NO 285

<211> LENGTH: 802
<212> TYPE: DNA
<213> ORGANISM: Chlamydia

<400> SEQUENCE: 285

```
ggatccgaat tcggcacgag ttagcttaat gtctttgtca tctctaccta catttgcagc      60
taattctaca ggcacaattg gaatcgttaa tttacgtcgc tgcctagaag agtctgctct     120
tgggaaaaaa gaatctgctg aattcgaaaa gatgaaaaac caattctcta acagcatggg     180
gaagatggag gaagaactgt cttctatcta ttccaagctc caagacgacg attacatgga     240
aggtctatcc gagaccgcag ctgccgaatt aagaaaaaaa ttcgaagatc tatctgcaga     300
atacaacaca gctcaagggc agtattacca aatattaaac caaagtaatc tcaagcgcat     360
gcaaaagatt atggaagaag tgaaaaaagc ttctgaaact gtgcgtattc aagaaggctt     420
gtcagtcctt cttaacgaag atattgtctt atctatcgat agttcggcag ataaaaccga     480
tgctgttatt aaagttcttg atgattcttt tcaaaataat taacatgcga agctagccga     540
ggagtgccgt atgtctcaat ccacttattc tcttgaacaa ttagctgatt ttttgaaagt     600
cgagtttcaa ggaaatggag ctactcttct ttccggagtt gaagagatcg aggaagcaaa     660
aacggcacac atcacattct tagataatga aaaatatgct aaacatttaa aatcatcgga     720
agctggcgct atcatcatat ctcgaacaca gtttcaaaaa tatcgagact tgaataaaaa     780
ctttcttatc acttctgagt ct                                              802
```

<210> SEQ ID NO 286
<211> LENGTH: 588
<212> TYPE: DNA
<213> ORGANISM: Chlamydia

<400> SEQUENCE: 286

```
ggatccgaat tcggcacgag gcaatattta ctcccaacat tacggttcca ataagcgat      60
aaggtcttct aataaggaag ttaatgtaag aggcttttt attgcttttc gtaaggtagt     120
attgcaaccg cacgcgattg aatgatacgc aagccatttc catcatggaa agaaccctt     180
ggacaaaaat acaaggagg ttcactccta accagaaaaa gggagagtta gtttccatgg     240
gttttccatta tatacacccg tttcacacaa ttaggagccg cgtctagtat ttggaataca     300
aattgtcccc aagcgaattt tgttcctgtt tcagggattt ctcctaattg ttctgtcagc     360
catccgccta tggtaacgca attagctgta gtaggaagat caactccaaa caggtctatag    420
aaatcagaaa gctcataggt gcctgcagca ataacaacat tcttgtctga gtgagcgaat     480
tgtttaaaag atgggcgatt atgagctacc tcatcagaga ctattttaaa tagatcattt     540
tgggtaatca atccttctat agacccatat tcatcaatga taatctcg                  588
```

<210> SEQ ID NO 287
<211> LENGTH: 489
<212> TYPE: DNA
<213> ORGANISM: Chlamydia
<220> FEATURE:
<221> NAME/KEY: misc_feature
<222> LOCATION: (1)...(489)
<223> OTHER INFORMATION: n = A,T,C or G

<400> SEQUENCE: 287

```
agtgcctatt gttttgcagg ctttgtctga tgatagcgat accgtacgtg agattgctgt      60
acaagtagct gttatgtatg gttctagttg cttactcgc gccgtgggcg atttagcgaa     120
aaatgattct tctattcaag tacgcatcac tgcttatcgt gctgcagccg tgttggagat     180
```

```
acaagatctt gtgcctcatt tacgagttgt agtccaaaat acacaattag atggaacgga    240
aagaagagaa gcttggagat ctttatgtgt tcttactcgg cctcatagtg gtgtattaac    300
tggcatagat caagctttaa tgacctgtga gatgttaaag gaatatcctg aaaagtgtac    360
ggaagaacag attcgtacat tattggctgc agatcatcca gaagtgcagg tagctacttt    420
acagatcatt ctgagaggag gtagagtatt ccggtcatct tctataatgg aatcggttct    480 cgtgccgnt                                                            489

<210> SEQ ID NO 288
<211> LENGTH: 191
<212> TYPE: DNA
<213> ORGANISM: Chlamydia

<400> SEQUENCE: 288
ggatccgaat tcaggatatg ctgttgggtt atcaataaaa agggttttgc cattttttaa     60
gacgactttg tagataacgc taggagctgt agcaataata tcgagatcaa attctctaga    120
gattctctca aagatgattt ctaagtgcag cagtcctaaa aatccacagc ggaacccaaa    180
tccgagagag t                                                          191

<210> SEQ ID NO 289
<211> LENGTH: 515
<212> TYPE: DNA
<213> ORGANISM: Chlamydia

<400> SEQUENCE: 289
ggatccgaat tcggcacgag gagcgacgtg aaatagtgga atcttcccgt attcttatta     60
cttctgcgtt gccttacgca aatggtcctt tgcattttgg acatattacc ggtgcttatt    120
tgcctgcaga tgtttatgcg cgttttcaga gactacaagg caaagaggtt ttgtatattt    180
gtggttctga tgaatacgga atcgcaatta cccttaatgc agagttggca ggcatggggt    240
atcaagaata tgtcgacatg tatcataagc ttcataaaga taccttcaag aaattgggaa    300
tttctgtaga tttcttttcc agaactacga acgcttatca tcctgctatt gtgcaagatt    360
tctatcgaaa cttgcaggaa cgcggactgg tagagaatca ggtgaccgaa cagctgtatt    420
ctgaggaaga agggaagttt ttagcggacc gttatgttgt aggtacttgt cccaagtgtg    480
ggtttgatcg agctcgagga gatgagtgtc agcag                               515

<210> SEQ ID NO 290
<211> LENGTH: 522
<212> TYPE: DNA
<213> ORGANISM: Chlamydia

<400> SEQUENCE: 290
ggatccgaat tcggcacgag ggaggaatgg aagggccctc cgattktama tctgctacca     60
tgccattcac tagaaactcc ataacagcgg ttttctctga tggcgagtaa gaagcaagca    120
tttgatgtaa attagcgcaa ttagagggg atgaggttac ttggaaatat aaggagcgaa    180
gcgatgaagg agatgtattt gctctggaag caaaggtttc tgaagctaac agaacattgc    240
gtcctccaac aatcgcctga ggattctggc tcatcagttg atgctttgcc tgaatgagag    300
cggacttaag tttcccatca gagggagcta tttgaattag ataatcaaga gctagatcct    360
ttattgtggg atcagaaaat ttacttgtga gcgcatcgag aatttcgtca gaagaagaat    420
catcatcgaa cgaattttc aatcctcgaa aatcttctcc agagacttcg aaagatcttc    480
```

```
ctgtgaaacg atcttcaaga ggagtatcgc cttttccyc tg                      522
```

<210> SEQ ID NO 291
<211> LENGTH: 1002
<212> TYPE: DNA
<213> ORGANISM: Chlamydia

<400> SEQUENCE: 291

```
atggcgacta acgcaattag atcggcagga agtgcagcaa gtaagatgct gctgccagtt    60
gccaaagaac cagcggctgt cagctccttt gctcagaaag ggatttattg tattcaacaa   120
ttttttacaa accctgggaa taagttagca aagtttgtag gggcaacaaa aagtttagat   180
aaatgcttta agctaagtaa ggcggttcct gactgtgtcg taggatcgct ggaagaggcg   240
ggatgcacag gggacgcatt gacctccgcg agaaacgccc agggtatgtt aaaaacaact   300
cgagaagttg ttgccttagc taatgtgctc aatggagctg ttccatctat cgttaactcg   360
actcagaggt gttaccaata cacacgtcaa gccttcgagt taggaagcaa gacaaaagaa   420
agaaaaacgc ctggggagta tagtaaaatg ctattaactc gaggtgatta cctattggca   480
gcttccaggg aagcttgtac ggcagtcggt gcaacgactt actcagcgac attcggtgtt   540
ttacgtccgt taatgttaat caataaactc acagcaaaac cattcttaga caaagcgact   600
gtaggcaatt ttggcacggc tgttgctgga attatgacca ttaatcatat ggcaggagtt   660
gctggtgctg ttggcggaat cgcattagaa caaaagctgt tcaaacgtgc gaaggaatcc   720
ctatacaatg agagatgtgc cttagaaaac caacaatctc agttgagtgg ggacgtgatt   780
ctaagcgcgg aaagggcatt acgtaaagaa cacgttgcta ctctaaaaag aaatgttta   840
actcttcttg aaaaagcttt agagttggta gtggatggag tcaaactcat tcctttaccg   900
attacagtgg cttgctccgc tgcaatttct ggagccttga cggcagcatc cgcaggaatt   960
ggcttatata gcatatggca gaaaacaaag tctggcaaat aa                    1002
```

<210> SEQ ID NO 292
<211> LENGTH: 333
<212> TYPE: PRT
<213> ORGANISM: Chlamydia

<400> SEQUENCE: 292

```
Met Ala Thr Asn Ala Ile Arg Ser Ala Gly Ser Ala Ala Ser Lys Met
  1               5                  10                  15

Leu Leu Pro Val Ala Lys Glu Pro Ala Ala Val Ser Ser Phe Ala Gln
             20                  25                  30

Lys Gly Ile Tyr Cys Ile Gln Gln Phe Phe Thr Asn Pro Gly Asn Lys
         35                  40                  45

Leu Ala Lys Phe Val Gly Ala Thr Lys Ser Leu Asp Lys Cys Phe Lys
     50                  55                  60

Leu Ser Lys Ala Val Ser Asp Cys Val Val Gly Ser Leu Glu Glu Ala
 65                  70                  75                  80

Gly Cys Thr Gly Asp Ala Leu Thr Ser Ala Arg Asn Ala Gln Gly Met
                 85                  90                  95

Leu Lys Thr Thr Arg Glu Val Val Ala Leu Ala Asn Val Leu Asn Gly
            100                 105                 110

Ala Val Pro Ser Ile Val Asn Ser Thr Gln Arg Cys Tyr Gln Tyr Thr
        115                 120                 125

Arg Gln Ala Phe Glu Leu Gly Ser Lys Thr Lys Glu Arg Lys Thr Pro
    130                 135                 140
```

```
Gly Glu Tyr Ser Lys Met Leu Leu Thr Arg Gly Asp Tyr Leu Leu Ala
145                 150                 155                 160

Ala Ser Arg Glu Ala Cys Thr Ala Val Gly Ala Thr Thr Tyr Ser Ala
            165                 170                 175

Thr Phe Gly Val Leu Arg Pro Leu Met Leu Ile Asn Lys Leu Thr Ala
            180                 185                 190

Lys Pro Phe Leu Asp Lys Ala Thr Val Gly Asn Phe Gly Thr Ala Val
        195                 200                 205

Ala Gly Ile Met Thr Ile Asn His Met Ala Gly Val Ala Gly Ala Val
    210                 215                 220

Gly Gly Ile Ala Leu Glu Gln Lys Leu Phe Lys Arg Ala Lys Glu Ser
225                 230                 235                 240

Leu Tyr Asn Glu Arg Cys Ala Leu Glu Asn Gln Gln Ser Gln Leu Ser
                245                 250                 255

Gly Asp Val Ile Leu Ser Ala Glu Arg Ala Leu Arg Lys Glu His Val
            260                 265                 270

Ala Thr Leu Lys Arg Asn Val Leu Thr Leu Leu Glu Lys Ala Leu Glu
        275                 280                 285

Leu Val Val Asp Gly Val Lys Leu Ile Pro Leu Pro Ile Thr Val Ala
    290                 295                 300

Cys Ser Ala Ala Ile Ser Gly Ala Leu Thr Ala Ala Ser Ala Gly Ile
305                 310                 315                 320

Gly Leu Tyr Ser Ile Trp Gln Lys Thr Lys Ser Gly Lys
                325                 330

<210> SEQ ID NO 293
<211> LENGTH: 7
<212> TYPE: DNA
<213> ORGANISM: Chlamydia

<400> SEQUENCE: 293 tgcaatc                                                                7

<210> SEQ ID NO 294
<211> LENGTH: 196
<212> TYPE: PRT
<213> ORGANISM: Chlamydia

<400> SEQUENCE: 294

Thr Met Gly Ser Leu Val Gly Arg Gln Ala Pro Asp Phe Ser Gly Lys
                5                   10                  15

Ala Val Val Cys Gly Glu Glu Lys Glu Ile Ser Leu Ala Asp Phe Arg
            20                  25                  30

Gly Lys Tyr Val Val Leu Phe Phe Tyr Pro Lys Asp Phe Thr Tyr Val
        35                  40                  45

Cys Pro Thr Glu Leu His Ala Phe Gln Asp Arg Leu Val Asp Phe Glu
    50                  55                  60

Glu His Gly Ala Val Val Leu Gly Cys Ser Val Asp Ile Glu Thr
65                  70                  75                  80

His Ser Arg Trp Leu Thr Val Ala Arg Asp Ala Gly Gly Ile Glu Gly
                85                  90                  95

Thr Glu Tyr Pro Leu Leu Ala Asp Pro Ser Phe Lys Ile Ser Glu Ala
            100                 105                 110

Phe Gly Val Leu Asn Pro Glu Gly Ser Leu Ala Leu Arg Ala Thr Phe
        115                 120                 125

Leu Ile Asp Lys His Gly Val Ile Arg His Ala Val Ile Asn Asp Leu
```

```
                130              135              140
Pro Leu Gly Arg Ser Ile Asp Glu Glu Leu Arg Ile Leu Asp Ser Leu
145                 150                  155                 160

Ile Phe Phe Glu Asn His Gly Met Val Cys Pro Ala Asn Trp Arg Ser
                165                 170                 175

Gly Glu Arg Gly Met Val Pro Ser Glu Glu Gly Leu Lys Glu Tyr Phe
            180                 185                 190

Gln Thr Met Asp
        195

<210> SEQ ID NO 295
<211> LENGTH: 181
<212> TYPE: PRT
<213> ORGANISM: Chlamydia

<400> SEQUENCE: 295

Lys Gly Gly Lys Met Ser Thr Thr Ile Ser Gly Asp Ala Ser Ser Leu
                 5                  10                  15

Pro Leu Pro Thr Ala Ser Cys Val Glu Thr Lys Ser Thr Ser Ser Ser
             20                  25                  30

Thr Lys Gly Asn Thr Cys Ser Lys Ile Leu Asp Ile Ala Leu Ala Ile
         35                  40                  45

Val Gly Ala Leu Val Val Ala Gly Val Leu Ala Leu Val Leu Cys
     50                  55                  60

Ala Ser Asn Val Ile Phe Thr Val Gly Ile Pro Ala Leu Ile Ile
 65                  70                  75                  80

Gly Ser Ala Cys Val Gly Ala Gly Ile Ser Arg Leu Met Tyr Arg Ser
                 85                  90                  95

Ser Tyr Ala Ser Leu Glu Ala Lys Asn Val Leu Ala Glu Gln Arg Leu
            100                 105                 110

Arg Asn Leu Ser Glu Glu Lys Asp Ala Leu Ala Ser Val Ser Phe Ile
        115                 120                 125

Asn Lys Met Phe Leu Arg Gly Leu Thr Asp Asp Leu Gln Ala Leu Glu
    130                 135                 140

Ala Lys Val Met Glu Phe Glu Ile Asp Cys Leu Asp Arg Leu Glu Lys
145                 150                 155                 160

Asn Glu Gln Ala Leu Leu Ser Asp Val Arg Leu Val Leu Ser Ser Tyr
                165                 170                 175

Thr Arg Trp Leu Asp
            180

<210> SEQ ID NO 296
<211> LENGTH: 124
<212> TYPE: PRT
<213> ORGANISM: Chlamydia

<400> SEQUENCE: 296

Ile Tyr Glu Val Met Asn Met Asp Leu Glu Thr Arg Arg Ser Phe Ala
                 5                  10                  15

Val Gln Gln Gly His Tyr Gln Asp Pro Arg Ala Ser Asp Tyr Asp Leu
             20                  25                  30

Pro Arg Ala Ser Asp Tyr Asp Leu Pro Arg Ser Pro Tyr Pro Thr Pro
         35                  40                  45

Pro Leu Pro Ser Arg Tyr Gln Leu Gln Asn Met Asp Val Glu Ala Gly
     50                  55                  60

Phe Arg Glu Ala Val Tyr Ala Ser Phe Val Ala Gly Met Tyr Asn Tyr
```

```
              65                  70                  75                  80
Val Val Thr Gln Pro Gln Glu Arg Ile Pro Asn Ser Gln Gln Val Glu
                    85                  90                  95

Gly Ile Leu Arg Asp Met Leu Thr Asn Gly Ser Gln Thr Phe Ser Asn
            100                 105                 110

Leu Met Gln Arg Trp Asp Arg Glu Val Asp Arg Glu
        115                 120

<210> SEQ ID NO 297
<211> LENGTH: 488
<212> TYPE: PRT
<213> ORGANISM: Chlamydia

<400> SEQUENCE: 297

Lys Gly Ser Leu Pro Ile Leu Gly Pro Phe Leu Asn Gly Lys Met Gly
                5                  10                  15

Phe Trp Arg Thr Ser Ile Met Lys Met Asn Arg Ile Trp Leu Leu Leu
            20                  25                  30

Leu Thr Phe Ser Ser Ala Ile His Ser Pro Val Arg Gly Glu Ser Leu
        35                  40                  45

Val Cys Lys Asn Ala Leu Gln Asp Leu Ser Phe Leu Glu His Leu Leu
    50                  55                  60

Gln Val Lys Tyr Ala Pro Lys Thr Trp Lys Glu Gln Tyr Leu Gly Trp
65                  70                  75                  80

Asp Leu Val Gln Ser Ser Val Ser Ala Gln Gln Lys Leu Arg Thr Gln
                85                  90                  95

Glu Asn Pro Ser Thr Ser Phe Cys Gln Gln Val Leu Ala Asp Phe Ile
            100                 105                 110

Gly Gly Leu Asn Asp Phe His Ala Gly Val Thr Phe Phe Ala Ile Glu
        115                 120                 125

Ser Ala Tyr Leu Pro Tyr Thr Val Gln Lys Ser Ser Asp Gly Arg Phe
    130                 135                 140

Tyr Phe Val Asp Ile Met Thr Phe Ser Ser Glu Ile Arg Val Gly Asp
145                 150                 155                 160

Glu Leu Leu Glu Val Asp Gly Ala Pro Val Gln Asp Val Leu Ala Thr
                165                 170                 175

Leu Tyr Gly Ser Asn His Lys Gly Thr Ala Ala Glu Glu Ser Ala Ala
            180                 185                 190

Leu Arg Thr Leu Phe Ser Arg Met Ala Ser Leu Gly His Lys Val Pro
        195                 200                 205

Ser Gly Arg Thr Thr Leu Lys Ile Arg Arg Pro Phe Gly Thr Thr Arg
    210                 215                 220

Glu Val Arg Val Lys Trp Arg Tyr Val Pro Glu Gly Val Gly Asp Leu
225                 230                 235                 240

Ala Thr Ile Ala Pro Ser Ile Arg Ala Pro Gln Leu Gln Lys Ser Met
                245                 250                 255

Arg Ser Phe Phe Pro Lys Lys Asp Asp Ala Phe His Arg Ser Ser Ser
            260                 265                 270

Leu Phe Tyr Ser Pro Met Val Pro His Phe Trp Ala Glu Leu Arg Asn
        275                 280                 285

His Tyr Ala Thr Ser Gly Leu Lys Ser Gly Tyr Asn Ile Gly Ser Thr
    290                 295                 300

Asp Gly Phe Leu Pro Val Ile Gly Pro Val Ile Trp Glu Ser Glu Gly
305                 310                 315                 320
```

```
Leu Phe Arg Ala Tyr Ile Ser Ser Val Thr Asp Gly Asp Gly Lys Ser
                325                 330                 335

His Lys Val Gly Phe Leu Arg Ile Pro Thr Tyr Ser Trp Gln Asp Met
            340                 345                 350

Glu Asp Phe Asp Pro Ser Gly Pro Pro Trp Glu Phe Ala Lys
        355                 360                 365

Ile Ile Gln Val Phe Ser Ser Asn Thr Glu Ala Leu Ile Ile Asp Gln
    370                 375                 380

Thr Asn Asn Pro Gly Gly Ser Val Leu Tyr Leu Tyr Ala Leu Leu Ser
385                 390                 395                 400

Met Leu Thr Asp Arg Pro Leu Glu Leu Pro Lys His Arg Met Ile Leu
                405                 410                 415

Thr Gln Asp Glu Val Val Asp Ala Leu Asp Trp Leu Thr Leu Leu Glu
            420                 425                 430

Asn Val Asp Thr Asn Val Glu Ser Arg Leu Ala Leu Gly Asp Asn Met
                435                 440                 445

Glu Gly Tyr Thr Val Asp Leu Gln Val Ala Glu Tyr Leu Lys Ser Phe
    450                 455                 460

Gly Arg Gln Val Leu Asn Cys Trp Ser Lys Gly Asp Ile Glu Leu Ser
465                 470                 475                 480

Thr Pro Ile Pro Leu Phe Gly Phe
                485

<210> SEQ ID NO 298
<211> LENGTH: 140
<212> TYPE: PRT
<213> ORGANISM: Chlamydia

<400> SEQUENCE: 298

Arg Ile Asp Ile Ser Ser Val Thr Phe Phe Ile Gly Ile Leu Leu Ala
                5                   10                  15

Val Asn Ala Leu Thr Tyr Ser His Val Leu Arg Asp Leu Ser Val Ser
            20                  25                  30

Met Asp Ala Leu Phe Ser Arg Asn Thr Leu Ala Val Leu Leu Gly Leu
        35                  40                  45

Val Ser Ser Val Leu Asp Asn Val Pro Leu Val Ala Ala Thr Ile Gly
    50                  55                  60

Met Tyr Asp Leu Pro Met Asn Asp Pro Leu Trp Lys Leu Ile Ala Tyr
65                  70                  75                  80

Thr Ala Gly Thr Gly Gly Ser Ile Leu Ile Gly Ser Ala Ala Gly
                85                  90                  95

Val Ala Tyr Met Gly Met Glu Lys Val Ser Phe Gly Trp Tyr Val Lys
            100                 105                 110

His Ala Ser Trp Ile Ala Leu Ala Ser Tyr Phe Gly Gly Leu Ala Val
        115                 120                 125

Tyr Phe Leu Met Glu Asn Cys Val Asn Leu Phe Val
    130                 135                 140

<210> SEQ ID NO 299
<211> LENGTH: 361
<212> TYPE: PRT
<213> ORGANISM: Chlamydia

<400> SEQUENCE: 299

His Gln Glu Ile Ala Asp Ser Pro Leu Val Lys Lys Ala Glu Glu Gln
                5                   10                  15
```

```
Ile Asn Gln Ala Gln Gln Asp Ile Gln Thr Ile Thr Pro Ser Gly Leu
            20                  25                  30

Asp Ile Pro Ile Val Gly Pro Ser Gly Ser Ala Ala Ser Ala Gly Ser
        35                  40                  45

Ala Ala Gly Ala Leu Lys Ser Ser Asn Asn Ser Gly Arg Ile Ser Leu
    50                  55                  60

Leu Leu Asp Asp Val Asp Asn Glu Met Ala Ala Ile Ala Met Gln Gly
65                  70                  75                  80

Phe Arg Ser Met Ile Glu Gln Phe Asn Val Asn Asn Pro Ala Thr Ala
                85                  90                  95

Lys Glu Leu Gln Ala Met Glu Ala Gln Leu Thr Ala Met Ser Asp Gln
            100                 105                 110

Leu Val Gly Ala Asp Gly Glu Leu Pro Ala Glu Ile Gln Ala Ile Lys
        115                 120                 125

Asp Ala Leu Ala Gln Ala Leu Lys Gln Pro Ser Ala Asp Gly Leu Ala
    130                 135                 140

Thr Ala Met Gly Gln Val Ala Phe Ala Ala Lys Val Gly Gly Gly
145                 150                 155                 160

Ser Ala Gly Thr Ala Gly Thr Val Gln Met Asn Val Lys Gln Leu Tyr
                165                 170                 175

Lys Thr Ala Phe Ser Ser Thr Ser Ser Ser Tyr Ala Ala Ala Leu
            180                 185                 190

Ser Asp Gly Tyr Ser Ala Tyr Lys Thr Leu Asn Ser Leu Tyr Ser Glu
        195                 200                 205

Ser Arg Ser Gly Val Gln Ser Ala Ile Ser Gln Thr Ala Asn Pro Ala
    210                 215                 220

Leu Ser Arg Ser Val Ser Arg Ser Gly Ile Glu Ser Gln Gly Arg Ser
225                 230                 235                 240

Ala Asp Ala Ser Gln Arg Ala Ala Glu Thr Ile Val Arg Asp Ser Gln
                245                 250                 255

Thr Leu Gly Asp Val Tyr Ser Arg Leu Gln Val Leu Asp Ser Leu Met
            260                 265                 270

Ser Thr Ile Val Ser Asn Pro Gln Ala Asn Gln Glu Glu Ile Met Gln
        275                 280                 285

Lys Leu Thr Ala Ser Ile Ser Lys Ala Pro Gln Phe Gly Tyr Pro Ala
    290                 295                 300

Val Gln Asn Ser Val Asp Ser Leu Gln Lys Phe Ala Ala Gln Leu Glu
305                 310                 315                 320

Arg Glu Phe Val Asp Gly Glu Arg Ser Leu Ala Glu Ser Gln Glu Asn
                325                 330                 335

Ala Phe Arg Lys Gln Pro Ala Phe Ile Gln Gln Val Leu Val Asn Ile
            340                 345                 350

Ala Ser Leu Phe Ser Gly Tyr Leu Ser
        355                 360

<210> SEQ ID NO 300
<211> LENGTH: 207
<212> TYPE: PRT
<213> ORGANISM: Chlamydia

<400> SEQUENCE: 300

Ser Ser Lys Ile Val Ser Leu Cys Glu Gly Ala Val Ala Asp Ala Arg
                 5                  10                  15

Met Cys Lys Ala Glu Leu Ile Lys Lys Glu Ala Asp Ala Tyr Leu Phe
            20                  25                  30
```

```
Cys Glu Lys Ser Gly Ile Tyr Leu Thr Lys Lys Glu Gly Ile Leu Ile
         35                  40                  45

Pro Ser Ala Gly Ile Asp Glu Ser Asn Thr Asp Gln Pro Phe Val Leu
     50                  55                  60

Tyr Pro Lys Asp Ile Leu Gly Ser Cys Asn Arg Ile Gly Glu Trp Leu
 65                  70                  75                  80

Arg Asn Tyr Phe Arg Val Lys Glu Leu Gly Val Ile Thr Asp Ser
                 85                  90                  95

His Thr Thr Pro Met Arg Arg Gly Val Leu Gly Ile Gly Leu Cys Trp
             100                 105                 110

Tyr Gly Phe Ser Pro Leu His Asn Tyr Ile Gly Ser Leu Asp Cys Phe
         115                 120                 125

Gly Arg Pro Leu Gln Met Thr Gln Ser Asn Leu Val Asp Ala Leu Ala
     130                 135                 140

Val Ala Ala Val Val Cys Met Gly Glu Gly Asn Glu Gln Thr Pro Leu
145                 150                 155                 160

Ala Val Ile Glu Gln Ala Pro Asn Met Val Tyr His Ser Tyr Pro Thr
                 165                 170                 175

Ser Arg Glu Glu Tyr Cys Ser Leu Arg Ile Asp Glu Thr Glu Asp Leu
             180                 185                 190

Tyr Gly Pro Phe Leu Gln Ala Val Thr Trp Ser Gln Glu Lys Lys
         195                 200                 205

<210> SEQ ID NO 301
<211> LENGTH: 183
<212> TYPE: PRT
<213> ORGANISM: Chlamydia

<400> SEQUENCE: 301

Ile Pro Pro Ala Pro Arg Gly His Pro Gln Ile Glu Val Thr Phe Asp
                 5                  10                  15

Ile Asp Ala Asn Gly Ile Leu His Val Ser Ala Lys Asp Ala Ala Ser
             20                  25                  30

Gly Arg Glu Gln Lys Ile Arg Ile Glu Ala Ser Ser Gly Leu Lys Glu
         35                  40                  45

Asp Glu Ile Gln Gln Met Ile Arg Asp Ala Glu Leu His Lys Glu Glu
     50                  55                  60

Asp Lys Gln Arg Lys Glu Ala Ser Asp Val Lys Asn Glu Ala Asp Gly
 65                  70                  75                  80

Met Ile Phe Arg Ala Glu Lys Ala Val Lys Asp Tyr His Asp Lys Ile
                 85                  90                  95

Pro Ala Glu Leu Val Lys Glu Ile Glu Glu His Ile Glu Lys Val Arg
             100                 105                 110

Gln Ala Ile Lys Glu Asp Ala Ser Thr Thr Ala Ile Lys Ala Ala Ser
         115                 120                 125

Asp Glu Leu Ser Thr Arg Met Gln Lys Ile Gly Glu Ala Met Gln Ala
     130                 135                 140

Gln Ser Ala Ser Ala Ala Ser Ser Ala Ala Asn Ala Gln Gly Gly
145                 150                 155                 160

Pro Asn Ile Asn Ser Glu Asp Leu Lys Lys His Ser Phe Ser Thr Arg
                 165                 170                 175

Pro Pro Ala Gly Gly Ser Ala
             180
```

```
<210> SEQ ID NO 302
<211> LENGTH: 232
<212> TYPE: PRT
<213> ORGANISM: Chlamydia

<400> SEQUENCE: 302
```

Met Thr Lys His Gly Lys Arg Ile Arg Gly Ile Gln Glu Thr Tyr Asp
                  5                  10                  15

Leu Ala Lys Ser Tyr Ser Leu Gly Glu Ala Ile Asp Ile Leu Lys Gln
             20                  25                  30

Cys Pro Thr Val Arg Phe Asp Gln Thr Val Asp Val Ser Val Lys Leu
         35                  40                  45

Gly Ile Asp Pro Arg Lys Ser Asp Gln Gln Ile Arg Gly Ser Val Ser
     50                  55                  60

Leu Pro His Gly Thr Gly Lys Val Leu Arg Ile Leu Val Phe Ala Ala
 65                  70                  75                  80

Gly Asp Lys Ala Ala Glu Ala Ile Glu Ala Gly Ala Asp Phe Val Gly
                 85                  90                  95

Ser Asp Asp Leu Val Glu Lys Ile Lys Gly Gly Trp Val Asp Phe Asp
            100                 105                 110

Val Ala Val Ala Thr Pro Asp Met Met Arg Glu Val Gly Lys Leu Gly
        115                 120                 125

Lys Val Leu Gly Pro Arg Asn Leu Met Pro Thr Pro Lys Ala Gly Thr
    130                 135                 140

Val Thr Thr Asp Val Val Lys Thr Ile Ala Glu Leu Arg Lys Gly Lys
145                 150                 155                 160

Ile Glu Phe Lys Ala Asp Arg Ala Gly Val Cys Asn Val Gly Val Ala
                165                 170                 175

Lys Leu Ser Phe Asp Ser Ala Gln Ile Lys Glu Asn Val Glu Ala Leu
            180                 185                 190

Cys Ala Ala Leu Val Lys Ala Lys Pro Ala Thr Ala Lys Gly Gln Tyr
        195                 200                 205

Leu Val Asn Phe Thr Ile Ser Ser Thr Met Gly Pro Gly Val Thr Val
    210                 215                 220

Asp Thr Arg Glu Leu Ile Ala Leu
225                 230

```
<210> SEQ ID NO 303
<211> LENGTH: 238
<212> TYPE: PRT
<213> ORGANISM: chlamydia

<400> SEQUENCE: 303
```

Ile Asn Ser Lys Leu Glu Thr Lys Asn Leu Ile Tyr Leu Lys Leu Lys
                  5                  10                  15

Ile Lys Lys Ser Phe Lys Met Gly Asn Ser Gly Phe Tyr Leu Tyr Asn
             20                  25                  30

Thr Gln Asn Cys Val Phe Ala Asp Asn Ile Lys Val Gly Gln Met Thr
         35                  40                  45

Glu Pro Leu Lys Asp Gln Gln Ile Ile Leu Gly Thr Thr Ser Thr Pro
     50                  55                  60

Val Ala Ala Lys Met Thr Ala Ser Asp Gly Ile Ser Leu Thr Val Ser
 65                  70                  75                  80

Asn Asn Pro Ser Thr Asn Ala Ser Ile Thr Ile Gly Leu Asp Ala Glu
                 85                  90                  95

Lys Ala Tyr Gln Leu Ile Leu Glu Lys Leu Gly Asp Gln Ile Leu Gly

```
                  100                 105                 110
Gly Ile Ala Asp Thr Ile Val Asp Ser Thr Val Gln Asp Ile Leu Asp
            115                 120                 125

Lys Ile Thr Thr Asp Pro Ser Leu Gly Leu Leu Lys Ala Phe Asn Asn
130                 135                 140

Phe Pro Ile Thr Asn Lys Ile Gln Cys Asn Gly Leu Phe Thr Pro Arg
145                 150                 155                 160

Asn Ile Glu Thr Leu Leu Gly Gly Thr Glu Ile Gly Lys Phe Thr Val
                165                 170                 175

Thr Pro Lys Ser Ser Gly Ser Met Phe Leu Val Ser Ala Asp Ile Ile
            180                 185                 190

Ala Ser Arg Met Glu Gly Val Val Leu Ala Leu Val Arg Glu Gly
        195                 200                 205

Asp Ser Lys Pro Tyr Ala Ile Ser Tyr Gly Tyr Ser Ser Gly Val Pro
    210                 215                 220

Asn Leu Cys Ser Leu Arg Thr Arg Ile Ile Asn Thr Gly Leu
225                 230                 235

<210> SEQ ID NO 304
<211> LENGTH: 133
<212> TYPE: PRT
<213> ORGANISM: Chlamydia

<400> SEQUENCE: 304

His Met His His His His His Met Ala Ser Ile Cys Gly Arg Leu
                5                   10                  15

Gly Ser Gly Thr Gly Asn Ala Leu Lys Ala Phe Phe Thr Gln Pro Ser
            20                  25                  30

Asn Lys Met Ala Arg Val Val Asn Lys Thr Lys Gly Met Asp Lys Thr
        35                  40                  45

Val Lys Val Ala Lys Ser Ala Ala Glu Leu Thr Ala Asn Ile Leu Glu
    50                  55                  60

Gln Ala Gly Gly Ala Gly Ser Ser Ala His Ile Thr Ala Ser Gln Val
65                  70                  75                  80

Ser Lys Gly Leu Gly Asp Thr Arg Thr Val Val Ala Leu Gly Asn Ala
                85                  90                  95

Phe Asn Gly Ala Leu Pro Gly Thr Val Gln Ser Ala Gln Ser Phe Phe
            100                 105                 110

Ser His Met Lys Ala Ala Ser Gln Lys Thr Gln Glu Gly Asp Glu Gly
        115                 120                 125

Leu Thr Ala Asp Leu
    130

<210> SEQ ID NO 305
<211> LENGTH: 125
<212> TYPE: PRT
<213> ORGANISM: Chlamydia

<400> SEQUENCE: 305

Met Ala Ser Ile Cys Gly Arg Leu Gly Ser Gly Thr Gly Asn Ala Leu
                5                   10                  15

Lys Ala Phe Phe Thr Gln Pro Ser Asn Lys Met Ala Arg Val Val Asn
            20                  25                  30

Lys Thr Lys Gly Met Asp Lys Thr Val Lys Val Ala Lys Ser Ala Ala
        35                  40                  45

Glu Leu Thr Ala Asn Ile Leu Glu Gln Ala Gly Gly Ala Gly Ser Ser
```

-continued

```
            50                  55                  60
Ala His Ile Thr Ala Ser Gln Val Ser Lys Gly Leu Gly Asp Thr Arg
 65                  70                  75                  80

Thr Val Val Ala Leu Gly Asn Ala Phe Asn Gly Ala Leu Pro Gly Thr
                 85                  90                  95

Val Gln Ser Ala Gln Ser Phe Phe Ser His Met Lys Ala Ala Ser Gln
                100                 105                 110

Lys Thr Gln Glu Gly Asp Glu Gly Leu Thr Ala Asp Leu
                115                 120                 125
```

*

COMPOUNDS AND METHODS FOR TREATMENT AND DIAGNOSIS OF CHLAMYDIAL INFECTION

REFERENCE TO RELATED APPLICATIONS

This application is a continuation-in-part of U.S. patent application Ser. No. 09/454,684, filed Dec. 3, 1999, which is a continuation-in-part of U.S. patent application Ser. No. 09/426,571, filed Oct. 22, 1999, which is a continuation-in-part of U.S. patent application Ser. No. 09/410,568, filed Oct. 1, 1999, which is a continuation-in-part of U.S. patent application Ser. No. 09/288,594, filed Apr. 8, 1999, which is a continuation-in-part of U.S. patent application Ser. No. 09/208,277, filed Dec. 8, 1998.

TECHNICAL FIELD

The present invention relates generally to the detection and treatment of Chlamydial infection. In particular, the invention is related to polypeptides comprising a Chlamydia antigen and the use of such polypeptides for the serodiagnosis and treatment of Chlamydial infection.

BACKGROUND OF THE INVENTION

Chlamydiae are intracellular bacterial pathogens that are responsible for a wide variety of important human and animal infections. *Chlamydia trachomatis* is one of the most common causes of sexually transmitted diseases and can lead to pelvic inflammatory disease (PID), resulting in tubal obstruction and infertility. *Chlamydia trachomatis* may also play a role in male infertility. In 1990, the cost of treating PID in the US was estimated to be $4 billion. Trachoma, due to ocular infection with *Chlamydia trachomatis,* is the leading cause of preventable blindness worldwide. *Chlamydia pneumonia* is a major cause of acute respiratory tract infections in humans and is also believed to play a role in the pathogenesis of atherosclerosis and, in particular, coronary heart disease. Individuals with a high titer of antibodies to *Chlamydia pneumonia* have been shown to be at least twice as likely to suffer from coronary heart disease as seronegative individuals. Chlamydial infections thus constitute a significant health problem both in the US and worldwide.

Chlamydial infection is often asymptomatic. For example, by the time a woman seeks medical attention for PID, irreversible damage may have already occurred resulting in infertility. There thus remains a need in the art for improved vaccines and pharmaceutical compositions for the prevention and treatment of Chlamydia infections. The present invention fulfills this need and further provides other related advantages.

SUMMARY OF THE INVENTION

The present invention provides compositions and methods for the diagnosis and therapy of Chlamydia infection. In one aspect, the present invention provides polypeptides comprising an immunogenic portion of a Chlamydia antigen, or a variant of such an antigen. Certain portions and other variants are immunogenic, such that the ability of the variant to react with antigen-specific antisera is not substantially diminished. Within certain embodiments, the polypeptide comprises an amino acid sequence encoded by a polynucleotide sequence selected from the group consisting of (a) a sequence of SEQ ID NO: 1, 15, 21–25, 44–64, 66–76, 79–88, 110–119, 120, 122, 124, 126, 128, 130, 132, 134, 136, 169–174, 181–188, 263, 265 and 267–290; (b) the complements of said sequences; and (c) sequences that hybridize to a sequence of (a) or (b) under moderately stringent conditions. In specific embodiments, the polypeptides of the present invention comprise at least a portion of a Chlamydial protein that includes an amino acid sequence selected from the group consisting of sequences recited in SEQ ID NO: 5–14, 17–20, 26, 28, 30–32, 34, 39–43, 65, 89–109, 138–158, 167, 168, 224–262, 246, 247, 254–256, 292, 294–305 and variants thereof.

The present invention further provides polynucleotides that encode a polypeptide as described above, or a portion thereof (such as a portion encoding at least 15 amino acid residues of a Chlamydial protein), expression vectors comprising such polynucleotides and host cells transformed or transfected with such expression vectors.

In a related aspect, polynucleotide sequences encoding the above polypeptides, recombinant expression vectors comprising one or more of these polynucleotide sequences and host cells transformed or transfected with such expression vectors are also provided.

In another aspect, the present invention provides fusion proteins comprising an inventive polypeptide, or, alternatively, an inventive polypeptide and a known Chlamydia antigen, as well as polynucleotides encoding such fusion proteins, in combination with a physiologically acceptable carrier or immunostimulant for use as pharmaceutical compositions and vaccines thereof.

The present invention further provides pharmaceutical compositions that comprise: (a) an antibody, both polyclonal and monoclonal, or antigen-binding fragment thereof that specifically binds to a Chlamydial protein; and (b) a physiologically acceptable carrier. Within other aspects, the present invention provides pharmaceutical compositions that comprise one or more Chlamydia polypeptides disclosed herein, or a polynucleotide molecule encoding such a polypeptide, and a physiologically acceptable carrier. The invention also provides vaccines for prophylactic and therapeutic purposes comprising one or more of the disclosed polypeptides and an immunostimulant, as defined herein, together with vaccines comprising one or more polynucleotide sequences encoding such polypeptides and an immunostimulant.

In yet another aspect, methods are provided for inducing protective immunity in a patient, comprising administering to a patient an effective amount of one or more of the above pharmaceutical compositions or vaccines.

In yet a further aspect, methods for the treatment of Chlamydia infection in a patient are provided, the methods comprising obtaining peripheral blood mononuclear cells (PBMC) from the patient, incubating the PBMC with a polypeptide of the present invention (or a polynucleotide that encodes such a polypeptide) to provide incubated T cells and administering the incubated T cells to the patient. The present invention additionally provides methods for the treatment of Chlamydia infection that comprise incubating antigen presenting cells with a polypeptide of the present invention (or a polynucleotide that encodes such a polypeptide) to provide incubated antigen presenting cells and administering the incubated antigen presenting cells to the patient. Proliferated cells may, but need not, be cloned prior to administration to the patient. In certain embodiments, the antigen presenting cells are selected from the group consisting of dendritic cells, macrophages, monocytes, B-cells, and fibroblasts. Compositions for the treatment of Chlamydia infection comprising T cells or antigen presenting cells that have been incubated with a polypeptide or polynucleotide of the present invention are also provided. Within related aspects, vaccines are provided that comprise: (a) an antigen presenting cell that expresses a polypeptide as described above and (b) an immunostimulant.

The present invention further provides, within other aspects, methods for removing Chlamydial-infected cells from a biological sample, comprising contacting a biological sample with T cells that specifically react with a Chlamydial protein, wherein the step of contacting is performed under conditions and for a time sufficient to permit the removal of cells expressing the protein from the sample.

Within related aspects, methods are provided for inhibiting the development of Chlamydial infection in a patient, comprising administering to a patient a biological sample treated as described above. In further aspects of the subject invention, methods and diagnostic kits are provided for detecting Chlamydia infection in a patient. In one embodiment, the method comprises: (a) contacting a biological sample with at least one of the polypeptides or fusion proteins disclosed herein; and (b) detecting in the sample the presence of binding agents that bind to the polypeptide or fusion protein, thereby detecting Chlamydia infection in the biological sample. Suitable biological samples include whole blood, sputum, serum, plasma, saliva, cerebrospinal fluid and urine. In one embodiment, the diagnostic kits comprise one or more of the polypeptides or fusion proteins disclosed herein in combination with a detection reagent. In yet another embodiment, the diagnostic kits comprise either a monoclonal antibody or a polyclonal antibody that binds with a polypeptide of the present invention.

The present invention also provides methods for detecting Chlamydia infection comprising: (a) obtaining a biological sample from a patient; (b) contacting the sample with at least two oligonucleotide primers in a polymerase chain reaction, at least one of the oligonucleotide primers being specific for a polynucleotide sequence disclosed herein; and (c) detecting in the sample a polynucleotide sequence that amplifies in the presence of the oligonucleotide primers. In one embodiment, the oligonucleotide primer comprises at least about 10 contiguous nucleotides of a polynucleotide sequence peptide disclosed herein, or of a sequence that hybridizes thereto.

In a further aspect, the present invention provides a method for detecting Chlamydia infection in a patient comprising: (a) obtaining a biological sample from the patient; (b) contacting the sample with an oligonucleotide probe specific for a polynucleotide sequence disclosed herein; and (c) detecting in the sample a polynucleotide sequence that hybridizes to the oligonucleotide probe. In one embodiment, the oligonucleotide probe comprises at least about 15 contiguous nucleotides of a polynucleotide sequence disclosed herein, or a sequence that hybridizes thereto.

These and other aspects of the present invention will become apparent upon reference to the following detailed description. All references disclosed herein are hereby incorporated by reference in their entirety as if each was incorporated individually.

Sequence Identifiers

SEQ ID NO: 1 is the determined DNA sequence for the *C. trachomatis* clone 1-B1-66.

SEQ ID NO: 2 is the determined DNA sequence for the *C. trachomatis* clone 4-D7-28.

SEQ ID NO: 3 is the determined DNA sequence for the *C. trachomatis* clone 3-G3-10.

SEQ ID NO: 4 is the determined DNA sequence for the *C. trachomatis* clone 10-C10-31.

SEQ ID NO: 5 is the predicted amino acid sequence for 1-B1-66.

SEQ ID NO: 6 is the predicted amino acid sequence for 4-D7-28.

SEQ ID NO: 7 is a first predicted amino acid sequence for 3-G3-10.

SEQ ID NO: 8 is a second predicted amino acid sequence for 3-G3-10.

SEQ ID NO: 9 is a third predicted amino acid sequence for 3-G3-10.

SEQ ID NO: 10 is a fourth predicted amino acid sequence for 3-G3-10.

SEQ ID NO: 11 is a fifth predicted amino acid sequence for 3-G3-10.

SEQ ID NO: 12 is the predicted amino acid sequence for 10-C10-31.

SEQ ID NO: 13 is the amino acid sequence of the synthetic peptide 1-B1-66/48-67.

SEQ ID NO: 14 is the amino acid sequence of the synthetic peptide 1-B1-66/58-77.

SEQ ID NO: 15 is the determined DNA sequence for the *C. trachomatis* serovar LGV II clone 2C7-8

SEQ ID NO: 16 is a DNA sequence of a putative open reading frame from a region of the *C. trachomatis* serovar D genome to which 2C7-8 maps SEQ ID NO: 17 is the predicted amino acid sequence encoded by the DNA sequence of SEQ ID NO: 16

SEQ ID NO: 18 is the amino acid sequence of the synthetic peptide CtC7.8-12

SEQ ID NO: 19 is the amino acid sequence of the synthetic peptide CtC7.8-13

SEQ ID NO: 20 is the predicted amino acid sequence encoded by a second putative open reading from *C. trachomatis* serovar D SEQ ID NO: 21 is the determined DNA sequence for clone 4C9-18 from *C. trachomatis* LGV II SEQ ID NO: 22 is the determined DNA sequence homologous to Lipoamide Dehydrogenase from *C. trachomatis* LGV II SEQ ID NO: 23 is the determined DNA sequence homologous to Hypothetical protein from *C. trachomatis* LGV II SEQ ID NO: 24 is the determined DNA sequence homologous to Ubiquinone Mehtyltransferase from *C. trachomatis* LGV II SEQ ID NO: 25 is the determined DNA sequence for clone 4C9-18#2 BL21 pLysS from *C. trachomatis* LGV II SEQ ID NO: 26 is the predicted amino acid sequence for 4C9-18#2 from *C. trachomatis* LGV II SEQ ID NO: 27 is the determined DNA sequence for Cp-SWIB from *C. pneumonia* strain TWAR SEQ ID NO: 28 is the predicted amino acid sequence for Cp-SWIB from *C. pneumonia* strain TWAR SEQ ID NO: 29 is the determined DNA sequence for Cp-S13 from *C. pneumonia* strain TWAR SEQ ID NO: 30 is the predicted amino acid sequence for Cp-S13 from *C. pneumonia* strain TWAR SEQ ID NO: 31 is the amino acid sequence for a 10 mer consensus peptide from CtC7.8-12 and CtC7.8-13

SEQ ID NO: 32 is the predicted amino acid sequence for clone 2C7-8 from *C. trachomatis* LGV II SEQ ID NO: 33 is the DNA sequence corresponding to nucleotides 597304-597145 of the *C. trachomatis* serovar D genome (NCBI, BLASTN search), which shows homology to clone 2C7-8

SEQ ID NO: 34 is the predicted amino acid sequence encoded by the sequence of SEQ ID NO: 33

SEQ ID NO: 35 is the DNA sequence for C.p. SWIB Nde (5'primer) from *C. pneumonia*

SEQ ID NO: 36 is the DNA sequence for C.p. SWIB EcoRI (3'primer) from *C. pneumonia*

SEQ ID NO : 37 is the DNA sequence for C.p. S13 Nde (5'primer) from *C. pneumonia*

SEQ ID NO: 38 is the DNA sequence for C.p. S13 EcoRI (3'primer) from *C. pneumonia*

SEQ ID NO: 39 is the amino acid sequence for CtSwib 52–67 peptide from *C. trachomatis* LGV II SEQ ID NO: 40 is the amino acid sequence for CpSwib 53–68 peptide from *C. pneumonia*

SEQ ID NO: 41 is the amino acid sequence for HuSwib 288–302 peptide from Human SWI domain SEQ ID NO: 42 is the amino acid sequence for CtSWI-T 822–837 peptide from the topoisomerase-SWIB fusion of *C. trachomatis*

SEQ ID NO: 43 is the amino acid sequence for CpSWI-T 828–842 peptide from the topoisomerase-SWIB fusion of *C. pneumonia*

SEQ ID NO: 44 is a first determined DNA sequence for the *C. trachomatis* LGV II clone 19783.3,jen.seq(1>509) CTL2#11-3', representing the 3' end.

SEQ ID NO: 45 is a second determined DNA sequence for the *C. trachomatis* LGV II clone 19783.4,jen.seq(1>481) CTL2#11-5', representing the 5' end.

SEQ ID NO: 46 is the determined DNA sequence for the *C. trachomatis* LGV II clone19784CTL2__12consensus.seq (1>427)CTL2#12.

SEQ ID NO: 47 is the determined DNA sequence for the *C. trachomatis* LGV II clone 19785.4,jen.seq(1>600) CTL2#16-5', representing the 5' end.

SEQ ID NO: 48 is a first determined DNA sequence for the *C. trachomatis* LGV II clone 19786.3,jen.seq(1>600) CTL2#18-3', representing the 3' end.

SEQ ID NO: 49 is a second determined DNA sequence for the *C. trachomatis* LGV II clone 19786.4,jen.seq(1>600) CTL2#18-5', representing the 5' end.

SEQ ID NO: 50 is the determined DNA sequence for the *C. trachomatis* LGV II clone 19788CTL2__21consensus.seq (1>406)CTL2#21.

SEQ ID NO: 51 is the determined DNA sequence for the *C. trachomatis* LGV II clone 19790CTL2__23consensus.seq (1>602)CTL2#23.

SEQ ID NO: 52 is the determined DNA sequence for the *C. trachomatis* LGV II clone 19791CTL2__24consensus.seq (1>145)CTL2#24.

SEQ ID NO: 53 is the determined DNA sequence for the *C. trachomatis* LGV II clone CTL2#4.

SEQ ID NO: 54 is the determined DNA sequence for the *C. trachomatis* LGV II clone CTL2#8b.

SEQ ID NO: 55 is the determined DNA sequence for the *C. trachomatis* LGV II clone15-G1-89, sharing homology to the lipoamide dehydrogenase gene CT557.

SEQ ID NO: 56 is the determined DNA sequence for the *C. trachomatis* LGV II clone 14-H1-4, sharing homology to the thiol specific antioxidant gene CT603.

SEQ ID NO: 57 is the determined DNA sequence for the *C. trachomatis* LGV II clone 12-G3-83, sharing homology to the hypothetical protein CT622.

SEQ ID NO: 58 is the determined DNA sequence for the *C. trachomatis* LGV II clone 12-B3-95, sharing homology to the lipoamide dehydrogenase gene CT557.

SEQ ID NO: 59 is the determined DNA sequence for the *C. trachomatis* LGV II clone 11-H4-28, sharing homology to the dnaK gene CT396.

SEQ ID NO: 60 is the determined DNA sequence for the *C. trachomatis* LGV II clone 11-H3-68, sharing partial homology to the PGP6-D virulence protein and L1 ribosomal gene CT318.

SEQ ID NO: 61 is the determined DNA sequence for the *C. trachomatis* LGV II clone 11-G1-34, sharing partial homology to the malate dehydrogenase gene CT376 and to the glycogen hydrolase gene CT042.

SEQ ID NO: 62 is the determined DNA sequence for the *C. trachomatis* LGV II clone 11-G10-46, sharing homology to the hypothetical protein CT610.

SEQ ID NO: 63 is the determined DNA sequence for the *C. trachomatis* LGV II clone 11-C12-91, sharing homology to the OMP2 gene CT443.

SEQ ID NO: 64 is the determined DNA sequence for the *C. trachomatis* LGV II clone 11-A3-93, sharing homology to the HAD superfamily gene CT103.

SEQ ID NO: 65 is the determined amino acid sequence for the *C. trachomatis* LGV II clone 14-H1-4, sharing homology to the thiol specific antioxidant gene CT603.

SEQ ID NO: 66 is the determined DNA sequence for the *C. trachomatis* LGV II clone CtL2#9.

SEQ ID NO: 67 is the determined DNA sequence for the *C. trachomatis* LGV II clone CtL2#7.

SEQ ID NO: 68 is the determined DNA sequence for the *C. trachomatis* LGV II clone CtL2#6.

SEQ ID NO: 69 is the determined DNA sequence for the *C. trachomatis* LGV II clone CtL2#5.

SEQ ID NO: 70 is the determined DNA sequence for the *C. trachomatis* LGV II clone CtL2#2.

SEQ ID NO: 71 is the determined DNA sequence for the *C. trachomatis* LGV II clone CtL2#1.

SEQ ID NO: 72 is a first determined DNA sequence for the *C. trachomatis* LGV II clone 23509.2CtL2#3-5', representing the 5' end.

SEQ ID NO: 73 is a second determined DNA sequence for the *C. trachomatis* LGV II clone 23509.1CtL2#3-3', representing the 3' end.

SEQ ID NO: 74 is a first determined DNA sequence for the *C. trachomatis* LGV II clone 22121.2CtL2#10-5', representing the 5' end.

SEQ ID NO: 75 is a second determined DNA sequence for the *C. trachomatis* LGV II clone 22121.1 CtL2#10-3', representing the 3' end.

SEQ ID NO: 76 is the determined DNA sequence for the *C. trachomatis* LGV II clone 19787.6CtL2#19-5', representing the 5' end.

SEQ ID NO: 77 is the determined DNA sequence for the *C. pneumoniae* LGV II clone CpS 13-His.

SEQ ID NO: 78 is the determined DNA sequence for the *C. pneumoniae* LGV II clone Cp_SWIB-His.

SEQ ID NO: 79 is the determined DNA sequence for the *C. trachomatis* LGV II clone 23-G7-68, sharing partial homology to the L11, L10 and L1 ribosomal protein.

SEQ ID NO: 80 is the determined DNA sequence for the *C. trachomatis* LGV II clone 22-F8-91, sharing homology to the pmpC gene.

SEQ ID NO: 81 is the determined DNA sequence for the *C. trachomatis* LGV II clone 21-E8-14, sharing homology to the CT610–CT613 genes.

SEQ ID NO: 82 is the determined DNA sequence for the *C. trachomatis* LGV II clone 19-F12-57, sharing homology to the CT858 and recA genes.

SEQ ID NO: 83 is the determined DNA sequence for the *C. trachomatis* LGV II clone 19-F12-53, sharing homology to the CT445 gene encoding glutamyl tRNA synthetase.

SEQ ID NO: 84 is the determined DNA sequence for the *C. trachomatis* LGV II clone 19-A5-54, sharing homology to the cryptic plasmid gene.

SEQ ID NO: 85 is the determined DNA sequence for the *C. trachomatis* LGV II clone 17-E11-72, sharing partial homology to the OppC_2 and pmpD genes.

SEQ ID NO: 86 is the determined DNA sequence for the *C. trachomatis* LGV II clone 17-C1-77, sharing partial homology to the CT857 and CT858 open reading frames.

SEQ ID NO: 87 is the determined DNA sequence for the *C. trachomatis* LGV II clone 15-H2-76, sharing partial homology to the pmpD and SycE genes, and to the CT089 ORF.

SEQ ID NO: 88 is the determined DNA sequence for the *C. trachomatis* LGV II clone 15-A3-26, sharing homology to the CT858 ORF.

SEQ ID NO: 89 is the determined amino acid sequence for the *C. pnuemoniae* clone Cp_SWIB-His.

SEQ ID NO: 90 is the determined amino acid sequence for the *C. trachomatis* LGV II clone CtL2_LPDA_FL.

SEQ ID NO: 91 is the determined amino acid sequence for the *C. pnuemoniae* clone CpS13-His.

SEQ ID NO: 92 is the determined amino acid sequence for the *C. trachomatis* LGV II clone CtL2_TSA_FL.

SEQ ID NO: 93 is the amino acid sequence for Ct-Swib 43–61 peptide from *C. trachomatis* LGV II.

SEQ ID NO: 94 is the amino acid sequence for Ct-Swib 48–67 peptide from *C. trachomatis* LGV II.

SEQ ID NO: 95 is the amino acid sequence for Ct-Swib 52–71 peptide from *C. trachomatis* LGV II.

SEQ ID NO: 96 is the amino acid sequence for Ct-Swib 58–77 peptide from *C. trachomatis* LGV II.

SEQ ID NO: 97 is the amino acid sequence for Ct-Swib 63–82 peptide from *C. trachomatis* LGV II.

SEQ ID NO: 98 is the amino acid sequence for Ct-Swib 51–66 peptide from *C. trachomatis* LGV II.

SEQ ID NO: 99 is the amino acid sequence for Cp-Swib 52-67 peptide from *C. pneumonia*.

SEQ ID NO: 100 is the amino acid sequence for Cp-Swib 37–51 peptide from *C. pneumonia*.

SEQ ID NO: 101 is the amino acid sequence for Cp-Swib 32–51 peptide from *C. pneumonia*.

SEQ ID NO: 102 is the amino acid sequence for Cp-Swib 37–56 peptide from *C. pneumonia*.

SEQ ID NO: 103 is the amino acid sequence for Ct-Swib 36–50 peptide from *C. trachomatis*.

SEQ ID NO: 104 is the amino acid sequence for Ct-S13 46–65 peptide from *C. trachomatis*.

SEQ ID NO: 105 is the amino acid sequence for Ct-S13 60–80 peptide from *C. trachomatis*.

SEQ ID NO: 106 is the amino acid sequence for Ct-S13 1–20 peptide from *C. trachomatis*.

SEQ ID NO: 107 is the amino acid sequence for Ct-S13 46–65 peptide from *C. trachomatis*.

SEQ ID NO; 108 is the amino acid sequence for Ct-S13 56–75 peptide from *C. trachomatis*.

SEQ ID NO: 109 is the amino acid sequence for Cp-S13 56–75 peptide from *C. pneumoniae*.

SEQ ID NO: 110 is the determined DNA sequence for the *C. trachomatis* LGV II clone 21-G12-60, containing partial open reading frames for hypothetical proteins CT875, CT229 and CT228.

SEQ ID NO: 111 is the determined DNA sequence for the *C. trachomatis* LGV II clone 22-B3-53, sharing homology to the C110 ORF of GroEL.

SEQ ID NO: 112 is the determined DNA sequence for the *C. trachomatis* LGV II clone 22-A1-49, sharing partial homology to the CT660 and CT659 ORFs.

SEQ ID NO: 113 is the determined DNA sequence for the *C. trachomatis* LGV II clone 17-E2-9, sharing partial homology to the CT611 and CT 610 ORFs.

SEQ ID NO: 114 is the determined DNA sequence for the *C. trachomatis* LGV II clone 17-C10-31, sharing partial homology to the CT858 ORF.

SEQ ID NO: 115 is the determined DNA sequence for the *C. trachomatis* LGV II clone 21-C7-66, sharing homology to the dnaK-like gene.

SEQ ID NO: 116 is the determined DNA sequence for the *C. trachomatis* LGV II clone 20-G3-45, containing part of the pmpB gene CT413.

SEQ ID NO: 117 is the determined DNA sequence for the *C. trachomatis* LGV II clone 18-C5-2, sharing homology to the S1 ribosomal protein ORF.

SEQ ID NO: 118 is the determined DNA sequence for the *C. trachomatis* LGV II clone 17-C5-19, containing part of the ORFs for CT431 and CT430.

SEQ ID NO: 119 is the determined DNA sequence for the *C. trachomatis* LGV II clone 16-D4-22, contains partial sequences of ORF3 and ORF4 of the plasmid for growth within mammalian cells.

SEQ ID NO: 120 is the determined full-length DNA sequence for the *C. trachomatis* serovar LGV II Cap1 gene CT529.

SEQ ID NO: 121 is the predicted full-length amino acid sequence for the *C. trachomatis* serovar LGV II Cap1 gene CT529.

SEQ ID NO: 122 is the determined full-length DNA sequence for the *C. trachomatis* serovar E Cap1 gene CT529.

SEQ ID NO: 123 is the predicted full-length amino acid sequence for the *C. trachomatis* serovar E Cap1 gene CT529.

SEQ ID NO: 124 is the determined full-length DNA sequence for the *C. trachomatis* serovar 1A Cap1 gene CT529.

SEQ ID NO: 125 is the predicted full-length amino acid sequence for the *C. trachomatis* serovar 1A Cap1 gene CT529.

SEQ ID NO: 126 is the determined full-length DNA sequence for the *C. trachomatis* serovar G Cap1 gene CT529.

SEQ ID NO: 127 is the predicted full-length amino acid sequence for the *C. trachomatis* serovar G Cap1 gene CT529.

SEQ ID NO: 128 is the determined full-length DNA sequence for the *C. trachomatis* serovar F1 NII Cap1 gene CT529.

SEQ ID NO: 129 is the predicted full-length amino acid sequence for the *C. trachomatis* serovar F1 NII Cap1 gene CT529.

SEQ ID NO: 130 is the determined full-length DNA sequence for the *C. trachomatis* serovar L1 Cap1 gene CT529.

SEQ ID NO: 131 is the predicted full-length amino acid sequence for the *C. trachomatis* serovar L1 Cap1 gene CT529.

SEQ ID NO: 132 is the determined full-length DNA sequence for the *C. trachomatis* serovar L3 Cap1 gene CT529.

SEQ ID NO: 133 is the predicted full-length amino acid sequence for the *C. trachomatis* serovar L3 Cap1 gene CT529.

SEQ ID NO: 134 is the determined full-length DNA sequence for the *C. trachomatis* serovar Ba Cap1 gene CT529.

SEQ ID NO: 135 is the predicted full-length amino acid sequence for the *C. trachomatis* serovar Ba Cap1 gene CT529.

SEQ ID NO: 136 is the determined full-length DNA sequence for the *C. trachomatis* serovar MOPN Cap1 gene CT529.

SEQ ID NO: 137 is the predicted full-length amino acid sequence for the *C. trachomatis* serovar MOPN Cap1 gene CT529.

SEQ ID NO: 138 is the determined amino acid sequence for the Cap1 CT529 ORF peptide #124–139 of *C. trachomatis* serovar L2.

SEQ ID NO: 139 is the determined amino acid sequence for the Cap1 CT529 ORF peptide #132–147 of *C. trachomatis* serovar L2.

SEQ ID NO: 140 is the determined amino acid sequence for the Cap1 CT529 ORF peptide #138–155 of *C. trachomatis* serovar L2.

SEQ ID NO: 141 is the determined amino acid sequence for the Cap1 CT529 ORF peptide #146–163 of *C. trachomatis* serovar L2.

SEQ ID NO: 142 is the determined amino acid sequence for the Cap1 CT529 ORF peptide #154–171 of *C. trachomatis* serovar L2.

SEQ ID NO: 143 is the determined amino acid sequence for the Cap1 CT529 ORF peptide #162–178 of *C. trachomatis* serovar L2.

SEQ ID NO: 144 is the determined amino acid sequence for the Cap1 CT529 ORF peptide #138–147 of *C. trachomatis* serovar L2.

SEQ ID NO: 145 is the determined amino acid sequence for the Cap1 CT529 ORF peptide #139–147 of *C. trachomatis* serovar L2.

SEQ ID NO: 146 is the determined amino acid sequence for the Cap1 CT529 ORF peptide #140–147 of *C. trachomatis* serovar L2.

SEQ ID NO: 147 is the determined amino acid sequence for the Cap1 CT529 ORF peptide #138–146 of *C. trachomatis* serovar L2.

SEQ ID NO: 148 is the determined amino acid sequence for the Cap1 CT529 ORF peptide #138–145 of *C. trachomatis* serovar L2.

SEQ ID NO: 149 is the determined amino acid sequence for the Cap1 CT529 ORF peptide #F140->I of *C. trachomatis* serovar L2.

SEQ ID NO: 150 is the determined amino acid sequence for the Cap1 CT529 ORF peptide ##S139>Ga of *C. trachomatis* serovar L2.

SEQ ID NO: 151 is the determined amino acid sequence for the Cap1 CT529 ORF peptide ##S139>Gb of *C. trachomatis* serovar L2.

SEQ ID NO: 152 is the determined amino acid sequence for the peptide #2 C7.8-6 of the 216aa ORF of *C. trachomatis* serovar L2.

SEQ ID NO: 153 is the determined amino acid sequence for the peptide #2 C7.8-7 of the 216aa ORF of *C. trachomatis* serovar L2.

SEQ ID NO: 154 is the determined amino acid sequence for the peptide #2 C7.8-8 of the 216aa ORF of *C. trachomatis* serovar L2.

SEQ ID NO: 155 is the determined amino acid sequence for the peptide #2 C7.8-9 of the 216aa ORF of *C. trachomatis* serovar L2.

SEQ ID NO: 156 is the determined amino acid sequence for the peptide #2 C7.8-10 of the 216aa ORF of *C. trachomatis* serovar L2.

SEQ ID NO: 157 is the determined amino acid sequence for the 53 amino acid residue peptide of the 216aa ORF within clone 2C7.8 of *C. trachomatis* serovar L2.

SEQ ID NO: 158 is the determined amino acid sequence for the 52 amino acid residue peptide of the CT529 ORF within clone 2C7.8 of *C. trachomatis* serovar L2.

SEQ ID NO: 159 is the determined DNA sequence for the 5' (forward) primer for cloning full-length CT529 serovar L2.

SEQ ID NO 160 is the determined DNA sequence for the 5' (reverse) primer for cloning full-length CT529 serovar L2.

SEQ ID NO: 161 is the determined DNA sequence for the 5' (forward) primer for cloning full-length CT529 for serovars other than L2 and MOPN.

SEQ ID NO: 162 is the determined DNA sequence for the 5' (reverse) primer for cloning full-length CT529 serovars other than L2 and MOPN.

SEQ ID NO: 163 is the determined DNA sequence for the 5' (forward) primer for cloning full-length CT529 serovar MOPN.

SEQ ID NO: 164 is the determined DNA sequence for the 5' (reverse) primer for cloning full-length CT529 serovar MOPN.

SEQ ID NO: 165 is the determined DNA sequence for the 5' (forward) primer for pBIB-KS.

SEQ ID NO: 166 is the determined DNA sequence for the 5' (reverse) primer for pBIB-KS.

SEQ ID NO: 167 is the determined amino acid sequence for the 9-mer epitope peptide Cap1 #139–147 from serovar L2.

SEQ ID NO: 168 is the determined amino acid sequence for the 9-mer epitope peptide Cap1 #139–147 from serovar D.

SEQ ID NO: 169 is the determined full-length DNA sequence for the *C. trachomatis* pmpI gene.

SEQ ID NO: 170 is the determined full-length DNA sequence for the *C. trachomatis* pmpG gene.

SEQ ID NO: 171 is the determined full-length DNA sequence for the *C. trachomatis* pmpE gene.

SEQ ID NO: 172 is the determined full-length DNA sequence for the *C. trachomatis* pmpD gene.

SEQ ID NO: 173 is the determined full-length DNA sequence for the *C. trachomatis* pmpC gene.

SEQ ID NO: 174 is the determined full-length DNA sequence for the *C. trachomatis* pmpB gene.

SEQ ID NO: 175 is the predicted full-length amino acid sequence for the *C. trachomatis* pmpI gene.

SEQ ID NO: 176 is the predicted full-length amino acid sequence for the *C. trachomatis* pmpG gene.

SEQ ID NO: 177 is the predicted full-length amino acid sequence for the *C. trachomatis* pmpE gene.

SEQ ID NO: 178 is the predicted full-length amino acid sequence for the *C. trachomatis* pmpD gene.

SEQ ID NO: 179 is the predicted full-length amino acid sequence for the *C. trachomatis* pmpC gene.

SEQ ID NO: 180 is the predicted full-length amino acid sequence for the *C. trachomatis* pmpB gene.

SEQ ID NO: 181 is the determined DNA sequence minus the signal sequence for the *C. trachomatis* pmpI gene.

SEQ ID NO: 182 is a subsequently determined full-length DNA sequence for the *C. trachomatis* pmpG gene.

SEQ ID NO: 183 is the determined DNA sequence minus the signal sequence for the *C. trachomatis* pmpE gene.

SEQ ID NO: 184 is a first determined DNA sequence representing the carboxy terminus for the *C. trachomatis* pmpD gene.

SEQ ID NO: 185 is a second determined DNA sequence representing the amino terminus minus the signal sequence for the *C. trachomatis* pmpD gene.

SEQ ID NO: 186 is a first determined DNA sequence representing the carboxy terminus for the *C. trachomatis* pmpC gene.

SEQ ID NO: 187 is a second determined DNA sequence representing the amino terminus minus the signal sequence for the *C. trachomatis* pmpC gene.

SEQ ID NO: 188 is the determined DNA sequence representing the *C. pneumoniae* serovar MOMPS pmp gene in a fusion molecule with Ra12.

SEQ ID NO: 189 is the predicted amino acid sequence minus the signal sequence for the *C. trachomatis* pmpI gene.

SEQ ID NO: 190 is subsequently predicted amino acid sequence for the *C. trachomatis* pmpG gene.

SEQ ID NO: 191 is the predicted amino acid sequence minus the signal sequence for the *C. trachomatis* pmpE gene.

SEQ ID NO: 192 is a first predicted amino acid sequence representing the carboxy terminus for the *C. trachomatis* pmpD gene.

SEQ ID NO: 193 is a second predicted amino acid sequence representing the Amino terminus minus the signal sequence for the *C. trachomatis* pmpD gene.

SEQ ID NO: 194 is a first predicted amino acid sequence representing the Carboxy terminus for the *C. trachomatis* pmpC gene.

SEQ ID NO: 195 is a second predicted amino acid sequence representing the Amino terminus for the *C. trachomatis* pmpC gene.

SEQ ID NO: 196 is the predicted amino acid sequence representing the *C. pneumoniae* serovar MOMPS pmp gene in a fusion molecule with Ra12.

SEQ ID NO: 197 is the determined DNA sequence for the 5' oligo primer for cloning the *C. trachomatis* pmpC gene in the SKB vaccine vector.

SEQ ID NO: 198 is the determined DNA sequence for the 3' oligo primer for cloning the *C. trachomatis* pmpC gene in the SKB vaccine vector.

SEQ ID NO: 199 is the determined DNA sequence for the insertion sequence for cloning the *C. trachomatis* pmpC gene in the SKB vaccine vector.

SEQ ID NO: 200 is the determined DNA sequence for the 5' oligo primer for cloning the *C. trachomatis* pmpD gene in the SKB vaccine vector.

SEQ ID NO: 201 is the determined DNA sequence for the 3' oligo primer for cloning the *C. trachomatis* pmpD gene in the SKB vaccine vector.

SEQ ID NO: 202 is the determined DNA sequence for the insertion sequence for cloning the *C. trachomatis* pmpD gene in the SKB vaccine vector.

SEQ ID NO: 203 is the determined DNA sequence for the 5' oligo primer for cloning the *C. trachomatis* pmpE gene in the SKB vaccine vector.

SEQ ID NO: 204 is the determined DNA sequence for the 3' oligo primer for cloning the *C. trachomatis* pmpE gene in the SKB vaccine vector.

SEQ ID NO: 205 is the determined DNA sequence for the 5' oligo primer for cloning the *C. trachomatis* pmpG gene in the SKB vaccine vector.

SEQ ID NO: 206 is the determined DNA sequence for the 3' oligo primer for cloning the *C. trachomatis* pmpG gene in the SKB vaccine vector.

SEQ ID NO: 207 is the determined DNA sequence for the 5' oligo primer for cloning the amino terminus portion of the *C. trachomatis* pmpC gene in the pET17b vector.

SEQ ID NO: 208 is the determined DNA sequence for the 3' oligo primer for cloning the amino terminus portion of the *C. trachomatis* pmpC gene in the pET17b vector.

SEQ ID NO: 209 is the determined DNA sequence for the 5' oligo primer for cloning the carboxy terminus portion of the *C. trachomatis* pmpC gene in the pET17b vector.

SEQ ID NO: 210 is the determined DNA sequence for the 3' oligo primer for cloning the carboxy terminus portion of the *C. trachomatis* pmpC gene in the pET17b vector.

SEQ ID NO: 211 is the determined DNA sequence for the 5' oligo primer for cloning the amino terminus portion of the *C. trachomatis* pmpD gene in the pET17b vector.

SEQ ID NO: 212 is the determined DNA sequence for the 3' oligo primer for cloning the amino terminus portion of the *C. trachomatis* pmpD gene in the pET17b vector.

SEQ ID NO: 213 is the determined DNA sequence for the 5' oligo primer for cloning the carboxy terminus portion of the *C. trachomatis* pmpD gene in the pET17b vector.

SEQ ID NO: 214 is the determined DNA sequence for the 3' oligo primer for cloning the carboxy terminus portion of the *C. trachomatis* pmpD gene in the pET17b vector.

SEQ ID NO: 215 is the determined DNA sequence for the 5' oligo primer for cloning the *C. trachomatis* pmpE gene in the pET17b vector.

SEQ ID NO: 216 is the determined DNA sequence for the 3' oligo primer for cloning the *C. trachomatis* pmpE gene in the pET17b vector.

SEQ ID NO: 217 is the determined DNA sequence for the insertion sequence for cloning the *C. trachomatis* pmpE gene in the pET17b vector.

SEQ ID NO: 218 is the amino acid sequence for the insertion sequence for cloning the *C. trachomatis* pmpE gene in the pET17b vector.

SEQ ID NO: 219 is the determined DNA sequence for the 5' oligo primer for cloning the *C. trachomatis* pmpG gene in the pET17b vector.

SEQ ID NO: 220 is the determined DNA sequence for the 3' oligo primer for cloning the *C. trachomatis* pmpG gene in the pET17b vector.

SEQ ID NO: 221 is the amino acid sequence for the insertion sequence for cloning the *C. trachomatis* pmpG gene in the pET17b vector.

SEQ ID NO: 222 is the determined DNA sequence for the 5' oligo primer for cloning the *C. trachomatis* pmpI gene in the pET17b vector.

SEQ ID NO: 223 is the determined DNA sequence for the 3' oligo primer for cloning the *C. trachomatis* pmpI gene in the pET17b vector.

SEQ ID NO: 224 is the determined amino acid sequence for the *C. pneumoniae* Swib peptide 1–20.

SEQ ID NO: 225 is the determined amino acid sequence for the *C. pneumoniae* Swib peptide 6–25.

SEQ ID NO: 226 is the determined amino acid sequence for the *C. pneumoniae* Swib peptide 12–31.

SEQ ID NO: 227 is the determined amino acid sequence for the *C. pneumoniae* Swib peptide 17–36.

SEQ ID NO: 228 is the determined amino acid sequence for the *C. pneumoniae* Swib peptide 22–41.

SEQ ID NO: 229 is the determined amino acid sequence for the *C. pneumoniae* Swib peptide 27–46.

SEQ ID NO: 230 is the determined amino acid sequence for the *C. pneumoniae* Swib peptide 42–61.

SEQ ID NO: 231 is the determined amino acid sequence for the *C. pneumoniae* Swib peptide 46–65.

SEQ ID NO: 232 is the determined amino acid sequence for the *C. pneumoniae* Swib peptide 51–70.

SEQ ID NO: 233 is the determined amino acid sequence for the *C. pneumoniae* Swib peptide 56–75.

SEQ ID NO: 234 is the determined amino acid sequence for the *C. pneumoniae* Swib peptide 61–80.

SEQ ID NO: 235 is the determined amino acid sequence for the *C. pneumoniae* Swib peptide 66–87.

SEQ ID NO: 236 is the determined amino acid sequence for the *C. trachomatis* OMCB peptide 103–122.

SEQ ID NO: 237 is the determined amino acid sequence for the *C. trachomatis* OMCB peptide 108–127.

SEQ ID NO: 238 is the determined amino acid sequence for the *C. trachomatis* OMCB peptide 113–132.

SEQ ID NO: 239 is the determined amino acid sequence for the *C. trachomatis* OMCB peptide 118–137.

SEQ ID NO: 240 is the determined amino acid sequence for the *C. trachomatis* OMCB peptide 123–143.

SEQ ID NO: 241 is the determined amino acid sequence for the *C. trachomatis* OMCB peptide 128–147.

SEQ ID NO: 242 is the determined amino acid sequence for the *C. trachomatis* OMCB peptide 133–152.

SEQ ID NO: 243 is the determined amino acid sequence for the *C. trachomatis* OMCB peptide 137–156.

SEQ ID NO: 244 is the determined amino acid sequence for the *C. trachomatis* OMCB peptide 142–161.

SEQ ID NO: 245 is the determined amino acid sequence for the *C. trachomatis* OMCB peptide 147–166.

SEQ ID NO: 246 is the determined amino acid sequence for the *C. trachomatis* OMCB peptide 152–171.

SEQ ID NO: 247 is the determined amino acid sequence for the *C. trachomatis* OMCB peptide 157–176.

SEQ ID NO: 248 is the determined amino acid sequence for the *C. trachomatis* OMCB peptide 162–181.

SEQ ID NO: 249 is the determined amino acid sequence for the *C. trachomatis* OMCB peptide 167–186.

SEQ ID NO: 250 is the determined amino acid sequence for the *C. trachomatis* OMCB peptide 171–190.

SEQ ID NO: 251 is the determined amino acid sequence for the *C. trachomatis* OMCB peptide 171–186.

SEQ ID NO: 252 is the determined amino acid sequence for the *C. trachomatis* OMCB peptide 175–186.

SEQ ID NO: 252 is the determined amino acid sequence for the *C. trachomatis* OMCB peptide 175–186.

SEQ ID NO: 253 is the determined amino acid sequence for the *C. pneumoniae* OMCB peptide 185–198.

SEQ ID NO: 254 is the determined amino acid sequence for the *C. trachomatis* TSA peptide 96–115.

SEQ ID NO: 255 is the determined amino acid sequence for the *C. trachomatis* TSA peptide 101–120.

SEQ ID NO: 256 is the determined amino acid sequence for the *C. trachomatis* TSA peptide 106–125.

SEQ ID NO: 257 is the determined amino acid sequence for the *C. trachomatis* TSA peptide 111–130.

SEQ ID NO: 258 is the determined amino acid sequence for the *C. trachomatis* TSA peptide 116–135.

SEQ ID NO: 259 is the determined amino acid sequence for the *C. trachomatis* TSA peptide 121–140.

SEQ ID NO: 260 is the determined amino acid sequence for the *C. trachomatis* TSA peptide 126–145.

SEQ ID NO: 261 is the determined amino acid sequence for the *C. trachomatis* TSA peptide 131–150.

SEQ ID NO: 262 is the determined amino acid sequence for the *C. trachomatis* TSA peptide 136–155.

SEQ ID NO: 263 is the determined full-length DNA sequence for the *C. trachomatis CT*529/Cap 1 gene serovar I.

SEQ ID NO: 264 is the predicted full-length amino sequence for the *C. trachomatis CT*529/Cap 1 gene serovar I.

SEQ ID NO: 265 is the determined full-length DNA sequence for the *C. trachomatis CT*529/Cap 1 gene serovar K.

SEQ ID NO: 266 is the predicted full-length amino sequence for the *C. trachomatis CT*529/Cap 1 gene serovar K.

SEQ ID NO: 267 is the determined DNA sequence for the *C. trachomatis* clone 17-G4-36 sharing homology to part of the ORF of DNA-directed RNA polymerase beta subunit-CT315 in serD.

SEQ ID NO: 268 is the determined DNA sequence for the partial sequence of the *C. trachomatis* CT016 gene in clone 2E10.

SEQ ID NO: 269 is the determined DNA sequence for the partial sequence of the *C. trachomatis* tRNA syntase gene in clone 2E10.

SEQ ID NO: 270 is the determined DNA sequence for the partial sequence for the *C. trachomatis* clpX gene in clone 2E10.

SEQ ID NO: 271 is a first determined DNA sequence for the *C. trachomatis* clone CtL2gam-30 representing the 5' end.

SEQ ID NO: 272 is a second determined DNA sequence for the *C. trachomatis clone CtL*2gam-30 representing the 3' end.

SEQ ID NO: 273 is the determined DNA sequence for the *C. trachomatis* clone CtL2gam-28.

SEQ ID NO: 274 is the determined DNA sequence for the *C. trachomatis* clone CtL2gam-27.

SEQ ID NO: 275 is the determined DNA sequence for the *C. trachomatis* clone CtL2gam-26.

SEQ ID NO: 276 is the determined DNA sequence for the *C. trachomatis* clone CtL2gam-24.

SEQ ID NO: 277 is the determined DNA sequence for the *C. trachomatis* clone CtL2gam-23.

SEQ ID NO: 278 is the determined DNA sequence for the *C. trachomatis* clone CtL2gam-21.

SEQ ID NO: 279 is the determined DNA sequence for the *C. trachomatis* clone CtL2gam-18.

SEQ ID NO: 280 is the determined DNA sequence for the *C. trachomatis* clone CtL2gam-17.

SEQ ID NO: 281 is a first determined DNA sequence for the *C. trachomatis* clone CtL2gam-15 representing the 5' end.

SEQ ID NO: 282 is a second determined DNA sequence for the *C. trachomatis clone CtL*2gam-15 representing the 3' end.

SEQ ID NO: 283 is the determined DNA sequence for the *C. trachomatis* clone CtL2gam-13.

SEQ ID NO: 284 is the determined DNA sequence for the *C. trachomatis* clone CtL2gam-10.

SEQ ID NO: 285 is the determined DNA sequence for the *C. trachomatis* clone CtL2gam-8.

SEQ ID NO: 286 is a first determined DNA sequence for the *C. trachomatis* clone CtL2gam-6 representing the 5' end.

SEQ ID NO: 287 is a second determined DNA sequence for the *C. trachomatis* clone CtL2gam-6 representing the 3' end.

SEQ ID NO: 288 is the determined DNA sequence for the *C. trachomatis* clone CtL2gam-5.

SEQ ID NO: 289 is the determined DNA sequence for the *C. trachomatis* clone CtL2gam-2.

SEQ ID NO: 290 is the determined DNA sequence for the *C. trachomatis* clone CtL2gam-1.

SEQ ID NO: 291 is the determined full-length DNA sequence for the *C. pneumoniae homologue of the CT*529 gene.

SEQ ID NO: 292 is the predicted full-length amino acid sequence for the *C. pneumoniae homologue of the CT*529 gene.

SEQ ID NO: 293 is the determined DNA sequence for the insertion sequence for cloning the *C. trachomatis* pmpG gene in the SKB vaccine vector.

SEQ ID NO: 294 is the amino acid sequence of an open reading frame of clone CT603.

SEQ ID NO: 295 is the amino acid sequence of a first open reading frame of clone CT875.

SEQ ID NO: 296 is the amino acid sequence of a second open reading frame of clone CT875.

SEQ ID NO: 297 is the amino acid sequence of a first open reading frame of clone CT858.

SEQ ID NO: 298 is the amino acid sequence of a second open reading frame of clone CT858.

SEQ ID NO: 299 is the amino acid sequence of an open reading frame of clone CT622.

SEQ ID NO: 300 is the amino acid sequence of an open reading frame of clone CT610.

SEQ ID NO: 301 is the amino acid sequence of an open reading frame of clone CT396.

SEQ ID NO: 302 is the amino acid sequence of an open reading frame of clone CT318.

SEQ ID NO: 303 is the amino acid sequence of an open reading frame of the ORF-3 protein of C. trachomatis.

SEQ ID NO: 304 is the amino acid sequence for C. trachomatis, serovar L2 rCt529c1-125 having a modified N-terminal sequence (6-His tag).

SEQ ID NO: 305 is the amino acid sequence for C. trachomatis, serovar L2 rCt529c1-125.

Figure 1:
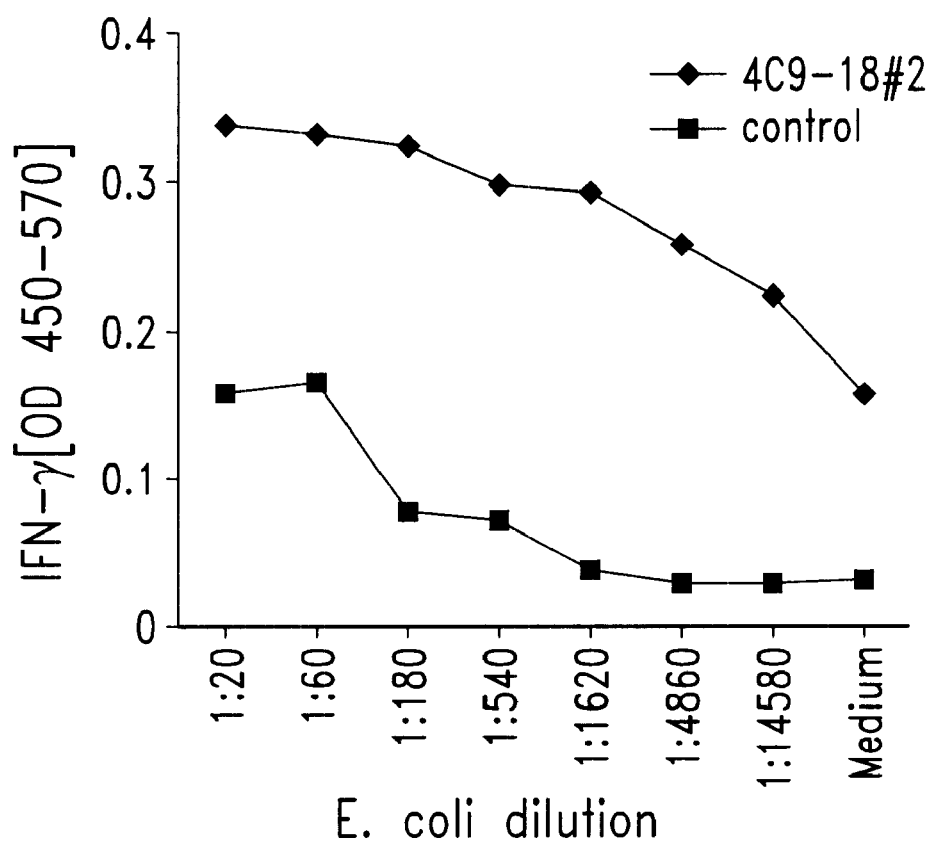
FIG. 1 illustrates induction of INF-γ from a Chlamydia-specific T cell line activated by target cells expressing clone 4C9-18#2.

Examples of immunogenic portions of antigens contemplated by the present invention include, for example, the T cell stimulating epitopes provided in SEQ ID NO: 9, 10, 18, 19, 31, 39, 93–96, 98, 100–102, 106, 108, 138–140, 158, 167, 168, 246, 247 and 254–256. Polypeptides comprising at least an immunogenic portion of one or more Chlamydia antigens as described herein may generally be used, alone or in combination, to detect Chlamydial infection in a patient.

The compositions and methods of the present invention also encompass variants of the above polypeptides and polynucleotide molecules. Such variants include, but are not limited to, naturally occurring allelic variants of the inventive sequences. In particular, variants include other Chlamydiae serovars, such as serovars D, E and F, as well as the several LGV serovars which share homology to the inventive polypeptide and polynucleotide molecules described herein. Preferably, the serovar homologues show 95–99% homology to the corresponding polypeptide sequence(s) described herein.

A polypeptide "variant," as used herein, is a polypeptide that differs from the recited polypeptide only in conservative substitutions and/or modifications, such that the antigenic properties of the polypeptide are retained. In a preferred embodiment, variant polypeptides differ from an identified sequence by substitution, deletion or addition of five amino acids or fewer. Such variants may generally be identified by modifying one of the above polypeptide sequences, and evaluating the antigenic properties of the modified polypeptide using, for example, the representative procedures described herein. In other words, the ability of a variant to react with antigen-specific antisera may be enhanced or unchanged, relative to the native protein, or may be diminished by less than 50%, and preferably less than 20%, relative to the native protein. Such variants may generally be identified by modifying one of the above polypeptide sequences and evaluating the reactivity of the modified polypeptide with antigen-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

As used herein, a "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. In a preferred embodiment, variant polypeptides differ from a native sequence by substitution, deletion or addition of five amino acids or fewer. Variants may also (or alternatively) be modified by, for example, the deletion or addition of amino acids that have minimal influence on the immunogenicity, secondary structure and hydropathic nature of the polypeptide. Variants may also, or alternatively, contain other modifications, including the deletion or addition of amino acids that have minimal influence on the antigenic properties, secondary structure and hydropathic nature of the polypeptide. For example, a polypeptide may be conjugated to a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

A polynucleotide "variant" is a sequence that differs from the recited nucleotide sequence in having one or more nucleotide deletions, substitutions or additions such that the immunogenicity of the encoded polypeptide is not diminished, relative to the native protein. The effect on the immunogenicity of the encoded polypeptide may generally be assessed as described herein. Such modifications may be readily introduced using standard mutagenesis techniques, such as oligonucleotide-directed site-specific mutagenesis as taught, for example, by Adelman et al. (*DNA,* 2:183, 1983). Nucleotide variants may be naturally occurring allelic variants as discussed below, or non-naturally occurring variants. The polypeptides provided by the present invention include variants that are encoded by polynucleotide sequences which are substantially homologous to one or more of the polynucleotide sequences specifically recited herein. "Substantial homology," as used herein, refers to polynucleotide sequences that are capable of hybridizing under moderately stringent conditions. Suitable moderately stringent conditions include prewashing in a solution of 5×SSC, 0.5% SDS, 1.0 mM EDTA (pH 8.0); hybridizing at 50° C.-65° C., 5×SSC, overnight or, in the event of cross-species homology, at 45° C. with 0.5×SSC; followed by washing twice at 65° C. for 20 minutes with each of 2×, 0.5× and 0.2×SSC containing 0.1% SDS. Such hybridizing polynucleotide sequences are also within the scope of this invention, as are nucleotide sequences that, due to code degeneracy, encode a polypeptide that is the same as a polypeptide of the present invention.

Two nucleotide or polypeptide sequences are said to be "identical" if the sequence of nucleotides or amino acid residues in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Resarch Foundation, Washington D.C. Vol. 5, Suppl. 3, pp. 345–358; Hein J. (1990) Unified Approach to Alignment and Phylogenes pp. 626–645 *Methods in Enzymology* vol. 183, Academic Press, Inc., San Diego, Calif.; Higgins, D. G. and Sharp, P. M. (1989) Fast and sensitive multiple sequence alignments on a microcomputer *CABIOS* 5:151–153; Myers, E. W. and Muller W. (1988) Optimal alignments in linear space *CABIOS* 4:11–17; Robinson, E. D. (1971) *Comb. Theor* 11:105; Santou, N. Nes, M. (1987) The neighbor joining method. A new method for reconstructing phylogenetic trees *Mol. Biol. Evol.* 4:406–425; Sneath, P. H. A. and Sokal, R. R. (1973) *Numerical Taxonomy—the Principles and Practice of Numerical Taxonomy,* Freeman Press, San Francisco, Calif.; Wilbur, W. J. and Lipman, D. J. (1983) Rapid similarity searches of nucleic acid and protein data banks *Proc. Natl. Acad., Sci. USA* 80:726–730.

Alternatively, optimal alignment of sequences for comparison may be conducted by the local identity algorithm of Smith and Waterman (1981) *Add. APL. Math* 2:482, by the identity alignment algorithm of Needleman and Wunsch (1970) J. Mol. Biol. 48:443, by the search for similarity methods of Pearson and Lipman (1988) Proc. Natl. Acad. Sci. (U.S.A.) 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, Wis.), or by inspection.

One illustrative example of algorithms that are suitable for determining percent sequence identity and sequence similarity are the BLAST and BLAST 2.0 algorithms, which are described in Altschul et al. (1977) Nuc. Acids Res. 25:3389–3402 and Altschul et al. (1990) J. Mol. Biol. 215:403–410, respectively. BLAST and BLAST 2.0 can be used, for example with the parameters described herein, to determine percent sequence identity for the polynucleotides and polypeptides of the invention. Software for performing BLAST analyses is publicly available through the National Center for Biotechnology Information (http://www.ncbi.nlm.nih.gov/) In one illustrative example, cumulative scores can be calculated using, for nucleotide sequences, the parameters M (reward score for a pair of matching residues; always >0) and N (penalty score for mismatching residues; always <0). For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a wordlength (W) of 11, and expectation (E) of 10, and the BLOSUM62 scoring matrix (see Henikoff and Henikoff (1989) Proc. Natl. Acad. Sci. USA 89:10915) alignments, (B) of 50, expectation (E) of 10, M=5, N=–4 and a comparison of both strands.

Preferably, the "percentage of sequence identity" is determined by comparing two optimally aligned sequences over a window of comparison of at least 20 positions, wherein the portion of the polynucleotide or amino acid sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Therefore, the present invention provides polynucleotide and polypeptide sequences having substantial identity to the sequences disclosed herein, for example those comprising at least 50% or more sequence identity, preferably at least 55%, 60%, 65%, 70%, 75%, 80%, 85%, 90%, 95%, 96%, 97%, 98%, or 99% or higher, sequence identity compared to a polynucleotide or polypeptide sequence of this invention using the methods described herein, (e.g., BLAST analysis using standard parameters, as described below). One skilled in this art will recognize that these values can be appropriately adjusted to determine corresponding identity of proteins encoded by two polynucleotide sequences by taking into account codon degeneracy, amino acid similarity, reading frame positioning and the like.

In additional embodiments, the present invention provides isolated polynucleotides or polypeptides comprising various lengths of contiguous stretches of sequence identical to or complementary to one or more of the sequences disclosed herein. For example, polynucleotides and polypeptides encompassed by this invention may comprise at least about 15, 20, 30, 40, 50, 75, 100, 150, 200, 300, 400, 500 or 1000 or more contiguous nucleotides of one or more of the disclosed sequences, as well as all intermediate lengths therebetween. It will be readily understood that "intermediate lengths", in this context, means any length between the quoted values, such as 16, 17, 18, 19, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000, and the like.

The polynucleotides of the present invention, or fragments thereof, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, illustrative DNA segments with total lengths of about 10,000, about 5000, about 3000, about 2,000, about 1,000, about 500, about 200, about 100, about 50 base pairs in length, and the like, (including all intermediate lengths) are contemplated to be useful in many implementations of this invention.

Also included in the scope of the present invention are alleles of the genes encoding the nucleotide sequences recited in herein. As used herein, an "allele" or "allellic sequence" is an alternative form of the gene which may result from at least one mutation in the nucleic acid sequence. Alleles may result in altered mRNAs or polypeptides whose structure or function may or may not be altered. Any given gene may have none, one, or many allelic forms.

Common mutational changes which give rise to alleles are generally ascribed to natural deletions, additions, or substitutions of nucleotides. Each of these types of changes may occur alone or in combination with the others, one or more times in a given sequence. In specific embodiments, the subject invention discloses polypeptides comprising at least an immunogenic portion of a Chlamydia antigen (or a variant of such an antigen), that comprises one or more of the amino acid sequences encoded by (a) a polynucleotide sequence selected from the group consisting of SEQ ID NO: 1–4, 15 21–25, 44–64, 66–76 and 79–88; (b) the complements of such DNA sequences or (c) DNA sequences substantially homologous to a sequence in (a) or (b). As discussed in the Examples below, several of the Chlamydia antigens disclosed herein recognize a T cell line that recognizes both Chlamydia trachomatis and Chlamydia pneumoniae infected monocyte-derived dendritic cells, indicating that they may represent an immunoreactive epitope shared by *Chlamydia trachomatis* and *Chlamydia pneumoniae*. The antigens may thus be employed in a vaccine for both *C. trachomatis* genital tract infections and for *C. pneumonia* infections. Further characterization of these Chlamydia antigens from *Chlamydia trachomatis* and *Chlamydia pneumonia* to determine the extent of cross-reactivity is provided in Example 6. Additionally, Example 4 describes cDNA fragments (SEQ ID NO: 15, 16 and 33) isolated from *C. trachomatis* which encode proteins (SEQ ID NO: 17–19 and 32) capable of stimulating a Chlamydia-specific murine CD8+ T cell line.

In general, Chlamydia antigens, and polynucleotide sequences encoding such antigens, may be prepared using any of a variety of procedures. For example, polynucleotide molecules encoding Chlamydia antigens may be isolated from a Chlamydia genomic or cDNA expression library by screening with a Chlamydia-specific T cell line as described below, and sequenced using techniques well known to those of skill in the art. Additionally, a polynucleotide may be identified, as described in more detail below, by screening a microarray of cDNAs for Chlamydia-associated expression (i.e., expression that is at least two fold greater in Chlamydia-infected cells than in controls, as determined using a representative assay provided herein). Such screens may be performed using a Synteni microarray (Palo Alto, Calif.) according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997). Alternatively, polypeptides may be amplified from cDNA prepared from cells expressing the proteins described herein. Such polynucleotides may be amplified via polymerase chain reaction (PCR). For this approach, sequence-specific primers may be designed based on the sequences provided herein, and may be purchased or synthesized.

Antigens may be produced recombinantly, as described below, by inserting a polynucleotide sequence that encodes the antigen into an expression vector and expressing the antigen in an appropriate host. Antigens may be evaluated for a desired property, such as the ability to react with sera obtained from a Chlamydia-infected individual as described herein, and may be sequenced using, for example, traditional Edman chemistry. See Edman and Berg, *Eur. J. Biochem.* 80:116–132, 1967.

Polynucleotide sequences encoding antigens may also be obtained by screening an appropriate Chlamydia cDNA or genomic DNA library for polynucleotide sequences that hybridize to degenerate oligonucleotides derived from partial amino acid sequences of isolated antigens. Degenerate oligonucleotide sequences for use in such a screen may be designed and synthesized, and the screen may be performed, as described (for example) in Sambrook et al., *Molecular Cloning. A Laboratory Manual,* Cold Spring Harbor Laboratories, Cold Spring Harbor, N.Y. (and references cited therein). Polymerase chain reaction (PCR) may also be employed, using the above oligonucleotides in methods well known in the art, to isolate a nucleic acid probe from a cDNA or genomic library. The library screen may then be performed using the isolated probe.

An amplified portion may be used to isolate a full length gene from a suitable library (e.g., a Chlamydia cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}$P) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual,* Cold Spring Harbor Laboratories, Cold Spring Harbor, N.Y., 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using techniques well known in the art (see, for example, Mullis et al., *Cold Spring Harbor Symp. Quant. Biol.* 51:263, 1987; Erlich ed., *PCR Technology,* Stockton Press, NY, 1989), and software well known in the art may also be employed. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl. Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111-19, 1991) and walking PCR (Parker et al., *Nucl. Acids. Res.* 19:3055–60, 1991). Transcription-Mediated Amplification, or TMA is another method that may be utilized for the amplification of DNA, rRNA, or mRNA, as described in Patent No. PCT/US91/03184. This autocatalytic and isothermic non-PCR based method utilizes two primers and two enzymes: RNA polymerase and reverse transcriptase. One primer contains a promoter sequence for RNA polymerase. In the first amplification, the promoter-primer hybridizes to the target rRNA at a defined site. Reverse transcriptase creates a DNA copy of the target rRNA by extension from the 3' end of the promoter-primer. The RNA in the resulting complex is degraded and a second primer binds to the DNA copy. A new strand of DNA is synthesized from the end of the primer by reverse transcriptase creating double stranded DNA. RNA polymerase recognizes the promoter sequence in the DNA template and initiates transcription. Each of the newly synthesized RNA amplicons re-enters the TMA process and serves as a template for a new round of replication leading to the expotential expansion of the RNA amplicon. Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence. Full length cDNA sequences may also be obtained by analysis of genomic fragments.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding a Chlamydial protein, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo (e.g., by transfecting antigen-presenting cells, such as dendritic cells, with a cDNA construct encoding a Chlamydial polypeptide, and administering the transfected cells to the patient).

A portion of a sequence complementary to a coding sequence (i.e., an antisense polynucleotide) may also be used as a probe or to modulate gene expression. cDNA constructs that can be transcribed into antisense RNA may also be introduced into cells of tissues to facilitate the production of antisense RNA. An antisense polynucleotide may be used, as described herein, to inhibit expression of a Chlamydial protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches,* Futura Publishing Co. (Mt. Kisco, N.Y.; 1994)). Alternatively, an antisense molecule may be designed to hybridize with a control region of a gene (e.g., promoter, enhancer or transcription initiation site), and block transcription of the gene; or to block translation by inhibiting binding of a transcript to ribosomes.

A portion of a coding sequence, or of a complementary sequence, may also be designed as a probe or primer to detect gene expression. Probes may be labeled with a variety of reporter groups, such as radionuclides and enzymes, and are preferably at least 10 nucleotides in length, more preferably at least 20 nucleotides in length and still more preferably at least 30 nucleotides in length. Primers, as noted above, are preferably 22–30 nucleotides in length.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Synthetic polypeptides having fewer than about 100 amino acids, and generally fewer than about 50 amino acids, may be generated using techniques well known in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Perkin Elmer/Applied BioSystems Division, Foster City, Calif., and may be operated according to the manufacturer's instructions.

As noted above, immunogenic portions of Chlamydia antigens may be prepared and identified using well known techniques, such as those summarized in Paul, *Fundamental Immunology,* 3d ed., Raven Press, 1993, pp. 243–247 and references cited therein. Such techniques include screening polypeptide portions of the native antigen for immunogenic properties. The representative ELISAs described herein may generally be employed in these screens. An immunogenic portion of a polypeptide is a portion that, within such representative assays, generates a signal in such assays that is substantially similar to that generated by the full length antigen. In other words, an immunogenic portion of a Chlamydia antigen generates at least about 20%, and preferably about 100%, of the signal induced by the full length antigen in a model ELISA as described herein.

Portions and other variants of Chlamydia antigens may be generated by synthetic or recombinant means. Variants of a native antigen may generally be prepared using standard mutagenesis techniques, such as oligonucleotide-directed site-specific mutagenesis. Sections of the polynucleotide sequence may also be removed using standard techniques to permit preparation of truncated polypeptides.

Recombinant polypeptides containing portions and/or variants of a native antigen may be readily prepared from a polynucleotide sequence encoding the polypeptide using a variety of techniques well known to those of ordinary skill in the art. For example, supernatants from suitable host/vector systems which secrete recombinant protein into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant protein.

Any of a variety of expression vectors known to those of ordinary skill in the art may be employed to express recombinant polypeptides as described herein. Expression may be achieved in any appropriate host cell that has been transformed or transfected with an expression vector containing a polynucleotide molecule that encodes a recombinant polypeptide. Suitable host cells include prokaryotes, yeast and higher eukaryotic cells. Preferably, the host cells employed are *E. coli,* yeast or a mammalian cell line, such as COS or CHO. The DNA sequences expressed in this manner may encode naturally occurring antigens, portions of naturally occurring antigens, or other variants thereof.

In general, regardless of the method of preparation, the polypeptides disclosed herein are prepared in an isolated, substantially pure, form. Preferably, the polypeptides are at least about 80% pure, more preferably at least about 90% pure and most preferably at least about 99% pure.

Within certain specific embodiments, a polypeptide may be a fusion protein that comprises multiple polypeptides as described herein, or that comprises at least one polypeptide as described herein and an unrelated sequence, such as a known Chlamydial protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein. A DNA sequence encoding a fusion protein of the present invention may be constructed using known recombinant DNA techniques to assemble separate DNA sequences encoding, for example, the first and second polypeptides, into an appropriate expression vector. The 3' end of a DNA sequence encoding the first polypeptide is ligated, with or without a peptide linker, to the 5' end of a DNA sequence encoding the second polypeptide so that the reading frames of the sequences are in phase to permit mRNA translation of the two DNA sequences into a single fusion protein that retains the biological activity of both the first and the second polypeptides.

A peptide linker sequence may be employed to separate the first and the second polypeptides by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad. Sci. USA* 83:8258–8562, 1986; U.S. Pat. Nos. 4,935,233 and 4,751,180. The linker sequence may be from 1 to about 50 amino acids in length. As an alternative to the use of a peptide linker sequence (when desired), one can utilize non-essential N-terminal amino acid regions (when present) on the first and second polypeptides to separate the functional domains and prevent steric hindrance.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen presenting cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae,* which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305. Additionally, the fusion protein Ra12 may be linked to the inventive polynucleotides to facilitate protein expression.

In another aspect, the present invention provides methods for using one or more of the above polypeptides or fusion proteins (or polynucleotides encoding such polypeptides or fusion proteins) to induce protective immunity against Chlamydial infection in a patient. As used herein, a "patient" refers to any warm-blooded animal, preferably a human. A patient may be afflicted with a disease, or may be free of detectable disease and/or infection. In other words, protective immunity may be induced to prevent or treat Chlamydial infection.

In this aspect, the polypeptide, fusion protein or polynucleotide molecule is generally present within a pharmaceutical composition or a vaccine. Pharmaceutical compositions may comprise one or more polypeptides, each of which may contain one or more of the above sequences (or variants thereof), and a physiologically acceptable carrier. Vaccines may comprise one or more of the above polypeptides and an immunostimulant, such as an adjuvant or a liposome (into which the polypeptide is incorporated). Such pharmaceutical compositions and vaccines may also contain other Chlamydia antigens, either incorporated into a combination polypeptide or present within a separate polypeptide.

Alternatively, a vaccine may contain polynucleotides encoding one or more polypeptides or fusion proteins as described above, such that the polypeptide is generated in situ. In such vaccines, the polynucleotides may be present within any of a variety of delivery systems known to those of ordinary skill in the art, including nucleic acid expression systems, bacterial and viral expression systems. Appropriate nucleic acid expression systems contain the necessary polynucleotide sequences for expression in the patient (such as a suitable promoter and terminating signal). Bacterial delivery systems involve the administration of a bacterium (such as Bacillus-Calmette-Guerrin) that expresses an immunogenic portion of the polypeptide on its cell surface. In a preferred embodiment, the polynucleotides may be introduced using a viral expression system (e.g., vaccinia or other pox virus, retrovirus, or adenovirus), which may involve the use of a non-pathogenic (defective) virus. Techniques for incorporating polynucleotides into such expression systems are well known to those of ordinary skill in the art. The polynucleotides may also be administered as "naked" plasmid vectors as described, for example, in Ulmer et al., Science 259:1745–1749, 1993 and reviewed by Cohen, Science 259:1691–1692, 1993. Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The uptake of naked polynucleotides may be increased by incorporating the polynucleotides into and/or onto biodegradable beads, which are efficiently transported into the cells. The preparation and use of such systems is well known in the art.

In a related aspect, a polynucleotide vaccine as described above may be administered simultaneously with or sequentially to either a polypeptide of the present invention or a known Chlamydia antigen. For example, administration of polynucleotides encoding a polypeptide of the present invention, either "naked" or in a delivery system as described above, may be followed by administration of an antigen in order to enhance the protective immune effect of the vaccine.

Polypeptides and polynucleotides disclosed herein may also be employed in adoptive immunotherapy for the treatment of Chlamydial infection. Adoptive immunotherapy may be broadly classified into either active or passive immunotherapy. In active immunotherapy, treatment relies on the in vivo stimulation of the endogenous host immune system with the administration of immune response-modifying agents (for example, vaccines, bacterial adjuvants, and/or cytokines).

In passive immunotherapy, treatment involves the delivery of biologic reagents with established immune reactivity (such as effector cells or antibodies) that can directly or indirectly mediate anti-Chlamydia effects and does not necessarily depend on an intact host immune system. Examples of effector cells include T lymphocytes (for example, CD8+ cytotoxic T-lymphocyte, CD4+ T-helper), killer cells (such as Natural Killer cells, lymphokine-activated killer cells), B cells, or antigen presenting cells (such as dendritic cells and macrophages) expressing the disclosed antigens. The polypeptides disclosed herein may also be used to generate antibodies or anti-idiotypic antibodies (as in U.S. Pat. No. 4,918,164), for passive immunotherapy.

The predominant method of procuring adequate numbers of T-cells for adoptive immunotherapy is to grow immune T-cells in vitro. Culture conditions for expanding single antigen-specific T-cells to several billion in number with retention of antigen recognition in vivo are well known in the art. These in vitro culture conditions typically utilize intermittent stimulation with antigen, often in the presence of cytokines, such as IL-2, and non-dividing feeder cells. As noted above, the immunoreactive polypeptides described herein may be used to rapidly expand antigen-specific T cell cultures in order to generate sufficient number of cells for immunotherapy. In particular, antigen-presenting cells, such as dendritic, macrophage, monocyte, fibroblast, or B-cells, may be pulsed with immunoreactive polypeptides, or polynucleotide sequence(s) may be introduced into antigen presenting cells, using a variety of standard techniques well known in the art. For example, antigen presenting cells may be transfected or transduced with a polynucleotide sequence, wherein said sequence contains a promoter region appropriate for increasing expression, and can be expressed as part of a recombinant virus or other expression system. Several viral vectors may be used to transduce an antigen presenting cell, including pox virus, vaccinia virus, and adenovirus; also, antigen presenting cells may be transfected with polynucleotide sequences disclosed herein by a variety of means, including gene-gun technology, lipid-mediated delivery, electroporation, osmotic shock, and particulate delivery mechanisms, resulting in efficient and acceptable expression levels as determined by one of ordinary skill in the art. For cultured T-cells to be effective in therapy, the cultured T-cells must be able to grow and distribute widely and to survive long term in vivo. Studies have demonstrated that cultured T-cells can be induced to grow in vivo and to survive long term in substantial numbers by repeated stimulation with antigen supplemented with IL-2 (see, for example, Cheever, M., et al, "Therapy With Cultured T Cells: Principles Revisited," *Immunological Reviews*, 157:177, 1997).

The polypeptides disclosed herein may also be employed to generate and/or isolate chlamydial-reactive T-cells, which can then be administered to the patient. In one technique, antigen-specific T-cell lines may be generated by in vivo immunization with short peptides corresponding to immunogenic portions of the disclosed polypeptides. The resulting antigen specific CD8+ or CD4+ T-cell clones may be isolated from the patient, expanded using standard tissue culture techniques, and returned to the patient.

Alternatively, peptides corresponding to immunogenic portions of the polypeptides may be employed to generate Chlamydia reactive T cell subsets by selective in vitro stimulation and expansion of autologous T cells to provide antigen-specific T cells which may be subsequently transferred to the patient as described, for example, by Chang et al, (*Crit. Rev. Oncol. Hematol.*, 22(3), 213, 1996). Cells of the immune system, such as T cells, may be isolated from the peripheral blood of a patient, using a commercially available cell separation system, such as Isolex™ System, available from Nexell Therapeutics, Inc. Irvine, Calif. The separated cells are stimulated with one or more of the immunoreactive polypeptides contained within a delivery vehicle, such as a microsphere, to provide antigen-specific T cells. The population of antigen-specific T cells is then expanded using standard techniques and the cells are administered back to the patient.

In other embodiments, T-cell and/or antibody receptors specific for the polypeptides disclosed herein can be cloned, expanded, and transferred into other vectors or effector cells for use in adoptive immunotherapy. In particular, T cells may be transfected with the appropriate genes to express the variable domains from chlamydia specific monoclonal antibodies as the extracellular recognition elements and joined to the T cell receptor signaling chains, resulting in T cell activation, specific lysis, and cytokine release. This enables the T cell to redirect its specificity in an MHC-independent manner. See for example, Eshhar, Z., *Cancer Immunol Immunother*, 45(3–4):131–6, 1997 and Hwu, P., et al, *Cancer Res*, 55(15):3369–73, 1995. Another embodiment may include the transfection of chlamydia antigen specific alpha and beta T cell receptor chains into alternate T cells, as in Cole, D J, et al, *Cancer Res*, 55(4):748–52, 1995.

In a further embodiment, syngeneic or autologous dendritic cells may be pulsed with peptides corresponding to at least an immunogenic portion of a polypeptide disclosed herein. The resulting antigen-specific dendritic cells may either be transferred into a patient, or employed to stimulate T cells to provide antigen-specific T cells which may, in turn, be administered to a patient. The use of peptide-pulsed dendritic cells to generate antigen-specific T cells and the subsequent use of such antigen-specific T cells to eradicate disease in a murine model has been demonstrated by Cheever et al, *Immunological Reviews*, 157:177, 1997). Additionally, vectors expressing the disclosed polynucleotides may be introduced into stem cells taken from the patient and clonally propagated in vitro for autologous transplant back into the same patient.

Within certain aspects, polypeptides, polynucleotides, T cells and/or binding agents disclosed herein may be incorporated into pharmaceutical compositions or immunogenic compositions (i.e., vaccines). Alternatively, a pharmaceutical composition may comprise an antigen-presenting cell (e.g. a dendritic cell) transfected with a Chlamydial polynucleotide such that the antigen presenting cell expresses a Chlamydial polypeptide. Pharmaceutical compositions comprise one or more such compounds and a physiologically acceptable carrier. Vaccines may comprise one or more such compounds and an immunostimulant. An immunostimulant may be any substance that enhances or potentiates an immune response to an exogenous antigen. Examples of immunostimulants include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other Chlamydial antigens may be present, either incorporated into a fusion polypeptide or as a separate compound, within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Numerous gene delivery techniques are well known in the art, such as those described by Rolland, *Crit. Rev. Therap. Drug Carrier Systems* 15:143–198, 1998, and references cited therein. Appropriate nucleic acid expression systems contain the necessary DNA sequences for expression in the patient (such as a suitable promoter and terminating signal). Bacterial delivery systems involve the administration of a bacterium (such as Bacillus-Calmette-Guerrin) that expresses an immnunogenic portion of the polypeptide on its cell surface or secretes such an epitope.

In a preferred embodiment, the DNA may be introduced using a viral expression system (e.g., vaccinia or other pox virus, retrovirus, adenovirus, baculovirus, togavirus, bacteriophage, and the like), which often involves the use of a non-pathogenic (defective), replication competent virus.

For example, many viral expression vectors are derived from viruses of the retroviridae family. This family includes the murine leukemia viruses, the mouse mammary tumor viruses, the human foamy viruses, Rous sarcoma virus, and the immunodeficiency viruses, including human, simian, and feline. Considerations when designing retroviral expression vectors are discussed in Comstock et al. (1997).

Excellent murine leukemia virus (MLV)-based viral expression vectors have been developed by Kim et al. (1998). In creating the MLV vectors, Kim et al. found that the entire gag sequence, together with the immediate upstream region, could be deleted without significantly affecting viral packaging or gene expression. Further, it was found that nearly the entire U3 region could be replaced with the immediately-early promoter of human cytomegalovirus without deleterious effects. Additionally, MCR and internal ribosome entry sites (IRES) could be added without adverse effects. Based on their observations, Kim et al. have designed a series of MLV-based expression vectors comprising one or more of the features described above.

As more has been learned about human foamy virus (HFV), characteristics of HFV that are favorable for its use as an expression vector have been discovered. These characteristics include the expression of pol by splicing and start of translation at a defined initiation codon. Other aspects of HFV viral expression vectors are reviewed in Bodem et al. (1997).

Murakami et al. (1997) describe a Rous sarcoma virus (RSV)-based replication-competent avian retrovirus vectors, IR1 and IR2 to express a heterologous gene at a high level. In these vectors, the IRES derived from encephalomyocarditis virus (EMCV) was inserted between the env gene and the heterologous gene. The IR1 vector retains the splice-acceptor site that is present downstream of the env gene while the IR2 vector lacks it. Murakami et al. have shown high level expression of several different heterologous genes by these vectors.

Recently, a number of lentivirus-based retroviral expression vectors have been developed. Kafri et al. (1997) have shown sustained expression of genes delivered directly into liver and muscle by a human immunodeficiency virus (HIV)-based expression vector. One benefit of the system is the inherent ability of HIV to transduce non-dividing cells. Because the viruses of Kafri et al. are pseudotyped with vesicular stomatitis virus G glycoprotein (VSVG), they can transduce a broad range of tissues and cell types.

A large number of adenovirus-based expression vectors have been developed, primarily due to the advantages offered by these vectors in gene therapy applications. Adenovirus expression vectors and methods of using such vectors are the subject of a number of United States patents, including U.S. Pat. Nos. 5,698,202, 5,616,326, 5,585,362, and 5,518,913, all incorporated herein by reference.

Additional adenoviral constructs are described in Khatri et al. (1997) and Tomanin et al. (1997). Khatri et al. describe novel ovine adenovirus expression vectors and their ability to infect bovine nasal turbinate and rabbit kidney cells as well as a range of human cell type, including lung and foreskin fibroblasts as well as liver, prostate, breast, colon and retinal lines. Tomanin et al. describe adenoviral expression vectors containing the T7 RNA polymerase gene. When introduced into cells containing a heterologous gene operably linked to a T7 promoter, the vectors were able to drive gene expression from the T7 promoter. The authors suggest that this system may be useful for the cloning and expression of genes encoding cytotoxic proteins.

Poxviruses are widely used for the expression of heterologous genes in mammalian cells, Over the years, the vectors have been improved to allow high expression of the heterologous gene and simplify the integration of multiple heterologous genes into a single molecule. In an effort to diminish cytopathic effects and to increase safety, vaccinia virus mutant and other poxviruses that undergo abortive infection in mammalian cells are receiving special attention (Oertli et al., 1997). The use of poxviruses as expression vectors is reviewed in Carroll and Moss (1997).

Togaviral expression vectors, which includes alphaviral expression vectors have been used to study the structure and function of proteins and for protein production purposes. Attractive features of togaviral expression vectors are rapid and efficient gene expression, wide host range, and RNA genomes (Huang, 1996). Also, recombinant vaccines based on alphaviral expression vectors have been shown to induce a strong humoral and cellular immune response with good immunological memory and protective effects (Tubulekas et al., 1997). Alphaviral expression vectors and their use are discussed, for example, in Lundstrom (1997).

In one study, Li and Garoff (1996) used Semliki Forest virus (SFV) expression vectors to express retroviral genes and to produce retroviral particles in BHK-21 cells. The particles produced by this method had protease and reverse transcriptase activity and were infectious. Furthermore, no helper virus could be detected in the virus stocks. Therefore, this system has features that are attractive for its use in gene therapy protocols.

Baculoviral expression vectors have traditionally been used to express heterologous proteins in insect cells. Examples of proteins include mammalian chemokine receptors (Wang et al., 1997), reporter proteins such as green fluorescent protein (Wu et al., 1997), and FLAG fusion proteins (Wu et al., 1997; Koh et al., 1997). Recent advances in baculoviral expression vector technology, including their use in virion display vectors and expression in mammalian cells is reviewed by Possee (1997). Other reviews on baculoviral expression vectors include Jones and Morikawa (1996) and O'Reilly (1997).

Other suitable viral expression systems are disclosed, for example, in Fisher-Hoch et al., Proc. Natl. Acad. Sci. USA 86:317–321, 1989; Flexner et al., Ann. N.Y. Acad. Sci. 569:86–103, 1989; Flexner et al., Vaccine 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, Biotechniques 6:616–627, 1988; Rosenfeld et al., Science 252:431–434, 1991; Kolls et al., Proc. Natl. Acad. Sci. USA 91:215–219, 1994; Kass-Eisler et al., Proc. Natl. Acad. Sci. USA 90:11498–11502, 1993; Guzman et al., Circulation 88:2838–2848, 1993; and Guzman et al., Cir. Res. 73:1202–1207, 1993. Techniques for incorporating DNA into such expression systems are well known to those of ordinary skill in the art. In other systems, the DNA may be introduced as "naked" DNA, as described, for example, in Ulmer et al., Science 259:1745–1749, 1993 and reviewed by Cohen, Science 259:1691–1692, 1993. The uptake of naked DNA may be increased by coating the DNA onto biodegradable beads, which are efficiently transported into the cells.

It will be apparent that a vaccine may comprise a polynucleotide and/or a polypeptide component, as desired. It will also be apparent that a vaccine may contain pharmaceutically acceptable salts of the polynucleotides and/or polypeptides provided herein. Such salts may be prepared from pharmaceutically acceptable non-toxic bases, including organic bases (e.g., salts of primary, secondary and tertiary amines and basic amino acids) and inorganic bases (e.g., sodium, potassium, lithium, ammonium, calcium and magnesium salts).While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, bacteriostats, chelating agents such as EDTA or glutathione, adjuvants (e.g., aluminum hydroxide), solutes that render the formulation isotonic, hypotonic or weakly hypertonic with the blood of a recipient, suspending agents, thickening agents and/or preservatives. Alternatively, compositions of the present invention may be formulated as a lyophilizate. Compounds may also be encapsulated within liposomes using well known technology.

Any of a variety of immunostimulants may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.); Merck Adjuvant 65 (Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF or interleukin-2, -7, or -12, may also be used as adjuvants.

Within the vaccines provided herein, under select circumstances, the adjuvant composition may be designed to induce an immune response predominantly of the Th1 type or Th2 type. High levels of Th1-type cytokines (e.g., IFN-$\gamma$, TNF$\alpha$, IL-2 and IL-12) tend to favor the induction of cell mediated immune responses to an administered antigen. In contrast, high levels of Th2-type cytokines (e.g., IL-4, IL-5, IL-6 and IL-10) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Corixa Corporation (Seattle, Wash.; see U.S. Pat. Nos. 4,436,727; 4,877,611; 4,866,034 and 4,912,094). CpG-containing oligonucleotides (in which the CpG dinucleotide is unmethylated) also induce a predominantly Th1 response. Such oligonucleotides are well known and are described, for example, in WO 96/02555 and WO 99/33488. Immunostimulatory DNA sequences are also described, for example, by Sato et al., *Science* 273:352, 1996. Another preferred adjuvant is a saponin, preferably QS21 (Aquila Biopharmaceuticals Inc., Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprise an oil-in-water emulsion and tocopherol. A particularly potent adjuvant formulation involving QS21, 3D-MPL and tocopherol in an oil-in-water emulsion is described in WO 95/17210.

Other preferred adjuvants include Montanide ISA 720 (Seppic, France), SAF (Chiron, Calif., United States), ISCOMS (CSL), MF-59 (Chiron), the SBAS series of adjuvants (e.g., SBAS-2 or SBAS-4, available from SmithKline Beecham, Rixensart, Belgium), Detox (Corixa Corporation; Seattle, Wash.), RC-529 (Corixa Corporation; Seattle, Wash.) and other aminoalkyl glucosaminide 4-phosphates (AGPs), such as those described in pending U.S. patent application Ser. Nos. 08/853,826 and 09/074,720, the disclosures of which are incorporated herein by reference in their entireties.

Any vaccine provided herein may be prepared using well known methods that result in a combination of antigen, immunostimulant and a suitable carrier or excipient. The compositions described herein may be administered as part of a sustained release formulation (i.e., a formulation such as a capsule, sponge or gel (composed of polysaccharides, for example) that effects a slow release of compound following administration). Such formulations may generally be prepared using well known technology (see, e.g., Coombes et al., *Vaccine* 14:1429–1438, 1996) and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane.

Carriers for use within such formulations are biocompatible, and may also be biodegradable; preferably the formulation provides a relatively constant level of active component release. Such carriers include microparticles of poly(lactide-co-glycolide), as well as polyacrylate, latex, starch, cellulose and dextran. Other delayed-release carriers include supramolecular biovectors, which comprise a non-liquid hydrophilic core (e.g., a cross-linked polysaccharide or oligosaccharide) and, optionally, an external layer comprising an amphiphilic compound, such as a phospholipid (see e.g., U.S. Pat. No. 5,151,254 and PCT applications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets Chlamydia-infected cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-Chlamydia effects per se and/or to be immunologically compatible with the receiver (i.e., matched HLA haplotype). APCs may generally be isolated from any of a variety of biological fluids and organs, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro), their ability to take up, process and present antigens with high efficiency, and their ability to activate naive T cell responses. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med.* 4:594–600, 1998).

Dendritic cells and progenitors may be obtained from peripheral blood, bone marrow, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce differentiation, maturation and proliferation of dendritic cells.

Dendritic cells are conveniently categorized as "immature" and "mature" cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor and mannose receptor. The mature phenotype is typically characterized by a lower expression of these markers, but a high expression of cell surface molecules responsible for T cell activation such as class I and class II MHC, adhesion molecules (e.g., CD54 and CD 11) and costimulatory molecules (e.g., CD40, CD80, CD86 and 4-1BB).

APCs may generally be transfected with a polynucleotide encoding a Chlamydial protein (or portion or other variant thereof) such that the Chlamydial polypeptide, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the Chlamydial polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Routes and frequency of administration of pharmaceutical compositions and vaccines, as well as dosage, will vary from individual to individual. In general, the pharmaceutical compositions and vaccines may be administered by injection (e.g., intracutaneous, intramuscular, intravenous or subcutaneous), intranasally (e.g., by aspiration) or orally. Between 1 and 3 doses may be administered for a 1–36 week period. Preferably, 3 doses are administered, at intervals of 3–4 months, and booster vaccinations may be given periodically thereafter. Alternate protocols may be appropriate for individual patients. A suitable dose is an amount of polypeptide or DNA that, when administered as described above, is capable of raising an immune response in an immunized patient sufficient to protect the patient from Chlamydial infection for at least 1–2 years. In general, the amount of polypeptide present in a dose (or produced in situ by the DNA in a dose) ranges from about 1 pg to about 100 mg per kg of host, typically from about 10 pg to about 1 mg, and preferably from about 100 pg to about 1 µg. Suitable dose sizes will vary with the size of the patient, but will typically range from about 0.1 mL to about 5 mL.

While any suitable carrier known to those of ordinary skill in the art may be employed in the pharmaceutical compositions of this invention, the type of carrier will vary depending on the mode of administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactic galactide) may also be employed as carriers for the pharmaceutical compositions of this invention. Suitable biodegradable microspheres are disclosed, for example, in U.S. Pat. Nos. 4,897,268 and 5,075,109.

In general, an appropriate dosage and treatment regimen provides the active compound(s) in an amount sufficient to provide therapeutic and/or prophylactic benefit. Such a response can be monitored by establishing an improved clinical outcome in treated patients as compared to non-treated patients. Increases in preexisting immune responses to a Chlamydial protein generally correlate with an improved clinical outcome. Such immune responses may generally be evaluated using standard proliferation, cytotoxicity or cytokine assays, which may be performed using samples obtained from a patient before and after treatment.

In another aspect, the present invention provides methods for using the polypeptides described above to diagnose Chlamydial infection. In this aspect, methods are provided for detecting Chlamydial infection in a biological sample, using one or more of the above polypeptides, either alone or in combination. For clarity, the term "polypeptide" will be used when describing specific embodiments of the inventive diagnostic methods. However, it will be clear to one of skill in the art that the fusion proteins of the present invention may also be employed in such methods.

As used herein, a "biological sample" is any antibody-containing sample obtained from a patient. Preferably, the sample is whole blood, sputum, serum, plasma, saliva, cerebrospinal fluid or urine. More preferably, the sample is a blood, serum or plasma sample obtained from a patient. The polypeptides are used in an assay, as described below, to determine the presence or absence of antibodies to the polypeptide(s) in the sample, relative to a predetermined cut-off value. The presence of such antibodies indicates previous sensitization to Chlamydia antigens which may be indicative of Chlamydia-infection.

In embodiments in which more than one polypeptide is employed, the polypeptides used are preferably complementary (i.e., one component polypeptide will tend to detect infection in samples where the infection would not be detected by another component polypeptide). Complementary polypeptides may generally be identified by using each polypeptide individually to evaluate serum samples obtained from a series of patients known to be infected with Chlamydia. After determining which samples test positive (as described below) with each polypeptide, combinations of two or more polypeptides may be formulated that are capable of detecting infection in most, or all, of the samples tested.

A variety of assay formats are known to those of ordinary skill in the art for using one or more polypeptides to detect antibodies in a sample. See, e.g., Harlow and Lane, *Antibodies: A Laboratory Manual*, Cold Spring Harbor Laboratory, 1988, which is incorporated herein by reference. In a preferred embodiment, the assay involves the use of polypeptide immobilized on a solid support to bind to and remove the antibody from the sample. The bound antibody may then be detected using a detection reagent that contains a reporter group. Suitable detection reagents include antibodies that bind to the antibody/polypeptide complex and free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide.

The solid support may be any solid material known to those of ordinary skill in the art to which the antigen may be attached. For example, the solid support may be a test well in a microtiter plate, or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681.

The polypeptides may be bound to the solid support using a variety of techniques known to those of ordinary skill in the art. In the context of the present invention, the term "bound" refers to both noncovalent association, such as adsorption, and covalent attachment (which may be a direct linkage between the antigen and functional groups on the support or may be a linkage by way of a cross-linking agent). Binding by adsorption to a well in a microtiter plate or to a membrane is preferred. In such cases, adsorption may be achieved by contacting the polypeptide, in a suitable buffer, with the solid support for a suitable amount of time. The contact time varies with temperature, but is typically between about 1 hour and 1 day. In general, contacting a well of a plastic microtiter plate (such as polystyrene or polyvinylchloride) with an amount of polypeptide ranging from about 10 ng to about 1 µg, and preferably about 100 ng, is sufficient to bind an adequate amount of antigen.

Covalent attachment of polypeptide to a solid support may generally be achieved by first reacting the support with a bifunctional reagent that will react with both the support and a functional group, such as a hydroxyl or amino group, on the polypeptide. For example, the polypeptide may be bound to supports having an appropriate polymer coating using benzoquinone or by condensation of an aldehyde group on the support with an amine and an active hydrogen on the polypeptide (see, e.g., Pierce Immunotechnology Catalog and Handbook, 1991, at A12–A13).

In certain embodiments, the assay is an enzyme linked immunosorbent assay (ELISA). This assay may be performed by first contacting a polypeptide antigen that has been immobilized on a solid support, commonly the well of a microtiter plate, with the sample, such that antibodies to the polypeptide within the sample are allowed to bind to the immobilized polypeptide. Unbound sample is then removed from the immobilized polypeptide and a detection reagent capable of binding to the immobilized antibody-polypeptide complex is added. The amount of detection reagent that remains bound to the solid support is then determined using a method appropriate for the specific detection reagent.

More specifically, once the polypeptide is immobilized on the support as described above, the remaining protein binding sites on the support are typically blocked. Any suitable blocking agent known to those of ordinary skill in the art, such as bovine serum albumin (BSA) or Tween 20™ (Sigma Chemical Co., St. Louis, Mo.) may be employed. The immobilized polypeptide is then incubated with the sample, and antibody is allowed to bind to the antigen. The sample may be diluted with a suitable diluent, such as phosphate-buffered saline (PBS) prior to incubation. In general, an appropriate contact time (i.e., incubation time) is that period of time that is sufficient to detect the presence of antibody within an HGE-infected sample. Preferably, the contact time is sufficient to achieve a level of binding that is at least 95% of that achieved at equilibrium between bound and unbound antibody. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. Detection reagent may then be added to the solid support. An appropriate detection reagent is any compound that binds to the immobilized antibody-polypeptide complex and that can be detected by any of a variety of means known to those in the art. Preferably, the detection reagent contains a binding agent (such as, for example, Protein A, Protein G, immunoglobulin, lectin or free antigen) conjugated to a reporter group. Preferred reporter groups include enzymes (such as horseradish peroxidase), substrates, cofactors, inhibitors, dyes, radionuclides, luminescent groups, fluorescent groups and biotin. The conjugation of binding agent to reporter group may be achieved using standard methods known to those of ordinary skill in the art. Common binding agents may also be purchased conjugated to a variety of reporter groups from many commercial sources (e.g., Zymed Laboratories, San Francisco, Calif., and Pierce, Rockford, Ill.).

The detection reagent is then incubated with the immobilized antibody-polypeptide complex for an amount of time sufficient to detect the bound antibody. An appropriate amount of time may generally be determined from the manufacturer's instructions or by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of anti-Chlamydia antibodies in the sample, the signal detected from the reporter group that remains bound to the solid support is generally compared to a signal that corresponds to a predetermined cut-off value. In one preferred embodiment, the cut-off value is the average mean signal obtained when the immobilized antigen is incubated with samples from an uninfected patient. In general, a sample generating a signal that is three standard deviations above the predetermined cut-off value is considered positive for Chlamydia-infection. In an alternate preferred embodiment, the cut-off value is determined using a Receiver Operator Curve, according to the method of Sackett et al., *Clinical Epidemiology: A Basic Science for Clinical Medicine,* Little Brown and Co., 1985, pp. 106–107. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for Chlamydial infection.

In a related embodiment, the assay is performed in a rapid flow-through or strip test format, wherein the antigen is immobilized on a membrane, such as nitrocellulose. In the flow-through test, antibodies within the sample bind to the immobilized polypeptide as the sample passes through the membrane. A detection reagent (e.g., protein A-colloidal gold) then binds to the antibody-polypeptide complex as the solution containing the detection reagent flows through the membrane. The detection of bound detection reagent may then be performed as described above. In the strip test format, one end of the membrane to which polypeptide is bound is immersed in a solution containing the sample. The sample migrates along the membrane through a region containing detection reagent and to the area of immobilized polypeptide. Concentration of detection reagent at the polypeptide indicates the presence of anti-Chlamydia antibodies in the sample. Typically, the concentration of detection reagent at that site generates a pattern, such as a line, that can be read visually. The absence of such a pattern indicates a negative result. In general, the amount of polypeptide immobilized on the membrane is selected to generate a visually discernible pattern when the biological sample contains a level of antibodies that would be sufficient to generate a positive signal in an ELISA, as discussed above. Preferably, the amount of polypeptide immobilized on the membrane ranges from about 25 ng to about 1 μg, and more preferably from about 50 ng to about 500 ng. Such tests can typically be performed with a very small amount (e.g., one drop) of patient serum or blood.

Of course, numerous other assay protocols exist that are suitable for use with the polypeptides of the present invention. The above descriptions are intended to be exemplary only. One example of an alternative assay protocol which may be usefully employed in such methods is a Western blot, wherein the proteins present in a biological sample are separated on a gel, prior to exposure to a binding agent. Such techniques are well known to those of skill in the art.

The present invention further provides agents, such as antibodies and antigen-binding fragments thereof, that specifically bind to a Chlamydial protein. As used herein, an antibody, or antigen-binding fragment thereof, is said to "specifically bind" to a Chlamydial protein if it reacts at a detectable level (within, for example, an ELISA) with a Chlamydial protein, and does not react detectably with unrelated proteins under similar conditions. As used herein, "binding" refers to a noncovalent association between two separate molecules such that a complex is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant may be determined using methods well known in the art.

Binding agents may be further capable of differentiating between patients with and without a Chlamydial infection using the representative assays provided herein. In other words, antibodies or other binding agents that bind to a Chlamydial protein will generate a signal indicating the presence of a Chlamydial infection in at least about 20% of patients with the disease, and will generate a negative signal indicating the absence of the disease in at least about 90% of individuals without infection. To determine whether a binding agent satisfies this requirement, biological samples (e.g., blood, sera, sputum urine and/or tissue biopsies) from patients with and without Chlamydial infection (as determined using standard clinical tests) may be assayed as described herein for the presence of polypeptides that bind to the binding agent. It will be apparent that a statistically significant number of samples with and without the disease should be assayed. Each binding agent should satisfy the above criteria; however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual,* Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual,* Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in site-specific regions by appropriate methods. It will be evident that the precise dose of the antibody/immunoconjugate will vary depending upon the antibody used, the antigen density, and the rate of clearance of the antibody.

Antibodies may be used in diagnostic tests to detect the presence of Chlamydia antigens using assays similar to those detailed above and other techniques well known to those of skill in the art, thereby providing a method for detecting Chlamydial infection in a patient.

Diagnostic reagents of the present invention may also comprise DNA sequences encoding one or more of the above polypeptides, or one or more portions thereof. For example, at least two oligonucleotide primers may be employed in a polymerase chain reaction (PCR) based assay to amplify Chlamydia-specific cDNA derived from a biological sample, wherein at least one of the oligonucleotide primers is specific for a DNA molecule encoding a polypeptide of the present invention. The presence of the amplified cDNA is then detected using techniques well known in the art, such as gel electrophoresis. Similarly, oligonucleotide probes specific for a DNA molecule encoding a polypeptide of the present invention may be used in a hybridization assay to detect the presence of an inventive polypeptide in a biological sample.

As used herein, the term "oligonucleotide primer/probe specific for a DNA molecule" means an oligonucleotide sequence that has at least about 80%, preferably at least about 90% and more preferably at least about 95%, identity to the DNA molecule in question. Oligonucleotide primers and/or probes which may be usefully employed in the inventive diagnostic methods preferably have at least about 10–40 nucleotides. In a preferred embodiment, the oligonucleotide primers comprise at least about 10 contiguous nucleotides of a DNA molecule encoding one of the polypeptides disclosed herein. Preferably, oligonucleotide probes for use in the inventive diagnostic methods comprise at least about 15 contiguous oligonucleotides of a DNA molecule encoding one of the polypeptides disclosed herein. Techniques for both PCR based assays and hybridization assays are well known in the art (see, for example, Mullis et al. Ibid; Ehrlich, Ibid). Primers or probes may thus be used to detect Chlamydia-specific sequences in biological samples. DNA probes or primers comprising oligonucleotide sequences described above may be used alone or in combination with each other.

The following Examples are offered by way of illustration and not by way of limitation.

EXAMPLE 1

Isolation o DNA Sequences Encoding Chlamydia Antigens

Chlamydia antigens of the present invention were isolated by expression cloning of a genomic DNA library of *Chlamydia trachomatis* LGV II essentially as described by Sanderson et al. (*J. Exp. Med.,* 1995, 182:1751–1757) and were shown to induce PBMC proliferation and IFN-γ in an immunoreactive T cell line.

A Chlamydia-specific T cell line was generated by stimulating PBMCs from a normal donor with no history of chlamydial genital tract infection with elementary bodies of *Chlamydia trachomatis* LGV II. This T cell line, referred to as TCL-8, was found to recognize both *Chlamydia trachomatis* and *Chlamydia pneumonia* infected monocyte-derived dendritic cells.

A randomly sheared genomic library of *Chlamydia trachomatis* LGV II was constructed in Lambda ZAP (Stratagene, La Jolla, Calif.) and the amplified library plated out in 96 well microtiter plates at a density of 30 clones/well. Bacteria were induced to express recombinant protein in the presence of 2 mM IPTG for 3 h, then pelleted and resuspended in 200 μl of RPMI 10% FBS. 10 μl of the induced bacterial suspension was transferred to 96 well plates containing autologous monocyte-derived dendritic cells. After a 2 h incubation, dendritic cells were washed to remove free *E. coli* and Chlamydia-specific T cells were added. Positive *E. coli* pools were identified by determining IFN-γ production and proliferation of the T cells in response to the pools.

Four positive pools were identified, which were broken down to yield four pure clones (referred to as 1-B1-66, 4-D7-28, 3-G3-10 and 10-C10-31), with insert sizes of 481 bp, 183 bp, 110 bp and 1400 bp, respectively. The determined DNA sequences for 1-B1-66, 4-D7-29, 3-G3-10 and 10-C10-31 are provided in SEQ ID NO: 1–4, respectively. Clone 1-B1-66 is approximately in region 536690 of the *C. trachomatis* genome (NCBI *C. trachomatis* database). Within clone 1-B1-66, an open reading frame (ORF) has been identified (nucleotides 115–375) that encodes a previously identified 9 kDa protein (Stephens, et al. Genbank Accession No. AE001320), the sequence of which is provided in SEQ ID NO: 5). Clone 4-D7-28 is a smaller region of the same ORF (amino acids 22–82 of 1-B1-66). Clone 3-G3-10 is approximately in region 74559 of the *C. trachomatis* genome. The insert is cloned in the antisense orientation with respect to its orientation in the genome. The clone 10-C10-31 contains an open reading frame that corresponds to a previously published sequence for S13 ribosomal protein from *Chlamydia trachomatis* (Gu, L. et al. *J. Bacteriology,* 177:2594–2601, 1995). The predicted protein sequences for 4-D7-28 and 10-C10-31 are provided in SEQ ID NO: 6 and 12, respectively. Predicted protein sequences for 3-G3-10 are provided in SEQ ID NO: 7–11.

In a related series of screening studies, an additional T cell line was used to screen the genomic DNA library of *Chlamydia trachomatis* LGV II described above. A Chlamydia-specific T cell line (TCT-1) was derived from a patient with a chlamydial genital tract infection by stimulating patient PBMC with autologous monocyte-derived dendritic cells infected with elementary bodies of *Chlamydia trachomatis* LGV II. One clone, 4C9-18 (SEQ ID NO: 21), containing a 1256 bp insert, elicited a specific immune response, as measured by standard proliferation assays, from the Chlamydia-specific T cell line TCT-1. Subsequent analysis revealed this clone to contain three known sequences: lipoamide dehydrogenase (Genbank Accession No. AE001326), disclosed in SEQ ID NO: 22; a hypothetical protein CT429 (Genbank Accession No. AE001316), disclosed in SEQ ID NO: 23; and part of an open reading frame of ubiquinone methyltransferase CT428 (Genbank Accession No. AE001316), disclosed in SEQ ID NO: 24.

In further studies involving clone 4C9-18 (SEQ ID NO: 21), the full-length amino acid sequence for lipoamide dehydrognase (SEQ ID NO: 22) from *C. trachomatis* (LGV II) was expressed in clone CtL2-LPDA-FL, as disclosed in SEQ ID NO: 90.

To further characterize the open reading frame containing the T cell stimulating epitope(s), a cDNA fragment containing nucleotides 1–695 of clone 4C9-18 with a cDNA sequence encoding a 6x-Histidine tag on the amino terminus was subcloned into the NdeI/EcoRI site of the pET17b vector (Novagen, Madison, Wis.), referred to as clone 4C9-18#2 BL21 pLysS (SEQ ID NO: 25, with the corresponding amino acid sequence provided in SEQ ID NO: 26) and transformed into E. coli. Selective induction of the transformed E. coli with 2 mM IPTG for three hours resulted in the expression of a 26 kDa protein from clone 4C9-18#2 BL21 pLysS, as evidenced by standard Coomassie-stained SDS-PAGE. To determine the immunogenicity of the protein encoded by clone 4C9-18#2 BL21 pLysS, E. coli expressing the 26 kDa protein were titered onto $1 \times 10^4$ monocyte-derived dendritic cells and incubated for two hours. The dendritic cell cultures were washed and $2.5 \times 10^4$ T cells (TCT-1) added and allowed to incubate for an additional 72 hours, at which time the level of IFN-γ in the culture supernatant was determined by ELISA. As shown in FIG. 1, the T-cell line TCT-1 was found to respond to induced cultures as measured by IFN-g, indicating a Chlamydia-specific T-cell response against the lipoamide dehydrogenase sequence, Similarly, the protein encoded by clone 4C9-18#2 BL21 pLysS was shown to stimulate the TCT-1 T-cell line by standard proliferation assays.

Subsequent studies to identify additional *Chlamydia trachomatis* antigens using the above-described CD4+ T-cell expression cloning technique yielded additional clones. The TCT-1 and TCL-8 Chlamydia-specific T-cell lines, as well as the TCP-21 T-cell line were utilized to screen the *Chlamydia trachomatis* LGVII genomic library. The TCP-21 T-cell line was derived from a patient having a humoral immune response to *Chlamydia pnuemoniae.* The TCT-1 cell line identified 37 positive pools, the TCT-3 cell line identified 41 positive pools and the TCP-21 cell line identified 2 positive pools. The following clones were derived from 10 of these positive pools. Clone 11-A3-93 (SEQ ID NO: 64), identified by the TCP-21 cell line, is a 1339 bp genomic fragment sharing homology to the HAD superfamily (CT103). The second insert in the same clone shares homology with the fab I gene (CT104) present on the complementary strand. Clone 11-C12-91 (SEQ ID NO: 63), identified using the TCP-21 cell line, has a 269 bp insert that is part of the OMP2 gene (CT443) and shares homology with the 60 kDa cysteine rich outer membrane protein of *C. pnuemoniae.*

Clone 11-G10-46, (SEQ ID NO: 62), identified using the TCT-3 cell line, contains a 688 bp insert that shares homology to the hypothetical protein CT610. Clone 11-G1-34, (SEQ ID NO: 61), identified using the TCT-3 cell line, has two partial open reading frames (ORF) with an insert size of 1215 bp. One ORF shares homology to the malate dehydrogenase gene (CT376), and the other ORF shares homology to the glycogen hydrolase gene (CT042). Clone 11-H3-68, (SEQ ID NO: 60), identified using the TCT-3 cell line, has two ORFs with a total insert size of 1180 bp. One partial ORF encodes the plasmid-encoded PGP6-D virulence protein while the second ORF is a complete ORF for the L1 ribosomal gene (CT318). Clone 11-H4-28, (SEQ ID NO: 59), identified using the TCT-3 cell line, has an insert size of 552 bp and is part of the ORF for the dnaK gene (CT396). Clone 12-B3-95, (SEQ ID NO: 58), identified using the TCT-1 cell line, has an insert size of 463 bp and is a part of the ORF for the lipoamide dehydrogenase gene (CT557). Clones 15-G1-89 and 12-B3-95 are identical, (SEQ ID NO: 55 and 58, respectively), identified using the TCT-1 cell line, has an insert size of 463 bp and is part of the ORF for the lipoamide dehydrogenase gene (CT557). Clone 12-G3-83, (SEQ ID NO: 57), identified using the TCT-1 cell line, has an insert size of 1537 bp and has part of the ORF for the hypothetical protein CT622.

Clone 23-G7-68, (SEQ ID NO: 79), identified using the TCT-3 cell line, contains a 950 bp insert and contains a small part of the L11 ribosomal ORF, the entire ORF for L1 ribosomal protein and a part of the ORF for L10 ribosomal protein. Clone 22-F 8-91, (SEQ ID NO: 80), identified using the TCT-1 cell line, contains a 395 bp insert that contains a part of the pmpC ORF on the complementary strand of the clone. Clone 21-E8-95, (SEQ ID NO: 81), identified using the TCT-3 cell line, contains a 2,085 bp insert which contains part of CT613 ORF, the complete ORF for CT612, the complete ORF for CT611 and part of the ORF for CT610. Clone 19-F12-57, (SEQ ID NO: 82), identified using the TCT-3 cell line, contains a 405 bp insert which contains part of the CT 858 ORF and a small part of the recA ORF. Clone 19-F12-53, (SEQ ID NO: 83), identified using the TCT-3 cell line, contains a 379 bp insert that is part of the ORF for CT455 encoding glutamyl tRNA synthetase. Clone 19-A5-54, (SEQ ID NO: 84), identified using the TCT-3 cell line, contains a 715 bp insert that is part of the ORF3 (complementary strand of the clone) of the cryptic plasmid. Clone 17-E11-72, (SEQ ID NO: 85), identified using the TCT-1 cell line, contains a 476 bp insert that is part of the ORF for Opp__2 and pmpD. The pmpD region of this clone is covered by the pmpD region of clone 15-H2-76. Clone 17-C1-77, (SEQ ID NO: 86), identified using the TCT-3 cell line, contains a 1551 bp insert that is part of the CT857 ORF, as well as part of the CT858 ORF. Clone 15-H2-76, (SEQ ID NO: 87), identified using the TCT-1 cell line, contains a 3,031 bp insert that contains a large part of the pmpD ORF, part of the CT089 ORF, as well as part of the ORF for SycE. Clone 15-A3–26, (SEQ ID NO: 88), contains a 976 bp insert that contains part of the ORF for CT858. Clone 17-G4-36, (SEQ ID NO: 267), identified using the TCT-10 cell line, contains a 680 bp insert that is in frame with beta-gal in the plasmid and shares homology to part of the ORF for DNA-directed RNA polymerase beta subunit (CT315 in SerD).

Several of the clones described above share homology to various polymorphic membrane proteins. The genomic sequence of *Chlamydia trachomatis* contains a family of nine polymorphic membrane protein genes, referred to as pmp. These genes are designated pmpA, pmpB, pmpC, pmpD, pmpE, pmpF, pmpG, pmpH and pmpI. Proteins expressed from these genes are believed to be of biological relevance in generating a protective immune response to a Chlamydial infection. In particular, pmpC, pmpD, pmpE and pmpI contain predictable signal peptides, suggesting they are outer membrane proteins, and therefore, potential immunological targets.

Based on the *Chlamydia trachomatis* LGVII serovar sequence, primer pairs were designed to PCR amplify the full-length fragments of pmpC, pmpD, pmpE, pmpG, pmpH and pmpI. The resulting fragments were subcloned into the DNA vaccine vector JA4304 or JAL, which is JA4304 with a modified linker (SmithKline Beecham, London, England). Specifically, PmpC was subcloned into the JAL vector using the 5' oligo GAT AGG CGC GCC GCA ATC ATG AAA TTT ATG TCA GCT ACT GCT G and the 3' oligo CAG AAC GCG TTT AGA ATG TCA TAC GAG CAC CGC A, as provided in SEQ ID NO: 197 and 198, respectively. PCR amplification of the gene under conditions well known in the art and ligation into the 5' ASCI/13' Mlul sites of the JAL vector was completed after inserting the short nucleotide sequence GCAATC (SEQ ID NO: 199) upstream of the ATG to create a Kozak-like sequence. The resulting expression vector contained the full-length pmpC gene comprising 5325 nucleotides (SEQ ID NO: 173) containing the hypothetical signal sequence, which encodes a 187 kD protein (SEQ ID NO: 179). The pmpD gene was subcloned into the JA4304 vaccine vector following PCR amplification of the gene using the following oligos: 5' oligo-TGC AAT CAT GAG TTC GCA GAA AGA TAT AAA AAG C (SEQ ID NO: 200) and 3' oligo-CAG AGC TAG CTT AAA AGA TCA ATC GCA ATC CAG TAT TC (SEQ ID NO: 201). The gene was ligated into the a 5' blunted HIII/3' Ml uI site of the JA4304 vaccine vector using standard techniques well known in the art. The CAATC (SEQ ID NO: 202) was inserted upstream of the ATG to create a Kozak-like sequence. This clone is unique in that the last threonine of the HindIII site is missing due to the blunting procedure, as is the last glycine of the Kozak-like sequence. The insert, a 4593 nucleotide fragment (SEQ ID NO: 172) is the full-length gene for pmpD containing the hypothetical signal sequence, which encodes a 161 kD protein (SEQ ID NO: 178). PmpE was subcloned into the JA4304 vector using the 5' oligo-TGC AAT CAT GAA AAA AGC GTT TTT CTT TTT C (SEQ ID NO: 203), and the 3' oligo-CAG AAC GCG TCT AGA ATC GCA GAG CAA TTT C (SEQ ID NO: 204). Following PCR amplification, the gene was ligated into the 5' blunted HIII/3' Ml uI site of JA4304. To facilitate this, a short nucleotide sequence, TGCAATC (SEQ ID NO: 293), was added upstream of the initiation codon for creating a Kozak-like sequence and reconstituting the HindIII site. The insert is the full-length pmpE gene (SEQ ID NO: 171) containing the hypothetical signal sequence. The pmpE gene encodes a 105 kD protein (SEQ ID NO: 177). The pmpG gene was PCR amplified using the 5' oligo-GTG CAA TCA TGA TTC CTC AAG GAA TTT ACG ( SEQ ID NO: 205), and the 3' oligo-CAG AAC GCG TTT AGA ACC GGA CTT TAC TTC C (SEQ ID NO: 206) and subcloned into the JA4304 vector. Similar cloning strategies were followed for the pmpI and pmpK genes. In addition, primer pairs were designed to PCR amplify the fill-length or overlapping fragments of the pmp genes, which were then subcloned for protein expression in the pET17b vector (Novagen, Madison, Wis.) and transfected into E. coli BL21 pLysS for expression and subsequent purification utilizing the histidine-nickel chromatographic methodology provided by Novagen. Several of the genes encoding the recombinant proteins, as described below, lack the native signal sequence to facilitate expression of the protein. Full-length protein expression of pmpC was accomplished through expression of two overlapping fragments, representing the amino and carboxy termini. Subcloning of the pmpC-amino terminal portion, which lacks the signal sequence, (SEQ ID NO: 187, with the corresponding amino acid sequence provided in SEQ ID NO: 195) used the 5' oligo-CAG ACA TAT GCA TCA CCA TCA CCA TCA CGA GGC GAG CTC GAT CCA AGA TC (SEQ ID NO: 207), and the 3' oligo-CAG AGG TAC CTC AGA TAG CAC TCT CTC CTA TTA AAG TAG G (SEQ ID NO: 208) into the 5' NdeI/3' KPN cloning site of the vector. The carboxy terminus portion of the gene, pmpC-carboxy terminal fragment (SEQ ID NO: 186, with the corresponding amino acid sequence provided in SEQ ID NO: 194), was subcloned into the 5' NheI/3' KPN cloning site of the expression vector using the following primers: 5' oligo-CAG AGC TAG CAT GCA TCA CCA TCA CCA TCA CGT TAA GAT TGA GAA CTT CTC TGG C (SEQ ID NO: 209), and 3' oligo-CAG AGG TAC CTT AGA ATG TCA TAC GAG CAC CGC AG (SEQ ID NO: 210). PmpD was also expressed as two overlapping proteins. The pmpD-amino terminal portion, which lacks the signal sequence, (SEQ ID NO: 185, with the corresponding amino acid sequence provided in SEQ ID NO: 193) contains the initiating codon of the pET17b and is expressed as a 80 kD protein. For protein expression and purification purposes, a six-histidine tag follows the initiation codon and is fused at the 28$^{th}$ amino acid (nucleotide 84) of the gene. The following primers were used, 5' oligo, CAG ACA TAT GCA TCA CCA TCA CCA TCA CGG GTT AGC (SEQ ID NO: 211), and the 3' oligo-CAG AGG TAC CTC AGC TCC TCC AGC ACA CTC TCT TC (SEQ ID NO-212), to splice into the 5' NdeI/3' KPN cloning site of the vector. The pmpD-carboxy terminus portion (SEQ ID NO: 184) was expressed as a 92 kD protein (SEQ ID NO: 192). For expression and subsequent purification, an additional methionine, alanine and serine was included, which represent the initiation codon and the first two amino acids from the pET17b vector. A six-histidine tag downstream of the methionine, alanine and serine is fused at the 691$^{st}$ amino acid (nucleotide 2073) of the gene. The 5' oligo-CAG AGC TAG CCA TCA CCA TCA CCA TCA CGG TGC TAT TTC TTG CTT ACG TGG (SEQ ID NO: 213) and the 3' oligo-CAG AGG TAC TTn AAA AGA TCA ATC GCA ATC CAG TAT TCG (SEQ ID NO: 214) were used to subclone the insert into the 5' NheI/3' KPN cloning site of the expression vector. PmpE was expressed as a 106 kD protein (SEQ ID NO: 183 with the corresponding amino acid sequence provided in SEQ ID NO: 191). The pmpE insert also lacks the native signal sequence. PCR amplification of the gene under conditions well known in the art was performed using the following oligo primers: 5' oligo-CAG AGG ATC CAC ATC ACC ATC ACC ATC ACG GAC TAG CTA GAG AGG TTC (SEQ ID NO: 215), and the 3' oligo-CAG AGA ATT CCT AGA ATC GCA GAG CAA TTT C (SEQ ID NO: 216), and the amplified insert was ligated into a 5' BamHI/3' EcoRI site of JA4304. The short nucleotide sequence, as provided in SEQ ID NO: 217, was inserted upstream of the initiation codon for creating the Kozak-like sequence and reconstituting the HindIII site. The expressed protein contains the initiation codon and the downstream 21 amino acids from the pET17b expression vector, i.e., MASMTG-GQQMGRDSSLVPSSDP (SEQ ID NO: 218). In addition, a six-histidine tag is included upstream of the sequence described above and is fused at the 28$^{th}$ amino acid (nucleotide 84) of the gene, which eliminates the hypothetical signal peptide. The sequences provided in SEQ ID NO: 183 with the corresponding amino acid sequence provided in SEQ ID NO: 191 do not include these additional sequences. The pmpG gene (SEQ ID NO: 182, with the corresponding amino acid sequence provided in SEQ ID No; 190) was PCR amplified under conditions well known in the art using the following oligo primers: 5' oligo-CAG AGG TAC CGC ATC ACC ATC ACC ATC ACA TGA TTC CTC AAG GAA TTT ACG (SEQ ID NO: 219), and the 3' oligo-CAG AGC GGC CGC TTA GAA CCG GAC TTT ACT TCC (SEQ ID NO: 220), and ligated into the 5' KPN/3' NotI cloning site of the expression vector. The expressed protein contains an additional amino acid sequence at the amino end, namely, MASMTGGQQNGRDSSLVPHHHHHH (SEQ ID NO: 221), which comprises the initiation codon and additional sequence from the pET17b expression vector. The pmpI gene (SEQ ID NO-181, with the corresponding amino acid sequence provided in SEQ ID No; 189) was PCR amplified under conditions well known in the art using the following oligo primers: 5' oligo-CAG AGC TAG CCA TCA CCA TCA CCA TCA CCT CTT TGG CCA GGA TCC C (SEQ ID NO: 222), and the 3' oligo-CAG AAC TAG TCT AGA ACC TGT AAG TGG TCC (SEQ ID NO: 223), and ligated into the expression vector at the 5' NheI/3' SpeI cloning site. The 95 kD expressed protein contains the initiation codon plus an additional alanine and serine from the pET17b vector at the amino end of the protein. In addition, a six-histidine tag is fused at the 21 st amino acid of the gene, which eliminates the hypothetical signal peptide.

Clone 14H1-4, (SEQ ID NO: 56), identified using the TCT-3 cell line, contains a complete ORF for the TSA gene, thiol specific antioxidant—CT603 (the CT603 ORF is a homolog of CPn0778 from C. pnuemoniae). The TSA open reading frame in clone 14-H1-4 was amplified such that the expressed protein possess an additional methionine and a 6×histidine tag (amino terminal end). This amplified insert was sub-cloned into the Nde/EcoRI sites of the pET17b vector. Upon induction of this clone with IPTG, a 22.6 kDa protein was purified by Ni-NTA agarose affinity chromatography. The determined amino acid sequence for the 195 amino acid ORF of clone 14-H1-4 encoding the TSA gene is provided in SEQ ID NO: 65. Further analysis yielded a full-length clone for the TSA gene, referred to as CTL2-TSA-FL, with the full-length amino acid sequence provided in SEQ ID NO: 92.

Further studies yielded 10 additional clones identified by the TCT-1 and TCT-3 T-cell lines, as described above. The clones identified by the TCT-1 line are: 16-D4-22, 17-C5-19, 18-C5-2, 20-G3-45 and 21-C7-66; clones identified by the TCT line are: 17-C10-11, 17-E2-9, 22-A1-49 and 22-B3-53. Clone 21-G12-60 was recognized by both the TCT-1 and TCT-3 T cell lines. Clone 16-D4-22 (SEQ ID NO: 119), identified using the TCT-1 cell line contains a 953 bp insert that contains two genes, parts of open reading frame 3 (ORF3) and ORF4 of the *C. trachomatis* plasmid for growth within mammalian cells. Clone 17-C5-19 (SEQ ID NO: 118), contains a 951 bp insert that contains part of the ORF for DT43 1, encoding for clpP_1 protease and part of the ORF for CT430 (diaminopimelate epimerase). Clone 18-C5-2 (SEQ ID NO: 117) is part of the ORF for S1 ribosomal protein with a 446 bp insert that was identified using the TCT-1 cell line. Clone 20-G3-45 (SEQ ID NO: 116), identified by the TCT-1 cell line, contains a 437 bp insert that is part of the pmpB gene (CT413). Clone 21-C7-66 (SEQ ID NO: 115), identified by the TCT-1 line, contains a 995bp insert that encodes part of the dnaK like protein. The insert of this clone does not overlap with the insert of the TCT-3 clone 11-H4-28 (SEQ ID NO: 59), which was shown to be part of the dnaK gene CT396 Clone 17-C10-31 (SEQ ID NO: 114), identified by the TCT-3 cell line, contains a 976 bp insert. This clone contains part of the ORF for CT858, a protease containing IRBP and DHR domains. Clone 17-E2-9 (SEQ ID NO: 113) contains part of ORFs for two genes, CT611 and CT610, that span a 1142 bp insert. Clone 22-A1-49 (SEQ ID NO: 112), identified using the TCT-3 line, also contains two genes in a 698 bp insert. Part of the ORF for CT660 (DNA gyrase{gyrA_2}) is present on the top strand where as the complete ORF for a hypothetical protein CT659 is present on the complementary strand. Clone 22-B3-53 (SEQ ID NO: 111), identified by the TCT1 line, has a 267 bp insert that encodes part of the ORF for GroEL (CT110). Clone 21-G12-60 (SEQ ID NO: 110), identified by both the TCT-1 and TCT-3 cell lines contains a 1461 bp insert that contains partial ORFs for hypothetical proteins CT875, CT229 and CT228.

Additional Chlamydia antigens were obtained by screening a genomic expression library of *Chlamydia trachomatis* (LGV II serovar) in Lambda Screen-1 vector (Novagen, Madison, Wis.) with sera pooled from several Chlamydia-infected individuals using techniques well known in the art. The following immuno-reactive clones were identified and the inserts containing Chlamydia genes sequenced: CTL2#1 (SEQ ID NO: 71); CTL2#2 (SEQ ID NO: 70); CTL2#3-5' (SEQ ID NO: 72, a first determined genomic sequence representing the 5' end); CTL2#3-3' (SEQ ID NO: 73, a second determined genomic sequence representing the 3' end); CTL2#4 (SEQ ID NO: 53); CTL2#5 (SEQ ID NO: 69); CTL2#6 (SEQ ID NO: 68); CTL2#7 (SEQ ID NO: 67); CTL2#8b (SEQ ID NO: 54); CTL2#9 (SEQ ID NO: 66); CTL2#10-5' (SEQ ID NO: 74, a first determined genomic sequence representing the 5' end); CTL2#10-3' (SEQ ID NO: 75, a second determined genomic sequence representing the 3' end); CTL2#11-5' (SEQ ID NO: 45, a first determined genomic sequence representing the 5' end); CTL2#11-3' (SEQ ID NO: 44, a second determined genomic sequence representing the 3' end); CTL2#12 (SEQ ID NO: 46); CTL2#16-5' (SEQ ID NO: 47); CTL2#18-5' (SEQ ID NO: 49, a first determined genomic sequence representing the 5' end); CTL2#18-3' (SEQ ID NO: 48, a second determined genomic sequence representing the 3, end); CTL2#19-5' (SEQ ID NO: 76, the determined genomic sequence representing the 5' end); CTL2#21 (SEQ ID NO: 50); CTL2#23 (SEQ ID NO: 51; and CTL2#24 (SEQ ID NO: 52).

Additional *Chlamydia trachomatis* antigens were identified by serological expression cloning. These studies used sera pooled from several Chlamydia-infected individuals, as described above, but, IgA,and IgM antibodies were used in addition to IgG as a secondary antibody. Clones screened by this method enhance detection of antigens recognized by an early immune response to a Chlamydial infection, that is a mucosal humoral immune response. The following immunoreactive clones were characterized and the inserts containing Chlamydia genes sequenced: CTL2gam-1 (SEQ ID NO: 290), CTL2gam-2 (SEQ ID NO: 289), CTL2gam-5 (SEQ ID NO: 288), CTL2gam-6-3' (SEQ ID NO: 287, a second determined genomic sequence representing the 3' end), CTL2gam-6-5' (SEQ ID NO: 286, a first determined genomic sequence representing the 5' end), CTL2gam-8 (SEQ ID NO: 285), CTL2gam-10 (SEQ ID NO: 284), CTL2gam-13 (SEQ ID NO: 283), CTL2gam-15-3' (SEQ ID NO: 282, a second determined genomic sequence representing the 3' end), CTL2gam-15–5' (SEQ ID NO: 281, a first determined genomic sequence representing the 5' end), CTL2gam-17 (SEQ ID NO: 280), CTL2gam-18 (SEQ ID NO: 279), CTL2gam-21 (SEQ ID NO: 278), CTL2gam-23 (SEQ ID NO: 277), CTL2gam-24 (SEQ ID NO: 276), CTL2gam-26 (SEQ ID NO: 275), CTL2gam-27 (SEQ ID NO: 274), CTL2gam-28 (SEQ ID NO: 273), CTL2gam-30–3' (SEQ ID NO: 272, a second determined genomic sequence representing the 3' end) and CTL2gam-30-5' (SEQ ID NO: 271, a first determined genomic sequence representing the 5' end).

EXAMPLE 2

Induction of T Cell Proliferation and Interferon-γProduction by Chlamydia Trachomatis Antigens The ability of recombinant *Chlamydia trachomatis* antigens to induce T cell proliferation and interferon-γ production is determined as follows.

Proteins are induced by IPTG and purified by Ni-NTA agarose affinity chromatograph (Webb et al., *J. Immunology* 157:5034–5041, 1996). The purified polypeptides are then screened for the ability to induce T-cell proliferation in PBMC preparations. PBMCs from *C. trachomatis* patients as well as from normal donors whose T-cells are known to proliferate in response to Chlamydia antigens, are cultured in medium comprising RPMI 1640 supplemented with 10% pooled human serum and 50 µg/ml gentamicin. Purified polypeptides are added in duplicate at concentrations of 0.5 to 10 µg/mL. After six days of culture in 96-well round-bottom plates in a volume of 200 µl, 50 µl of medium is removed from each well for determination of IFN-γ levels, as described below The plates are then pulsed with 1 µCi/well of tritiated thymidine for a further 18 hours, harvested and tritium uptake determined using a gas scintillation counter. Fractions that result in proliferation in both replicates three fold greater than the proliferation observed in cells cultured in medium alone are considered positive.

IFN-γ is measured using an enzyme-linked immunosorbent assay (ELISA). ELISA plates are coated with a mouse monoclonal antibody directed to human IFNγ (PharMingen, San Diego, Calif.) in PBS for four hours at room temperature. Wells are then blocked with PBS containing 5% (W/V) non-fat dried milk for 1 hour at room temperature. The plates are washed six times in PBS/0.2% TWEEN-20 and samples diluted 1:2 in culture medium in the ELISA plates are incubated overnight at room temperature. The plates are again washed and a polyclonal rabbit anti-human IFN-γ serum diluted 1:3000 in PBS/10% normal goat serum is added to each well. The plates are then incubated for two hours at room temperature, washed and horseradish peroxidase-coupled anti-rabbit IgG (Sigma Chemical So., St. Louis, Mo.) is added at a 1:2000 dilution in PBS/5% non-fat dried milk. After a further two hour incubation at room temperature, the plates are washed and TMB substrate added. The reaction is stopped after 20 min with 1 N sulfuric acid. Optical density is determined at 450 nm using 570 nm as a reference wavelength. Fractions that result in both replicates giving an OD two fold greater than the mean OD from cells cultured in medium alone, plus 3 standard deviations, are considered positive.

Using the above methodology, recombinant 1B1-66 protein (SEQ ID NO: 5) as well as two synthetic peptides corresponding to amino acid residues 48–67 (SEQ ID NO: 13; referred to as 1-B1-66/48-67) and 58–77 (SEQ ID NO: 14, referred to as 1B1-66/58-77), respectively, of SEQ ID NO: 5, were found to induce a proliferative response and IFN-γ production in a Chlamydia-specific T cell line used to screen a genomic library of C. trachomatis LGV II.

Figure 8:
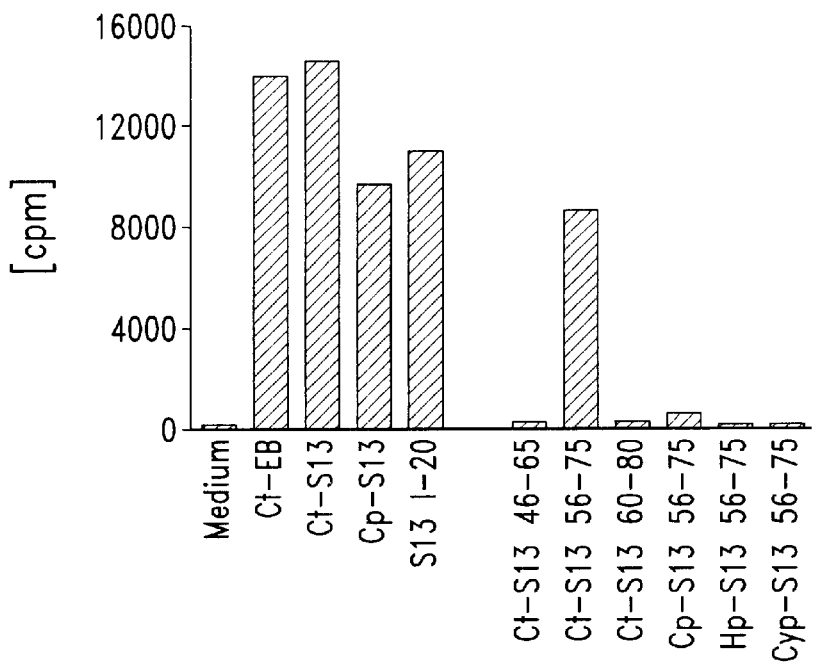

Further studies have identified a C. trachomatis-specific T-cell epitope in the ribosomal S13 protein. Employing standard epitope mapping techniques well known in the art, two T-cell epitopes in the ribosomal S13 protein (rS13) were identified with a Chlamydia-specific T-cell line from donor CL-8 (T-cell line TCL-8 EB/DC). FIG. 8 illustrates that the first peptide, rS13 1–20 (SEQ ID NO: 106), is 100% identical with the corresponding C. pneumoniae sequence, explaining the cross-reactivity of the T-cell line to recombinant C. trachomatis- and C. pneumoniae-rS13. The response to the second peptide rS13 56–75 (SEQ ID NO: 108) is C. trachomatis-specific, indicating that the rS13 response in this healthy asymptomatic donor was elicited by exposure to C. trachomatis and not to C. pneumoniae, or any other microbial infection.

As described in Example 1, Clone 11-C12-91 (SEQ ID NO: 63), identified using the TCP-21 cell line, has a 269 bp insert that is part of the OMP2 gene (CT443) and shares homology with the 60 kDa cysteine rich outer membrane protein of C. pneumoniae, referred to as OMCB. To further define the reactive epitope(s), epitope mapping was performed using a series of overlapping peptides and the immunoassay previously described. Briefly, proliferative responses were determined by stimulating $2.5 \times 10^4$ TCP-21 T-cells in the presence of $1 \times 10^4$ monocyte-derived dendritic cells with either non-infectious elementary bodies derived from C. trachomatis and C. pneumoniae, or peptides derived from the protein sequence of C. trachomatis or C. pneumoniae OMCB protein (0.1 µg/ml). The TCP-21 T-cells responded to epitopes CT-OMCB #167-186, CT-OMCB #171-190, CT-OMCB #171-186, and to a lesser extent, CT-OMCB #175-186 (SEQ ID NO: 249-252, respectively). Notably, the TCP-21 T-cell line also gave a proliferative response to the homologous C. pneumoniae peptide CP-OMCB #171-186 (SEQ ID NO. 253), which was equal to or greater than the response to the C. trachomatis peptides. The amino acid substitutions in position two (i.e., Asp for Glu) and position four (i.e., Cys for Ser) did not alter the proliferative response of the T-cells and therefore demonstrating this epitope to be a cross-reactive epitope between C. trachomatis and C. pneumoniae.

To further define the epitope described above, an additional T-cell line, TCT-3, was used in epitope mapping experiments. The immunoassays were performed as described above, except that only peptides from C. trachomatis were tested. The T-cells gave a proliferative response to two peptides, CT-OMCB #152-171 and CT-OMCB #157-176 (SEQ ID NO: 246 and 247, respectively), thereby defining an additional immunogenic epitope in the cysteine rich outer membrane protein of C. trachomatis.

Clone 14H1-4, (SEQ ID NO: 56, with the corresponding full-length amino acid sequence provided in SEQ ID NO: 92), was identified using the TCT-3 cell line in the CD4 T-cell expression cloning system previously described, and was shown to contain a complete ORF for the, thiol specific antioxidant gene (CT603), referred to as TSA. Epitope mapping immunoassays were performed, as described above, to further define the epitope. The TCT-3 T-cells line exhibited a strong proliferative response to the overlapping peptides CT-TSA #96-115, CT-TSA #101-120 and CT-TSA #106-125 (SEQ ID NO: 254–256, respectively) demonstrating an immunoreactive epitope in the thiol specific antioxidant gene of C. trachomatis serovar LGVII.

EXAMPLE 3

Preparation o Synthetic Polypeptides

Polypeptides may be synthesized on a Millipore 9050 peptide synthesizer using FMOC chemistry with HPTU (O-Benzotriazole-N,N,N',N'-tetramethyluronium hexafluorophosphate) activation. A Gly-Cys-Gly sequence may be attached to the amino terminus of the peptide to provide a method of conjugating or labeling of the peptide. Cleavage of the peptides from the solid support may be carried out using the following cleavage mixture: trifluoroacetic acid:ethanedithiol:thioanisole:water:phenol (40:1:2:2:3). After cleaving for 2 hours, the peptides may be precipitated in cold methyl-t-butyl-ether. The peptide pellets may then be dissolved in water containing 0.1% trifluoroacetic acid (TFA) and lyophilized prior to purification by C18 reverse phase HPLC. A gradient of 0-60% acetonitrile (containing 0.1% TFA) in water (containing 0.1% TFA) may be used to elute the peptides. Following lyophilization of the pure fractions, the peptides may be characterized using electrospray mass spectrometry and by amino acid analysis.

EXAMPLE 4

Figure 2:
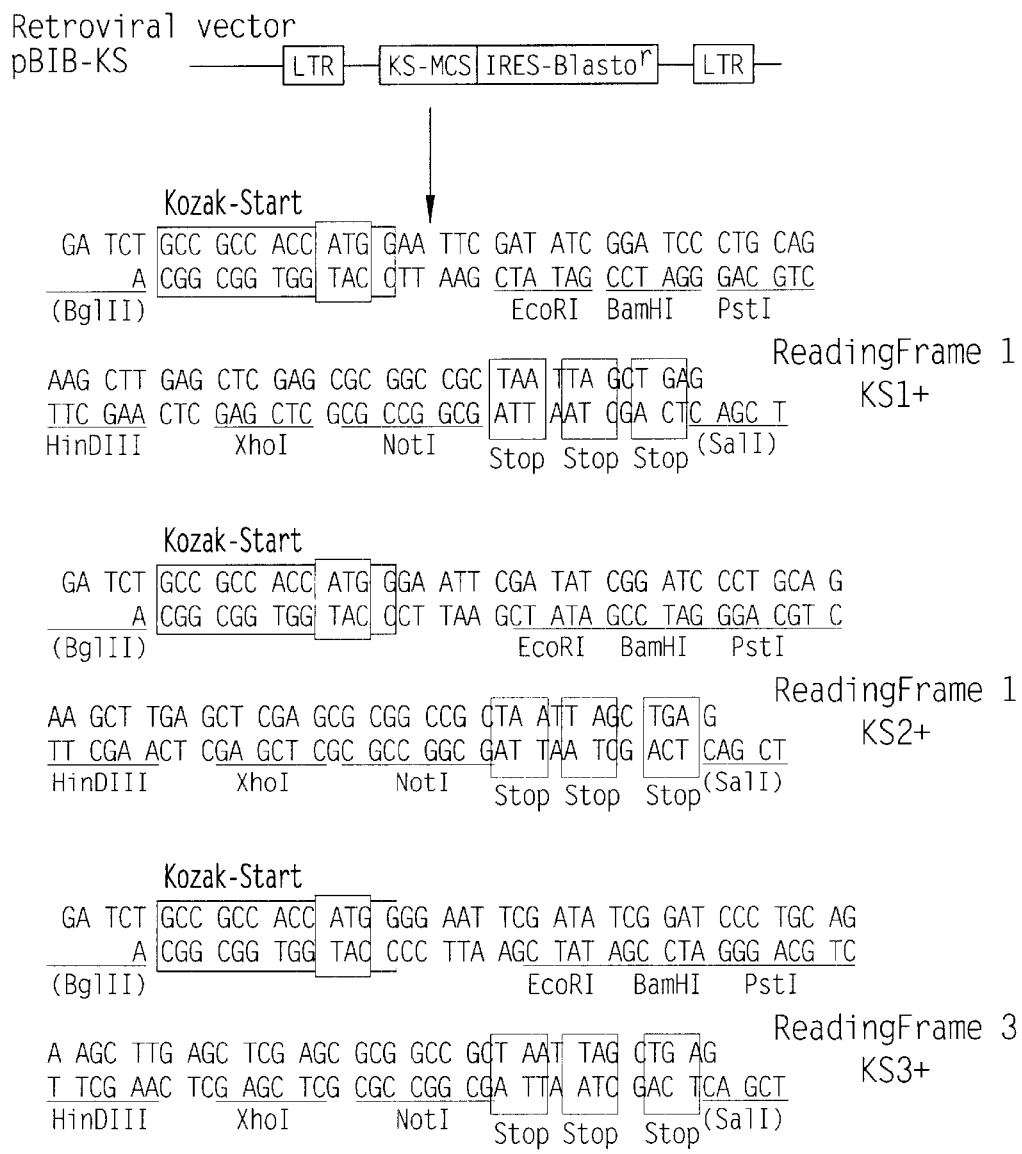
FIG. 2 illustrates retroviral vectors pBIB-KS1,2,3 modified to contain a Kosak translation initiation site and stop codons.

Isolation and Characterization of DNA Sequences Encoding Chlamydia Antigens Using Retroviral Expression Vector Systems and Subsequent Immunological Analysis A genomic library of Chlamydia trachomatis LGV II was constructed by limited digests using BamHI, BglII, BstYi and MboI restriction enzymes. The restriction digest fragments were subsequently ligated into the BamHI site of the retroviral vectors pBIB-KS1,2,3. This vector set was modified to contain a Kosak translation initiation site and stop codons in order to allow expression of proteins from short DNA genomic fragments, as shown in FIG. 2. DNA pools of 80 clones were prepared and transfected into the retroviral packaging line Phoenix-Ampho, as described in Pear, W. S., Scott, M. L. and Nolan, G. P., Generation of High Titre, Helper-free Retroviruses by Transient Transfection. Methods in Molecular Medicine: Gene Therapy Protocols, Humana Press, Totowa, N.J., pp. 41–57. The Chlamydia library in retroviral form was then transduced into H2-Ld expressing P815 cells, which were then used as target cells to stimulate an antigen specific T-cell line.

A Chlamydia-specific, murine $H2^d$ restricted CD8+ T-cell line was expanded in culture by repeated rounds of stimulation with irradiated C. trachomatis-infected J774 cells and irradiated syngeneic spleen cells, as described by Starnbach, M., in J. Immunol., 153:5183, 1994. This Chlamydia-specific T-cell line was used to screen the above Chlamydia genomic library expressed by the retrovirally-transduced P815 cells. Positive DNA pools were identified by detection of IFN-γ production using Elispot analysis (see Lalvani et al., J. Experimental Medicine 186:859–865, 1997).

Two positive pools, referred to as 2C7 and 2E10, were identified by IFN-γ Elispot assays. Stable transductants of P815 cells from pool 2C7 were cloned by limiting dilution and individual clones were selected based upon their capacity to elicit IFN-γ production from the Chlamydia-specific CTL line. From this screening process, four positive clones were selected, referred to as 2C7-8, 2C7-9, 2C7-19 and 2C7-21. Similarly the positive pool 2E10 was further screened, resulting in an additional positive clone, which contains three inserts. The three inserts are fragments of the CT016, tRNA syntase and clpX genes (SEQ ID NO: 268–270, respectively).

Transgenic DNA from these four positive 2C7 clones were PCR amplified using pBIB-KS specific primers to selectively amplify the Chlamydia DNA insert. Amplified inserts were gel purified and sequenced. One immunoreactive clone, 2C7-8 (SEQ ID NO: 15, with the predicted amino acid sequence provided in SEQ ID NO: 32), is a 160 bp fragment with homology to nucleotides 597304–597145 of Chlamydia trachomatis, serovar D (NCBI, BLASTN search; SEQ ID NO: 33, with the predicted amino acid sequence provided in SEQ ID NO: 34). The sequence of clone 2C7-8 maps within two putative open reading frames from the region of high homology described immediately above, and in particular, one of these putative open reading frames, consisting of a 298 amino acid fragment (SEQ ID NO: 16, with the predicted amino acid sequence provided in SEQ ID NO: 17), was demonstrated to exhibit immunological activity.

Full-length cloning of the 298 amino acid fragment (referred to as CT529 and/or the Cap1 gene) from serovar L2 was obtained by PCR amplification using 5'-ttttgaagcaggtaggtgaatatg (forward) (SEQ ID NO: 159) and 5'-ttaagaaatttaaaaaatccctta (reverse) (SEQ ID NO: 160) primers, using purified C. trachomatis L2 genomic DNA as template. This PCR product was gel-purified, cloned into pCRBlunt (Invitrogen, Carlsbad, Calif.) for sequencing, and then subcloned into the EcoRI site of pBIB-KMS, a derivative of pBIB-KS for expression. The Chlamydia pnuemoniae homlogue of CT529 is provided in SEQ ID NO: 291, with the corresponding amino acid sequence provided in SEQ ID NO: 292.

Full-length DNA encoding various CT529 serovars were amplified by PCR from bacterial lysates containing $10^5$ IFU, essentially as described (Denamur, E., C. Sayada, A. Souriau, J. Orfila, A. Rodolakis and J. Elion. 1991. J. Gen. Microbiol. 137: 2525). The following serovars were amplified as described: Ba (SEQ ID NO: 134, with the corresponding predicted amino acid sequence provided in SEQ ID NO: 135); E (BOUR) and E (MTW447) (SEQ ID NO: 122, with the corresponding predicted amino acid sequence provided in SEQ ID NO: 123); F (NI1) (SEQ ID NO: 128, with the corresponding predicted amino acid sequence provided in SEQ ID NO: 129); G; (SEQ ID NO: 126, with the corresponding predicted amino acid sequence provided in SEQ ID NO: 127); Ia (SEQ ID NO: 124, with the corresponding predicted amino acid sequence provided in SEQ ID NO: 125); L1 (SEQ ID NO: 130, with the corresponding predicted amino acid sequence provided in SEQ ID NO: 131); L3 (SEQ ID NO: 132, with the corresponding predicted amino acid sequence provided in SEQ ID NO: 133); I (SEQ ID NO: 263, with the corresponding predicted amino acid sequence provided in SEQ ID NO: 264); K (SEQ ID NO: 265, with the corresponding predicted amino acid sequence provided in SEQ ID NO: 266); and MoPn (SEQ ID NO: 136, with the corresponding predicted amino acid sequence provided in SEQ ID NO: 137). PCR reactions were performed with Advantage Genomic PCR Kit (Clontech, Palo Alto, Calif.) using primers specific for serovar L2 DNA (external to the ORF). Primers sequences were 5'-ggtataatatotctctaaattttg (forward-SEQ ID NO: 161) and 5'-agataaaaaaggctgtttc' (reverse-SEQ ID NO: 162) except for MoPn which required 5'-ttttgaagcaggtaggtgaatatg (forward-SEQ ID NO: 163) and 5'-tttacaataagaaaagctaagcactttgt (reverse-SEQ ID NO: 164). PCR amplified DNA was purified with QIAquick PCR purification kit (Qiagen, Valencia, Calif.) and cloned in pCR2.1 (Invitrogen, Carlsbad, Calif.) for sequencing.

Sequencing of DNA derived from PCR amplified inserts of immunoreactive clones was done on an automated sequencer (ABI 377) using both a pBIB-KS specific forward primer 5'-ccttacacagtcctgctgac (SEQ ID NO: 165) and a reverse primer 3'-gtttccgggccctcacattg (SEQ ID NO: 166). PCRBlunt cloned DNA coding for CT529 serovar L2 and pCR2.1 cloned DNA coding for CT529 serovar Ba, E (BOUR), E (MTW447), F (NI1), G, Ia, K, L1, L3 and MoPn were sequenced using T7 promoter primer and universal M13 forward and M13 reverse primers.

Figure 3:
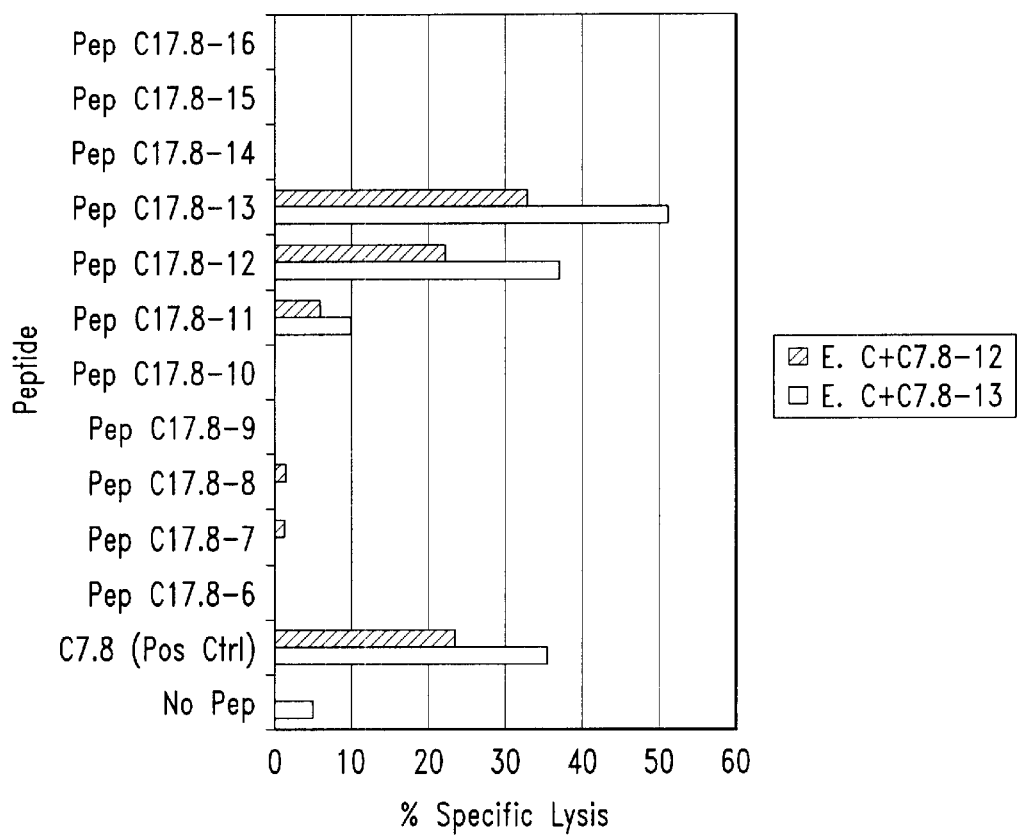
FIG. 3 shows spec reactivity of the full length polypeptide. Such screens may generally be performed using methods well known to those of ordinary skill in the art, such as those described in Harlow and Lane, *Antibodies: A Laboratory Manual,* Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.
Figure 5:
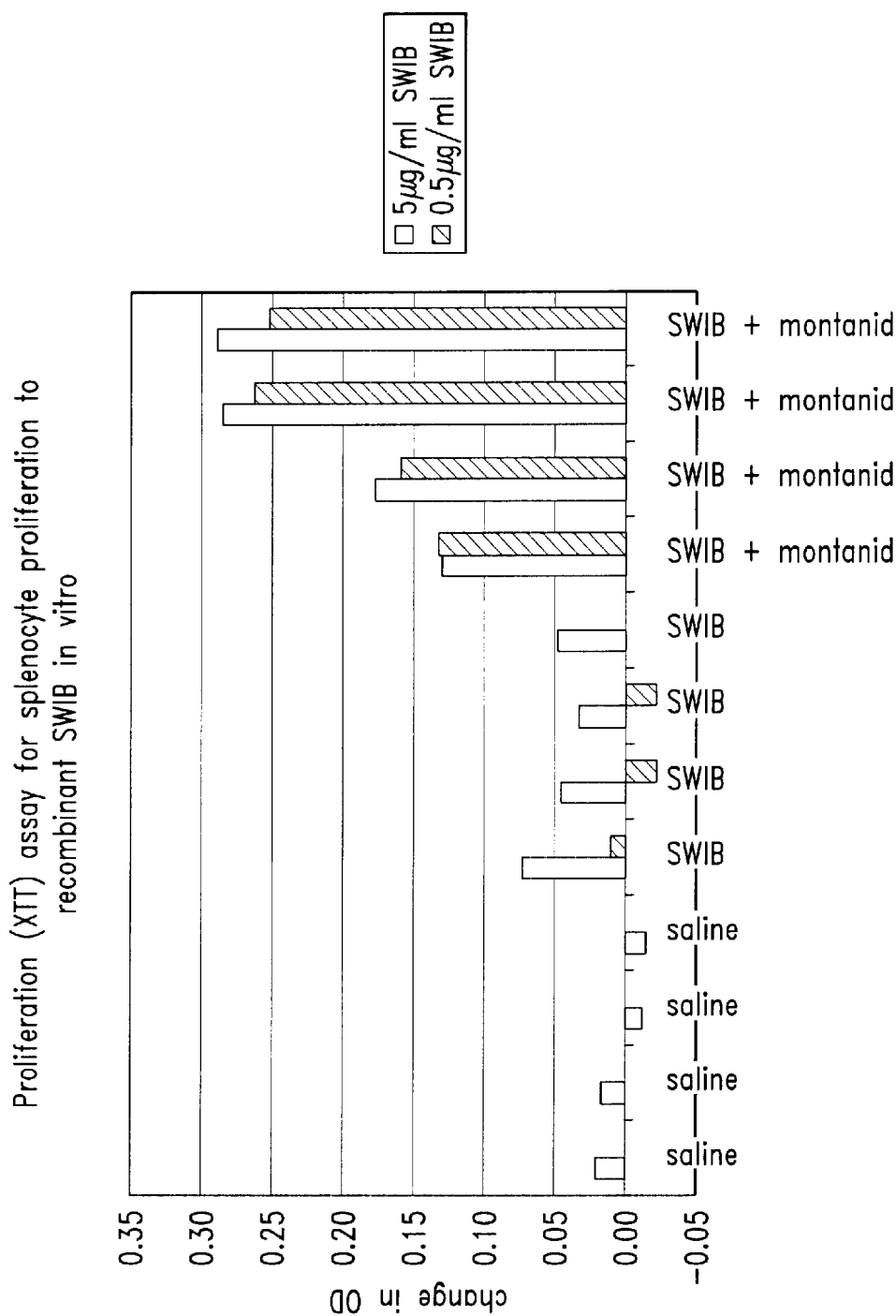

To determine if these two putative open reading frames (SEQ ID NO: 16 and 20) encoded a protein with an associated immunological function, overlapping peptides (17–20 amino acid lengths) spanning the lengths of the two open reading frames were synthesized, as described in Example 3. A standard chromium release assay was utilized to determine the per cent specific lysis of peptide-pulsed $H2^d$ restricted target cells. In this assay, aliquots of P815 cells ($H2^d$) were labeled at 37° C. for one hour with 100 µCi of $^{51}$Cr in the presence or absence of 1 µg/ml of the indicated peptides. Following this incubation, labeled P815 cells were washed to remove excess $^{51}$Cr and peptide, and subsequently plated in duplicate in microculture plates at a concentration of 1,000 cells/well. Effector CTL (Chlamydia-specific CD8 T cells) were added at the indicated effector-:target ratios. Following a 4 hour incubation, supernatants were harvested and measured by gamma-counter for release of $^{51}$Cr into the supernatant. Two overlapping peptides from the 298 amino acid open reading frame did specifically stimulate the CTL line. The peptides represented in SEQ ID NO: 138–156 were synthesized, representing the translation of the L2 homologue of the serovar D open reading frame for CT529 (Cap1 gene) and 216 amino acid open reading frame. As shown in FIG. 3, peptides CtC7.8-12 (SEQ ID NO: 18, also referred to as Cap1#132-147, SEQ ID NO: 139) and CtC7.8-13 (SEQ ID NO: 19, also referred to as Cap1#138-155, SEQ ID NO: 140) were able to elicit 38 to 52% specific lysis, respectively, at an effector to target ratio of 10:1. Notably, the overlap between these two peptides contained a predicted H2$^d$ (K$^d$ and L$^d$) binding peptide. A 10 amino acid peptide was synthesized to correspond to this overlapping sequence (SEQ ID NO: 31) and was found to generate a strong immune response from the anti-Chlamydia CTL line by elispot assay. Significantly, a search of the most recent Genbank database revealed no proteins have previously been described for this gene. Therefore, the putative open reading frame encoding clone 2C7-8 (SEQ ID NO: 15) defines a gene which encompasses an antigen from Chlamydia capable of stimulating antigen-specific CD8+ T-cells in a MHC-I restricted manner, demonstrating this antigen could be used to develop a vaccine against Chlamydia.

To confirm these results and to further map the epitope, truncated peptides (SEQ ID NO: 138–156) were made and tested for recognition by the T-cells in an IFN-g ELISPOT assay. Truncations of either Ser139 (Cap1#140-147, SEQ ID NO: 146) or Leu147 (Cap1#138-146, SEQ ID NO: 147) abrogate T-cell recognition. These results indicate that the 9-mer peptide Cap1#139-147 (SFIGGITYL, SEQ ID NO: 145) is the minimal epitope recognized by the Chlamydia-specific T-cells.

Sequence alignments of Cap1 (CT529) from selected serovars of *C. trachomatis* (SEQ ID NO: 121, 123, 125, 127, 129, 131, 133, 135, 137 and 139) shows one of the amino acid differences is found in position 2 of the proposed epitope. The homologous serovar D peptide is SIIGGITYL (SEQ ID NO: 168). The ability of SFIGGITYL and SIIGGITYL to target cells for recognition by the Chlamydia specific T-cells was compared. Serial dilutions of each peptide were incubated with P815 cells and tested for recognition by the T-cells in a $^{51}Cr$ release assay, as described above. The Chlamydia-specific T-cells recognize the serovar L2 peptide at a minimum concentration of 1 nM and the serovar D peptide at a minimum concentration of 10 nM.

Further studies have shown that a Cap1#139-147-specific T-cell clone recognizes *C. trachomatis* infected cells. To confirm that Cap1#139-147 is presented on the surface of Chlamydia infected cells, Balb-3T3 ($H-2^d$) cells were infected with *C. trachomatis* serovar L2 and tested to determine whether these cells are recognized by a CD8+ T-cell clone specific for Cap1#139-147 epitope (SEQ ID NO: 145). The T-cell clone specific for Cap1#139-147 epitope was obtained by limiting dilution of the line 69 T-cells. The T-cell clone specifically recognized the Chlamydia infected cells. In these experiments, target cells were *C. trachomatis* infected (positive control) or uninfected Balb/3T3 cells, showing 45%, 36% and 30% specific lysis at 30:1, 10:1 and 3:1 effector to target ratios, respectively; or Cap1#139-147 epitope (SEQ ID NO: 145) coated, or untreated P815 cells, showing 83%, 75% and 58% specific lysis at 30:1, 10:1 and 3:1 effector to target ratios, respectively (negative controls having less than 5% lysis in all cases). This data suggests that the epitope is presented during infection.

In vivo studies show Cap1#139-147 epitope-specific T-cells are primed during murine infection with *C. trachomatis*. To determine if infection with *C. trachomatis* primes a Cap1#139-147 epitope-specific T-cell response, mice were infected i.p. with $10^8$ IFU of *C. trachomatis* serovar L2. Two weeks after infection, the mice were sacrificed and spleen cells were stimulated on irradiated syngeneic spleen cells pulsed with Cap1#139-147 epitope peptide. After 5 days of stimulation, the cultures were used in a standard $^{51}Cr$ release assay to determine if there were Cap1#139-147 epitope-specific T-cells present in the culture. Specifically, spleen cells from a *C. trachomatis* serovar L2 immunized mouse or a control mouse injected with PBS after a 5 days culture with Cap1#139-147 peptide-coated syngeneic spleen cells and CD8+ T-cells able to specifically recognize Cap1#139-147 epitope gave 73%, 60% and 32% specific lysis at a30:1, 10:1 and 3:1 effector to target ratios, respectively. The control mice had a percent lysis of approximately 10% at a 30:1 effector to target ratio, and steadily declining with lowering E:T ratios. Target cells were Cap1#139-147 peptide-coated, or untreated P815 cells. These data suggest that Cap1#139-147 peptide-specific T-cells are primed during murine infection with *C. trachomatis.*

Studies were performed demonstrating that Ct529 (referred to herein as Cap-1) localizes to the inclusion membrane of *C. trachomatis*-infected cells and is not associated with elementary bodies or reticulate bodies. As described above, Cap-1 was identified as a product from Chlamydia that stimulates CD8+ CTL. These CTL are protective in a murine model of infection, thus making Cap-1 a good vaccine candidate. Further, since these CTL are MHC-T restricted, the Cap-1 gene must have access to the cytosol of infected cells, which may be a unique characteristic of specific Chlamydial gene products. Therefore, determination of the cellular localization of the gene products would be useful in characterizing Cap-1 as a vaccine candidate. To detect the intracellular localization of Cap-1, rabbit polyclonal antibodies directed against a recombinant polypeptide encompassing the N-terminal 125 amino acids of Cap-1 (SEQ ID NO: 305, with the amino acid sequence including the N-terminal 6-His tag provided in SEQ ID NO: 304) were used to stain McCoy cells infected with Chlamydial.

Rabbit-anti-Cap-1 polyclonal antibodies were obtained by hyper-immunization of rabbits with a recombinant polypeptide, rCt529c1-125 (SEQ ID NO: 305) encompassing the N-terminal portion of Cap-1. Recombinant rCt529e1-125 protein was obtained from *E. coli* transformed with a pET expression plasmid (as described above) encoding the nucleotides 1–375 encoding the N-terminal 1–125 amino acids of Cap-1. Recombinant protein was purified by Ni-NTA using techniques well known in the art. For a positive control antiserum, polyclonal antisera directed against elementary bodies were made by immunization of rabbits with purified *C. trachomatis* elementary bodies (Biodesign, Sacco, Me). Pre-immune sera derived from rabbits prior to immunization with the Cap-1 polypeptide was used as a negative control.

Immunocytochemistry was performed on McCoy cell monolayers grown on glass coverslips inoculated with either *C. trachomatis* serovar L2 or *C. psitacci*, strain 6BC, at a concentration of $10^6$ IFU (Inclusion Forming Units) per ml. After 2 hours, medium was aspirated and replaced with fresh RP-10 medium supplemented with cycloheximide (1.0 $\mu$g/ml). Infected cells were incubated at in 7% $CO_2$ for 24 hours and fixed by aspirating medium, rinsing cells once with PBS and methanol fixation for 5 minutes. For antigen staining, fixed cell monolayers were washed with PBS and incubated at 37° C. for 2 hours with 1:100 dilutions of specific or control antisera. Cells were rinsed with PBS and incubated for 1 hour with fluorescein isothiocyanate (FITC)-labeled, anti-rabbit IgG (KPL, Gaithersburg) and stained with Evans blue (0.05%) in PBS. Fluorescence was observed with a 100X objective (Zeiss epifluorescence microscope), and photographed (Nikon UFX-11A camera).

Results from this study show Cap-1 localizes to the inclusion membrane of C. trachomatis-infected cells. Cap-1 specific antibody labeled the inclusion membranes of C. trachomatis-infected cells, but not Chlamydial elementary bodies contained in these inclusions or released by the fixation process. Conversely, the anti-elementary body antibody clearly labeled the bacterial bodies, not only within the inclusions, but those released by the fixation process. Specificity of the anti-Cap-1 antibody is demonstrated by the fact that it does not stain C. psittaci-infected cells. Specificity of the Cap-1 labeling is also shown by the absence of reactivity in pre-immune sera. These results suggest that Cap-1 is released from the bacteria and becomes associated with the Chlamydial inclusion membrane. Therefore, Cap-1 is a gene product which may be useful for stimulating CD8+ T cells in the development of a vaccine against infections caused by Chlamydia.

The relevance of the Cap-1 gene as a potential CTL antigen in a vaccine against Chlamydia infection is further illustrated by two additional series of studies. First, CTL specific for the MHC-I epitope of Cap-1 CT529 #138-147 peptide of C. trachomatis (SEQ ID NO: 144) have been shown to be primed to a high frequency during natural infection. Specifically, Balb/C mice were inoculated with $10^6$ I.F.U. of C. trachomatis, serova L2. After 2 weeks, spleens were harvested and quantified by Elispot analysis for the number of IFN-γ secreting cells in response to Cap-1 #138-147 peptide-pulsed antigen presenting cells. In two experiments, the number of IFN-γ-secreting cells in $10^5$ splenocytes was about 1% of all CD8+ T-cells. This high frequency of responding CD8+ CTL to the MHC-1 epitope (Cap-1 CT529 #138-147 peptide) suggest that Cap-1 is highly immunogenic in infections.

Results from a second series of studies have shown that the Cap-1 protein is almost immediately accessible to the cytosol of the host cell upon infection. This is shown in a time-course of Cap-1 CT529 #138-147 peptide presentation. Briefly, 3T3 cells were infected with *C. trachomatis* serovar L2 for various lengths of time, and then tested for recognition by Cap-1 CT529 #138-147 peptide-specific CTL. The results show that *C. trachomatis*-infected 3T3 cells are targeted for recognition by the antigen-specific CTL after only 2 hours of infection. These results suggest that Cap-1 is an early protein synthesized in the development of *C. trachomatis* elementary bodies to reticulate bodies. A CD8+ CTL immune response directed against a gene product expressed early in infection may be particularly efficacious in a vaccine against Chlamydia infection.

EXAMPLE 5

Generation of Antibody and T-cell Responses in Mice Immunized With Chlamydia Angigens Immunogenicity studies were conducted to determine the antibody and CD4+ T cell responses in mice immunized with either purified SWIB or S13 proteins formulated with Montanide adjuvant, or DNA-based immunizations with pcDNA-3 expression vectors containing the DNA sequences for SWIB or S13. SWIB is also referred to as clone 1-B1-66 (SEQ ID NO: 1, with the corresponding amino acid sequence provided in SEQ ID NO: 5), and S13 ribosomal protein is also referred to as clone 10-C10-31 (SEQ ID NO: 4, with the corresponding amino acid sequence provided in SEQ ID NO: 12). In the first experiment, groups of three C57BL/6 mice were immunized twice and monitored for antibody and CD4+ T-cell responses. DNA immunizations were intradermal at the base of the tail and polypeptide immunizations were administered by subcutaneous route. Results from standard $^3$H-incorporation assays of spleen cells from immunized mice shows a strong proliferative response from the group immunized with purified recombinant SWIB polypeptide (SEQ ID NO: 5). Further analysis by cytokine induction assays, as previously described, demonstrated that the group immunized with SWIB polypeptide produced a measurable IFN-γ and IL-4 response. Subsequent ELISA-based assays to determine the predominant antibody isotype response in the experimental group immunized with the SWIB polypeptide were performed. FIG. 4 illustrates the SWIB-immunized group gave a humoral response that was predominantly IgG1.

In a second experiment, C3H mice were immunized three times with 10 μg purified SWIB protein (also referred to as clone 1-B1-66, SEQ ID NO: 5) formulated in either PBS or Montanide at three week intervals and harvested two weeks after the third immunization. Antibody titers directed against the SWIB protein were determined by standard ELISA-based techniques well known in the art, demonstrating the SWIB protein formulated with Montanide adjuvant induced a strong humoral immune response. T-cell proliferative responses were determined by a XTT-based assay (Scudiero, et al, *Cancer Research,* 1988, 48:4827). As shown in FIG. 5, splenocytes from mice immunized with the SWIB polypeptide plus Montanide elicited an antigen specific proliferative response. In addition, the capacity of splenocytes from immunized animals to secrete IFN-γ in response to soluble recombinant SWIB polypeptide was determined using the cytokine induction assay previously described. The splenocytes from all animals in the group immunized with SWIB polypeptide formulated with montanide adjuvant secreted IFN-γ in response to exposure to the SWIB Chlamydia antigen, demonstrating an Chlamydia-specific immune response.

In a further experiment, C3H mice were immunized at three separate time points at the base of the tail with 10 μg of purified SWIB or S13 protein (*C. trachomatis*, SWIB protein, clone 1-B1-66, SEQ ID NO: 5, and S13 protein, clone 10-C10-31, SEQ ID NO: 4) formulated with the SBAS2 adjuvant (SmithKline Beecham, London, England). Antigen-specific antibody titers were measured by ELISA, showing both polypeptides induced a strong IgG response, ranging in titers from $1\times10^{-4}$ to $1\times10^{-5}$. The IgG1 and IgG2a components of this response were present in fairly equal amounts. Antigen-specific T-cell proliferative responses, determined by standard $^3$H-incorporation assays on spleen cells isolated from immunized mice, were quite strong for SWIB (50,000 cpm above the negative control) and even stronger for s13 (100,000 cpm above the negative control). The IFNγ production was assayed by standard ELISA techniques from supernatant from the proliferating culture. In vitro restimulation of the culture with S13 protein induced high levels of IFNγ production, approximately 25 ng/ml versus 2 ng/ml for the negative control. Restimulation with the SWIB protein also induced IFNγ, although to a lesser extent.

In a related experiment, C3H mice were immunized at three separate time points with 10 μg of purified SWIB or S13 protein (*C. trachomatis*, SWIB protein, clone 1-B1-66, SEQ ID NO: 5, and S13 protein, clone 10-C10-31, SEQ ID NO: 4) mixed with 10 µg of Cholera Toxin. Mucosal immunization was through intranasal inoculation. Antigen-specific antibody responses were determined by standard ELISA techniques. Antigen-specific IgG antibodies were present in the blood of SWIB-immunized mice, with titers ranging from $1 \times 10^{-3}$ to $1 \times 10^{-4}$ but non-detectable in the S13-immunized animals. Antigen-specific T-cell responses from isolated splenocytes, as measured by IFNγ production, gave similar results to those described immediately above for systemic immunization.

An animal study was conducted to determine the immunogenicity of the CT529 serovar LGVII CTL epitope, defined by the CT529 110 consensus peptide (CSFIGGITYL—SEQ ID NO: 31), which was identified as an H2-Kd restricted CTL epitope. BALB/c mice (3 mice per group) were immunized three times with 25 µg of peptide combined with various adjuvants. The peptide was administered systemically at the base of the tail in either SKB Adjuvant System SBAS-2", SBAS-7 (SmithKline Beecham, London, England) or Montanide. The peptide was also administered intranasally mixed with 10 ug of Cholera Toxin (CT). Naive mice were used as a control. Four weeks after the 3rd immunization, spleen cells were restimulated with LPS-blasts pulsed with 10 ug/ml CT529 10 mer consensus peptide at three different effector to LPS-blasts ratios: 6, 1.5 and 0.4 at $1 \times 10^6$ cell/ml. After 2 restimulations, effector cells were tested for their ability to lyse peptide pulsed P815 cells using a standard chromium release assay. A non-relevant peptide from chicken egg ovalbumin was used as a negative control. The results demonstrate that a significant immune response was elicited towards the CT529 10 mer consensus peptide and that antigen-specific T-cells capable of lysing peptide-pulsed targets were elicited in response to immunization with the peptide. Specifically, antigen-specific lytic activities were found in the SBAS-7 and CT adjuvanted group while Montanide and SBAS-2" failed to adjuvant the CTL epitope immunization.

EXAMPLE 6

Expression and Characterization of *Chlamydia Pneumoniae* Genes

The human T-cell line, TCL-8, described in Example 1, recognizes *Chlamydia trachomatis* as well as *Chlamydia pneumonia* infected monocyte-derived dendritic cells, suggesting *Chlamydia trachomatis* and pneumonia may encode cross-reactive T-cell epitopes. To isolate the *Chlamydia pneumonia* genes homologous to *Chlamydia trachomatis* LGV II clones 1B1-66, also referred to as SWIB (SEQ ID NO: 1) and clone 10C10-31, also referred to as S13 ribosomal protein (SEQ ID NO: 4), HeLa 229 cells were infected with *C. pneumonia* strain TWAR (CDC/CWL-029). After three days incubation, the *C. pneumonia*-infected HeLa cells were harvested, washed and resuspended in 200 µl water and heated in a boiling water bath for 20 minutes. Ten microliters of the disrupted cell suspension was used as the PCR template.

*C. pneumonia* specific primers were designed for clones 1B1-66 and 10C10-31 such that the 5' end had a 6x-Histidine tag and a Nde I site inserted, and the 3' end had a stop codon and a BamHI site included (FIG. 6). The PCR products were amplified and sequenced by standard techniques well known in the art. The *C. pneumonia*-specific PCR products were cloned into expression vector pET17B (Novagen, Madison, Wis.) and transfected into *E. coli* BL21 pLysS for expression and subsequent purification utilizing the histidine-nickel chromatographic methodology provided by Novagen. Two proteins from *C. pneumonia* were thus generated, a 10–11 kDa protein referred to as CpSWIB (SEQ ID NO: 27, and SEQ ID NO: 78 having a 6xHis tag, with the corresponding amino acid sequence provided in SEQ ID NO: 28, respectively), a 15 kDa protein referred to as CpS13 (SEQ ID NO: 29, and SEQ ID NO: 77, having a 6xHis tag, with the corresponding amino acid sequence provided in SEQ ID NO: 30 and 91, respectively).

EXAMPLE 7

Induction of T Cell Proliferation and Interferon-γ Production by *Chlamydia Pneumoniae* Antigens The ability of recombinant Chlamydia pneumoniae antigens to induce T cell proliferation and interferon-γ production is determined as follows.

Proteins are induced by IPTG and purified by Ni-NTA agarose affinity chromatography (Webb et al., *J. Immunology* 157:5034–5041, 1996). The purified polypeptides are then screened for the ability to induce T-cell proliferation in PBMC preparations. PBMCs from *C. pneumoniae* patients as well as from normal donors whose T-cells are known to proliferate in response to Chlamydia antigens, are cultured in medium comprising RPMI 1640 supplemented with 10% pooled human serum and 50 µg/ml gentamicin. Purified polypeptides are added in duplicate at concentrations of 0.5 to 10 µg/mL. After six days of culture in 96-well round-bottom plates in a volume of 200 µl, 50 µl of medium is removed from each well for determination of IFN-γ levels, as described below. The plates are then pulsed with 1 µCi/well of tritiated thymidine for a further 18 hours, harvested and tritium uptake determined using a gas scintillation counter. Fractions that result in proliferation in both replicates three fold greater than the proliferation observed in cells cultured in medium alone are considered positive.

IFN-γ was measured using an enzyme-linked immunosorbent assay (ELISA). ELISA plates are coated with a mouse monoclonal antibody directed to human IFN-γ (PharMingen, San Diego, Calif.) in PBS for four hours at room temperature. Wells are then blocked with PBS containing 5% (W/V) non-fat dried milk for 1 hour at room temperature. The plates are washed six times in PBS/0.2% TWEEN-20 and samples diluted 1:2 in culture medium in the ELISA plates are incubated overnight at room temperature. The plates are again washed and a polyclonal rabbit anti-human IFN-γ serum diluted 1:3000 in PBS/10% normal goat serum is added to each well. The plates are then incubated for two hours at room temperature, washed and horseradish peroxidase-coupled anti-rabbit IgG (Sigma Chemical So., St. Louis, Mo.) is added at a 1:2000 dilution in PBS/5% non-fat dried milk. After a further two hour incubation at room temperature, the plates are washed and TMB substrate added. The reaction is stopped after 20 min with 1 N sulfuric acid. Optical density is determined at 450 nm using 570 nm as a reference wavelength. Fractions that result in both replicates giving an OD two fold greater than the mean OD from cells cultured in medium alone, plus 3 standard deviations, are considered positive.

A human anti-Chlamydia T-cell line (TCL-8) capable of cross-reacting to *C. trachomatis* and *C. pneumonia* was used to determine whether the expressed proteins described in the example above, (i.e., CpSWIB, SEQ ID NO: 27, and SEQ ID NO: 78 having a 6xHis tag, with the corresponding amino acid sequence provided in SEQ ID NO: 28, respectively, and the 15 kDa protein referred to as CpS13 SEQ ID NO: 29, and SEQ ID NO: 77, having a 6xHis tag, with the corresponding amino acid sequence provided in SEQ ID NO: 30 and 91, respectively), possessed T-cell epitopes common to both *C. trachomatis* and *C. pneumonia*. Briefly, *E. coli* expressing Chlamydial proteins were titered on 1×10$^4$ monocyte-derived dendritic cells. After two hours, the dendritic cells cultures were washed and 2.5×10$^4$ T cells (TCL-8) added and allowed to incubate for an additional 72 hours. The amount of INF-γ in the culture supernatant was then determined by ELISA. As shown in FIGS. 7A and 7B, the TCL-8 T-cell line specifically recognized the S13 ribosomal protein from both *C. trachomatis* and *C. pneumonia* as demonstrated by the antigen-specific induction of IFN-γ, whereas only the SWIB protein from *C. trachomatis* was recognized by the T-cell line. To validate these results, the T cell epitope of *C. trachomatis* SWIB was identified by epitope mapping using target cells pulsed with a series of overlapping peptides and the T-cell line TCL-8. 3H-thymidine incorporation assays demonstrated that the peptide, referred to as C.t.SWIB 52-67, of SEQ ID NO: 39 gave the strongest proliferation of the TCL-8 line. The homologous peptides corresponding to the SWIB of *C. pneumoniae* sequence (SEQ ID NO: 40), the topoisomerase-SWIB fusion of *C. pneumoniae* (SEQ ID NO: 43) and *C. trachomatis* (SEQ ID NO: 42) as well as the human SWI domain (SEQ ID NO: 41) were synthesized and tested in the above assay. The T-cell line TCL-8 only recognized the *C. trachomatis* peptide of SEQ ID NO: 39 and not the corresponding *C. pneumoniae* peptide (SEQ ID NO: 40), or the other corresponding peptides described above (SEQ ID NO: 41–43).

Chlamydia-specific T cell lines were generated from donor CP-21 with a positive serum titer against *C. pneumoniae* by stimulating donor PBMC with either *C. trachomatis* or *C. pneumoniae*-infected monocyte-derived dendritic cells, respectively. T-cells generated against *C. pneumoniae* responded to recombinant *C. pneumoniae*-SWIB but not *C. trachomatis*-SWIB, whereas the T-cell line generated against *C. trachomatis* did not respond to either *C. trachomatis*- or *C. pneumoniae*-SWIB (see FIG. 9). The *C. pneumoniae*-SWIB specific immune response of donor CP-21 confirms the *C. pneumoniae* infection and indicates the elicitation of *C. pneumoniae*-SWIB specific T-cells during in vivo *C. pneumoniae* infection.

Epitope mapping of the T-cell response to *C. pneumoniae*-SWIB has shown that Cp-SWIB-specific T-cells responded to the overlapping peptides Cp-SWIB 32-51 (SEQ ID NO: 101) and Cp-SWIB 37-56 (SEQ ID NO: 102), indicating a *C. pneumoniae*-SWIB-specific T-cell epitope Cp-SWIB 37-51 (SEQ ID NO: 100).

In additional experiments, T-cell lines were generated from donor CP1, also a *C. pneumoniae* seropositive donor, by stimulating PBMC with non-infectious elementary bodies from *C. trachomatis* and *C. pneumoniae*, respectively. In particular, proliferative responses were determined by stimulating 2.5×10$^4$ T-cells in the presence of 1×10$^4$ monocyte-derived dendritic cells and non-infectious elementary bodies derived from *C. trachomatis* and *C. pneumoniae*, or either recombinant *C. trachomatis* or *C. pneumoniae* SWIB protein. The T-cell response against SWIB resembled the data obtained with T-cell lines from CP-21 in that *C. pneumoniae*-SWIB, but not *C. trachomatis*-SWIB elicited a response by the *C. pneumoniae* T-cell line. In addition, the *C. trachomatis* T-cell line did not proliferate in response to either *C. trachomatis* or *C. pneumoniae* SWIB, though it did proliferate in response to both CT and CP elementary bodies. As described in Example 1, Clone 11-C12-91 (SEQ ID NO: 63), identified using the TCP-21 cell line, has a 269 bp insert that is part of the OMP2 gene (CT443) and shares homology with the 60 kDa cysteine rich outer membrane protein of *C. pneumoniae*, referred to as OMCB. To further define the reactive epitope(s), epitope mapping was performed using a series of overlapping peptides and the immunoassay previously described. Briefly, proliferative responses were determined by stimulating 2.5× 10$^4$ TCP-21 T-cells in the presence of 1×10$^4$ monocyte-derived dendritic cells with either non-infectious elementary bodies derived from *C. trachomatis* and *C. pneumoniae*, or peptides derived from the protein sequence of *C. trachomatis* or *C. pneumoniae* OMCB protein (0.1 μg/ml). The TCP-21 T-cells responded to epitopes CT-OMCB #167–186, CT-OMCB #171–190, CT-OMCB #171–186, and to a lesser extent, CT-OMCB #175–186 (SEQ ID NO: 249–252, respectively). Notably, the TCP-21 T-cell line also gave a proliferative response to the homologous *C. pneumoniae* peptide CP-OMCB #171-186 (SEQ ID NO: 253), which was equal to or greater than the response to the to the *C. trachomatis* peptides. The amino acid substitutions in position two (i.e., Asp for Glu) and position four (i.e., Cys for Ser) did not alter the proliferative response of the T-cells and therefore demonstrating this epitope to be a cross-reactive epitope between *C. trachomatis* and *C. pneumoniae*.

EXAMPLE 8

Immune Responses of Human PBMC and T-cell Lines Against Chlamydia Antigens

The examples provided herein suggest that there is a population of healthy donors among the general population that have been infected with *C. trachomatis* and generated a protective immune response controlling the *C. trachomatis* infection. These donors remained clinically asymptomatic and seronegative for *C. trachomatis*. To characterize the immune responses of normal donors against chlamydial antigens which had been identified by CD4 expression cloning, PBMC obtained from 12 healthy donors were tested against a panel of recombinant chlamydial antigens including *C. trachomatis*-, *C. pneumoniae*-SWIB and *C. trachomatis*-, *C. pneumoniae*-S13. The data are summarized in Table I below. All donors were seronegative for *C. trachomatis*, whereas 6/12 had a positive *C. pneumoniae* titer. Using a stimulation index of >4 as a positive response, 11/12 of the subjects responded to *C. trachomatis* elementary bodies and 12/12 responded to *C. pneumoniae* elementary bodies. One donor, AD104, responded to recombinant *C. pneumoniae*-S13 protein, but not to recombinant *C. trachomatis*-S13 protein, indicating a *C. pneumoniae*-specific response. Three out of 12 donors had a *C. trachomatis*-SWIB, but not a *C. pneumoniae*-SWIB specific response, confirming a *C. trachomatis* infection. *C. trachomatis* and *C. pneumoniae*-S13 elicited a response in 8/12 donors suggesting a chlamydial infection. These data demonstrate the ability of SWIB and S13 to elicit a T-cell response in PBMC of normal study subjects.

TABLE I

Immune response of normal study subjects against Chlamydia

| Donor | Sex | Chlamydia IgG titer | CT EB | CP EB | CT Swib | CP Swib | CT S13 | CP S13 | CT lpdA | CT TSA |
|---|---|---|---|---|---|---|---|---|---|---|
| AD100 | male | negative | ++ | +++ | + | − | ++ | ++ | − | n.t. |
| AD104 | female | negative | +++ | ++ | − | − | − | ++ | − | n.t. |
| AD108 | male | CP 1:256 | ++ | ++ | + | +/− | + | + | + | n.t. |
| AD112 | female | negative | ++ | ++ | + | − | + | − | +/− | n.t. |
| AD120 | male | negative | − | + | − | − | − | − | − | n.t. |
| AD124 | female | CP 1:128 | ++ | ++ | − | − | − | − | − | n.t. |
| AD128 | male | CP 1:512 | + | ++ | − | − | ++ | + | ++ | − |
| AD132 | female | negative | ++ | ++ | − | − | + | + | − | − |
| AD136 | female | CP 1:128 | + | ++ | − | − | +/− | − | − | − |
| AD140 | male | CP 1:256 | ++ | ++ | − | − | + | + | − | − |
| AD142 | female | CP 1:512 | ++ | ++ | − | − | + | + | + | − |
| AD146 | female | negative | ++ | ++ | − | − | ++ | + | + | − |

CT=*Chlamydia trachomatis*; CP=*Chlamydia pneumoniae*; EB=Chlamydia elementary bodies; Swib=recombinant Chlamydia Swib protein; S13=recombinant chlamydia S13 protein, lpdA=recombinant Chlamydia lpdA protein; TSA=recombinant Chlamydia TSA protein. Values represent results from standard proliferation assays. Proliferative responses were determined by stimulating $3 \times 10^5$ PBMC with $1 \times 10^4$ monocyte-derived dendritic cells pre-incubated with the respective recombinant antigens or elementary bodies (EB). Assays were harvested after 6 days with a $^3$H-thymidine pulse for the last 18 h.

| SI: Stimulation index | | |
|---|---|---|
| +/−: | SI~ | 4 |
| +: | SI> | 4 |
| ++: | SI | 10–30 |
| +++: | SI> | 30 |

Figure 11:
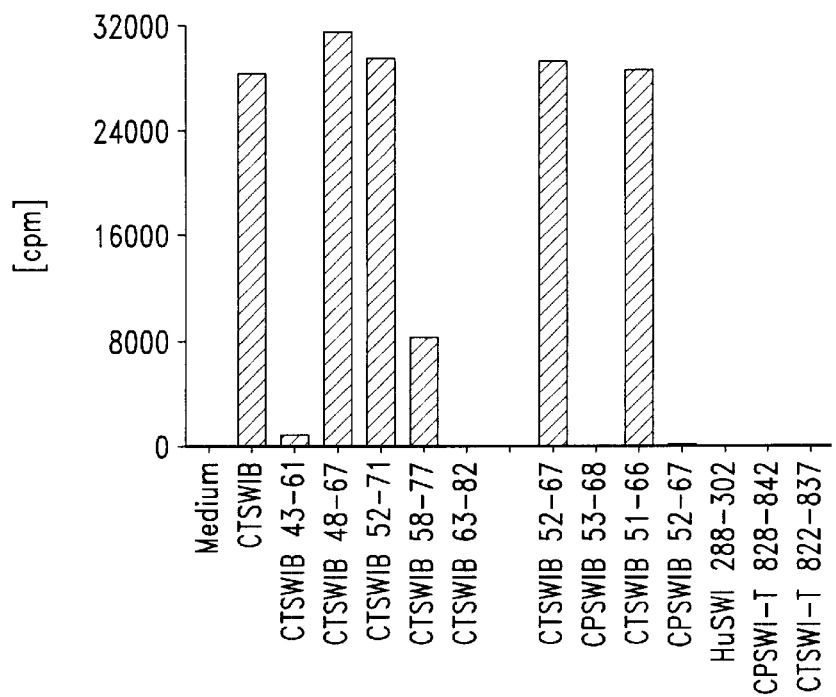

In a first series of experiments, T-cell lines were generated from a healthy female individual (CT-10) with a history of genital exposure to *C. trachomatis* by stimulating T-cells with *C. trachomatis* LGV II elementary bodies as previously described. Although the study subject was exposed to *C. trachomatis*, she did not seroconvert and did not develop clinical symptoms, suggesting donor CT-10 may have developed a protective immune response against *C. trachomatis*. As shown in FIG. 10, a primary Chlamydia-specific T-cell line derived from donor CT-10 responded to *C. trachomatis*-SWIB, but not *C. pneumoniae*-SWIB recombinant proteins, confirming the exposure of CT-10 to *C. trachomatis*. Epitope mapping of the T-cell response to *C. trachomatis*-SWIB showed that this donor responded to the same epitope Ct-SWIB 52-67 (SEQ ID NO: 39) as T-cell line TCL-8, as shown in FIG. 11.

Additional T-cell lines were generated as described above for various *C. trachomatis* patients. A summary of the patients' clinical profile and proliferative responses to various *C. trachomatis* and *C. pneumoniae* elementary bodies and recombinant proteins are summarized in Table II.

TABLE II

Proliferative response of *C. trachomatis* patients

| Patients | Clinical manifestation | IgG titer | CT EB | CP EB | CT Swib | CP Swib | CT S13 | CP S13 | CT lpdA | CT TSA |
|---|---|---|---|---|---|---|---|---|---|---|
| CT-1 | NGU | negative | + | + | − | − | ++ | ++ | ++ | + |
| CT-2 | NGU | negative | ++ | ++ | − | − | + | +/− | − | − |
| CT-3 | asymptomatic shed Eb Dx was KPV | Ct 1:512 Cp 1:1024 Cps 1:256 | + | + | − | − | + | − | + | − |
| CT-4 | asymptomatic shed Eb | Ct 1:1024 | + | + | − | − | − | − | − | − |
| CT-5 | BV | Ct 1:256 Cp 1:256 | ++ | ++ | − | − | + | − | − | − |
| CT-6 | perinial rash discharge | Cp 1:1024 | + | + | − | − | − | − | − | − |
| CT-7 | BV genital ulcer | Ct 1:512 Cp 1:1024 | + | + | − | − | + | + | + | − |
| CT-8 | Not known | Not tested | ++ | ++ | − | − | − | − | − | − |
| CT-9 | asymptomatic | Ct 1:128 Cp 1:128 | +++ | ++ | − | − | ++ | + | + | − |
| CT-10 | Itch mild vulvar | negative | ++ | ++ | − | − | − | − | − | − |
| CT-11 | BV. abnormal pap | Ct 1:512 | +++ | +++ | − | − | +++ | +/− | ++ | + |
| CT-12 | asymptomatic | Cp 1:512 | ++ | ++ | − | − | ++ | + | + | − |

NGU=Non-Gonococcal Urethritis; BV=Bacterial Vaginosis; CT=*Chlamydia trachomatis*; CP=*Chlamydia pneumoniae*, EB=Chlamydia elementary bodies; Swib=recombinant Chlamydia Swib protein; S13=recombinant Chlamydia S13 protein; lpdA=recombinant Chlamydia lpdA protein TSA= recombinant Chlamydia TSA protein Values represent results from standard proliferation assays. Proliferative responses were determined by stimulating $3\times10^5$ PBMC with $1\times10^4$ monocyte-derived dendritic cells pre-incubated with the respective recombinant antigens or elementary bodies (EB). Assays were harvested after 6 days with a $^3$H-thymidine pulse for the last 18 hours.

| SI: Stimulation index | | |
|---|---|---|
| +/−: | SI~ | 4 |
| +: | SI> | 4 |
| ++: | SI | 10–30 |
| +++: | SI> | 30 |

Using the panel of asymptomatic (as defined above) study subjects and *C. trachomatis* patients, as summarized in Tables I and II, a comprehensive study of the immune responses of PBMC derived from the two groups was conducted. Briefly, PBMCs from *C. pneumoniae* patients as well as from normal donors are cultured in medium comprising RPMI 1640 supplemented with 10% pooled human serum and 50 µg/ml gentamicin. Purified polypeptides, a panel of recombinant chlamydial antigens including *C. trachomatis*-, *C. pneumoniae*-SWIB and S13, as well as. *C. trachomatis* lpdA and TSA are added in duplicate at concentrations of 0.5 to 10 µg/mL. After six days of culture in 96-well round-bottom plates in a volume of 200 µl, 50 µl of medium is removed from each well for determination of IFN-γ levels, as described below. The plates are then pulsed with 1 µCi/well of tritiated thymidine for a further 18 hours, harvested and tritium uptake determined using a gas scintillation counter. Fractions that result in proliferation in both replicates three fold greater than the proliferation observed in cells cultured in medium alone are considered positive.

Proliferative responses to the recombinant Chlamydial antigens demonstrated that the majority of asymptomatic donors and *C. trachomatis* patients recognized the *C. trachomatis* S13 antigen (8/12) and a majority of the *C. trachomatis* patients recognized the *C. pneumonia* S13 antigen (8/12), with 4/12 asymptomatic donors also recognizing the *C. pneumonia* S13 antigen. Also, six out of twelve of the *C. trachomatis* patients and four out of twelve of the asymptomatic donors gave a proliferative response to the lpdA antigen of *C. trachomatis*. These results demonstrate that the *C. trachomatis* and *C. pneumonia* S13 antigen, *C. trachomatis* Swib antigen and the *C. trachomatis* lpdA antigen are recognized by the asymptomatic donors, indicating these antigens were recognized during exposure to Chlamydia and an immune response elicited against them. This implies these antigens may play a role in conferring protective immunity in a human host. In addition, the *C. trachomatis* and *C. pneumonia* S13 antigen is recognized equally well among the *C. trachomatis* patients, therefore indicating there may be epitopes shared between *C. trachomatis* and *C. pneumonia* in the S13 protein. Table III summarizes the results of these studies.

TABLE III

| Antigen | Normal Donors | C.t. Patients |
|---|---|---|
| C.t-Swib | 3/12 | 0/12 |
| C.p.-Swib | 0/12 | 0/12 |
| C.t.-S13 | 8/12 | 8/12 |
| C.p.-S13 | 4/12 | 8/12 |
| IpdA | 4/12 | 6/12 |
| TSA | 0/12 | 2/12 |

A series of studies were initiated to determine the cellular immune response to short-term T-cell lines generated from asymptomatic donors and *C. trachomatis* patients. Cellular immune responses were measured by standard proliferation assays and IFN-γ, as described in Example 7. Specifically, the majority of the antigens were in the form of single *E. coli* clones expressing Chlamydial antigens, although some recombinant proteins were also used in the assays. The single *E. coli* clones were titered on $1\times10^4$ monocyte-derived dendritic cells and after two hours, the culture was washed and $2.5\times10^4$ T-cells were added. The assay using the recombinant proteins were performed as previously described. Proliferation was determined after four days with a standard $^3$H-thymidine pulse for the last 18 hours. Induction of IFN-γ was determined from culture supernatants harvested after four days using standard ELISA assays, as described above. The results show that all the *C. trachomatis* antigens tested, except for C.T. Swib, elicited a proliferative response from one or more different T-cell lines derived form *C. trachomatis* patients. In addition, proliferative responses were elicited from both the *C. trachomatis* patients and asymptomatic donors for the following Chlamydia genes, CT622, groEL, pmpD, CT610 and rS13.

The 12G3-83 clone also contains sequences to CT734 and CT764 in addition to CT622, and therefore these gene sequence may also have immunoreactive epitopes. Similarly, clone 21G12-60 contains sequences to the hypothetical protein genes CT229 and CT228 in addition to CT875; and 15H2-76 also contains sequences from CT812 and CT088, as well as sharing homology to the sycE gene. Clone 11H3-61 also contains sequences sharing homology to the PGP6-D virulence protein.

TABLE IV

| Clone | C.t. Antigen (putative*) | TCL from Asymp. Donors | TCL from C.t. Patients | SEQ ID NO:: |
|---|---|---|---|---|
| 1B1-66 (*E. coli*) | Swib | 2/2 | 0/4 | 5 |
| 1B1-66 (protein) | Swib | 2/2 | 0/4 | 5 |
| 12G3-83 (*E. coli*) | CT622* | 2/2 | 4/4 | 57 |
| 22B3-53 (*E. coli*) | groEL | 1/2 | 4/4 | 111 |
| 22B3-53 (protein) | groEL | 1/2 | 4/4 | 111 |
| 15H2-76 (*E. coli*) | PmpD* | 1/2 | 3/4 | 87 |
| 11H3-61 (*E. coli*) | rL1* | 0/2 | 3/4 | 60 |
| 14H1-4 (*E. coli*) | TSA | 0/2 | 3/4 | 56 |
| 14H1-4 (protein) | TSA | 0/2 | 3/4 | 56 |
| 11G10-46 (*E. coli*) | CT610 | 1/2 | 1/4 | 62 |
| 10C10-17 (*E. coli*) | rS13 | 1/2 | 1/4 | 62 |
| 10C10-17 (protein) | rS13 | 1/2 | 1/4 | 62 |
| 21G12-60 (*E. coli*) | CT875* | 0/2 | 2/4 | 110 |
| 11H4-32 (*E. coli*) | dnaK | 0/2 | 2/4 | 59 |
| 21C7-8 (*E. coli*) | dnaK | 0/2 | 2/4 | 115 |
| 17C10-31 (*E. coli*) | CT858 | 0/2 | 2/4 | 114 |

EXAMPLE 9

Protective Studies Using Chlamydia Antigens

Protection studies were conducted in mice to determine whether immunization with chlamydial antigens can impact on the genital tract disease resulting from chlamydial inoculation. Two models were utilized; a model of intravaginal inoculation that uses a human isolate containing a strain of *Chlamydia psittaci* (MTW447), and a model of intrauterine inoculation that involves a human isolate identified as *Chlamydia trachomatis*, serovar F (strain NI1). Both strains induce inflammation in the upper genital tract, which resemble endometritis and salpingitis caused by *Chlamydia trachomatis* in women. In the first experiment, C3H mice (4 mice per group) were immunized three times with 100 $\mu$g of pcDNA-3 expression vector containing *C. trachomatis* SWIB DNA (SEQ ID NO: 1, with the corresponding amino acid sequence provided in SEQ ID NO: 5). Inoculations were at the base of the tail for systemic immunization. Two weeks after the last immunization, animals were progesterone treated and infected, either thru the vagina or by injection of the inoculum in the uterus. Two weeks after infection, the mice were sacrificed and genital tracts sectioned, stained and examined for histopathology. Inflammation level was scored (from + for very mild, to +++++ for very severe). Scores attributed to each single oviduct/ovary were summed and divided by the number of organs examined to get a mean score of inflammation for the group. In the model of uterine inoculation, negative control-immunized animals receiving empty vector showed consistent inflammation with an ovary/oviduct mean inflammation score of 6.12, in contrast to 2.62 for the DNA-immunized group. In the model of vaginal inoculation and ascending infection, negative control-immunized mice had an ovary/oviduct mean inflammation score of 8.37, versus 5.00 for the DNA-immunized group. Also, in the later model, vaccinated mice showed no signs of tubal occlusion while negative control vaccinated groups had inflammatory cells in the lumen of the oviduct.

In a second experiment, C3H mice (4 mice per group) were immunized three times with 50 $\mu$g of pcDNA-3 expression vector containing *C. trachomatis* SWIB DNA (SEQ ID NO: 1, with the corresponding amino acid sequence provided in SEQ ID NO: 5) encapsulated in Poly Lactide co-Glycolide microspheres (PLG); immunizations were made intra-peritoneally. Two weeks after the last immunization, animal were progesterone treated and infected by inoculation of *C. psittaci* in the vagina. Two weeks after infection, mice were sacrificed and genital tracts sectioned, stained and examined for histopathology. Inflammation level was scored as previously described. Scores attributed to each single oviduct/ovary were summed and divided by the number of examined organs to get a mean of inflammation for the group. Negative control-immunized animals receiving PLG-encapsulated empty vector showed consistent infammation with an ovary/oviduct mean inflammation score of 7.28, versus 5.71 for the PLG-encapsulated DNA immunized group. Inflammation in the peritoneum was 1.75 for the vaccinated group versus 3. 75 for the control.

In a third experiment, C3H mice (4 per group) were immunized three times with 10 $\mu$g of purified recombinant protein, either SWIB (SEQ ID NO: 1, with the corresponding amino acid sequence provided in SEQ ID NO: 5, or S13 (SEQ ID NO: 4, with the corresponding amino acid sequence provided in SEQ ID NO: 12) mixed with Cholera Toxin (CT); the preparation was administered intranasally upon anaesthesia in a 20 uL volume. Two weeks after the last immunization, animal were progesterone treated and infected, either by vaginal inoculation of *C. psittaci* or by injection of *C. trachomatis* serovar F in the uterus. Two weeks after infection, the mice were sacrificed and genital tracts sectioned, stained and examined for histopathology. The degree of inflammation was scored as described above. Scores attributed to each single oviduct/ovary were summed and divided by the number of examined organs to get a mean score of inflammation for the group. In the model of uterine inoculation, negative control-immunized animals receiving cholera toxin alone showed an ovary/oviduct mean inflammation score of 4.25 (only 2 mice analyzed; 2 other died) versus 5.00 for the s13 plus cholera toxin-immunized group, and 1.00 for the SWIB plus cholera toxin, Untreated infected animals had an ovary/oviduct mean inflammation score of 7. In the model of vaginal inoculation and ascending infection, negative control-immunized mice had an ovary/oviduct mean inflammation score of 7.37 versus 6.75 for the s13 plus cholera toxin-immunized group and 5.37 for the SWIB plus cholera toxin-immunized group. Untreated infected animals had an ovary /oviduct mean inflammation score of 8.

The three experiments described above suggest that SWIB-specific protection is obtainable. This protective effect is more marked in the model of homologous infection but is still present when in a heterologous challenge infection with *C. psittaci.*

Although the present invention has been described in some detail by way of illustration and example for purposes of clarity of understanding, changes and modifications can be carried out without departing from the scope of the invention which is intended to be limited only by the scope of the appended claims.

What is claimed is:

1. An isolated polypeptide comprising an amino acid sequence set forth in any one of SEQ ID NOs:304–305.

2. A fusion protein comprising a polypeptide according to claim 1.

3. An isolated polynucleotide encoding a fusion protein according to claim 2.

4. A pharmaceutical composition comprising a polypeptide according to claim 1, and a physiologically acceptable carrier.

5. A vaccine comprising a polypeptide according to claim 1, and an immunostimulant.

6. The vaccine of claim 5, wherein the immunostimulant is an adjuvant.

7. A method for stimulating an immune response in a patient, comprising administering to a patient a pharmaceutical composition according to claim 4, wherein an immune response to Chlamydia is induced.

8. A method for stimulating an immune response in a patient, comprising administering to a patient a vaccine according to claim 5, wherein an immune response to Chlamydia is induced.

9. A method for detecting Chlamydia infection in a patient, comprising:

(a) obtaining a biological sample from the patient;

(b) contacting the sample with a polypeptide comprising an immunogenic portion of a Chlamydia antigen, wherein said antigen comprises an amino acid sequence set forth in any one of SEQ ID NOs: 304–305; and (c) detecting the presence of antibodies that bind to the polypeptide.

10. A method for detecting Chlamydia infection in a patient, comprising:

(a) obtaining a biological sample from the patient;

(b) contacting the sample with a fusion protein comprising a polypeptide, the polypeptide comprising an immunogenic portion of a Chlamydia antigen, wherein said antigen comprises an amino acid sequence set forth in any one of SEQ ID NOs: 304–305; and (c) detecting the presence of antibodies that bind to the fusion protein.

11. The method of any one of claims 9 and 10 wherein the biological sample is selected from the group consisting of whole blood, serum, plasma, saliva, cerebrospinal fluid and urine.

12. A method for detecting Chlamydia infection in a biological sample, comprising:

(a) contacting the biological sample with a binding agent which is capable of binding to a polypeptide comprising an immunogenic portion of a Chlamydia antigen, wherein said antigen comprises an amino acid sequence set forth in any one of SEQ ID NOs:304–305; and (b) detecting in the sample a polypeptide that binds to the binding agent, thereby detecting Chlamydia infection in the biological sample.

13. The method of claim 12, wherein the binding agent is a monoclonal antibody.

14. The method of claim 12, wherein the binding agent is a polyclonal antibody.

15. A diagnostic kit comprising:

(a) a polypeptide comprising an immunogenic portion of a Chlamydia antigen, wherein said antigen comprises an amino acid sequence set forth in any one of SEQ ID NOs:304–305; and (b) a detection reagent.

16. A diagnostic kit comprising:

(a) a fusion protein comprising a polypeptide, the polypeptide comprising an immunogenic portion of a Chlamydia antigen, wherein said antigen comprises an amino acid sequence set forth in any one of SEQ ID NOs: 304–305; and (b) a detection reagent.

17. The kit of claims 15 or 16 wherein the polypeptide is immobilized on a solid support.

18. The kit of claims 15 or 16 wherein the detection reagent comprises a reporter group conjugated to a binding agent.

19. The kit of claim 18 wherein the binding agent is selected from the group consisting of anti-immunoglobulins, Protein G, Protein A and lectins.

20. The kit of claim 18 wherein the reporter group is selected from the group consisting of radioisotopes, fluorescent groups, luminescent groups, enzymes, biotin and dye particles.

21. A diagnostic kit comprising:

(a) at least one antibody, or antigen-binding fragment thereof, according to claim 7 or claim 8; and (b) a detection reagent.

22. A method for stimulating an immune response in a patient, comprising administering to a patient a polypeptide comprising an amino acid sequence having at least 90% identity with the amino acid sequence of SEQ ID NO:305, wherein an immune response to Chlamydia is induced.

* * * * *